US012605453B2

(12) United States Patent
Kim et al.

(10) Patent No.: US 12,605,453 B2
(45) Date of Patent: Apr. 21, 2026

(54) CP2C-TARGETING PEPTIDE-BASED ANTICANCER AGENT

(71) Applicants: Industry-University Cooperation Foundation Hanyang University, Seoul (KR); Konkuk University Glocal Industry-Academic Collaboration Foundation, Chungju-si (KR); Korea National University of Education Industry-Academy Cooperation Foundation, Cheongwon-gun (KR)

(72) Inventors: Chul Geun Kim, Seoul (KR); Min Young Kim, Seoul (KR); Chan Gil Kim, Chungju-si (KR); Seung Han Son, Incheon (KR); Ji Sook Kim, Uijeongbu-si (KR); Sung Woo Choi, Gimpo-si (KR); Seol Eui Lee, Seoul (KR); Min Sung Chung, Seoul (KR); Dong Sun Park, Cheongju-si (KR); Sang Won Lee, Seoul (KR); Jae Min Jeong, Seoul (KR); Dong Ho Choi, Seoul (KR); Ki Seok Jang, Seoul (KR)

(73) Assignees: Industry-University Cooperation Foundation Hanyang University, Seoul (KR); Konkuk University Glocal Industry-Academic Collaboration Foundation, Chungju-si (KR); Korea National University of Education Industry-Academy Cooperation Foundation, Cheongwon-gun (KR)

( * ) Notice: Subject to any disclaimer, the term of this patent is extended or adjusted under 35 U.S.C. 154(b) by 891 days.

(21) Appl. No.: 17/600,760

(22) PCT Filed: Apr. 1, 2020

(86) PCT No.: PCT/KR2020/004467
§ 371 (c)(1),
(2) Date: Oct. 1, 2021

(87) PCT Pub. No.: WO2020/204605
PCT Pub. Date: Oct. 8, 2020

(65) Prior Publication Data
US 2022/0160888 A1 May 26, 2022

(30) Foreign Application Priority Data
Apr. 1, 2019 (KR) ........................ 10-2019-0038023
Jul. 16, 2019 (KR) ........................ 10-2019-0085790

(51) Int. Cl.
A61K 47/64 (2017.01)
A61K 47/54 (2017.01)
A61K 47/65 (2017.01)
A61P 35/00 (2006.01)
C07K 14/00 (2006.01)

(52) U.S. Cl.
CPC ............ *A61K 47/64* (2017.08); *A61K 47/542* (2017.08); *A61K 47/65* (2017.08); *A61P 35/00* (2018.01)

(58) Field of Classification Search
CPC ................................. A61K 47/64; C07K 14/00
See application file for complete search history.

(56) References Cited

U.S. PATENT DOCUMENTS

| | | | |
|---|---|---|---|
| 10,143,660 B2 | 12/2018 | Nel et al. | |
| 10,611,797 B2 | 4/2020 | Kim et al. | |
| 2006/0205771 A1 | 9/2006 | Noble et al. | |
| 2013/0280298 A1* | 10/2013 | Leclerc ................. | A61K 39/29 424/209.1 |
| 2015/0211021 A1 | 7/2015 | De Mollerat Du Jeu | |
| 2018/0086788 A1* | 3/2018 | Kim ........................ | A23L 33/40 |

FOREIGN PATENT DOCUMENTS

| | | | | |
|---|---|---|---|---|
| CN | 104479002 A | | 4/2015 | |
| CN | 107624116 A | * | 1/2018 | ............. A23L 33/18 |
| EP | 2 028 270 A2 | | 2/2009 | |
| KR | 10-2015-0064097 A | | 6/2015 | |
| KR | 10-1841339 B1 | | 3/2018 | |
| KR | 10-2018-0094112 A | | 8/2018 | |
| WO | 2004/110341 A2 | | 12/2004 | |
| WO | 2014/046983 A1 | | 3/2014 | |
| WO | WO-2016159627 | * | 10/2016 | ............. A23L 33/18 |
| WO | WO-2016159627 A1 | * | 10/2016 | ............. A23L 33/18 |
| WO | WO-2018044012 A1 | * | 3/2018 | ............. A23L 33/18 |

OTHER PUBLICATIONS

Pujals et al., 2008, Proline-rich, amphipathic cell-penetrating peptides, Advanced Drug Delivery Reviews, 60: 473-484.*
Zhang et al., 2012, Converting Peptides into Drug Leads by Lipidation, Current Medicinal Chemistry, 19: 1602-1618.*
Lauta, 2000, Pharmacological elements in clinical applications of synthetic peptides, Fundam Clin Pharmacol, 14: 425-442.*
Chinese Office Action dated Oct. 26, 2023 in Chinese Application No. 202080039723.6.
Wang et al., "Advances in Research on Modification of Protein and Peptide Drugs with Fatty Acids", Progress in Pharmaceutical Sciences, 2015, vol. 39, No. 9, pp. 651-658 (8 page total).
Ying Li et al., "Variant fatty acid-like molecules Conjugation, novel approaches for extending the stability of therapeutic peptides", Scientific Reports, Dec. 11, 2015, pp. 1-9 (9 pages total).

(Continued)

*Primary Examiner* — Amber D Steele
(74) *Attorney, Agent, or Firm* — Sughrue Mion, PLLC

(57) ABSTRACT

The presented invention relates to a CP2c-targeting peptide-based anticancer agent. A CP2c-targeting peptide according to the presented invention binds to transcription factor CP2c to inhibit the formation of transcription factor CP2c complexes (CP2c homotetramer and CP2c/CP2b/PIAS1 heterohexamer), thereby inducing cancer cell-specific cell death. A fatty acid is bound to the peptide to ensure stability enabling long-term sustenance in vivo.

5 Claims, 134 Drawing Sheets
Specification includes a Sequence Listing.

(56) References Cited

OTHER PUBLICATIONS

Jin Youn Lee, "Effects of DHA-conjugation on the anticancer function of CP2c-targeting peptide", Thesis for the Master of Science, Hanyang University, Aug. 2019 (60 pages total).

Extended European Search Report issued Mar. 28, 2023 in European Application No. 20783202.3.

Esben M. Bech, et al., "Chemical Strategies for Half-Life Extension of Biopharmaceuticals: Lipidation and Its Alternatives", ACS Medicinal Chemistry Letters, 2018, pp. 577-580, vol. 9.

Office Action issued from Korean Patent Application No. 10-2019-0085790 issued on Oct. 23, 2020.

International Search Report for PCT/KR2020/004467 dated Jul. 13, 2020 (PCT/ISA/210).

* cited by examiner

[FIG 1]
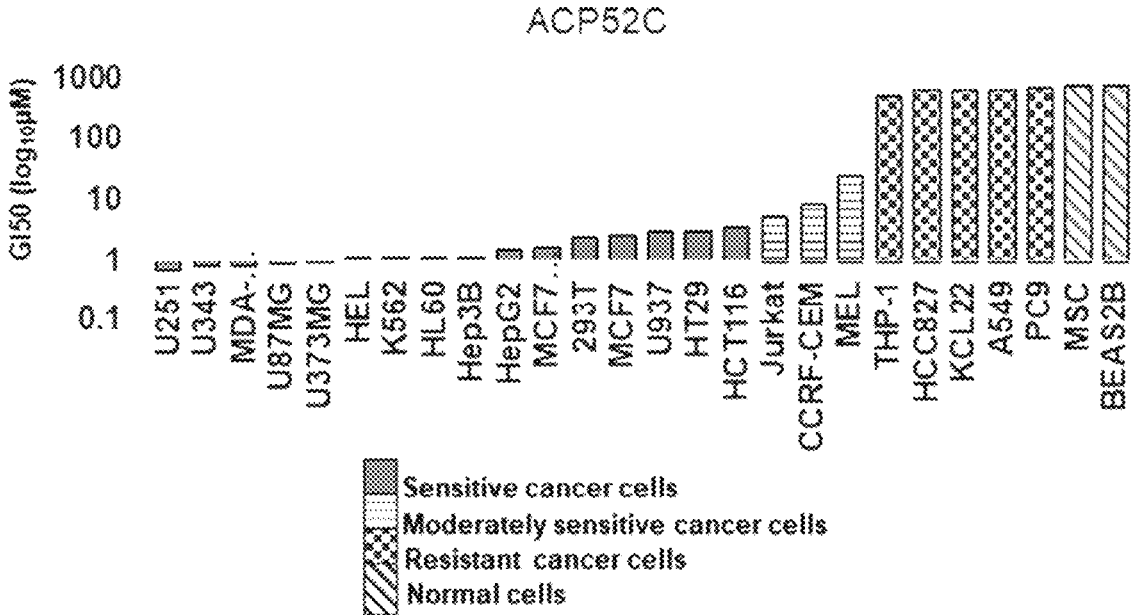

[FIG 2a]
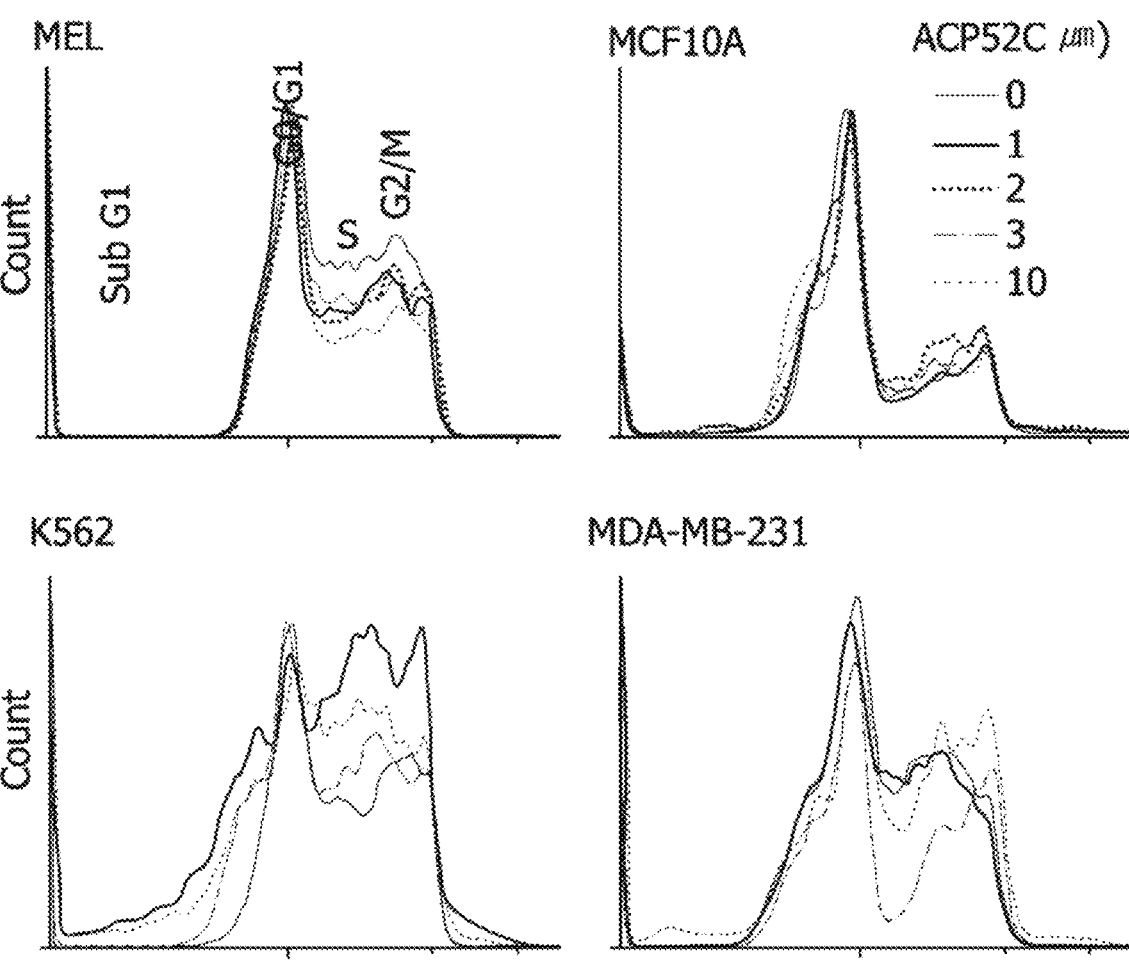

[FIG 2b]
B
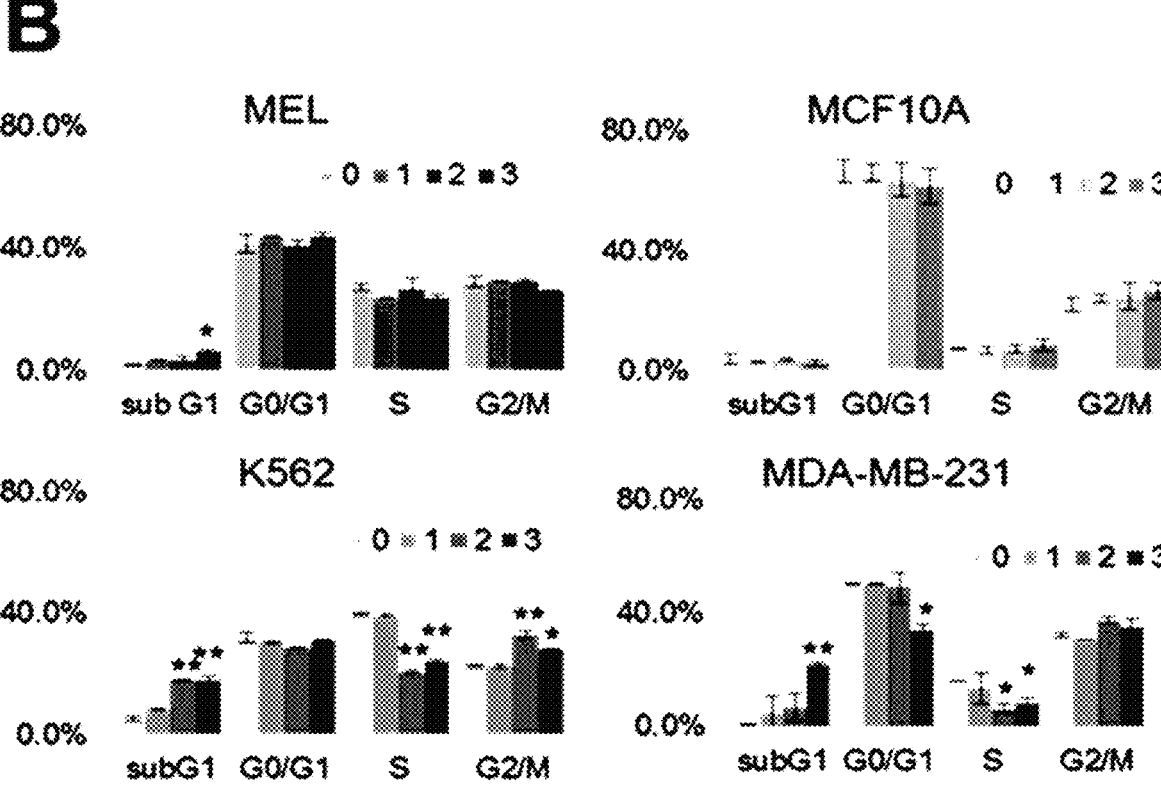

【FIG 2c】
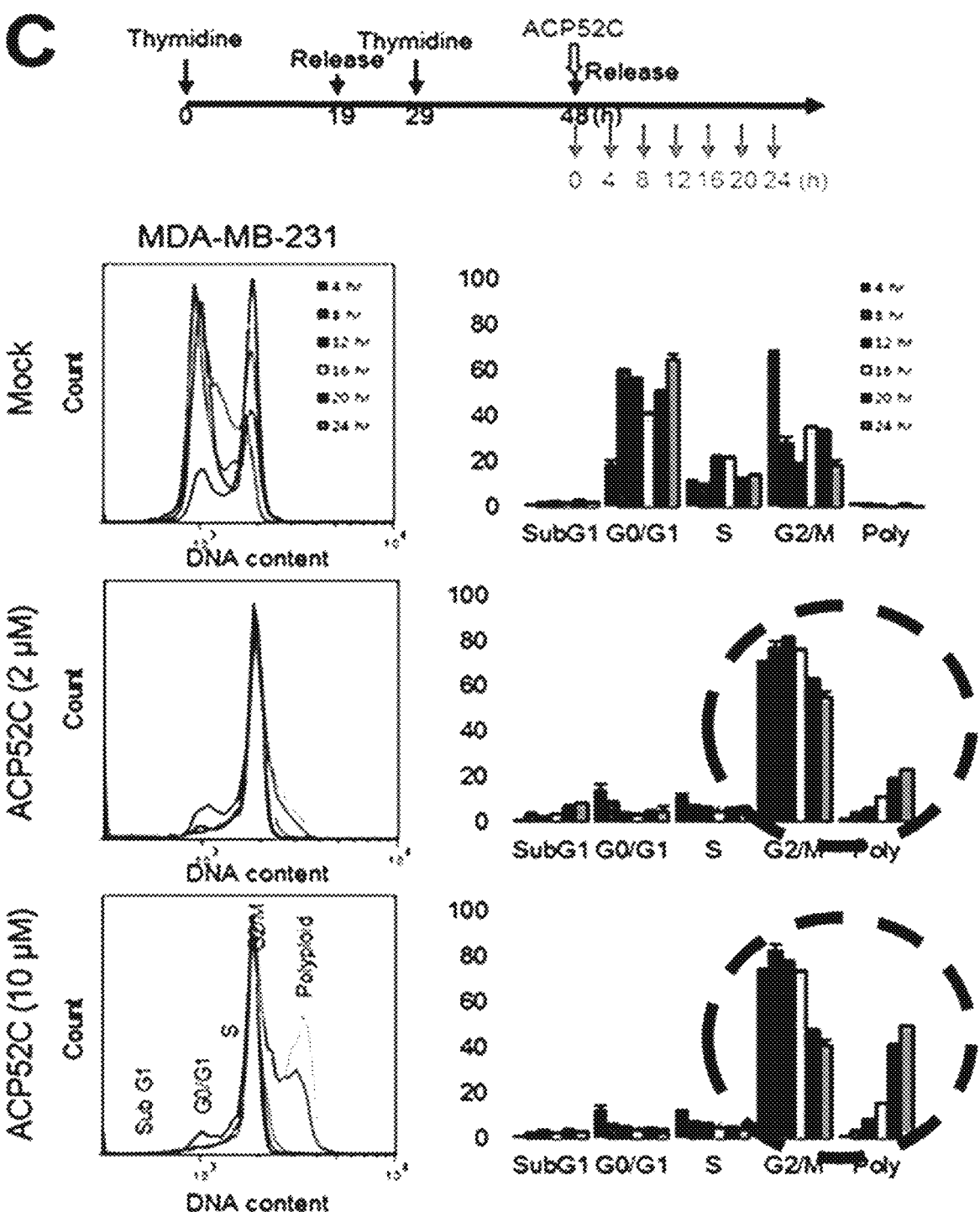

【FIG 2d】
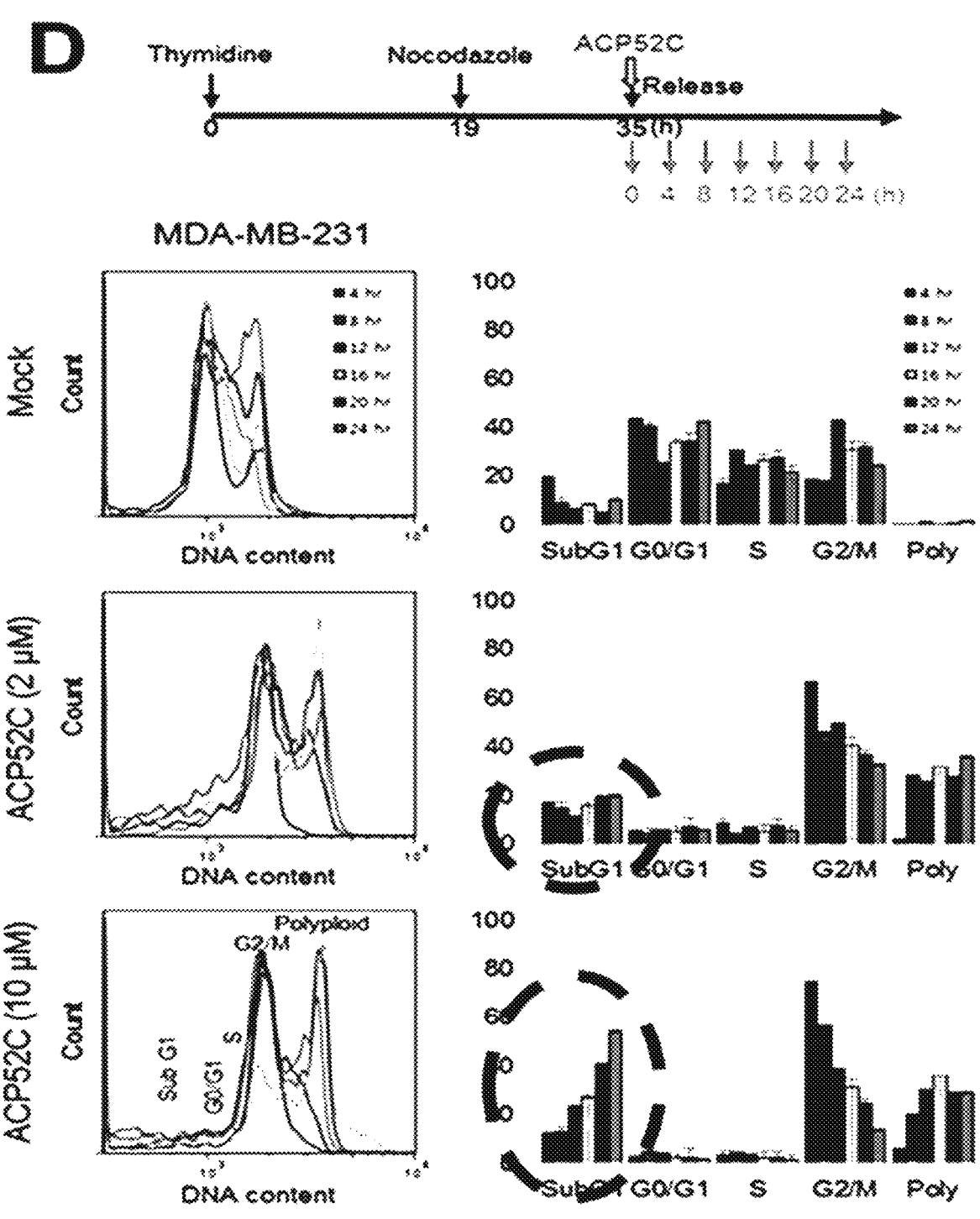

[FIG 3a]
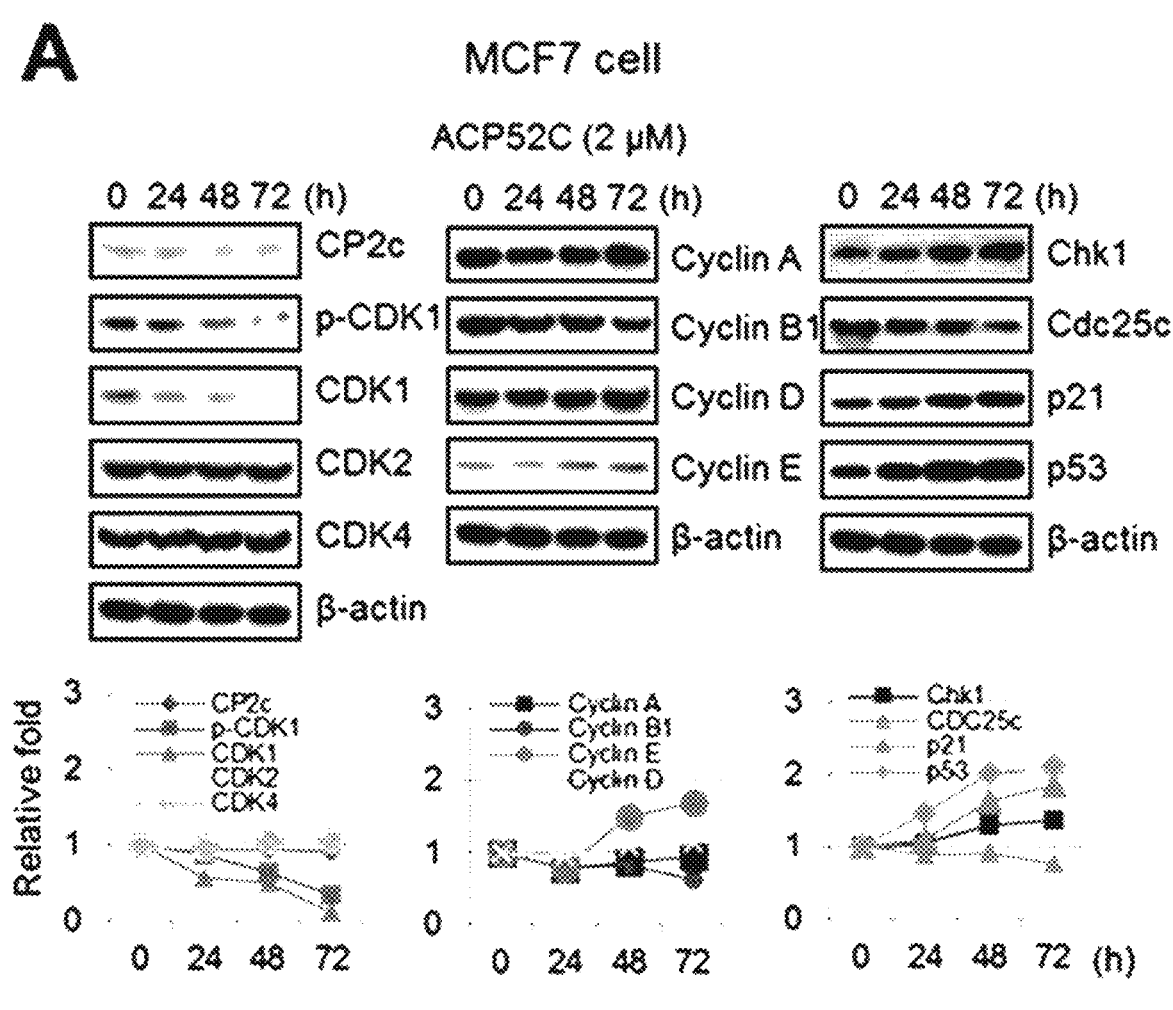

[FIG 3b]
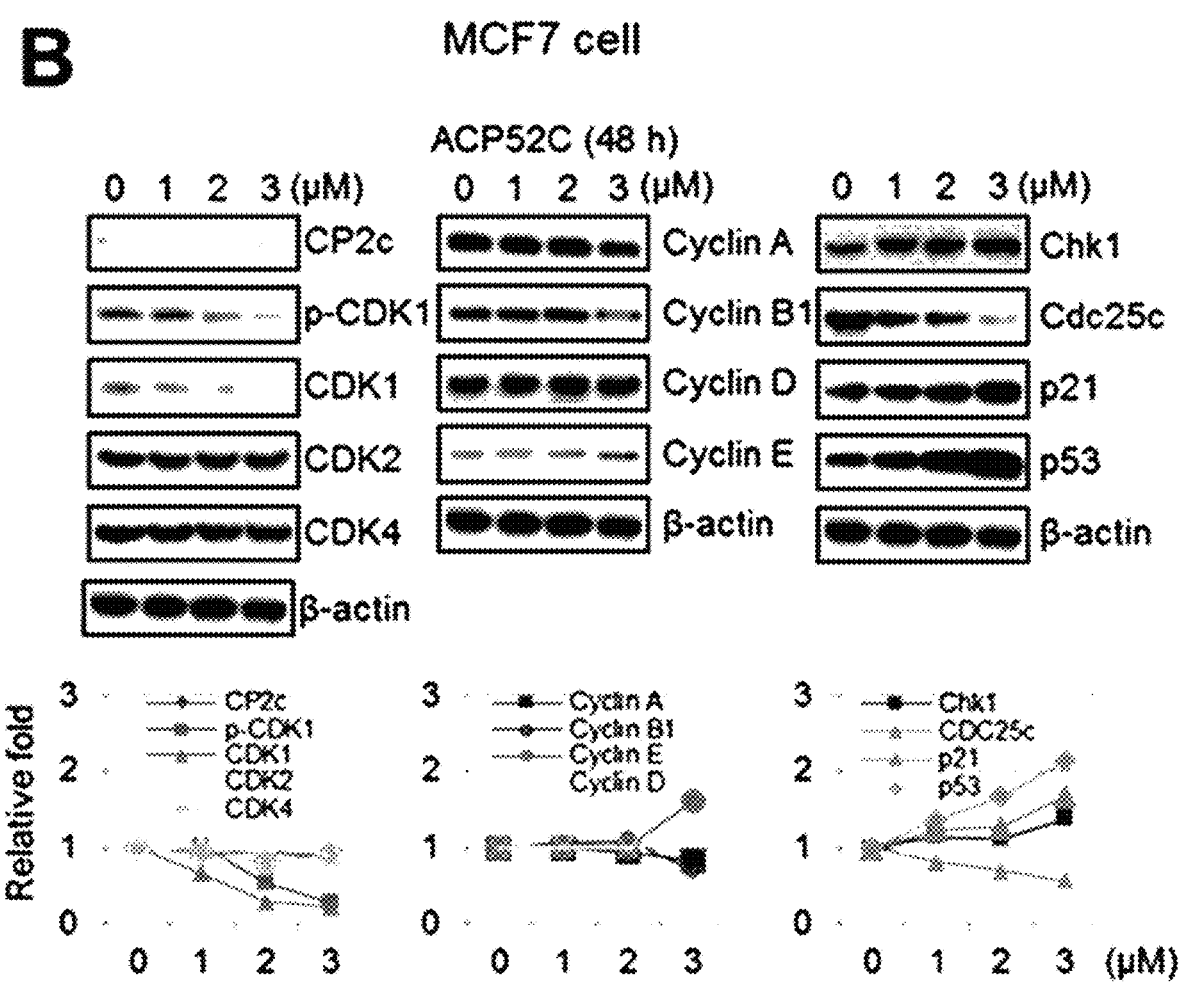

【FIG 3c】
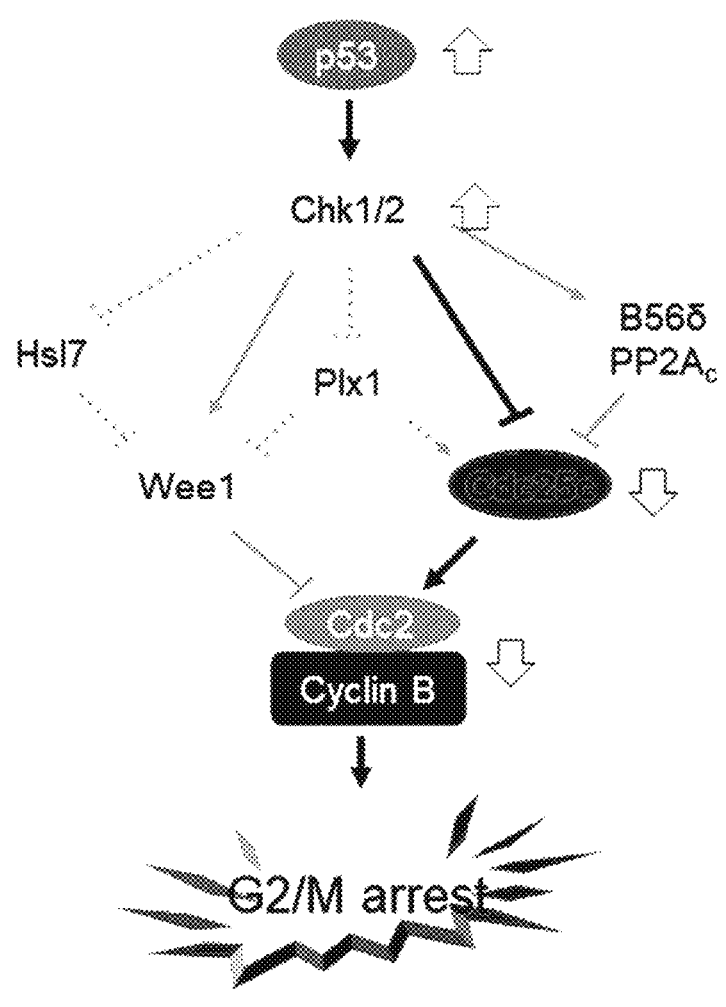

【FIG 4a】
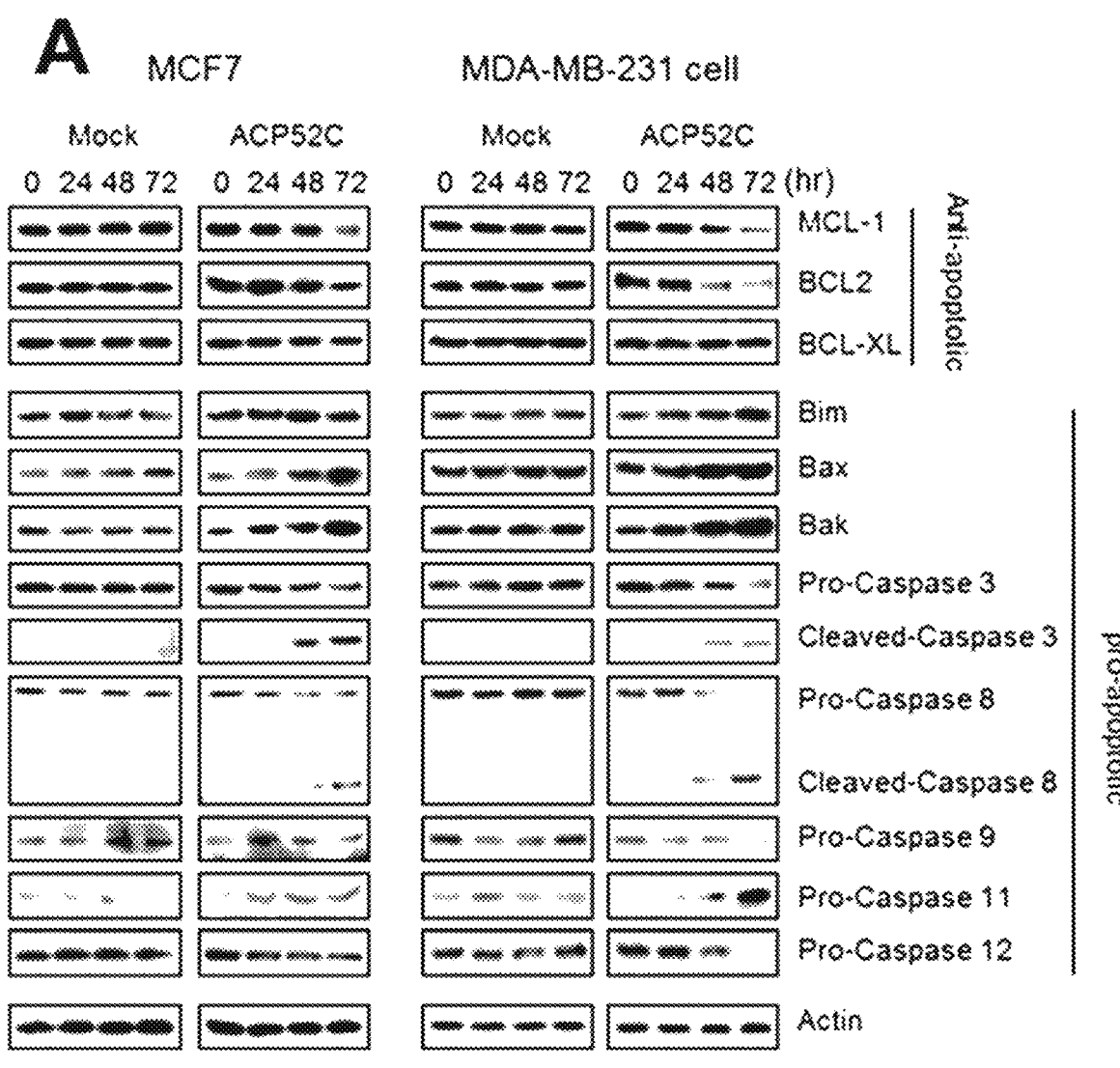

【FIG 4b】
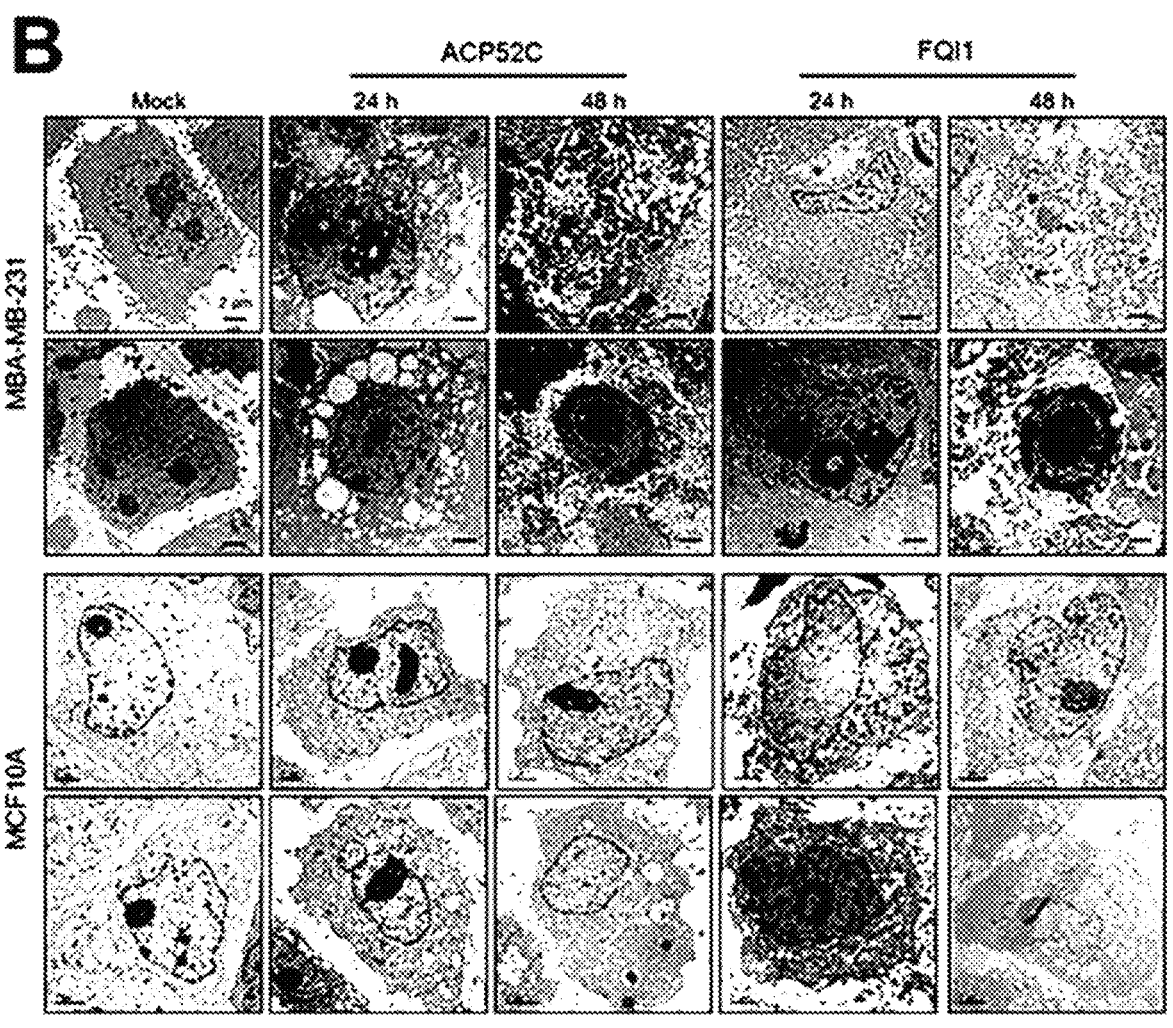

【FIG 4c】
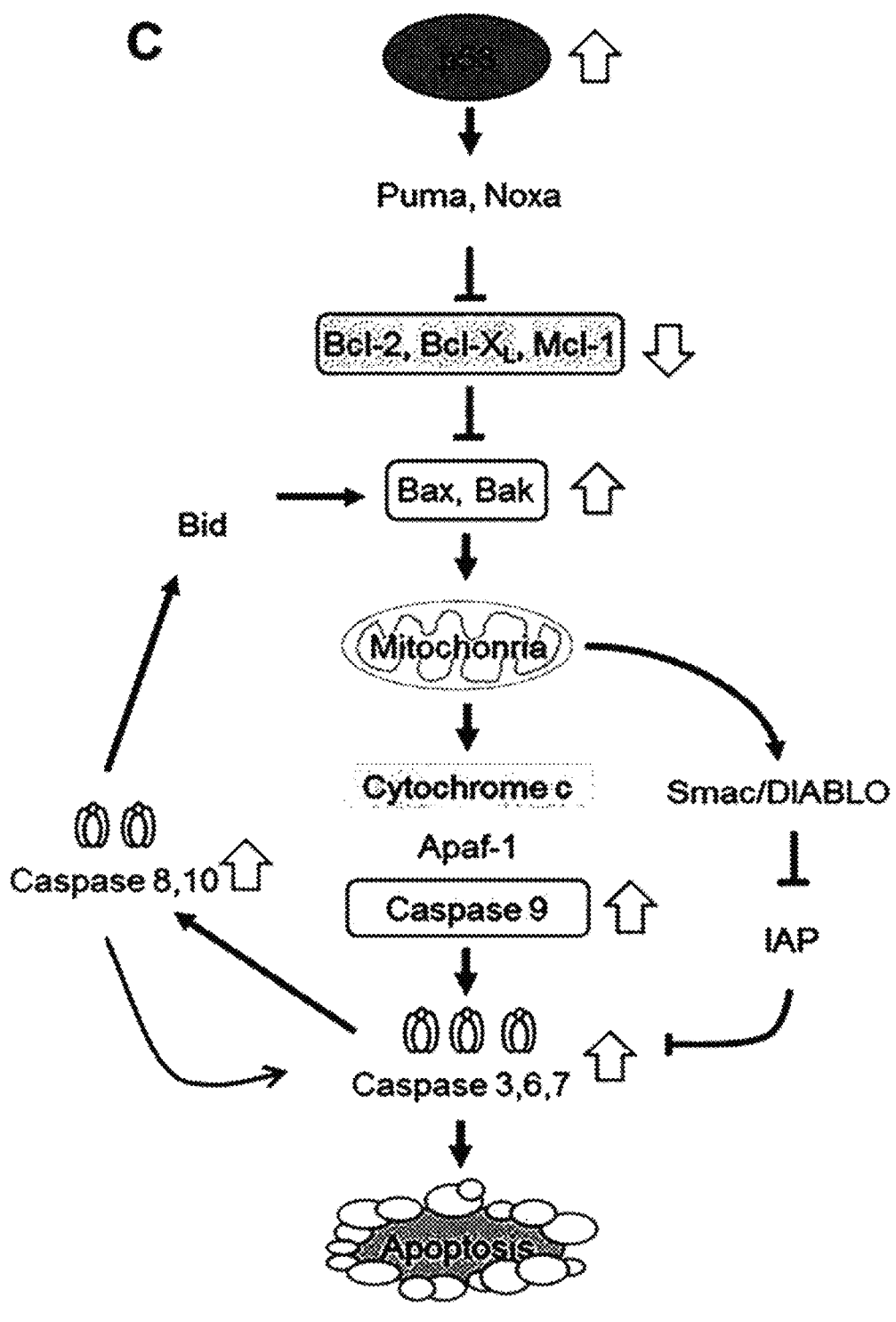

【FIG 5】
Cellular efficacy of ACP52C
- Cytosol → nucleus → cytosol → degradation
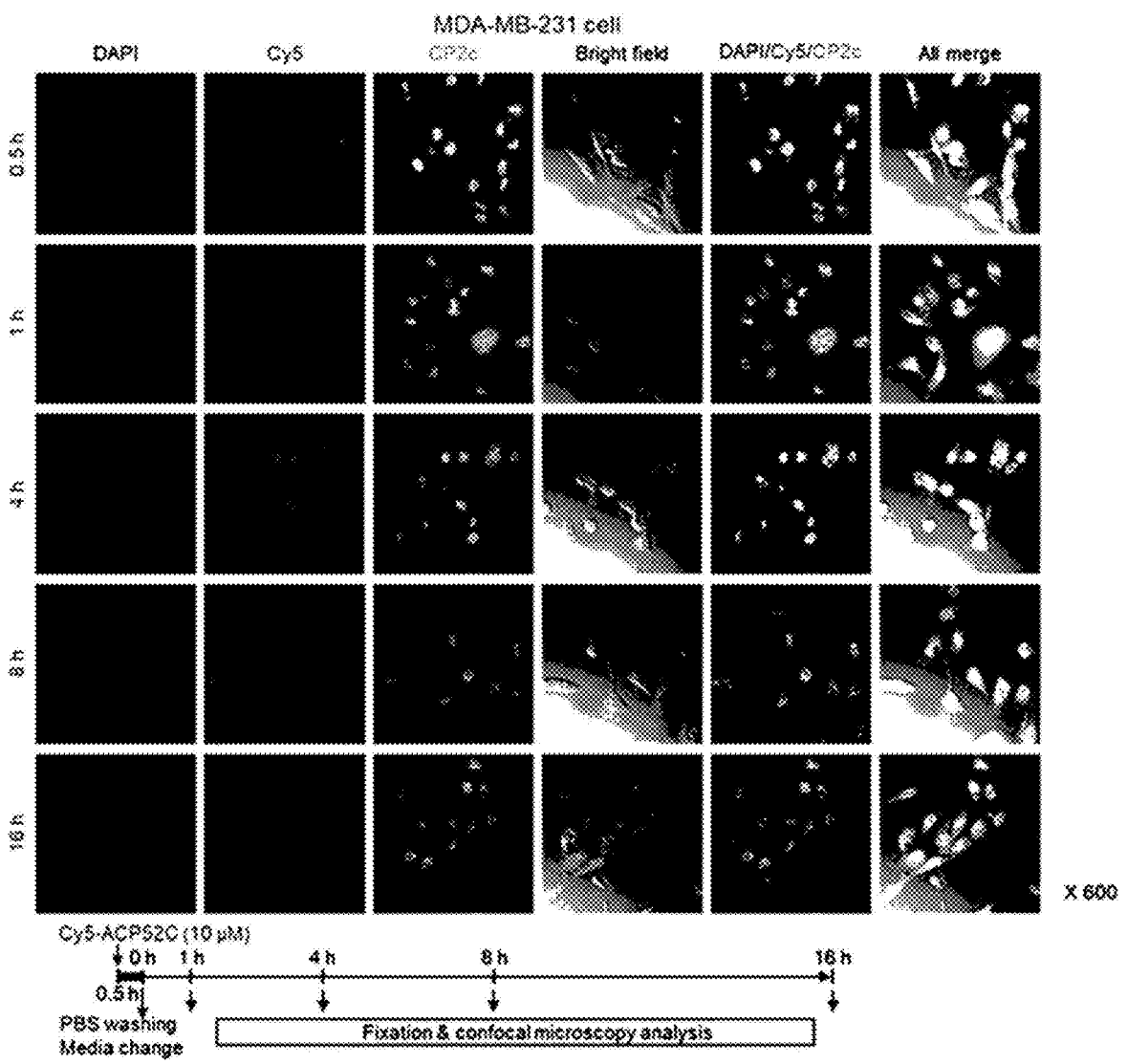

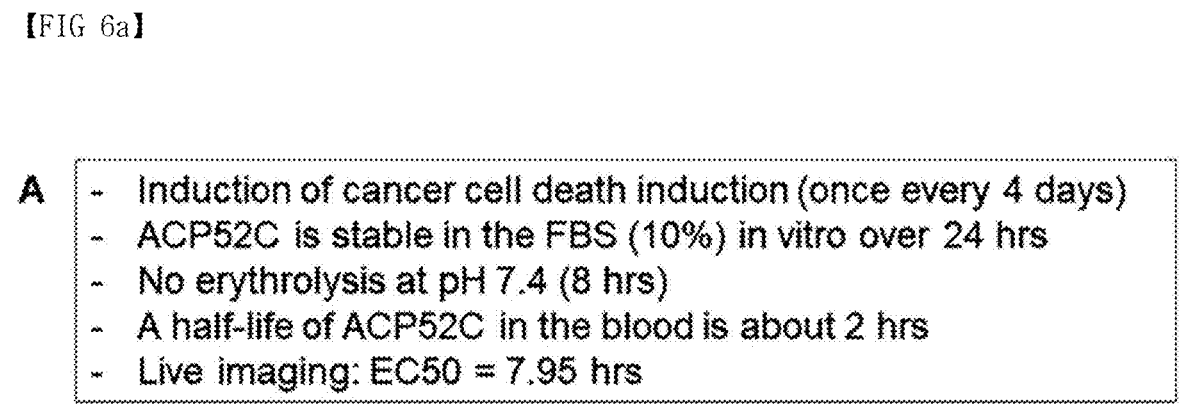

【FIG 6a】

A
- Induction of cancer cell death induction (once every 4 days)
- ACP52C is stable in the FBS (10%) in vitro over 24 hrs
- No erythrolysis at pH 7.4 (8 hrs)
- A half-life of ACP52C in the blood is about 2 hrs
- Live imaging: EC50 = 7.95 hrs

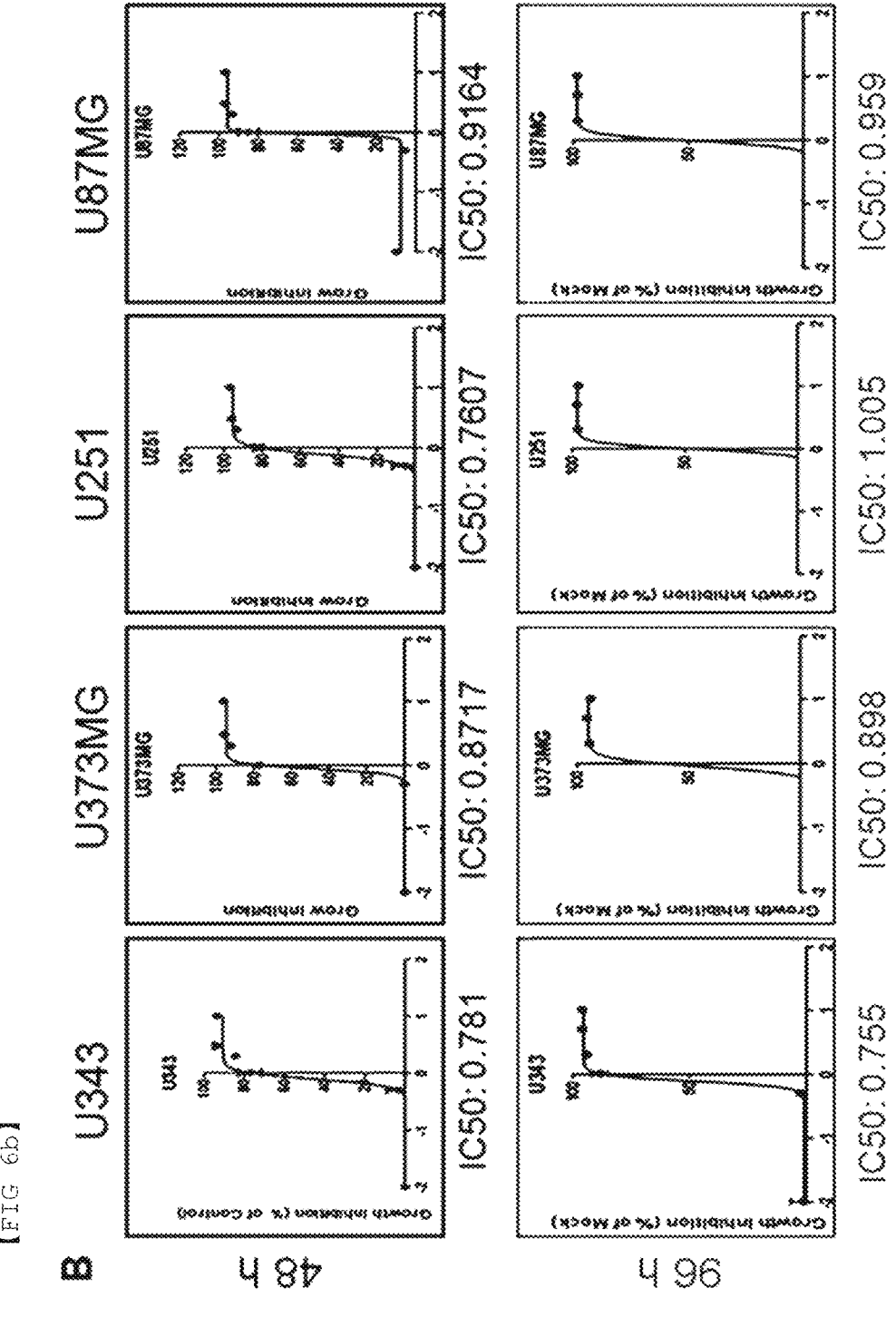
[FIG 6b]

[FIG 6c]
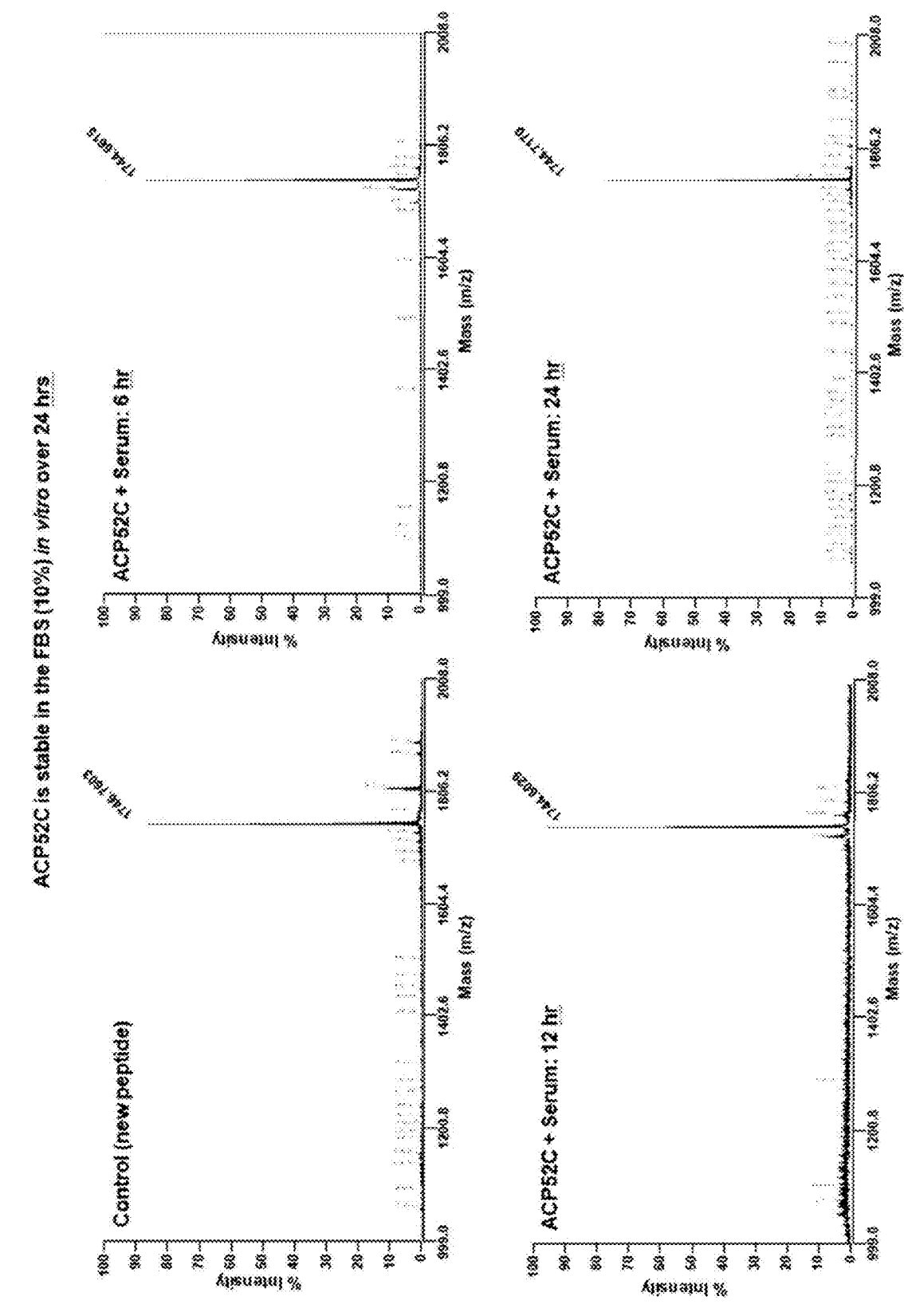

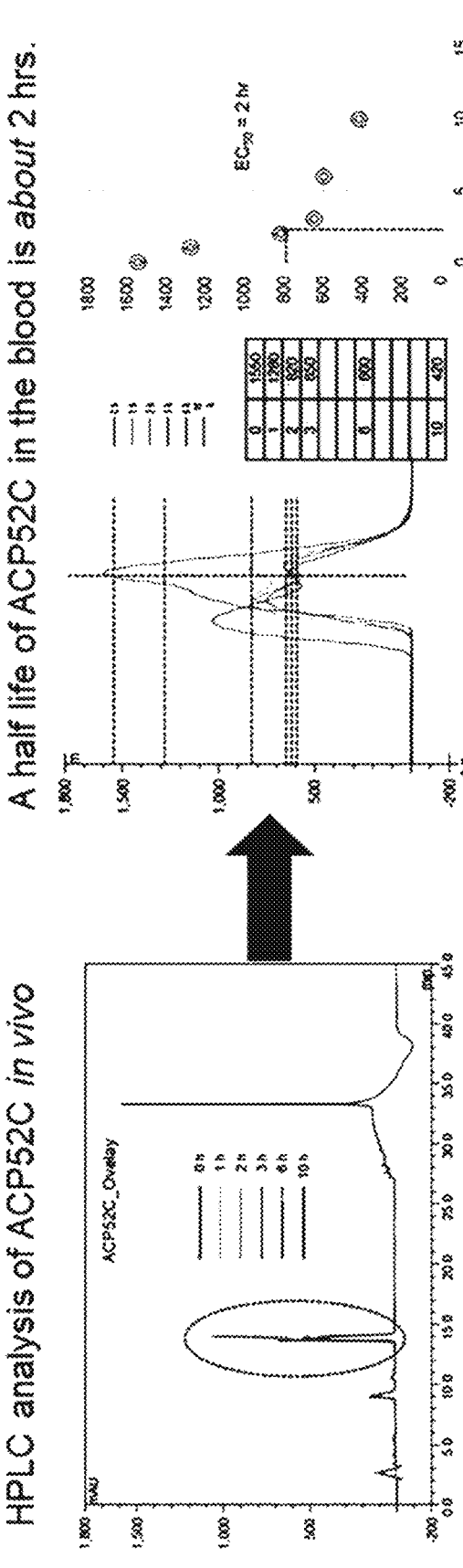
[FIG 6d]

[FIG 6e]
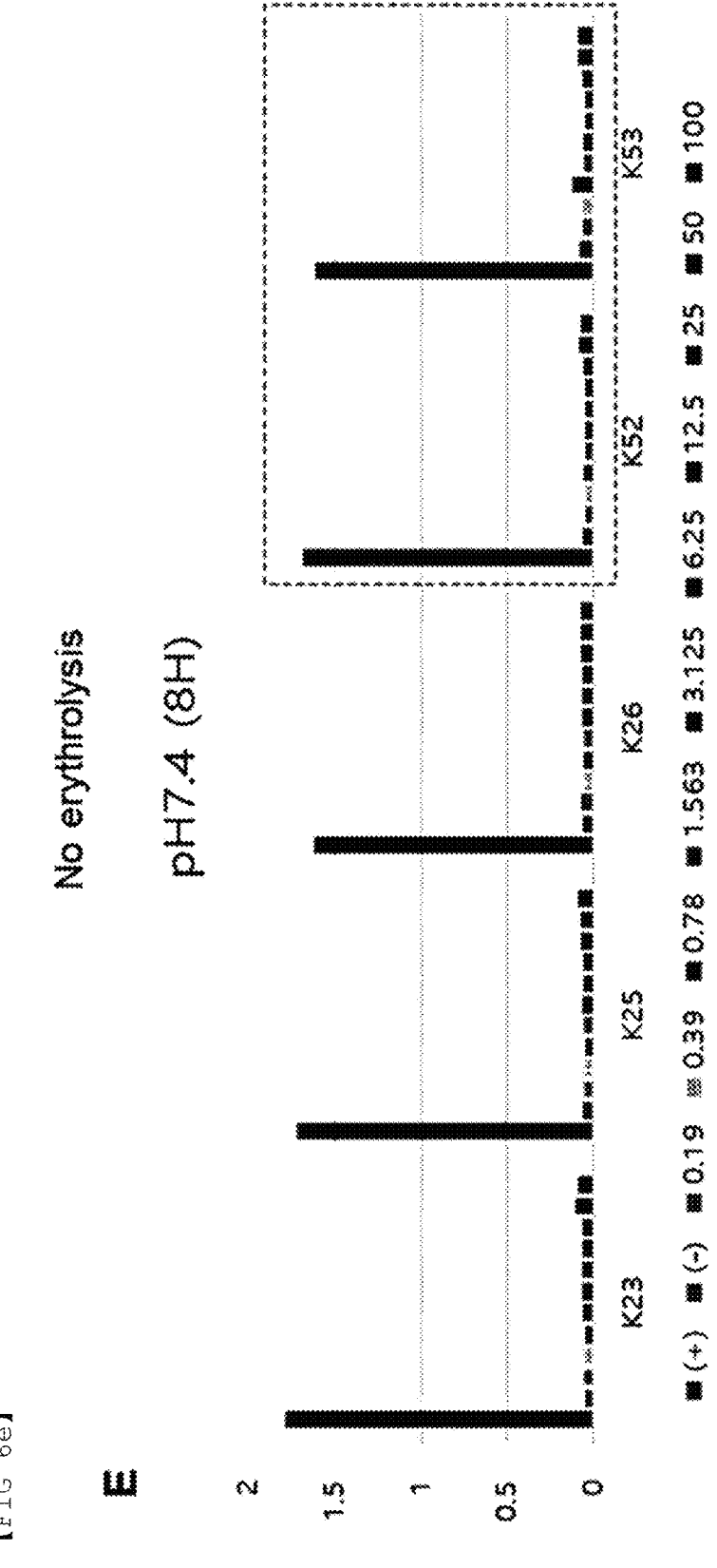

[FIG 6f]
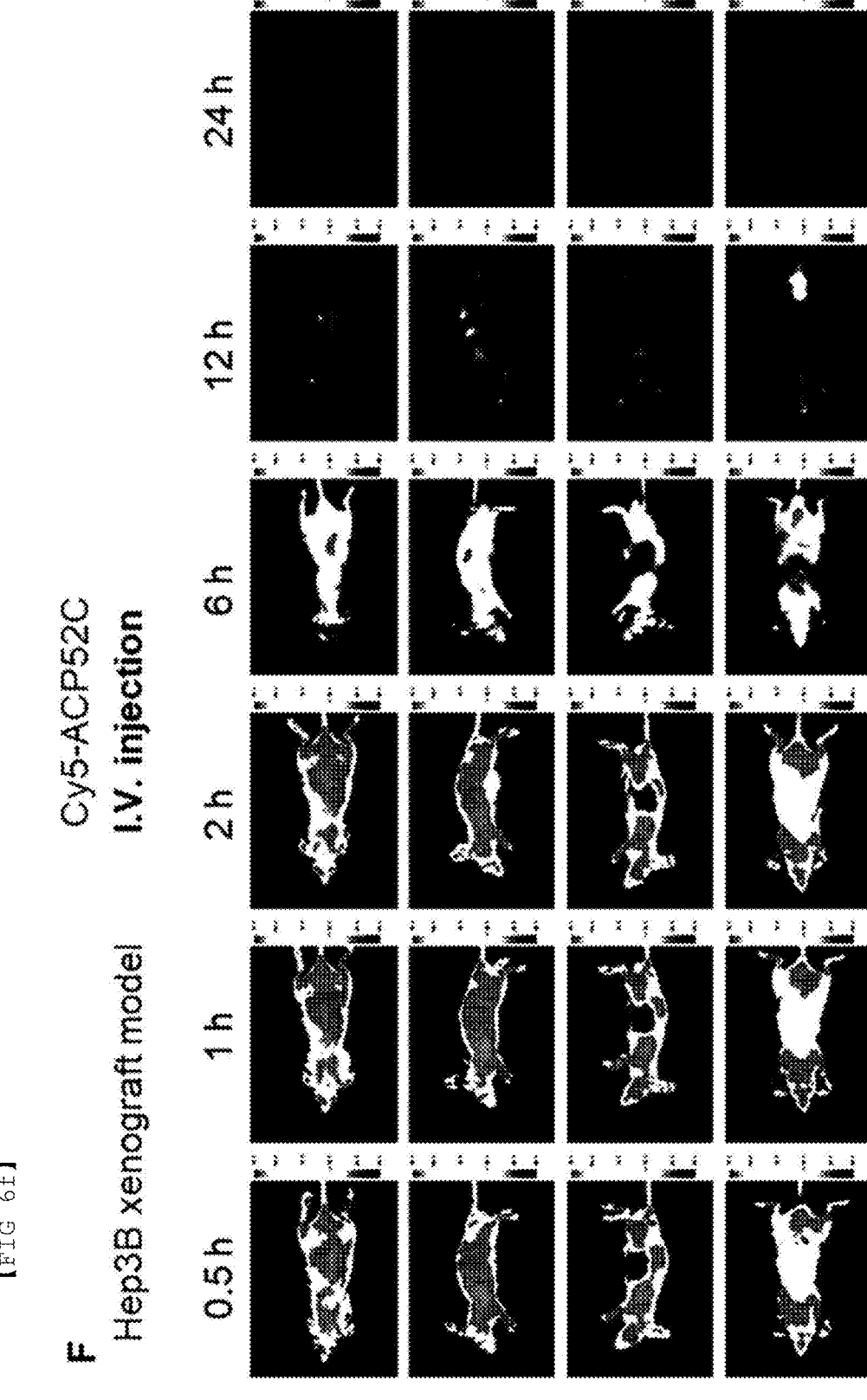

【FIG 6g】
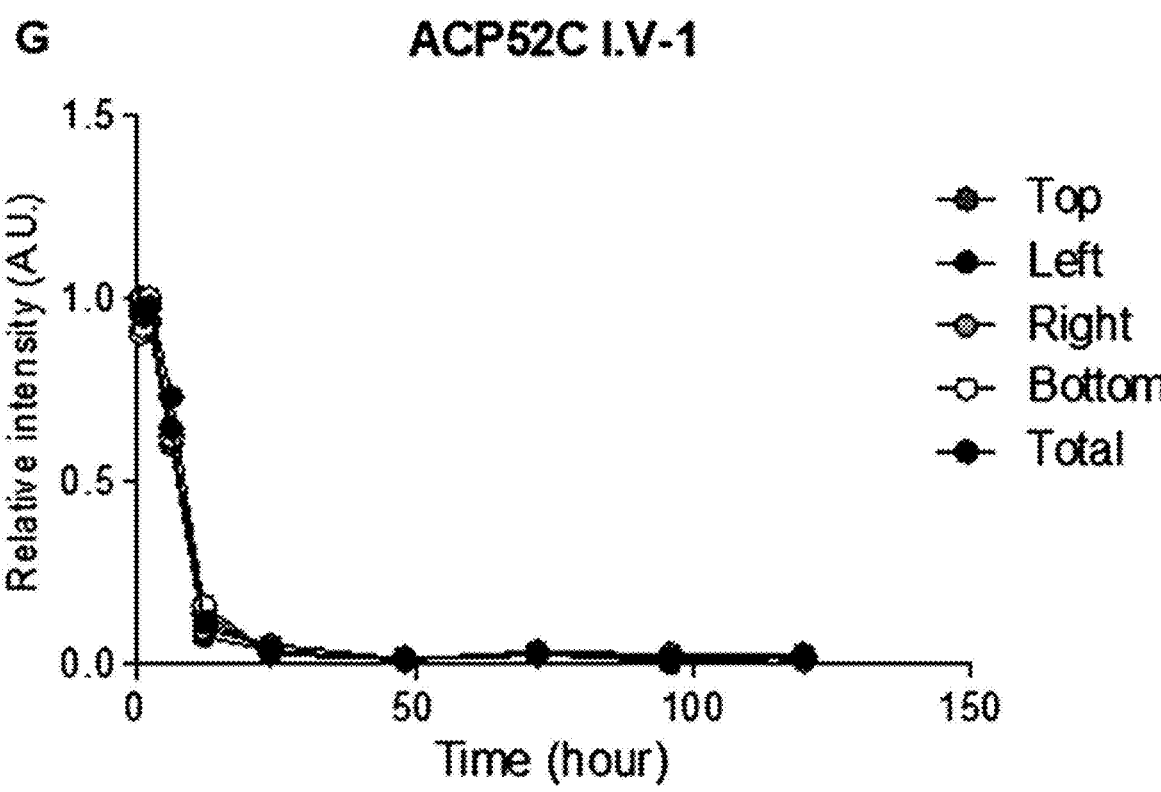

[FIG 6h]
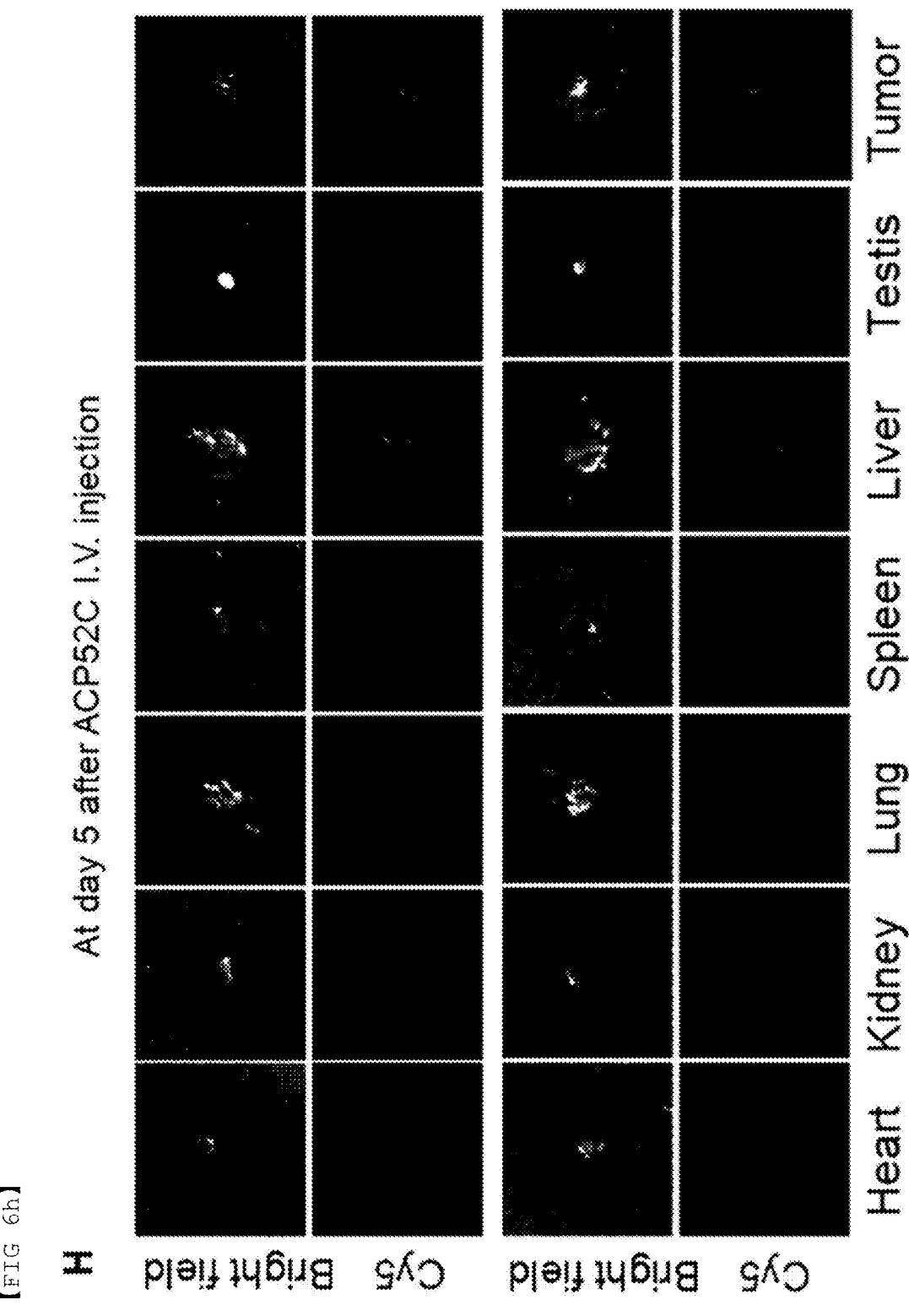

FIG. 7

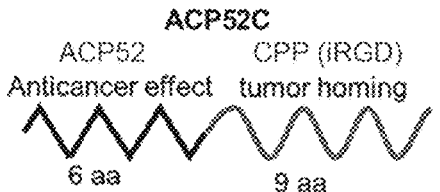

ACP52C

ACP52       CPP (iRGD)

Anticancer effect    tumor homing 6 aa       9 aa

[Effectiveness] Cancer cell specific apoptosis
[Safety] No side effect to normal cells
[peptide drug] many merits
[MOA] well known (multi-faceted)
[Stability] need to be improved (about 6 h in vivo)

| no | name | sequence | |
|----|------|----------|---|
| 1 | C16-ACP52Cn (ACP52CG) | Ac-K(E-pal)-GG-NYPQRPCRGDKGPDC-NH2 | (SEQ ID NO: 17) |
| 2 | C16-GFLG-ACP52Cn (ACP52CK) | Ac-K(EGLFG-pal)-GG-NYPQRPCRGDKGPDC-NH2 | (SEQ ID NO: 18) |
| 3 | C16-ACP52Cm (ACP52GK) | Ac-NYPQRP-GG-K(E-pal)-GGCRGDKGPDC-NH2 | (SEQ ID NO: 19) |
| 4 | yC16-ACP52Cm (ACP52CGK) | Ac-NYPQRP-GG-K(yE-pal)-GGCRGDKGPDC-NH2 | (SEQ ID NO: 20) |

(SEQ ID NO: 16)

【FIG 9a】
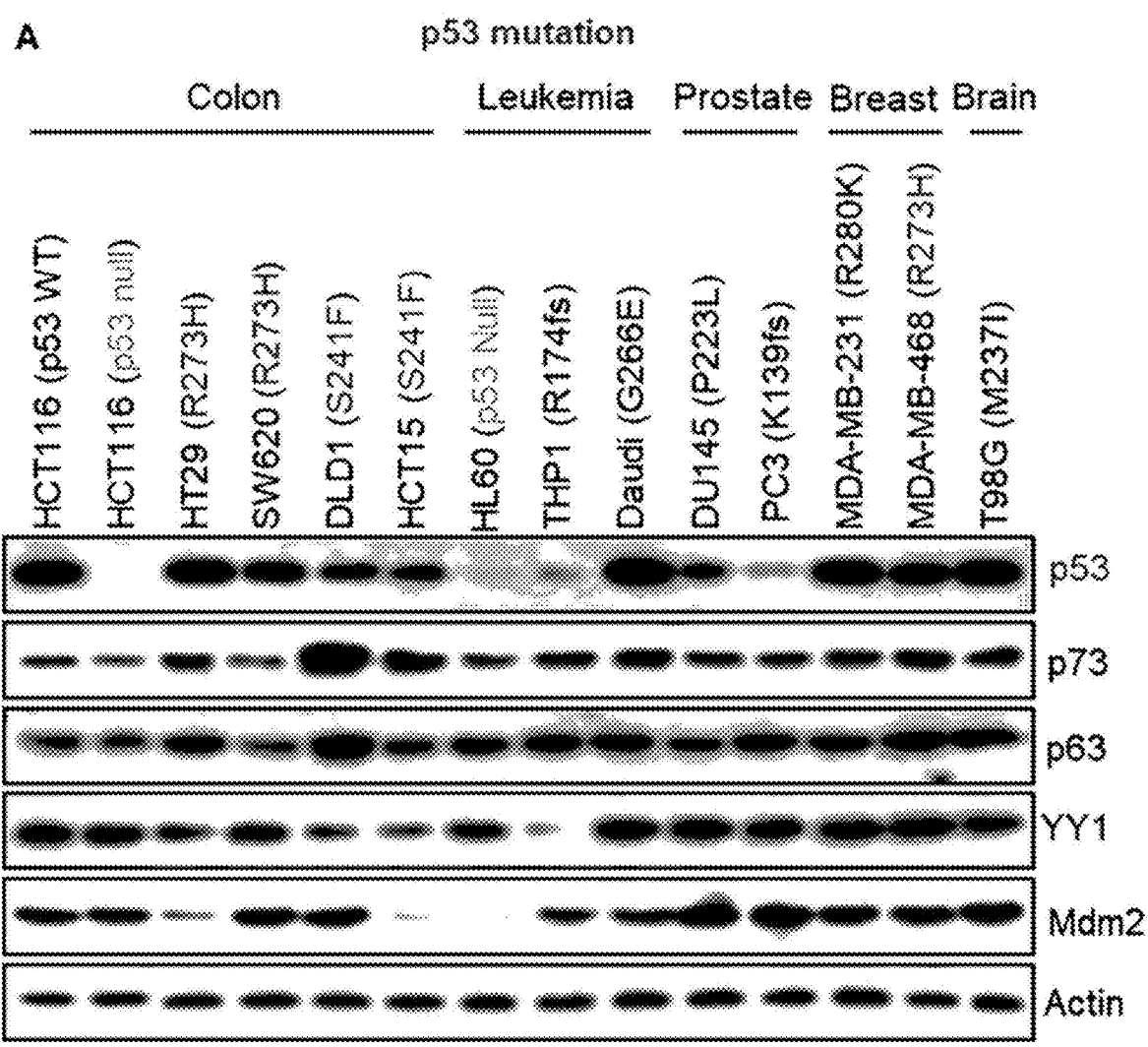

【FIG 10a】
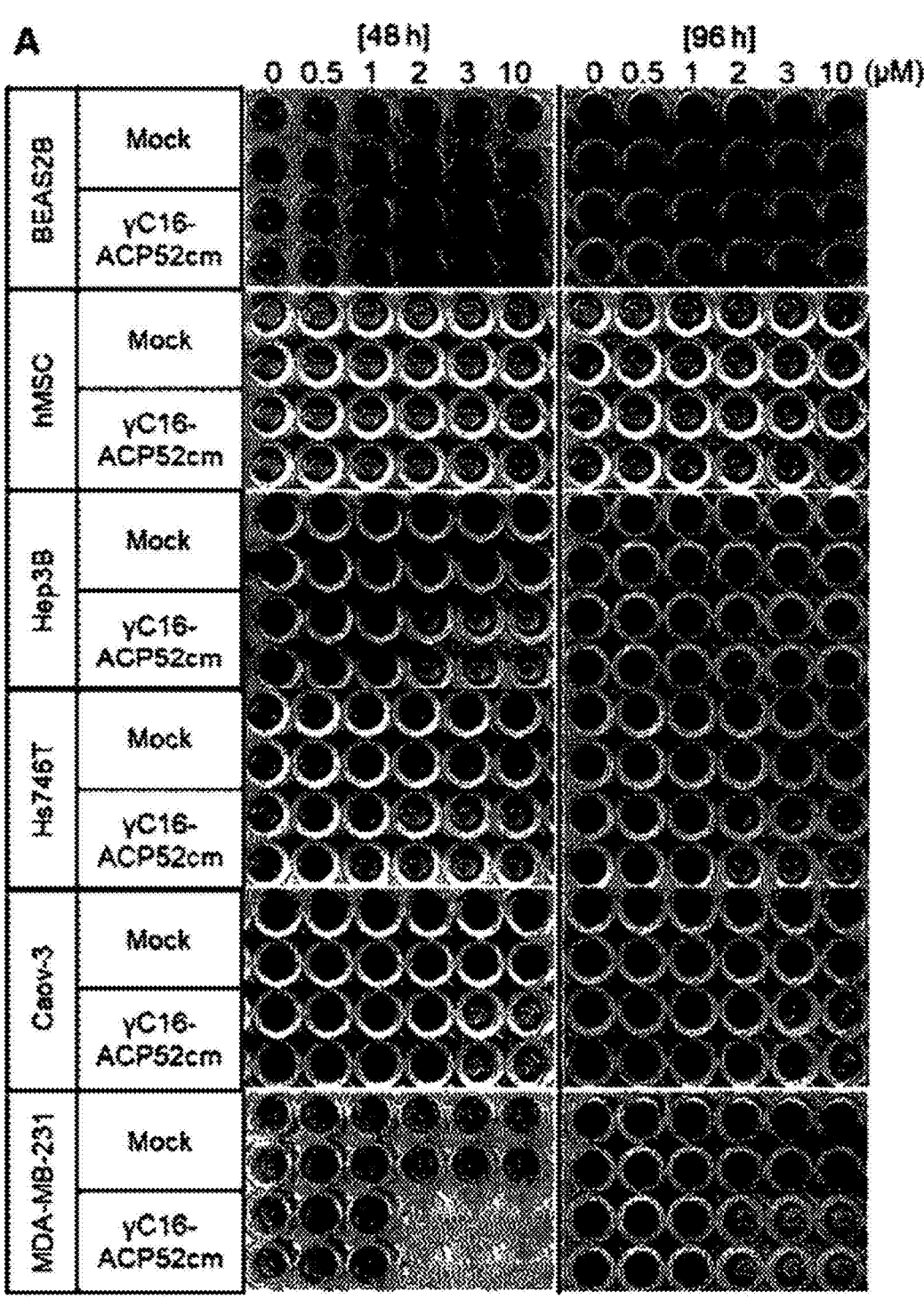

【FIG 10b】
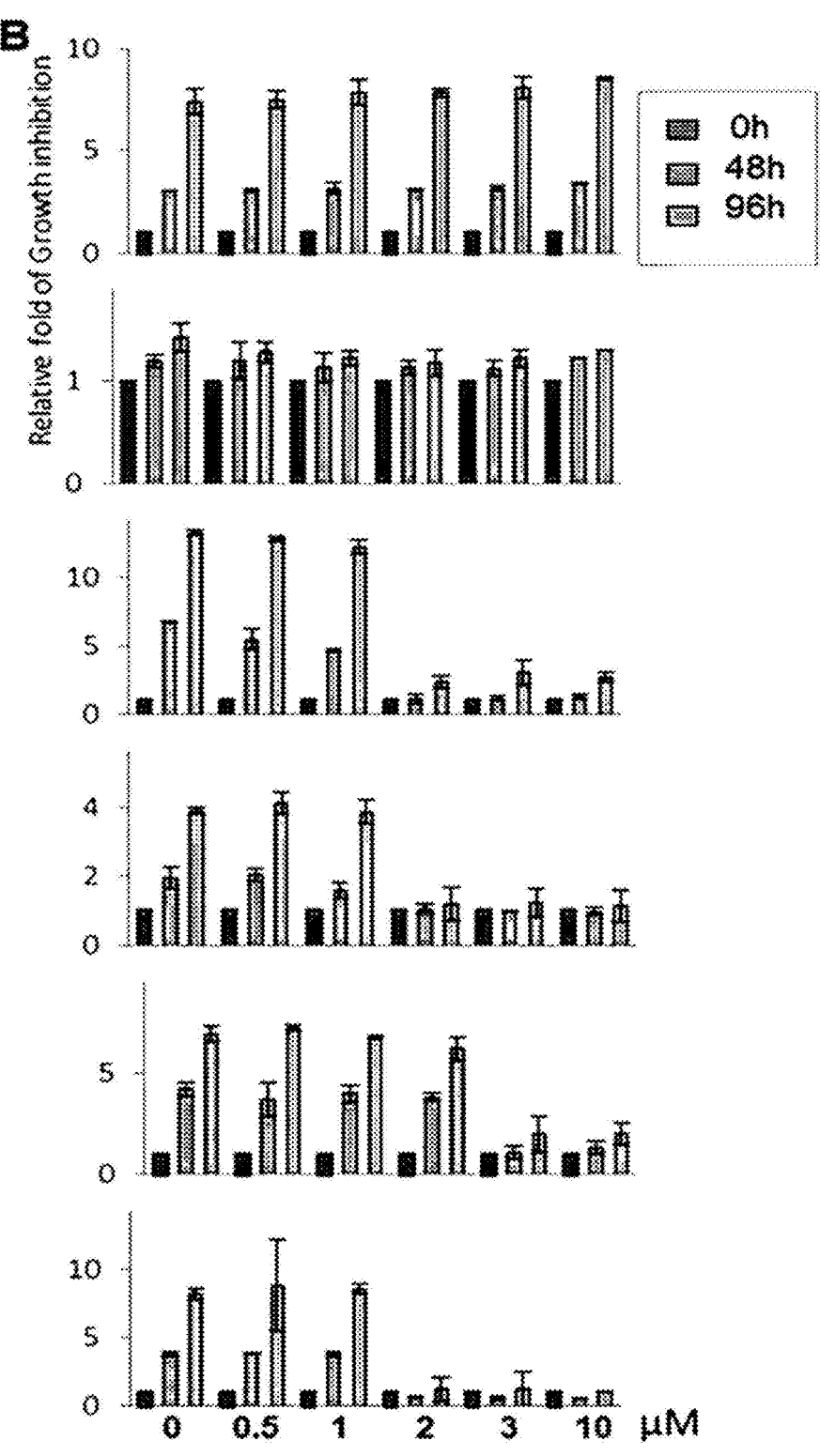

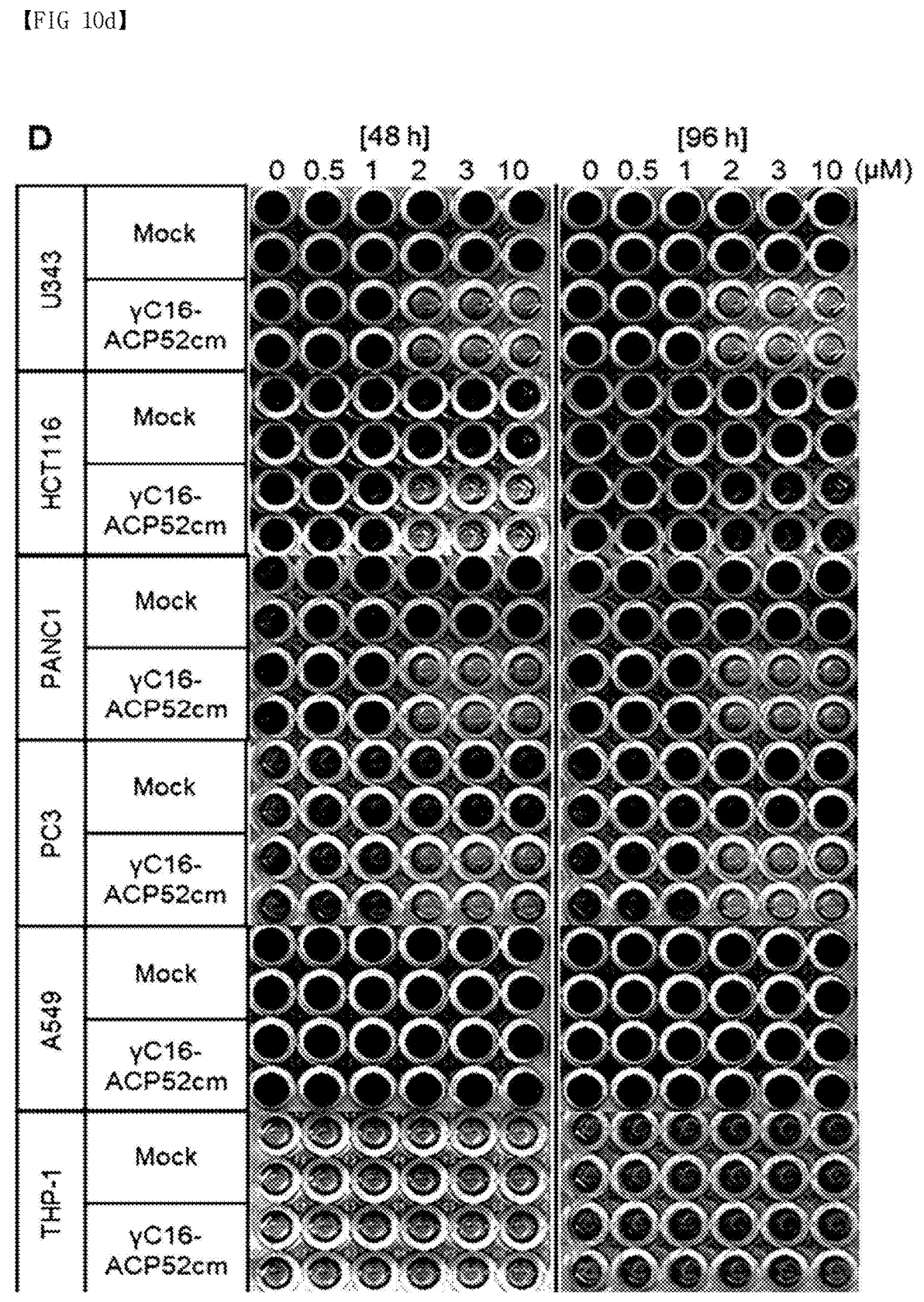

【FIG 10d】

【FIG 10e】
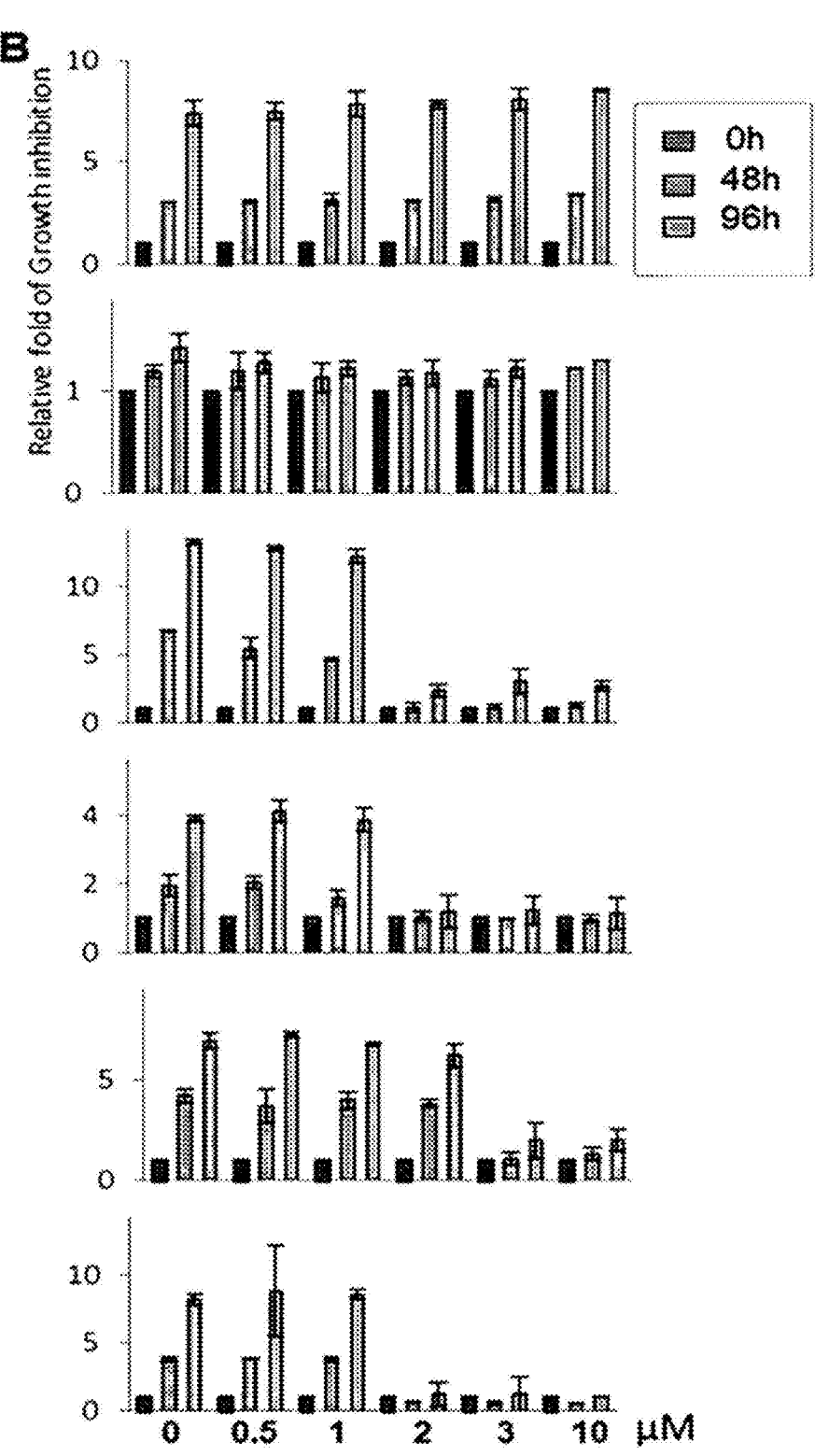

【FIG 10g】
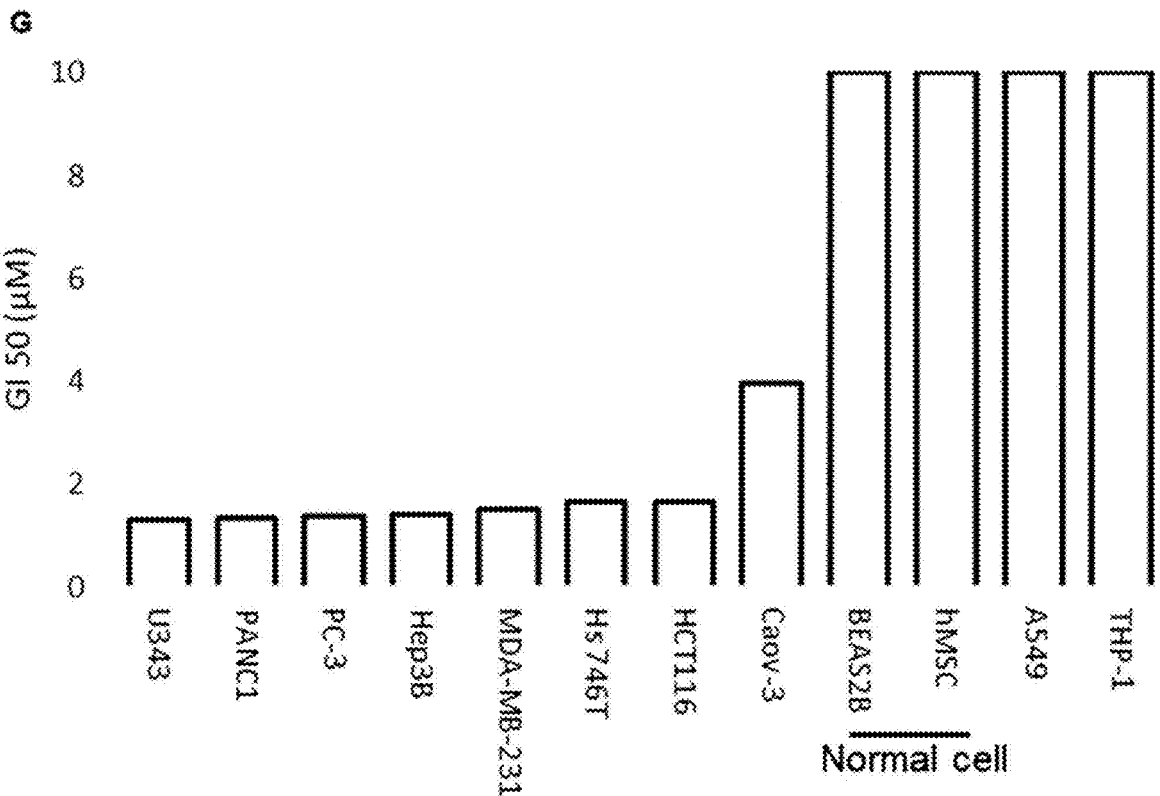

【FIG 11a】
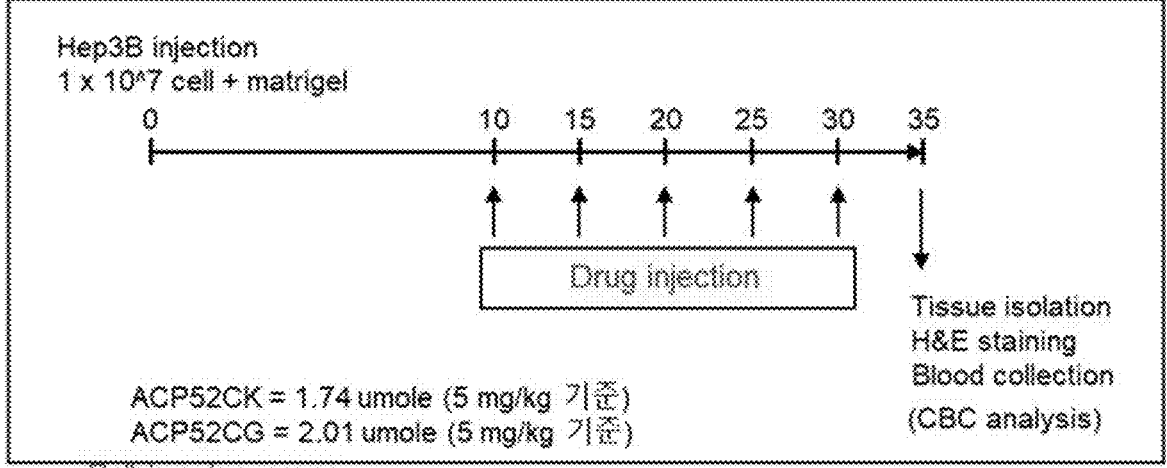
【FIG 11b】
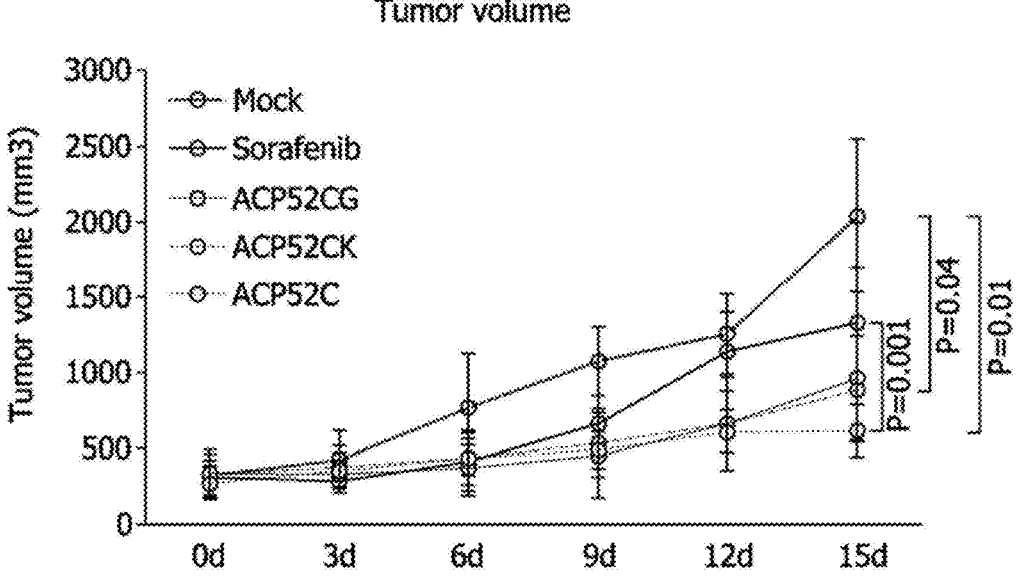

[FIG 11c]
c
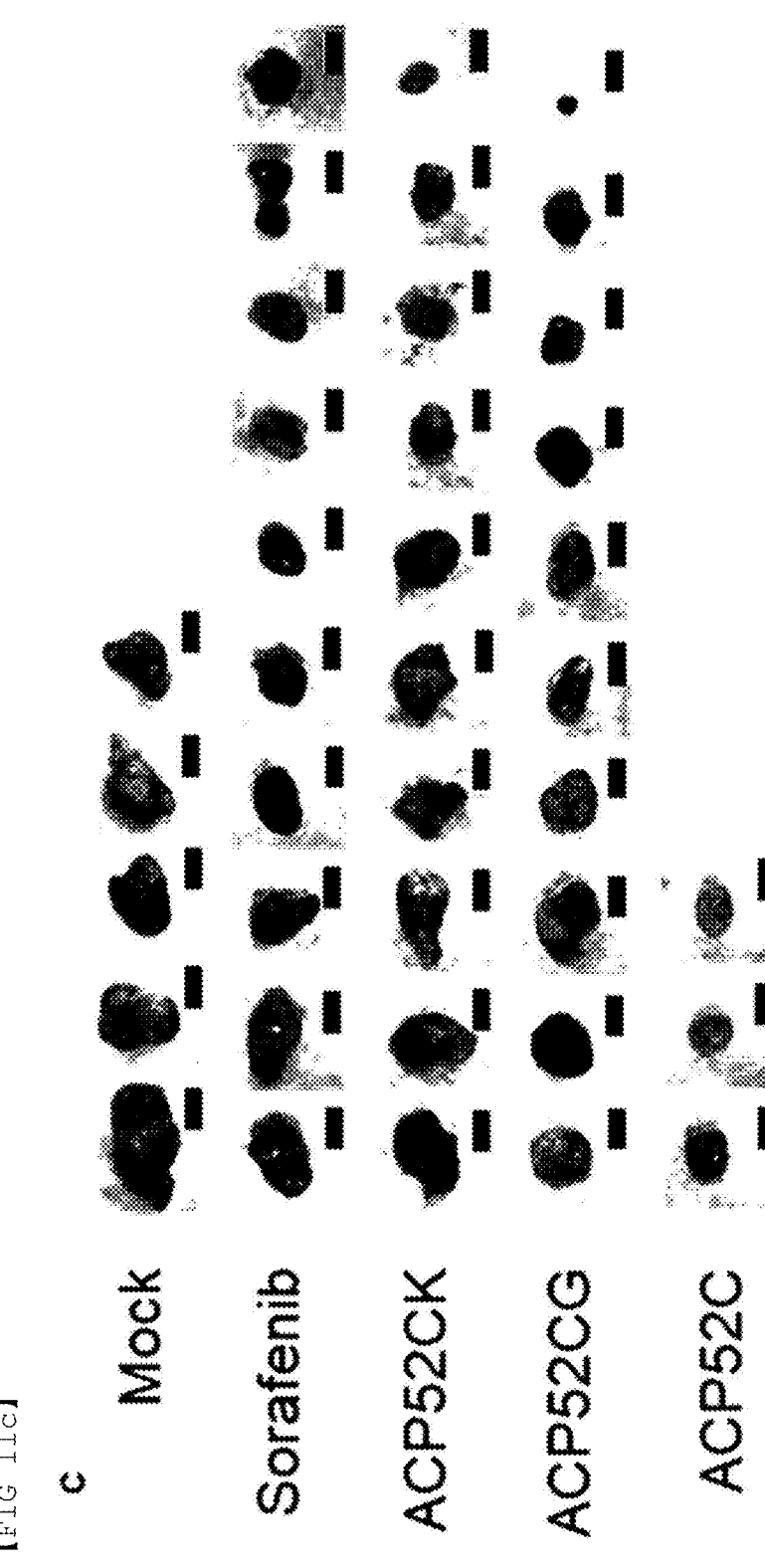
Mock
Sorafenib
ACP52CK
ACP52CG
ACP52C

【FIG 11d】
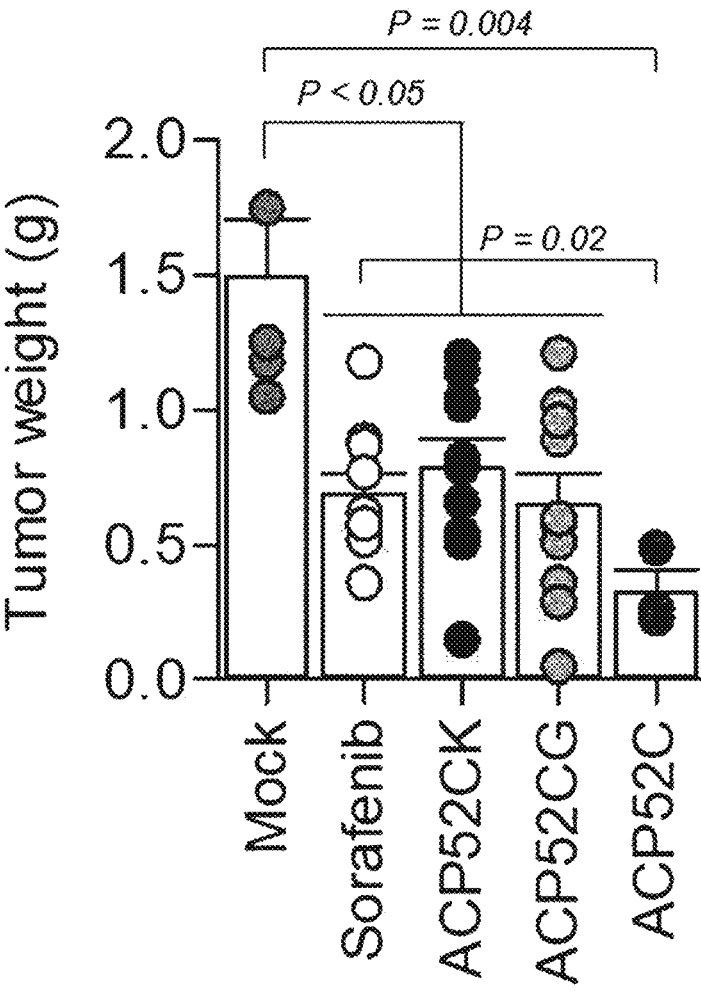

[FIG 11e]
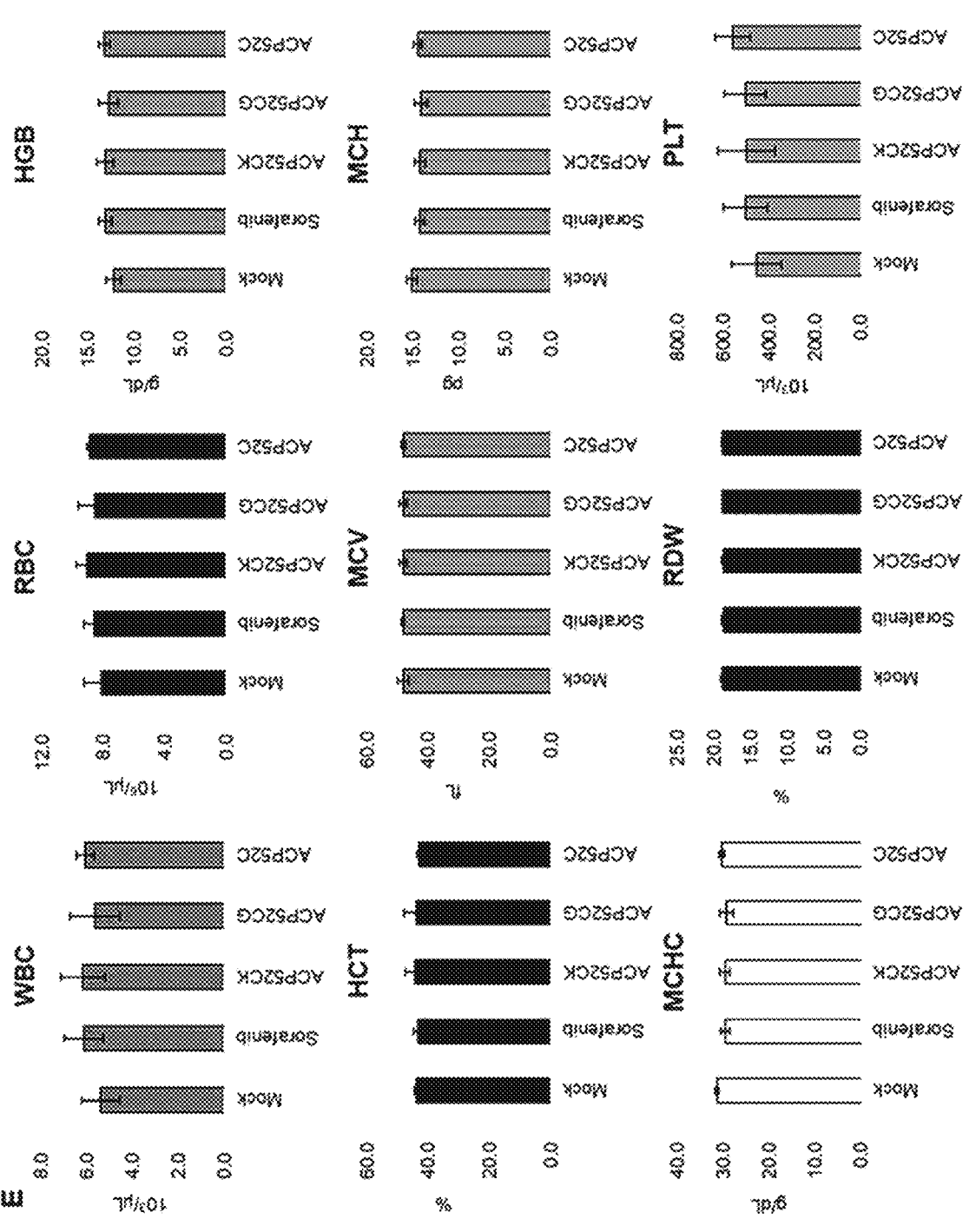

【FIG 12a】
A
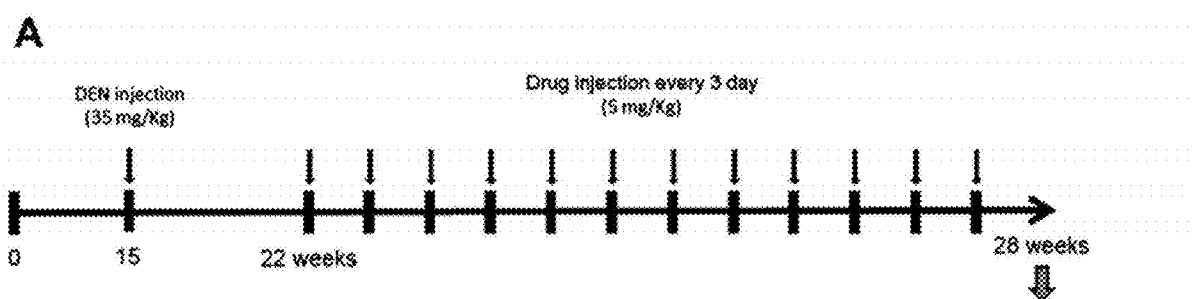
DEN injection
(35 mg/Kg)
Drug injection every 3 day
(5 mg/Kg)
0      15      22 weeks      28 weeks
* Mouse strain = C57BL/6
Termination (sacrifice)
- Dissect major organs
- Liver weight measure
- H/E staining of Liver tissue
- IHC against AFP Ab (Liver tissue)

[FIG 13a]
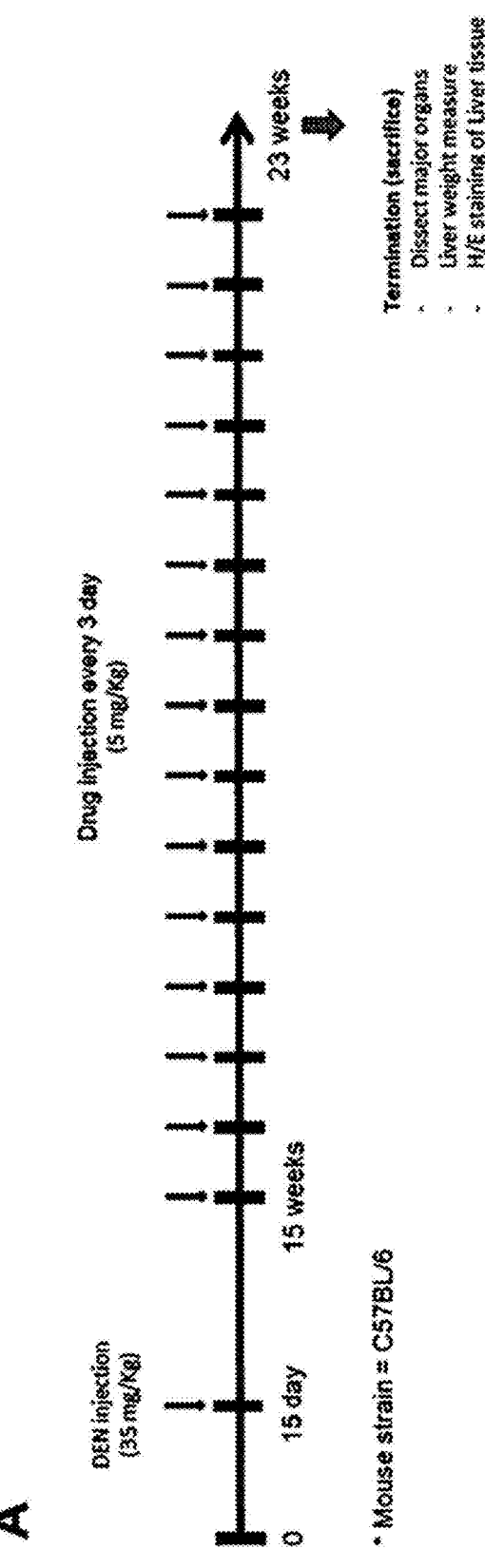

[FIG 13b]
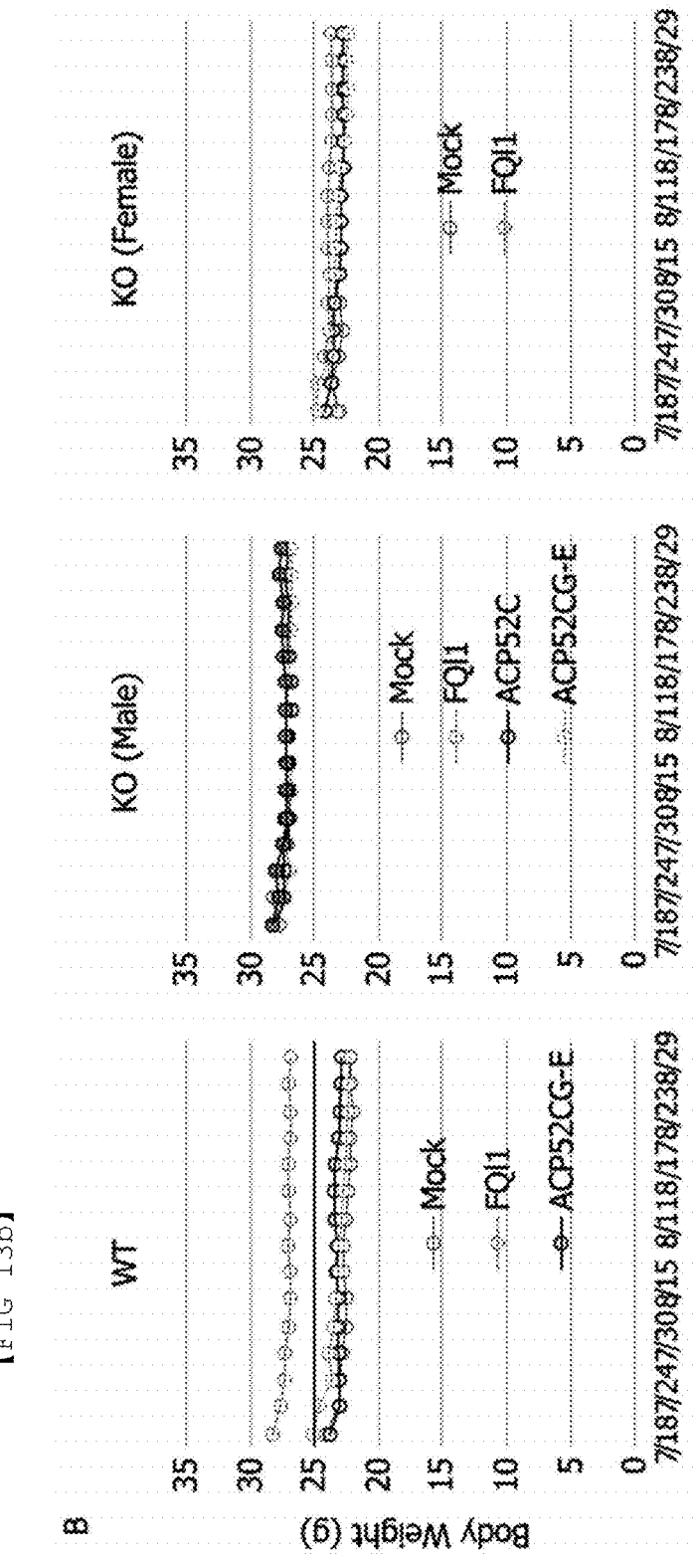

【FIG 14a】
A
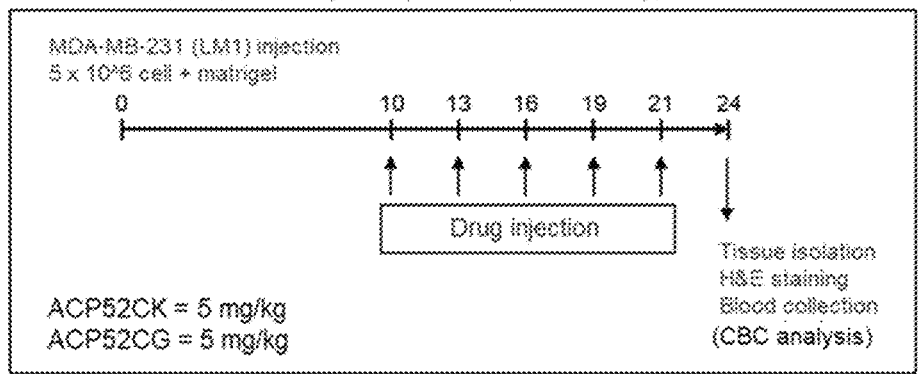
MDA-MB-231 (LM1) cell xenograft experiment (interval 3 day)
MDA-MB-231 (LM1) injection
5 × 10^6 cell + matrigel
Drug injection
ACP52CK = 5 mg/kg
ACP52CG = 5 mg/kg
Tissue isolation
H&E staining
Blood collection
(CBC analysis)
NPG (NOD-Prkdc^scid IL2vg^-/-) mouse
【FIG 14b】
B
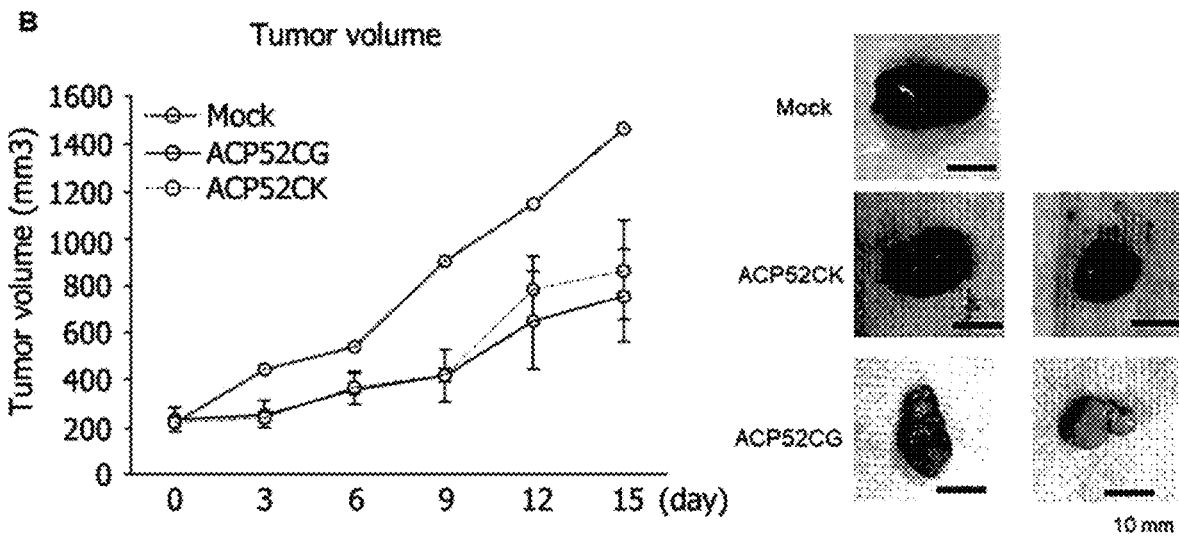
Tumor volume

[FIG 14c]
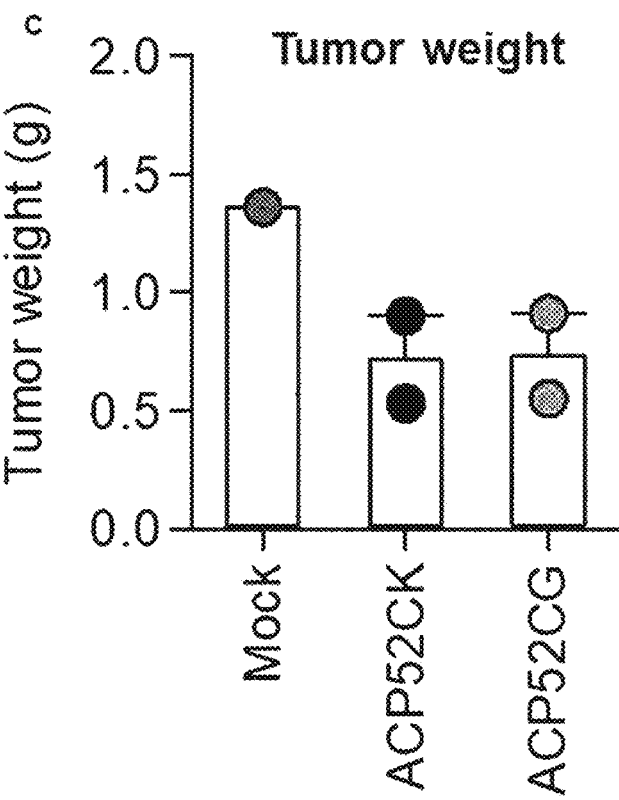

[FIG 14d]
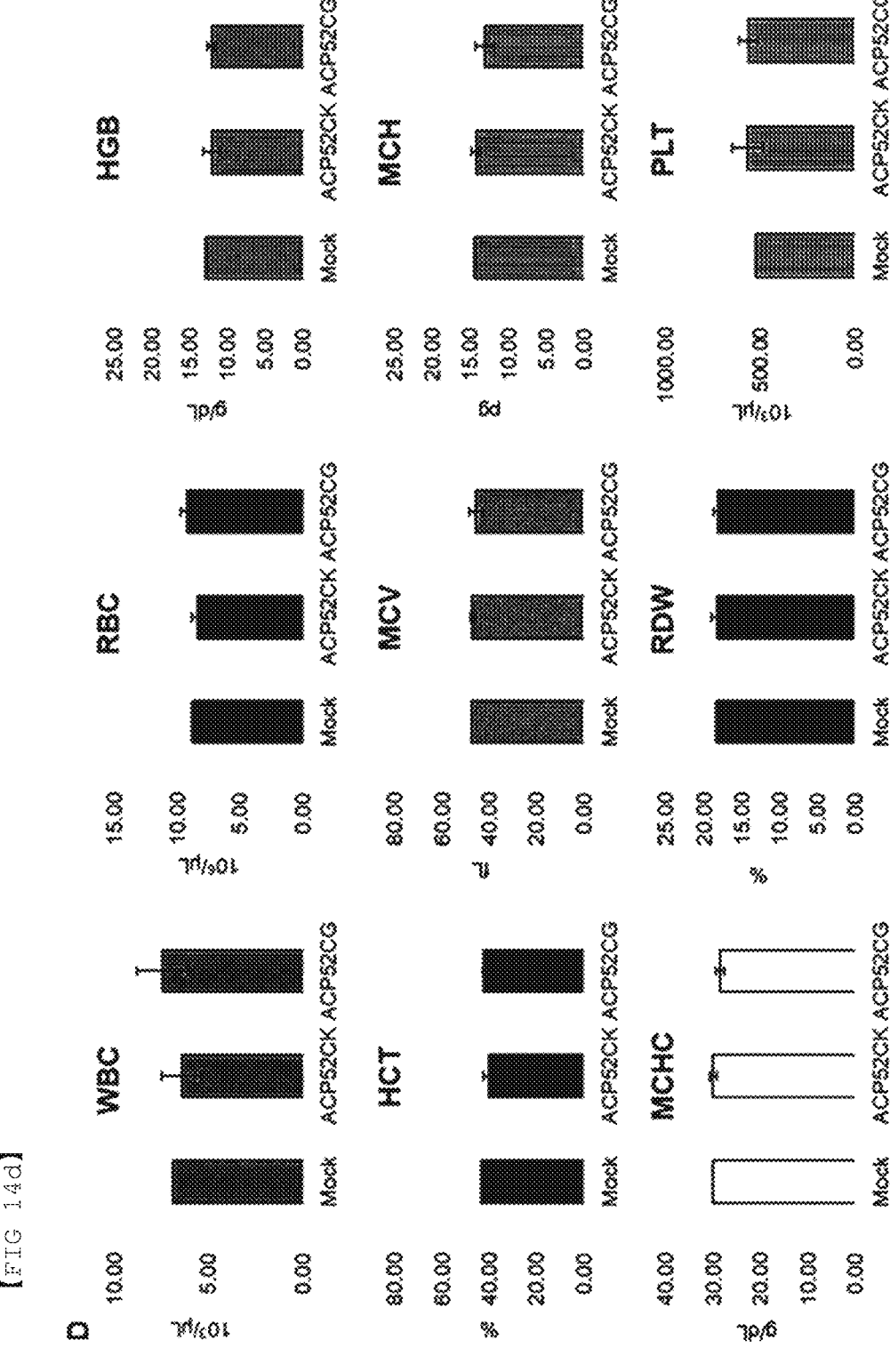

【FIG 15a】
A
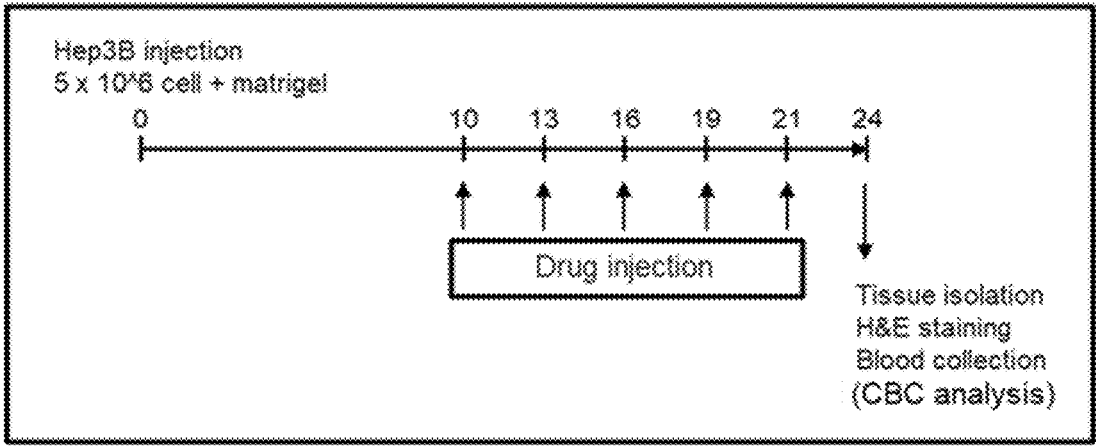

【FIG 15b】
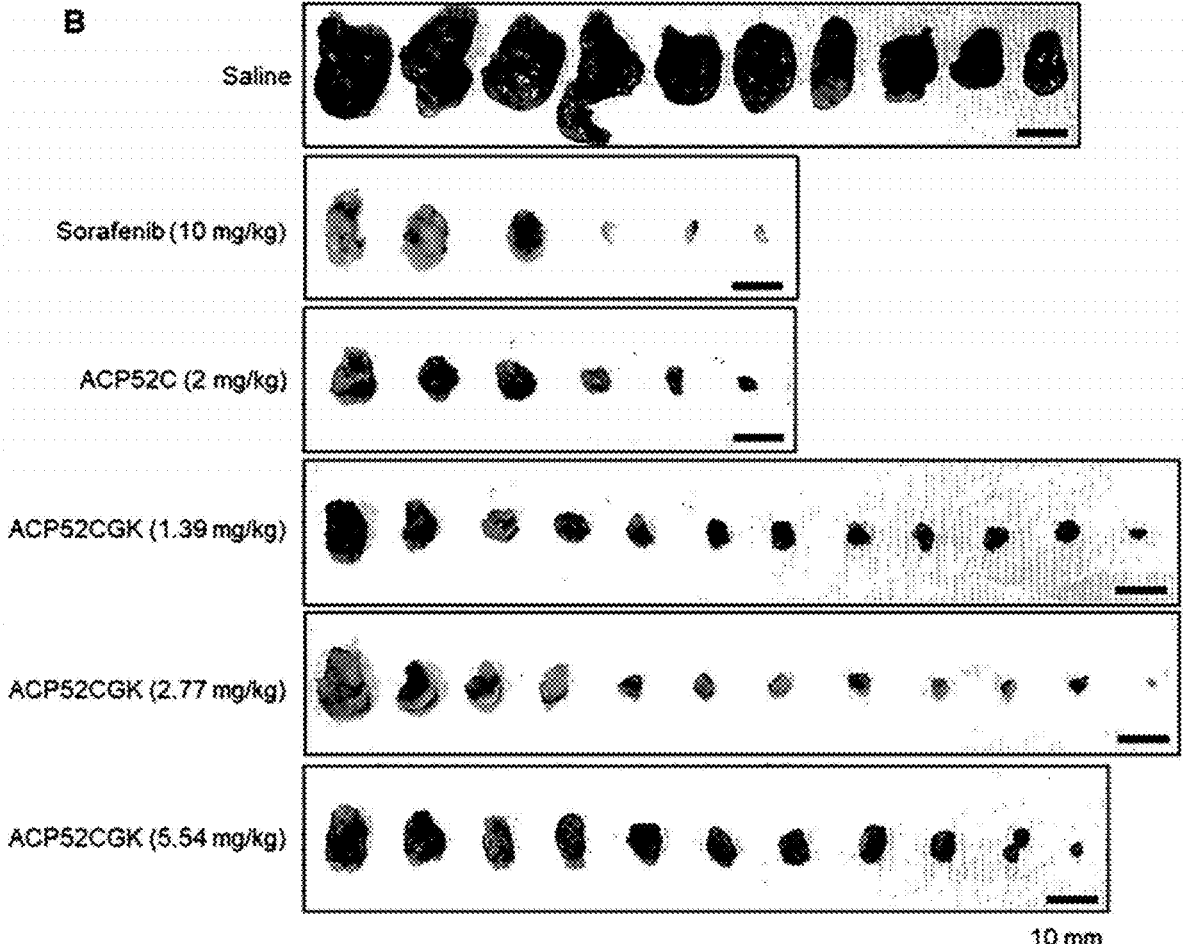

[FIG 15c]
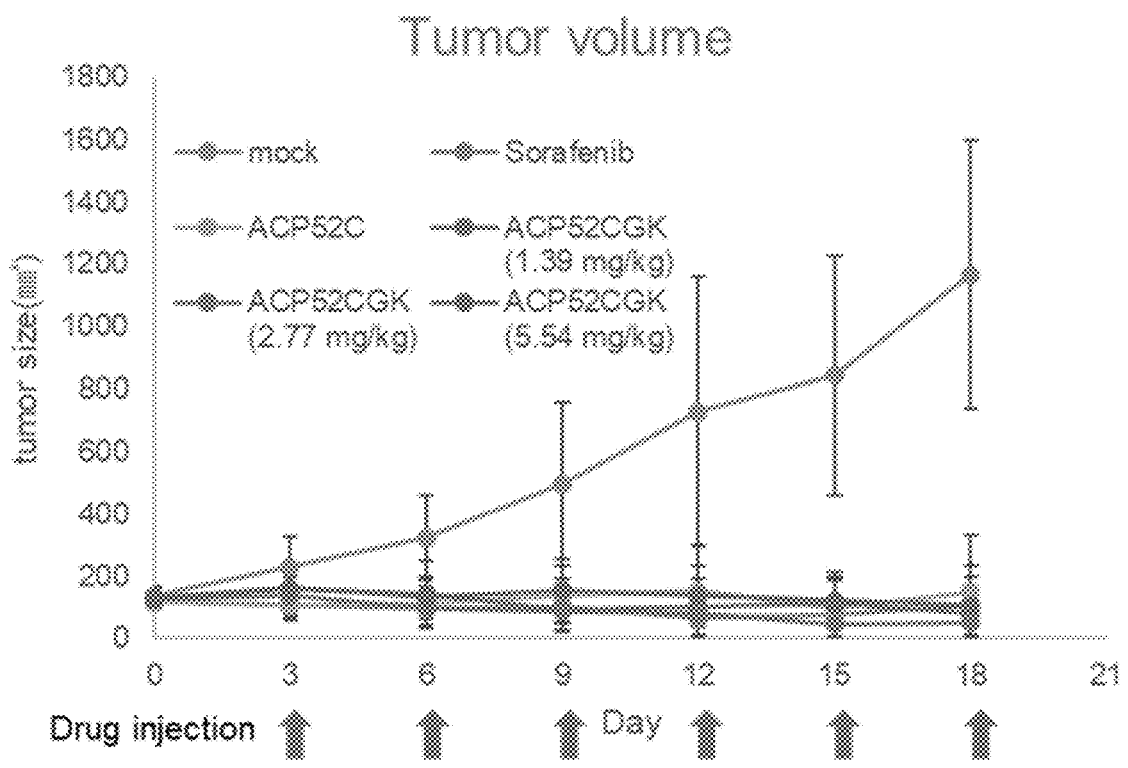

【FIG 15d】
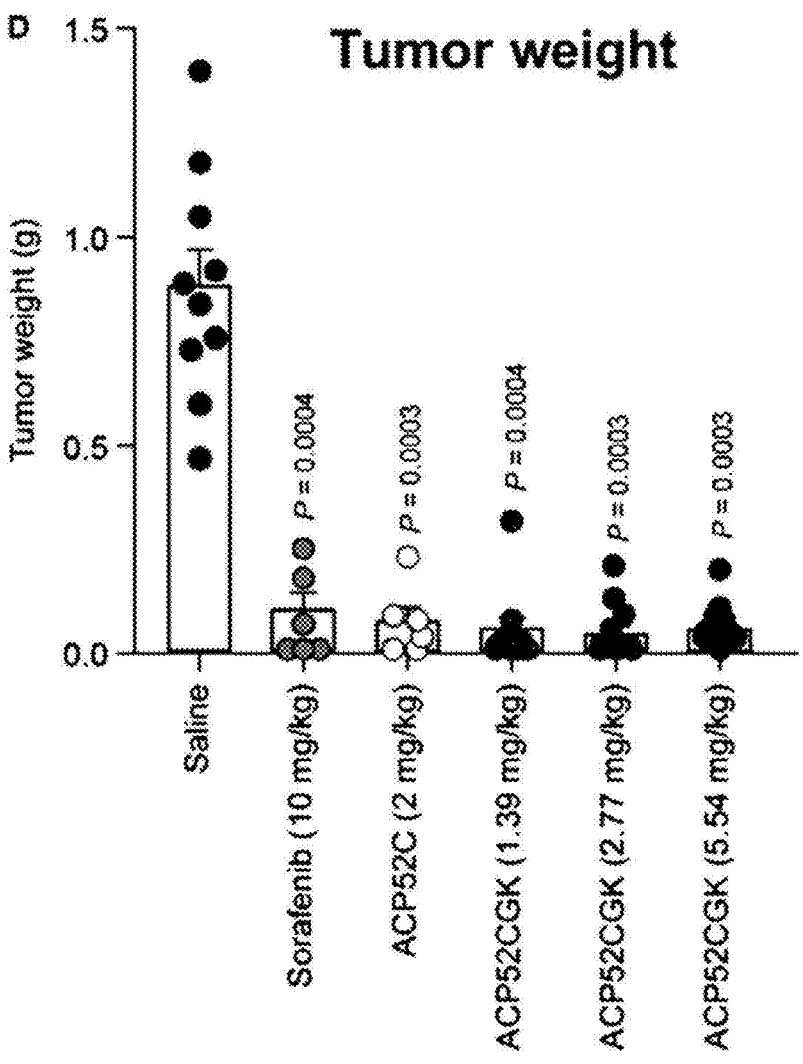

【FIG 15e】
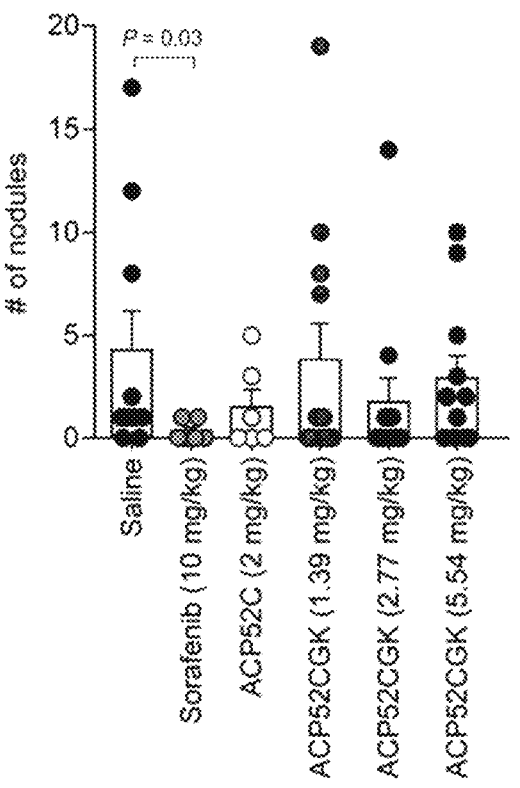

【FIG 15f】
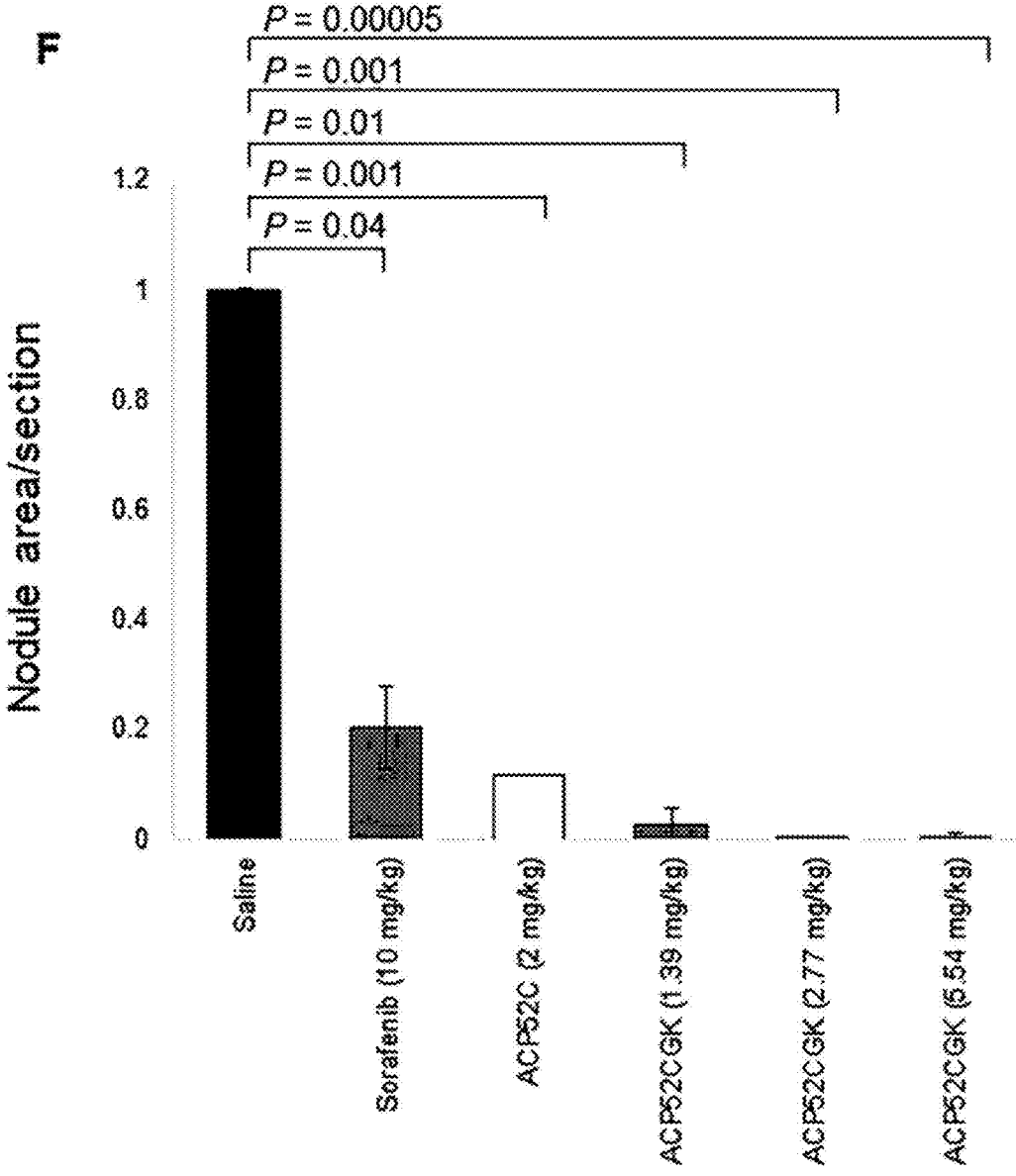

【FIG 15g】
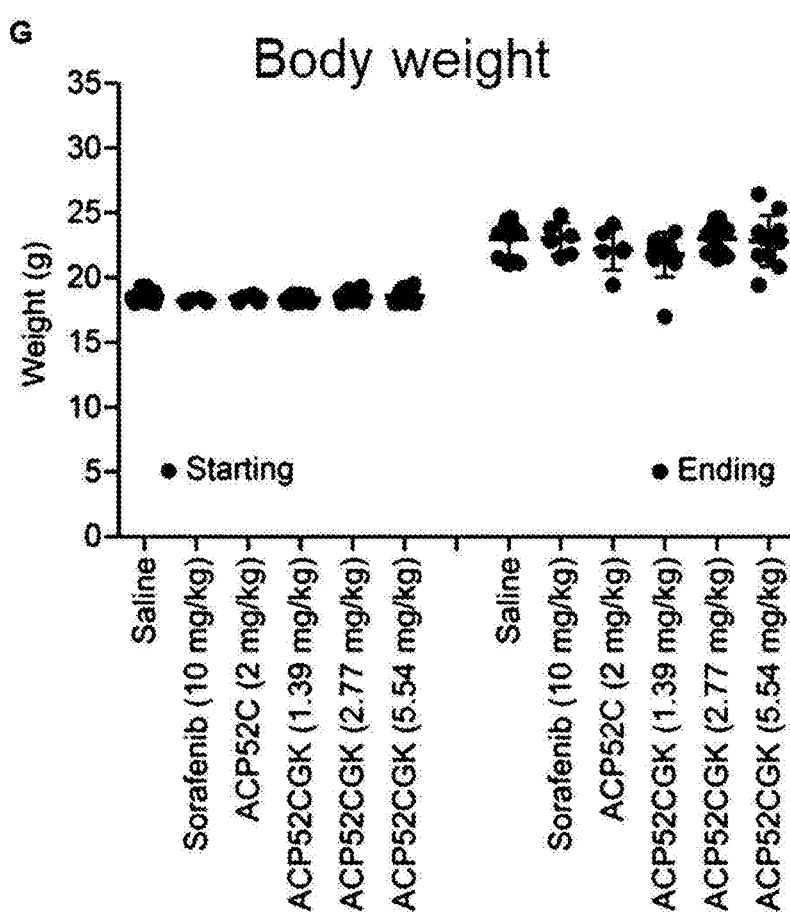

【FIG 15h】
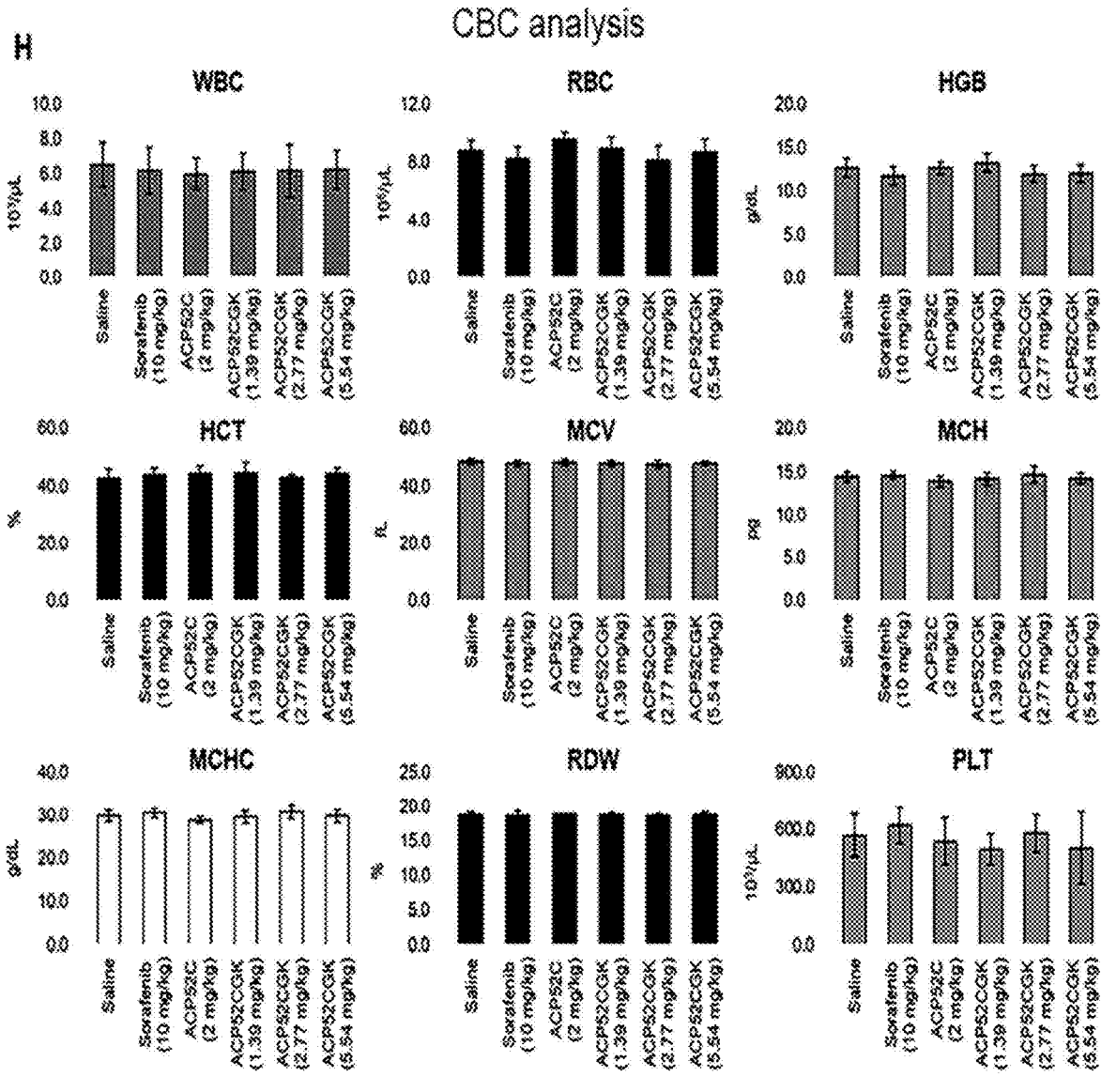

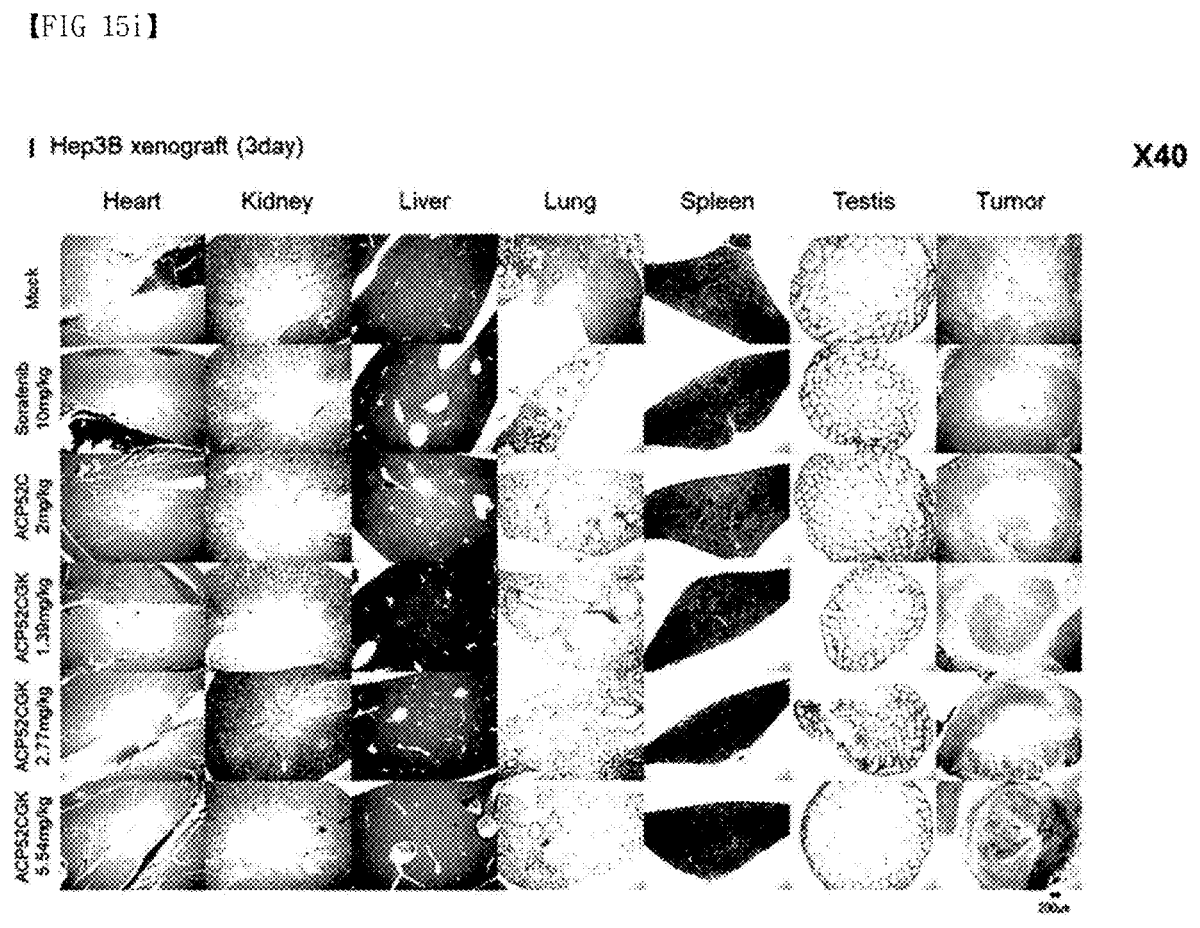

【FIG 15i】

Hep3B xenograft (3day)     X40

[FIG 15j]
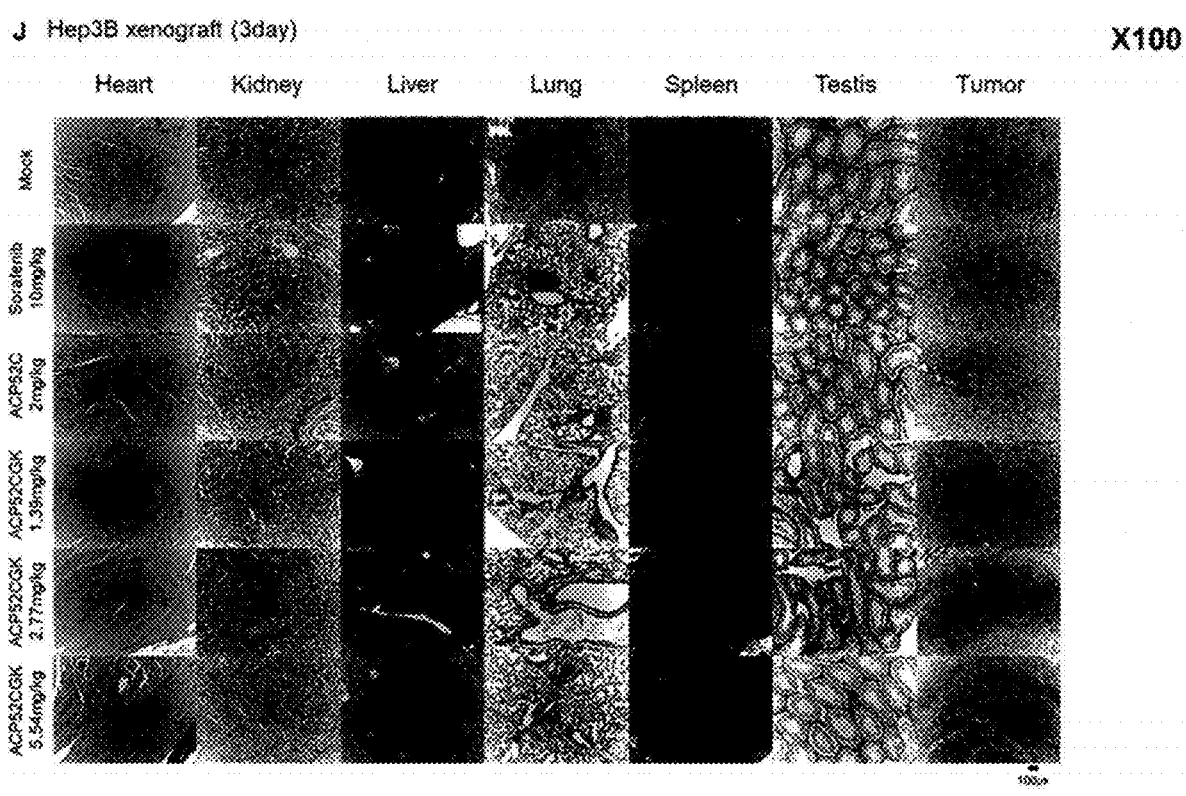

【FIG 16a】
A
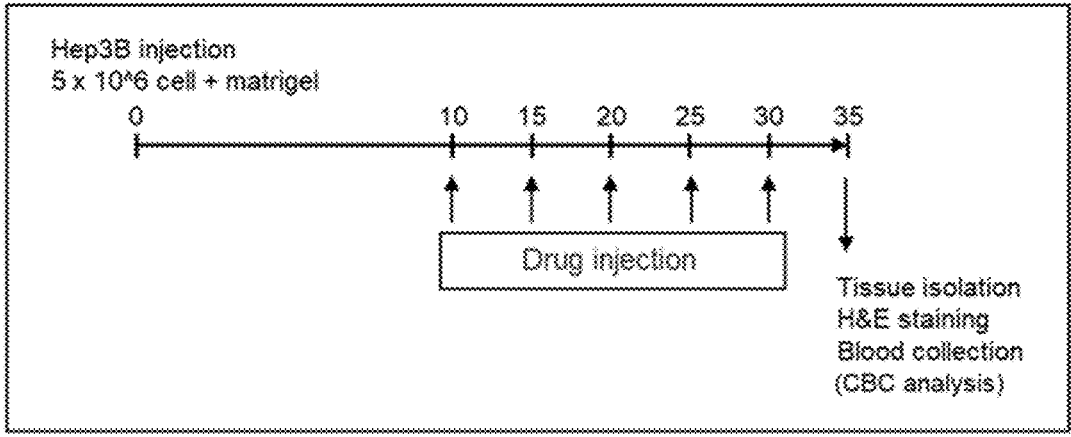
Hep3B cell xenograft experiment (interval 5 day, 3 different doses)
Hep3B injection
5 x 10^6 cell + matrigel
Drug injection
Tissue isolation
H&E staining
Blood collection
(CBC analysis)
Balb/c nu/nu mouse 【FIG 16b】
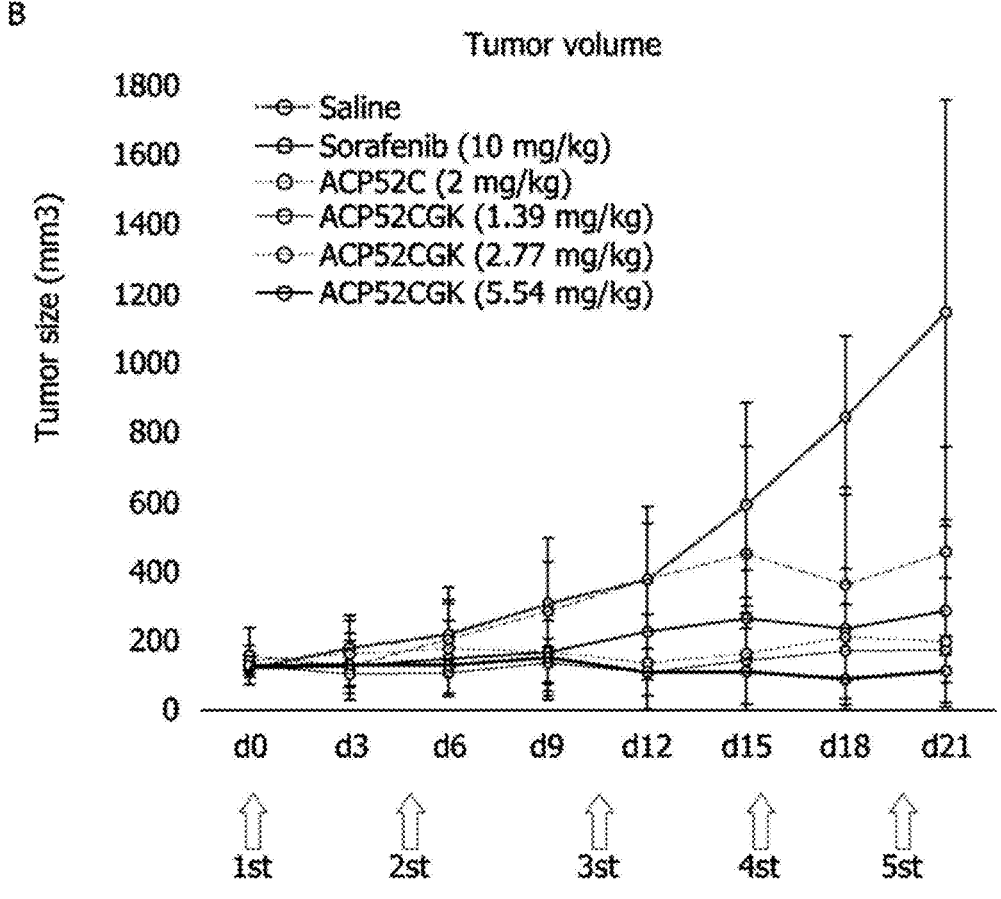

【FIG 16c】
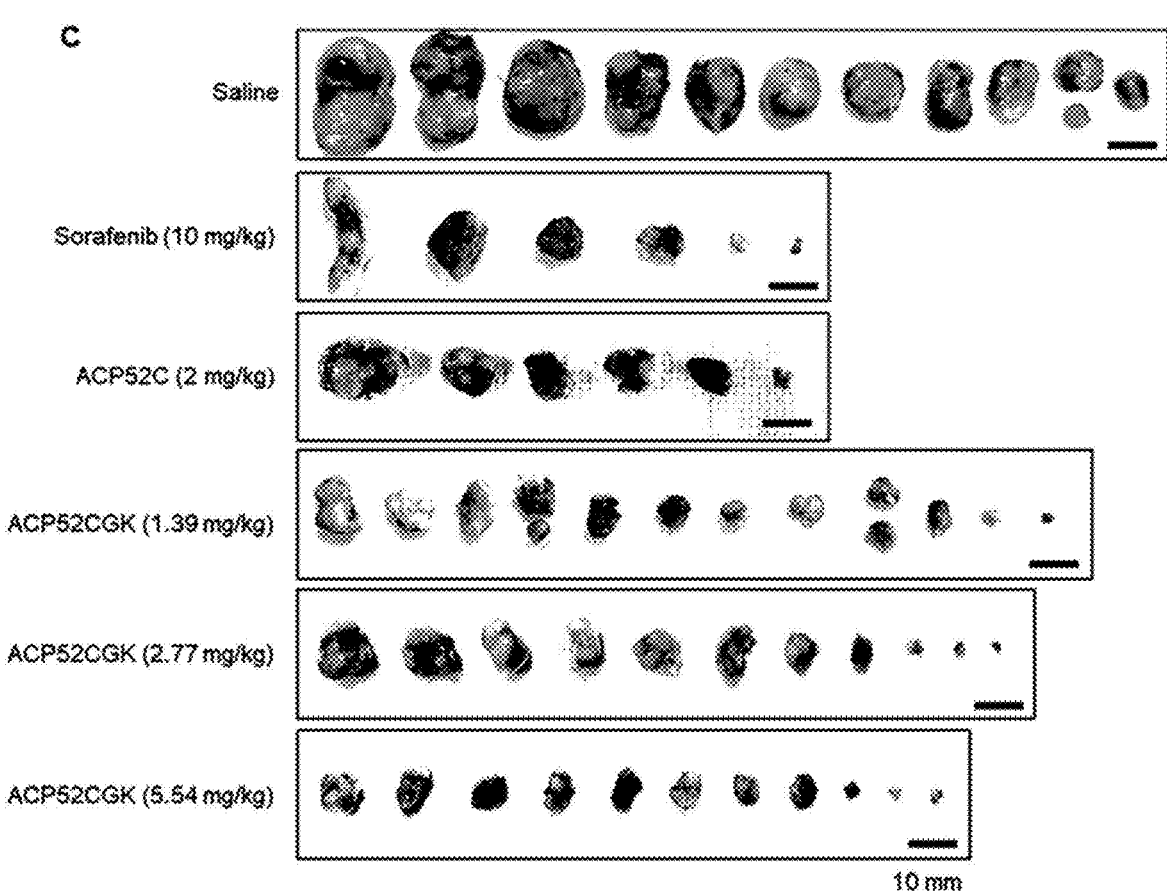

【FIG 16d】
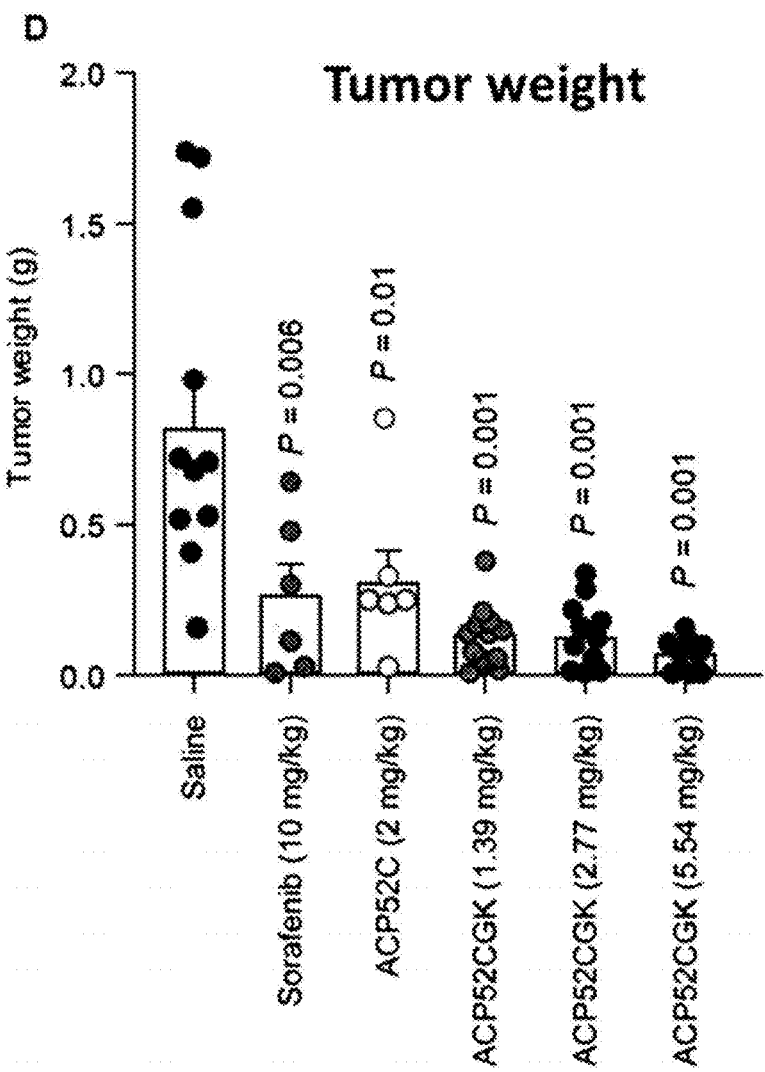

【FIG 16e】
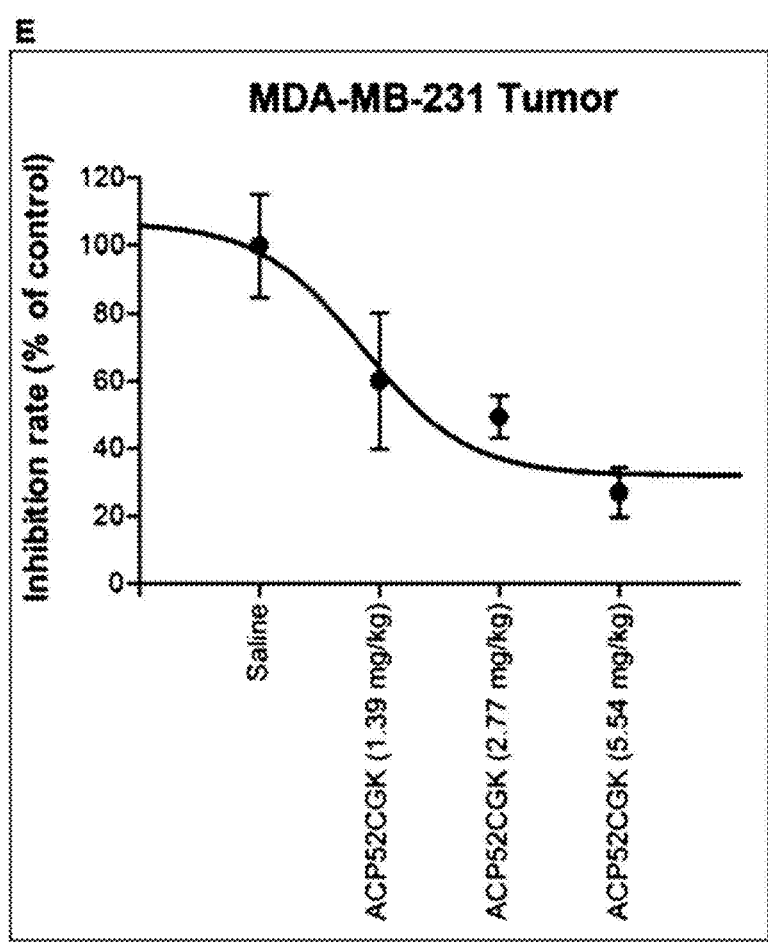

【FIG 16f】
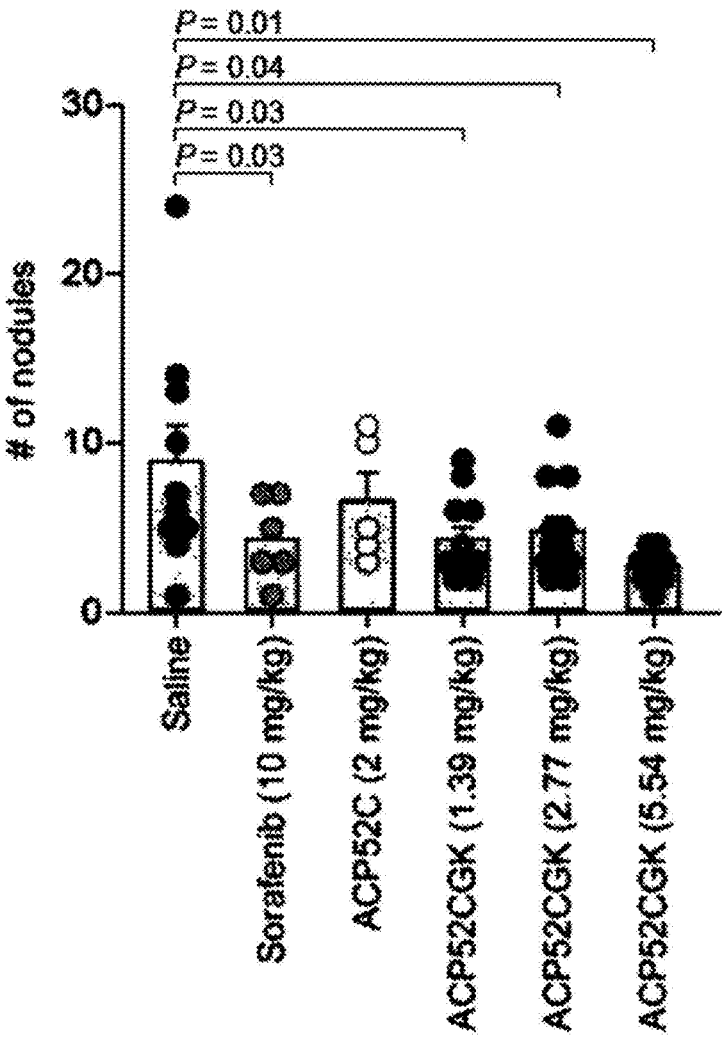

【FIG 16g】
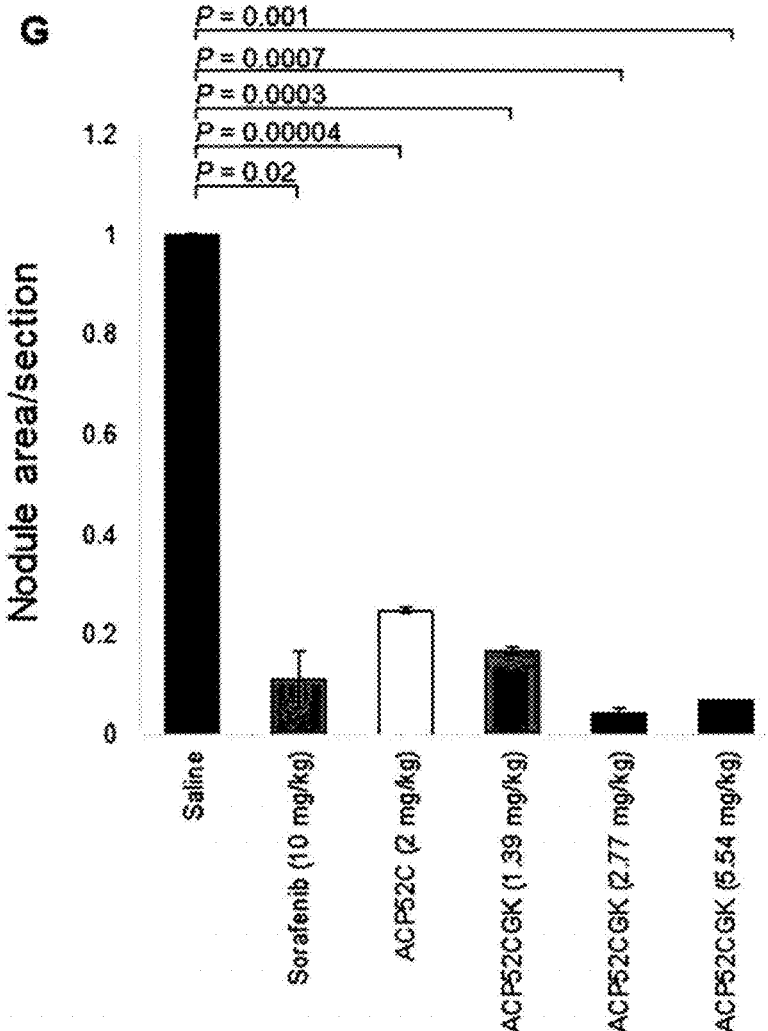
Examined by H/E-stained lung section
N = 4 (2 heads; tissue 2 pieces each)

【FIG 16h】
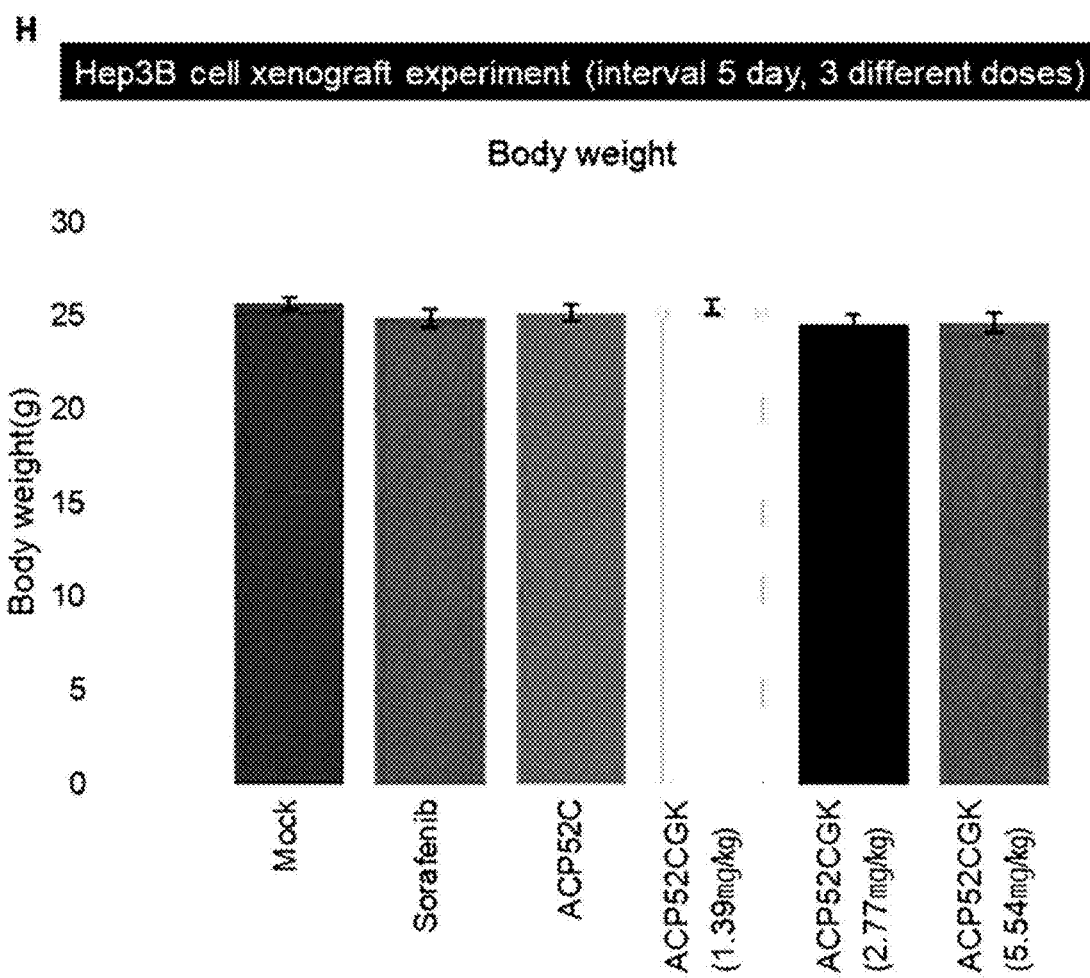

【FIG 16i】
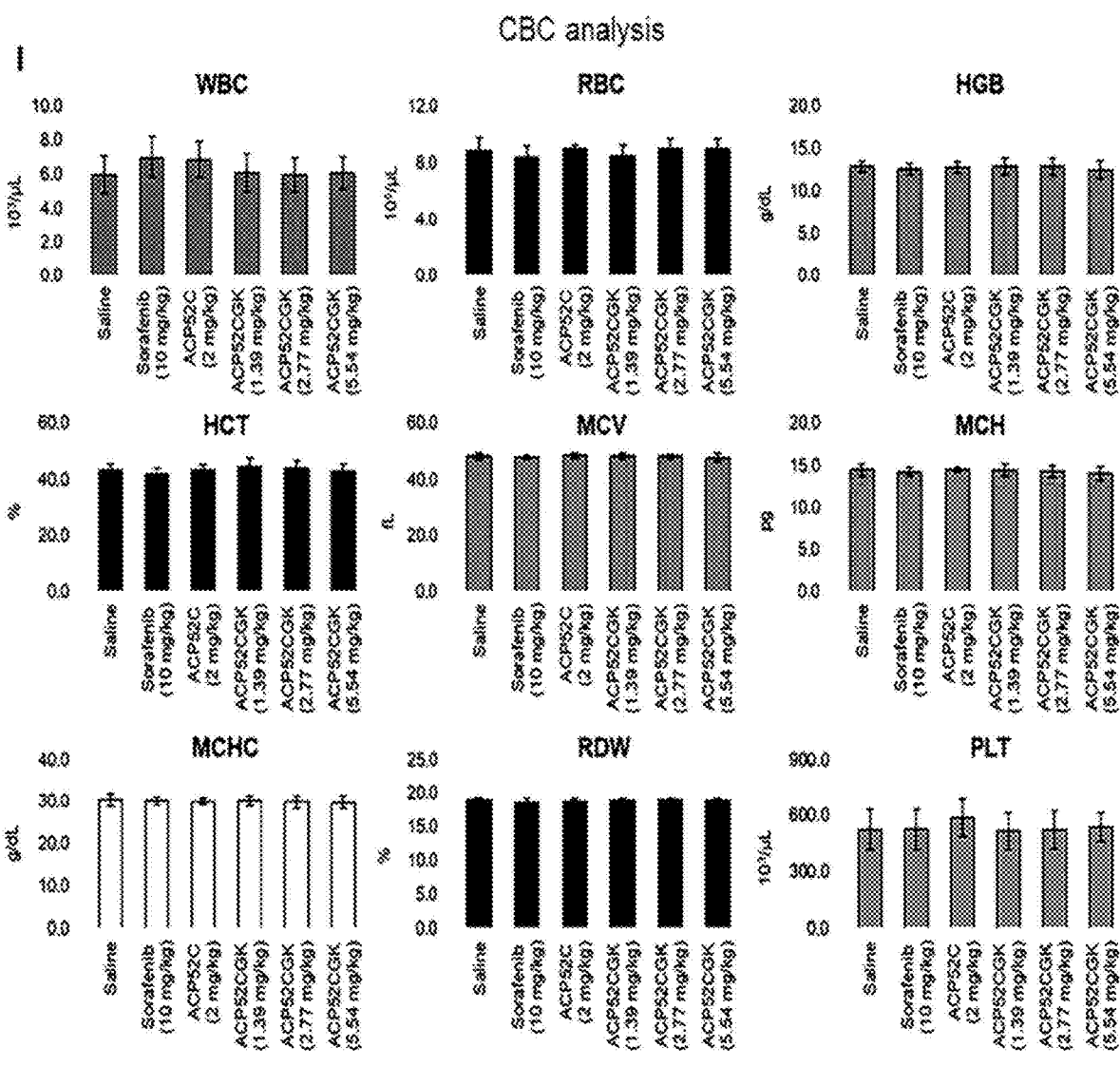

Hep3B cell xenograft experiment (interval 5 day, 3 different doses)

【FIG 16k】
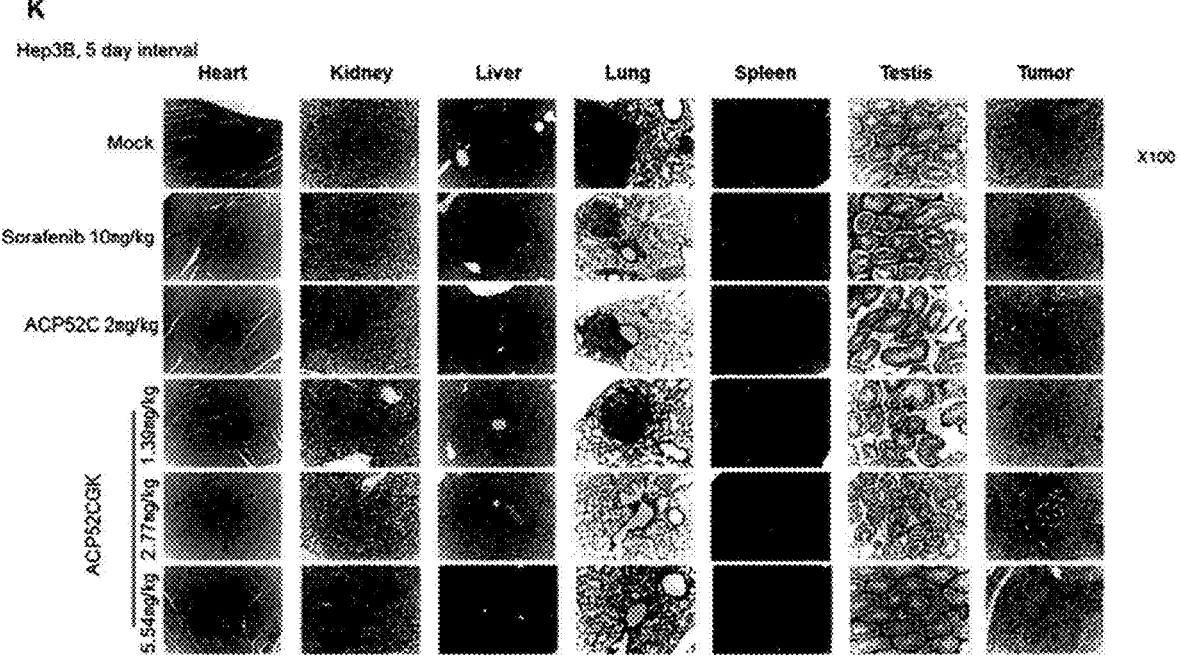
【FIG 17a】
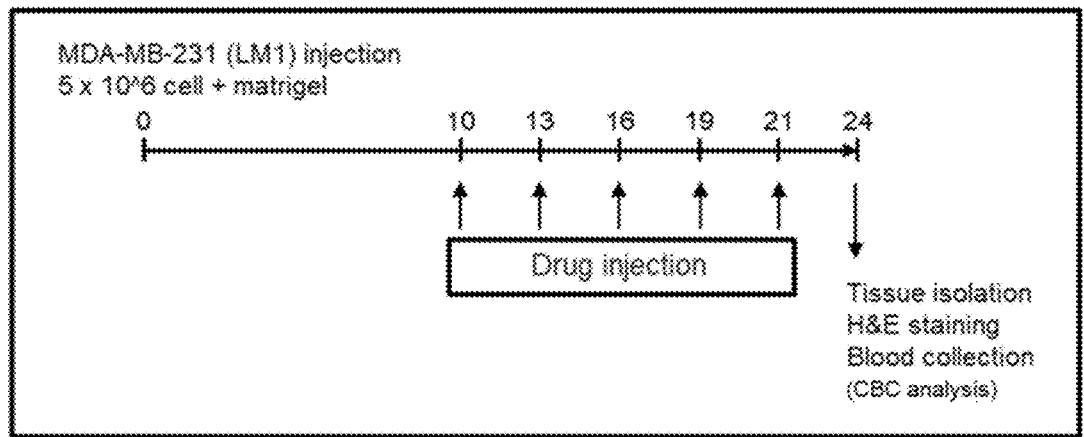

【FIG 17b】
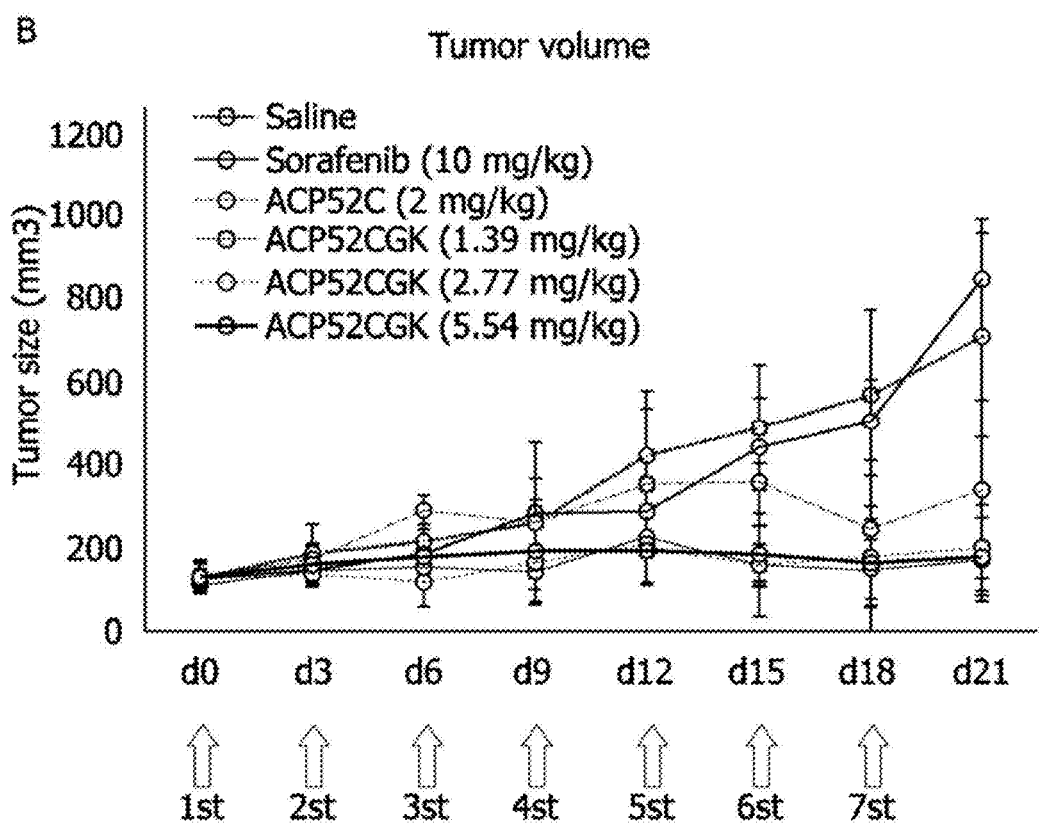

【FIG 17c】
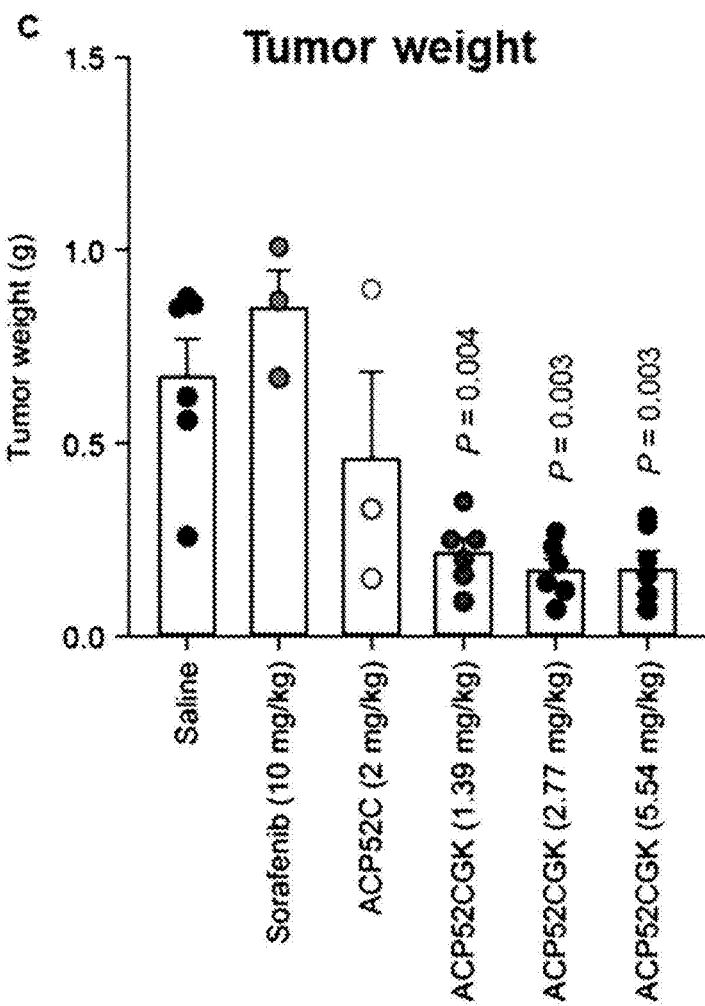

【FIG 17d】
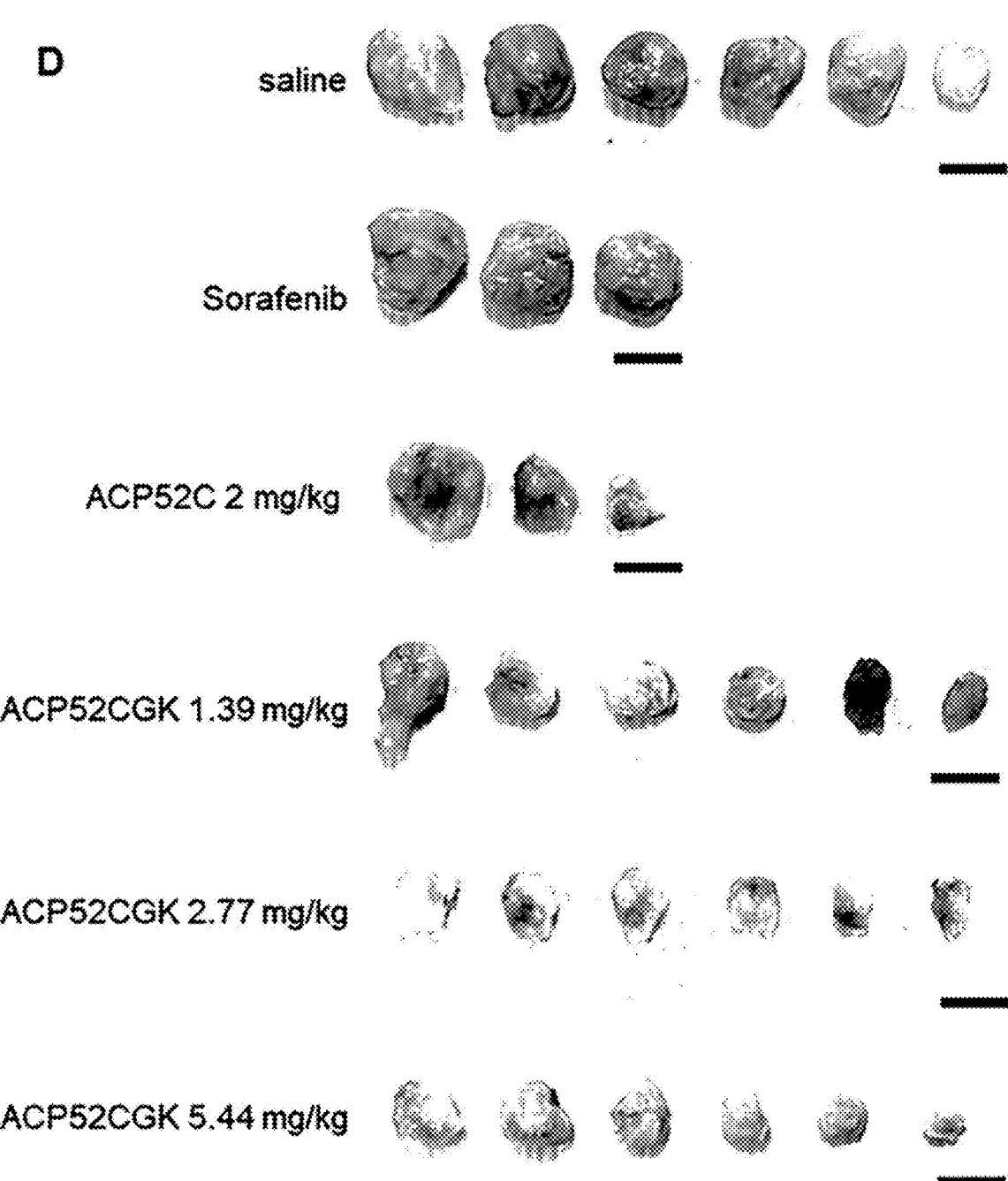
10 mm

【FIG 17e】
E Lung metastasis
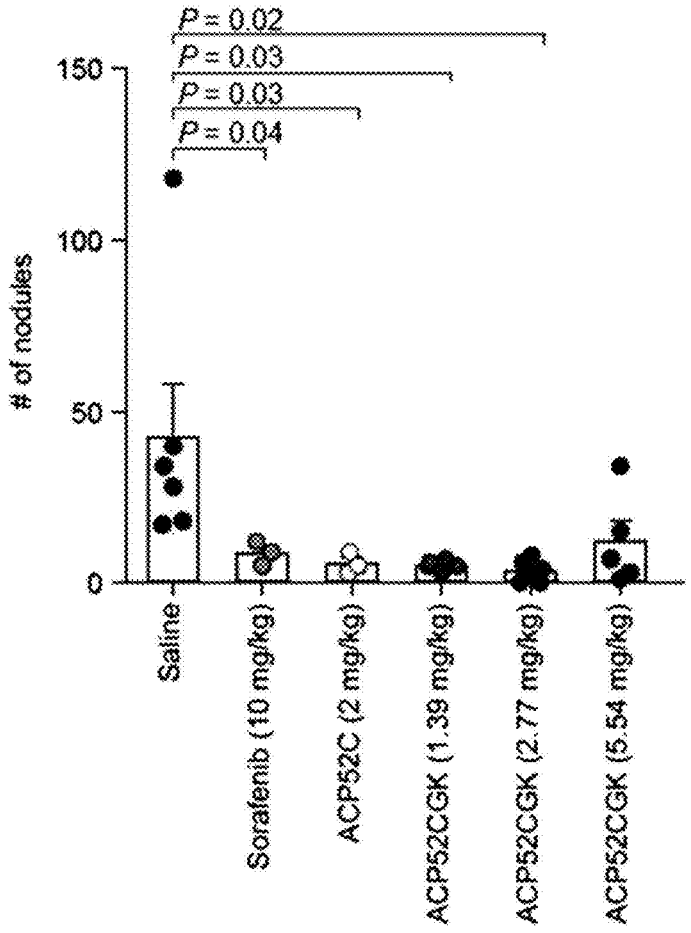
MDA-MB-231 LM1 xenograft (day 3 interval)

[FIG 17f]
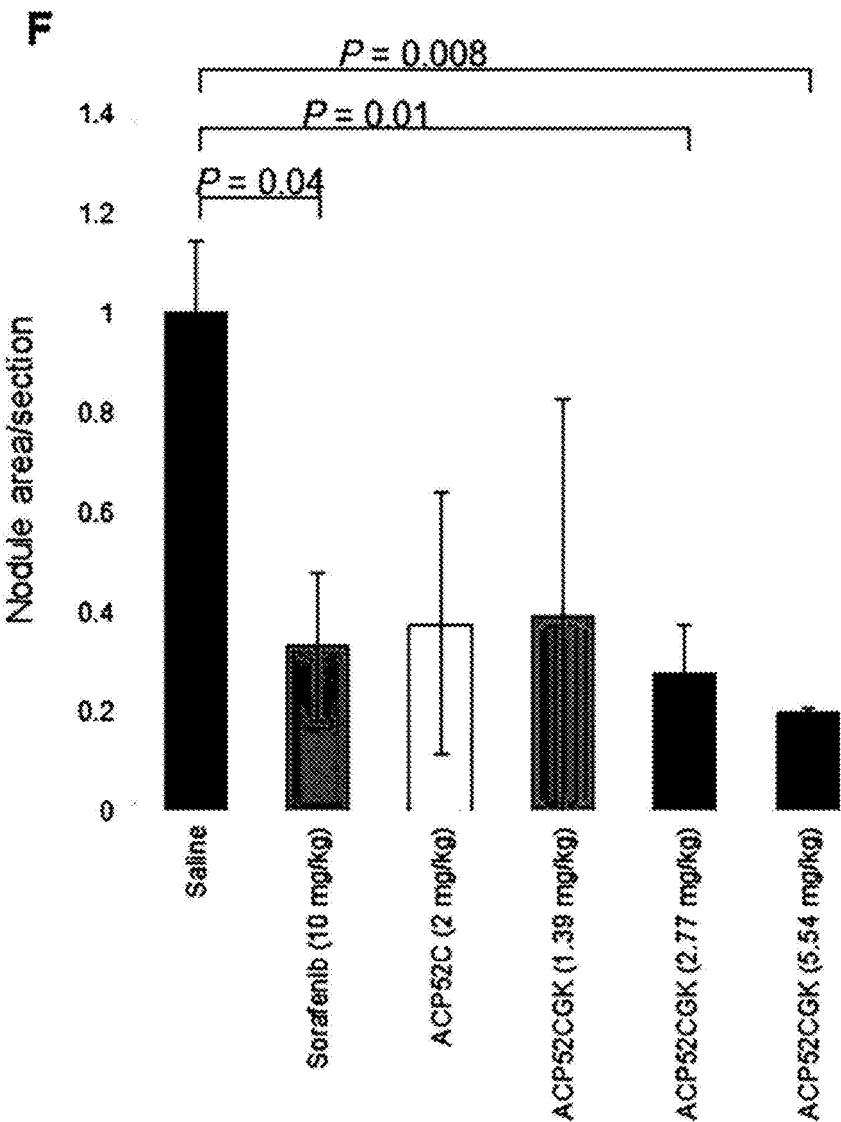

【FIG 17g】
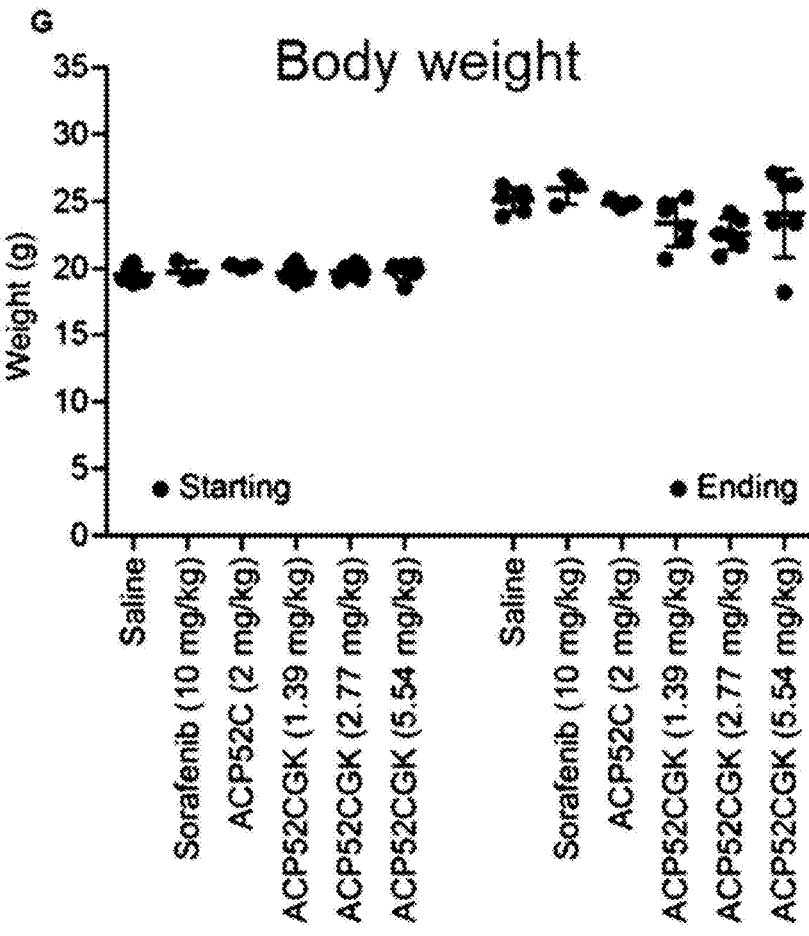

【FIG 17h】
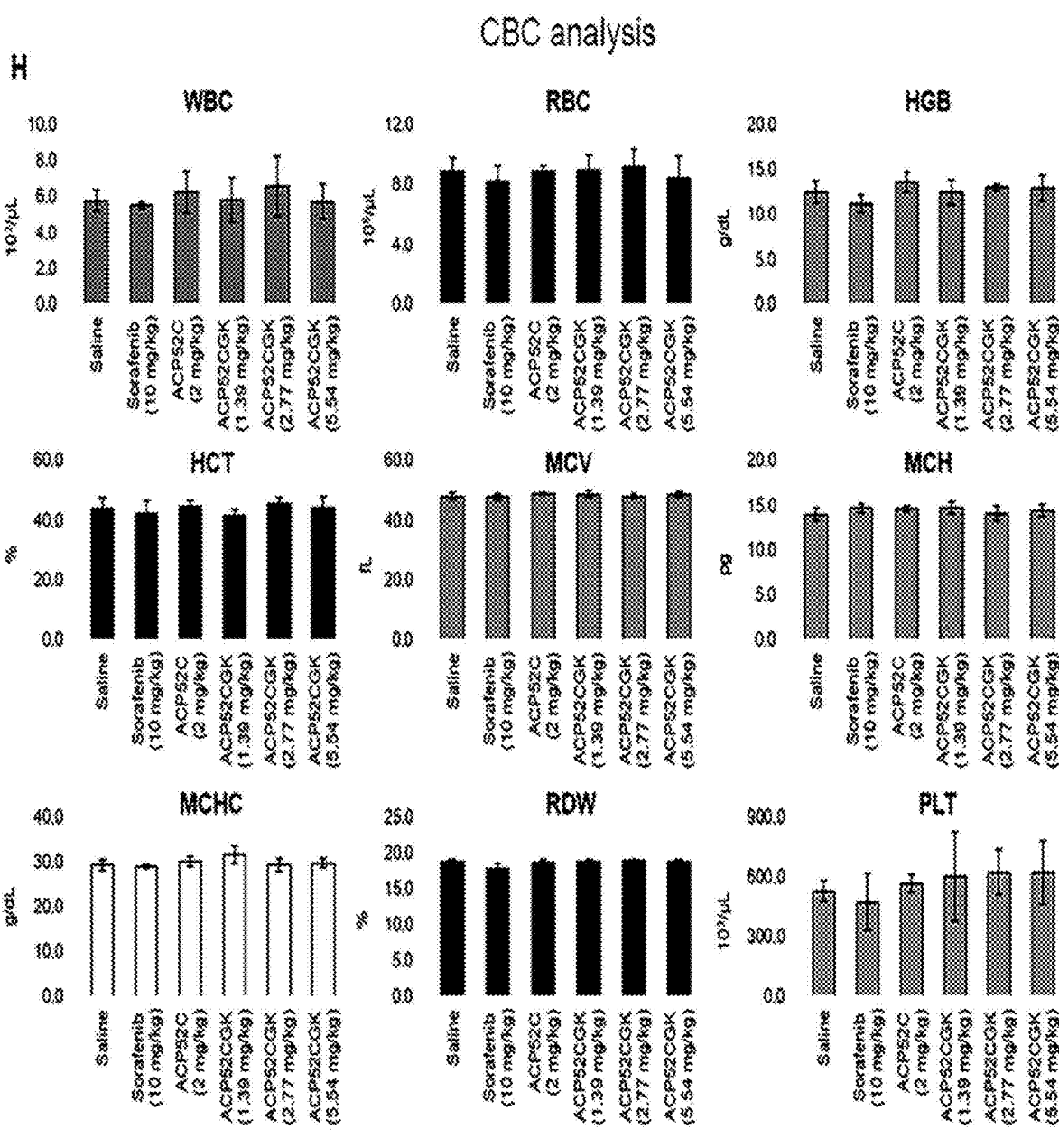

[FIG 17i]
MDA-MB-231 xenograft (3day)
X40
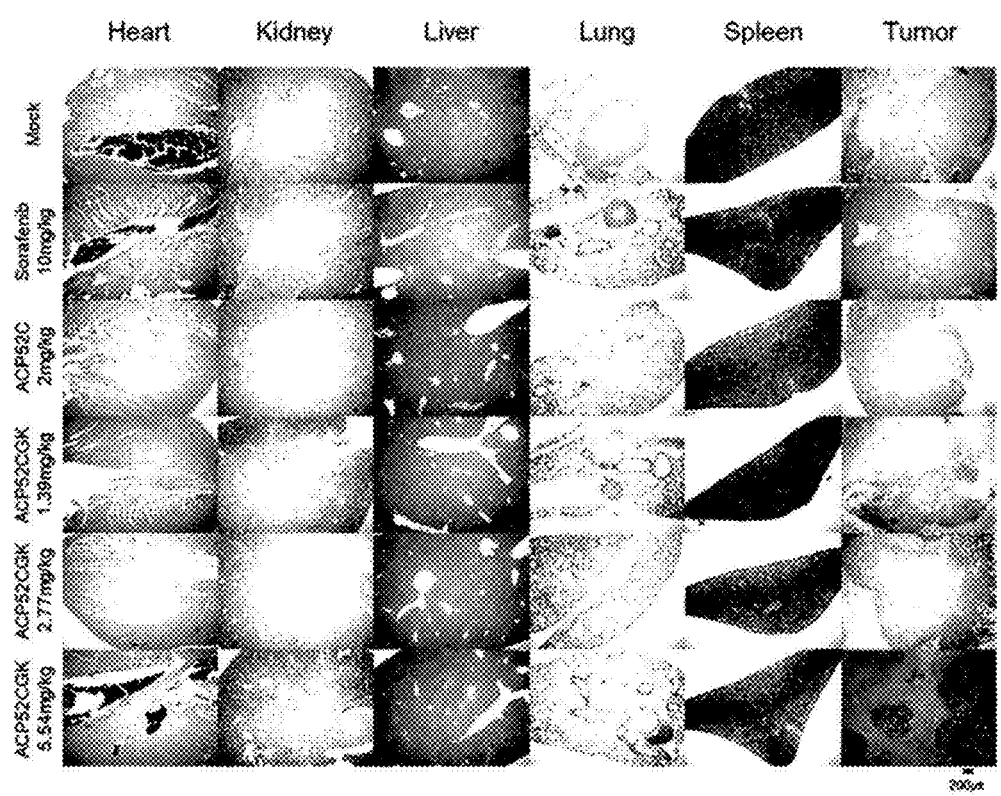

【FIG 17j】
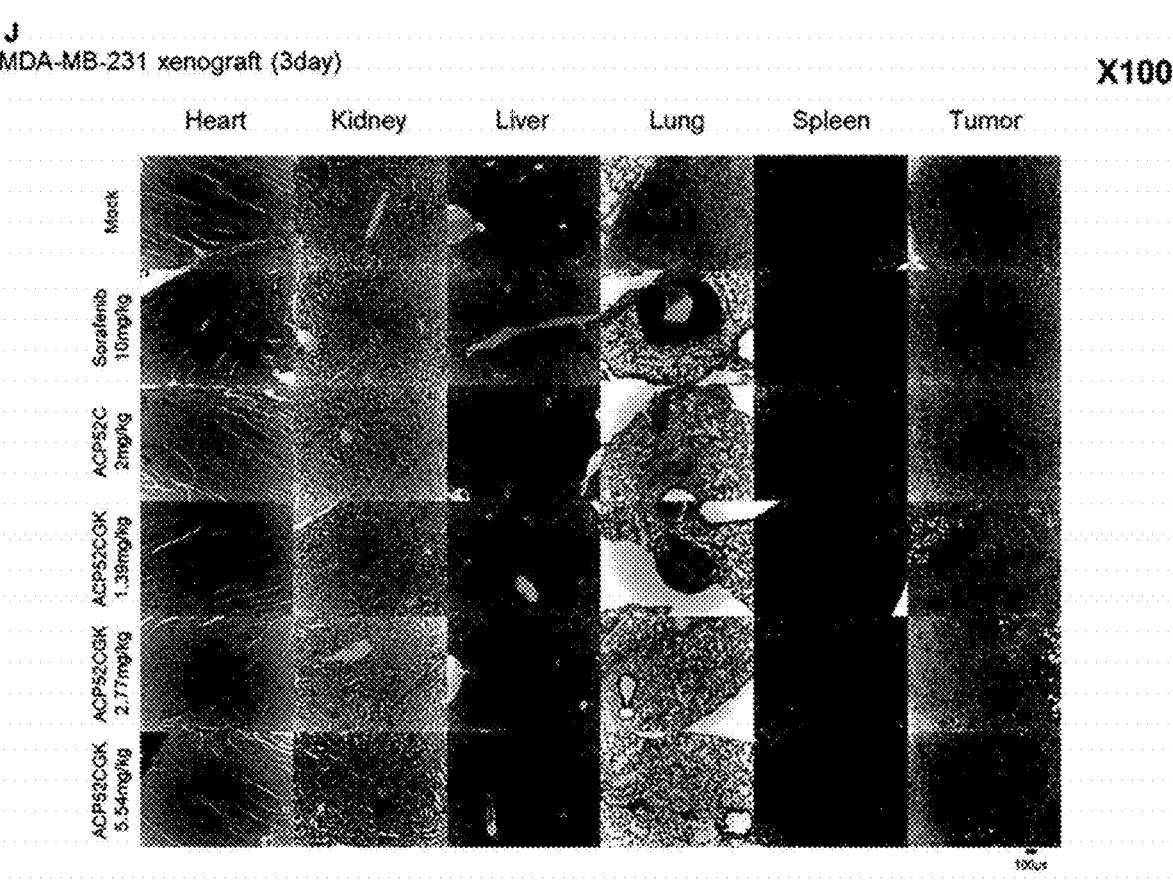

【FIG 18a】
A
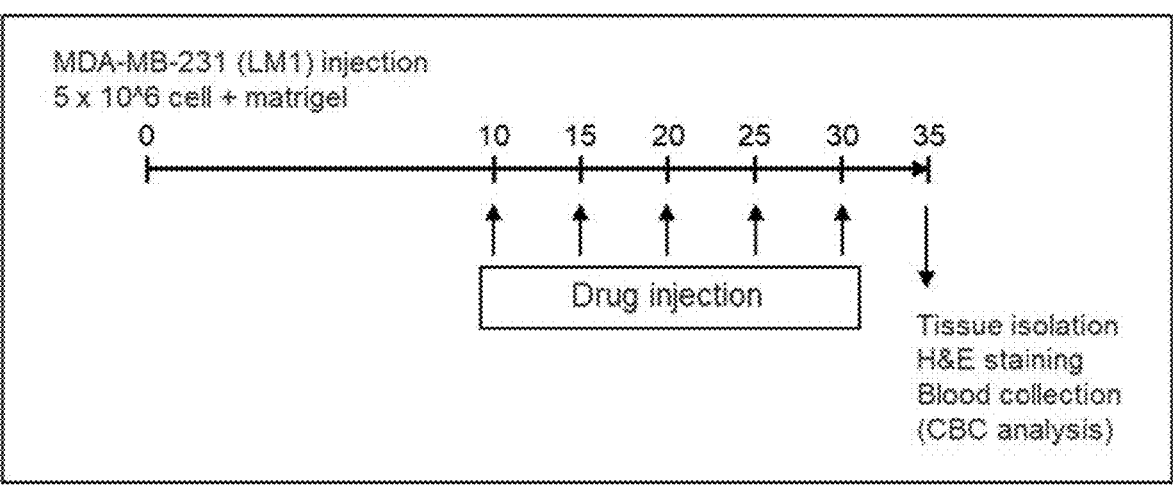
NPG (NOD-Prkdc^SCID^IL2yg^-/-^) mouse

【FIG 18b】
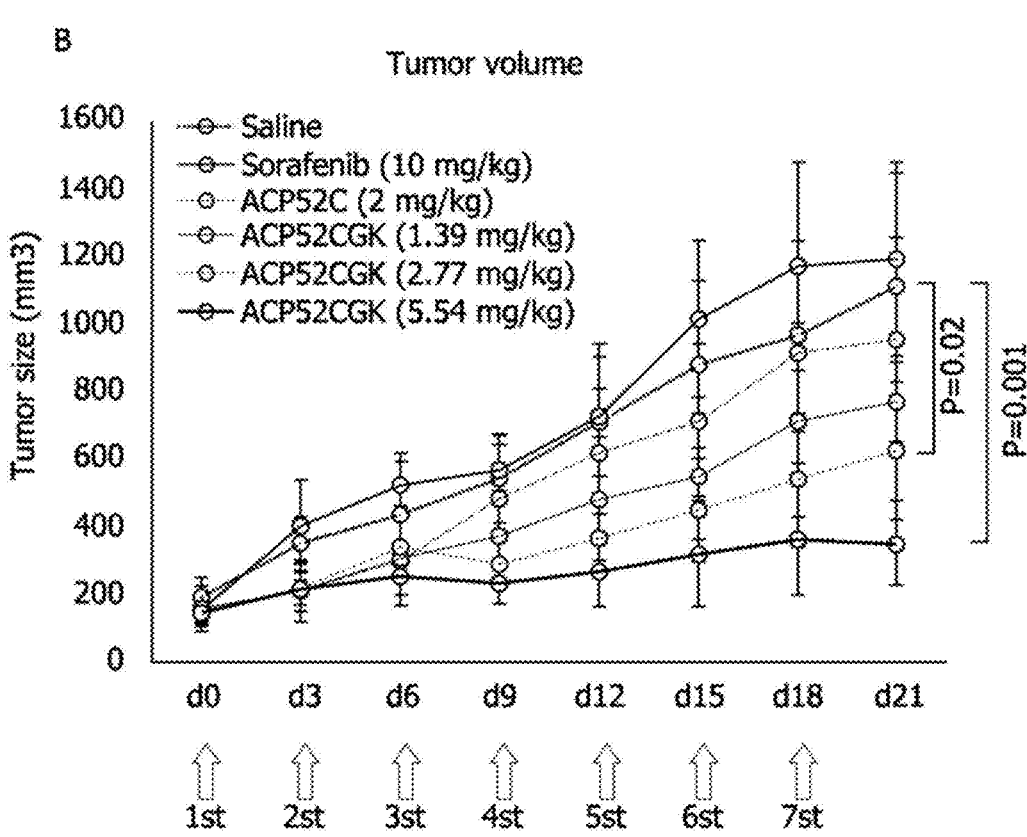

【FIG 18c】
C
Saline
Sorafenib (10 mg/kg)
ACP52C (2 mg/kg)
ACP52CGK (1.39 mg/kg)
ACP52CGK (2.77 mg/kg)
ACP52CGK (5.54 mg/kg)
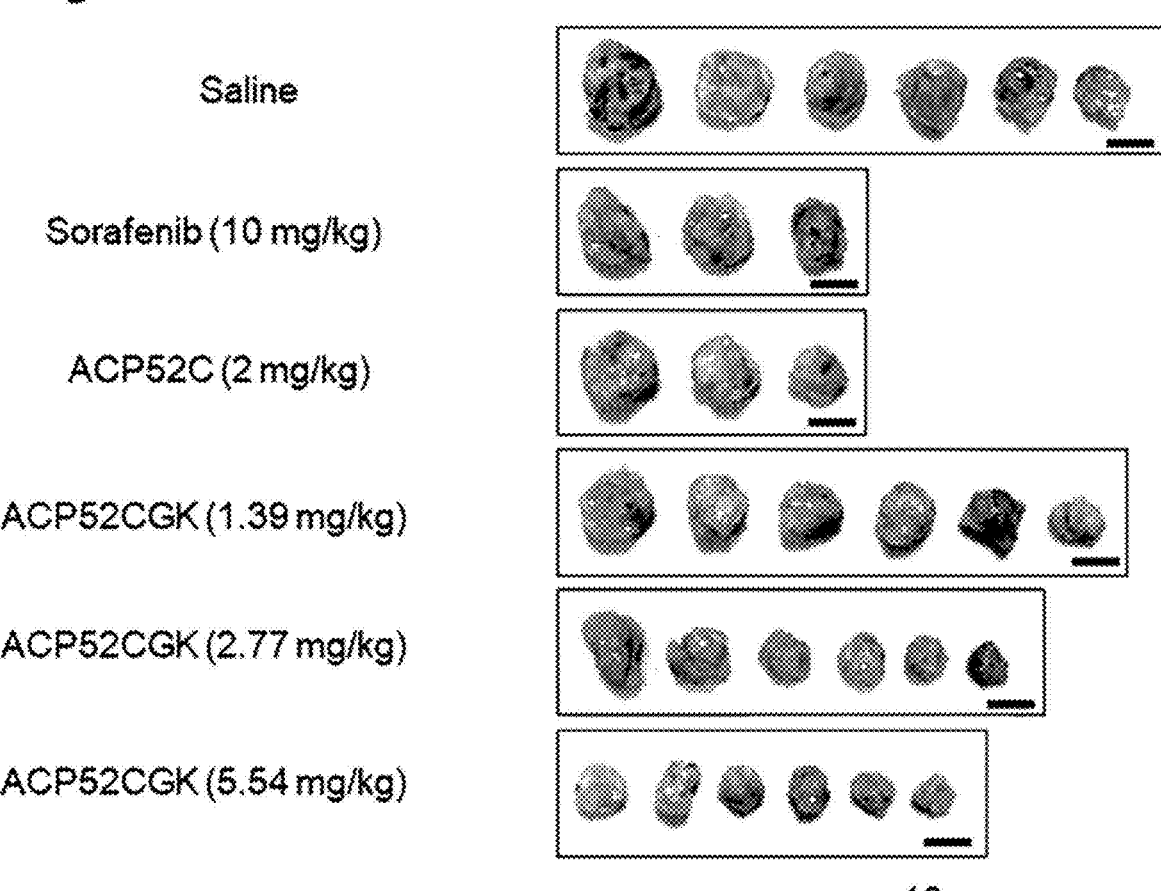
10 mm 【FIG 18d】
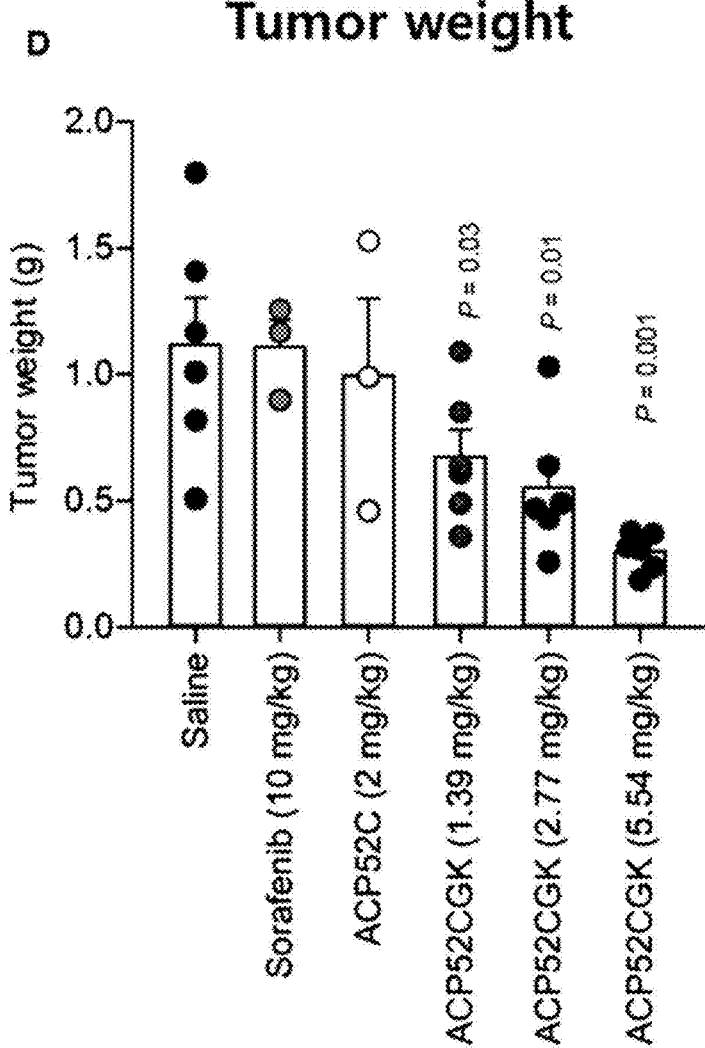

【FIG 18e】
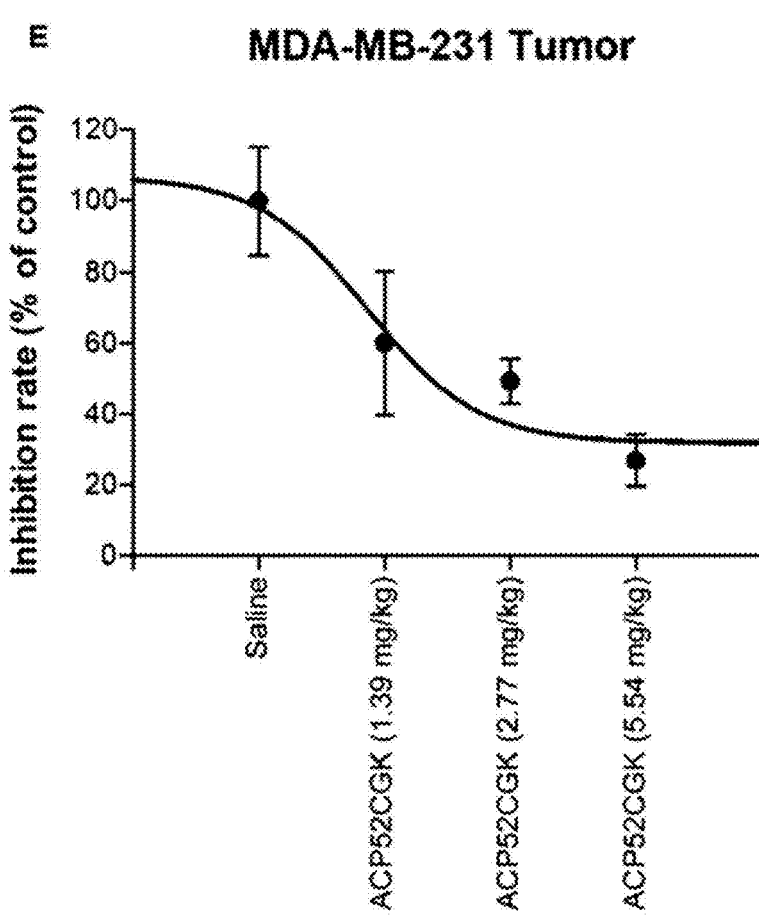

【FIG 18f】
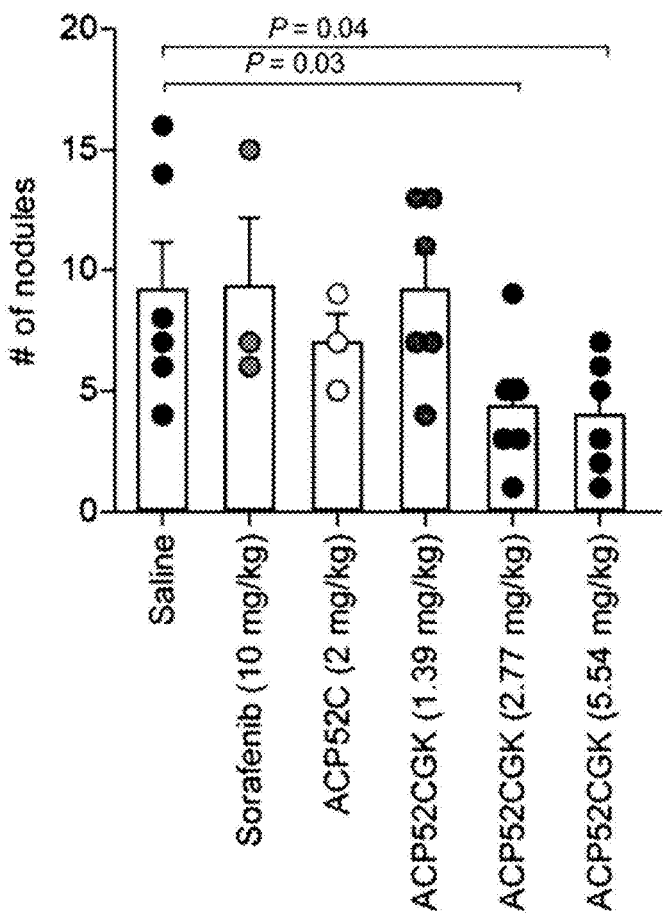
F     Lung metastasis
MDA-MB-231 LM1 xenograft (day 5 interval)
Examined by eye (lung surface)

【FIG 18g】
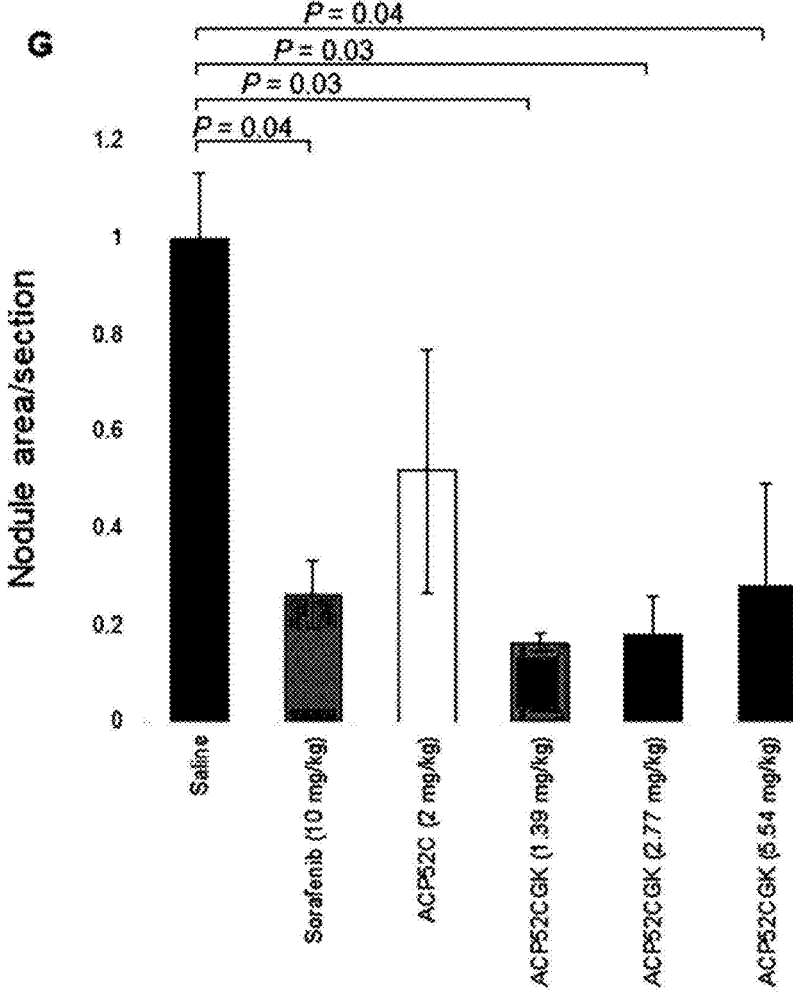
Examined by H/E-stained lung section
N = 4 (2 heads; tissue 2 pieces each)

【FIG 18h】
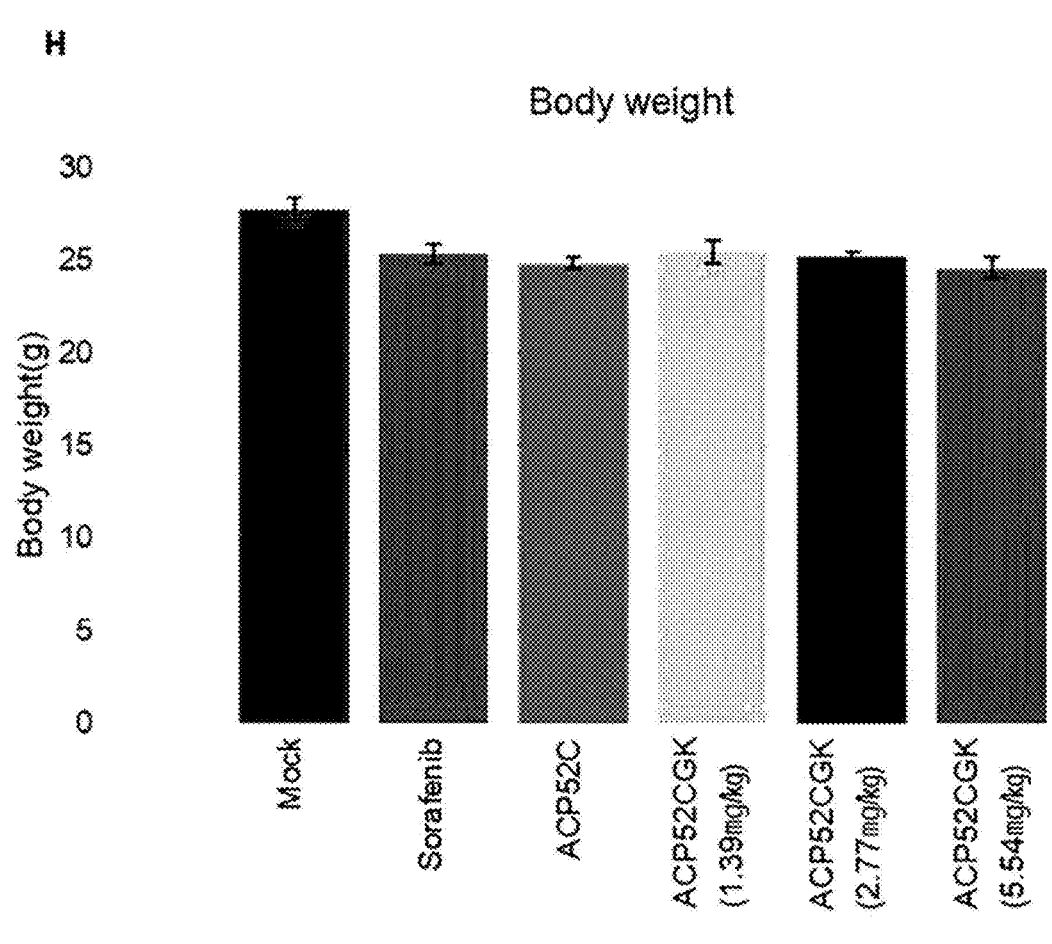

【FIG 18i】
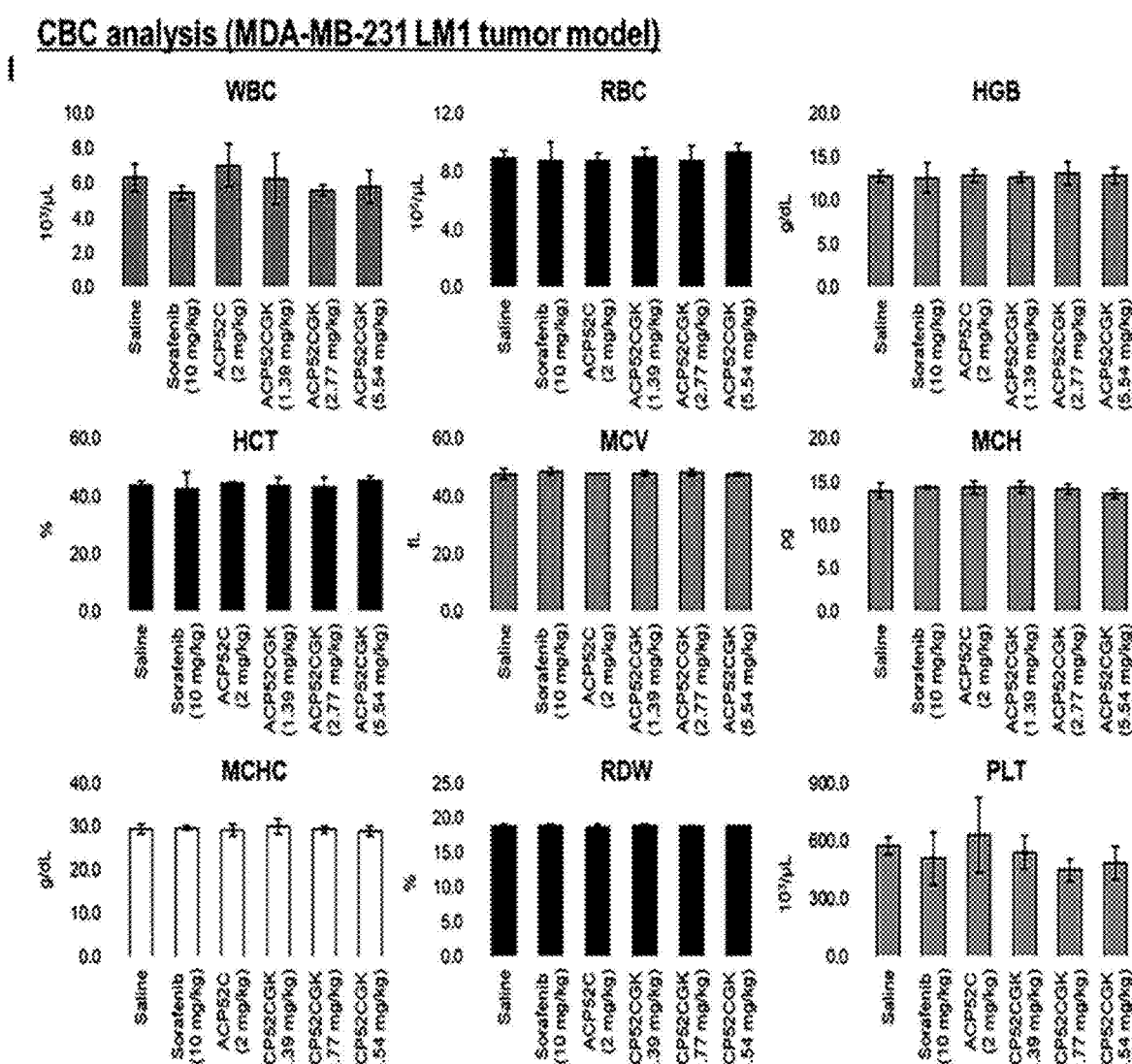

[FIG 18j]
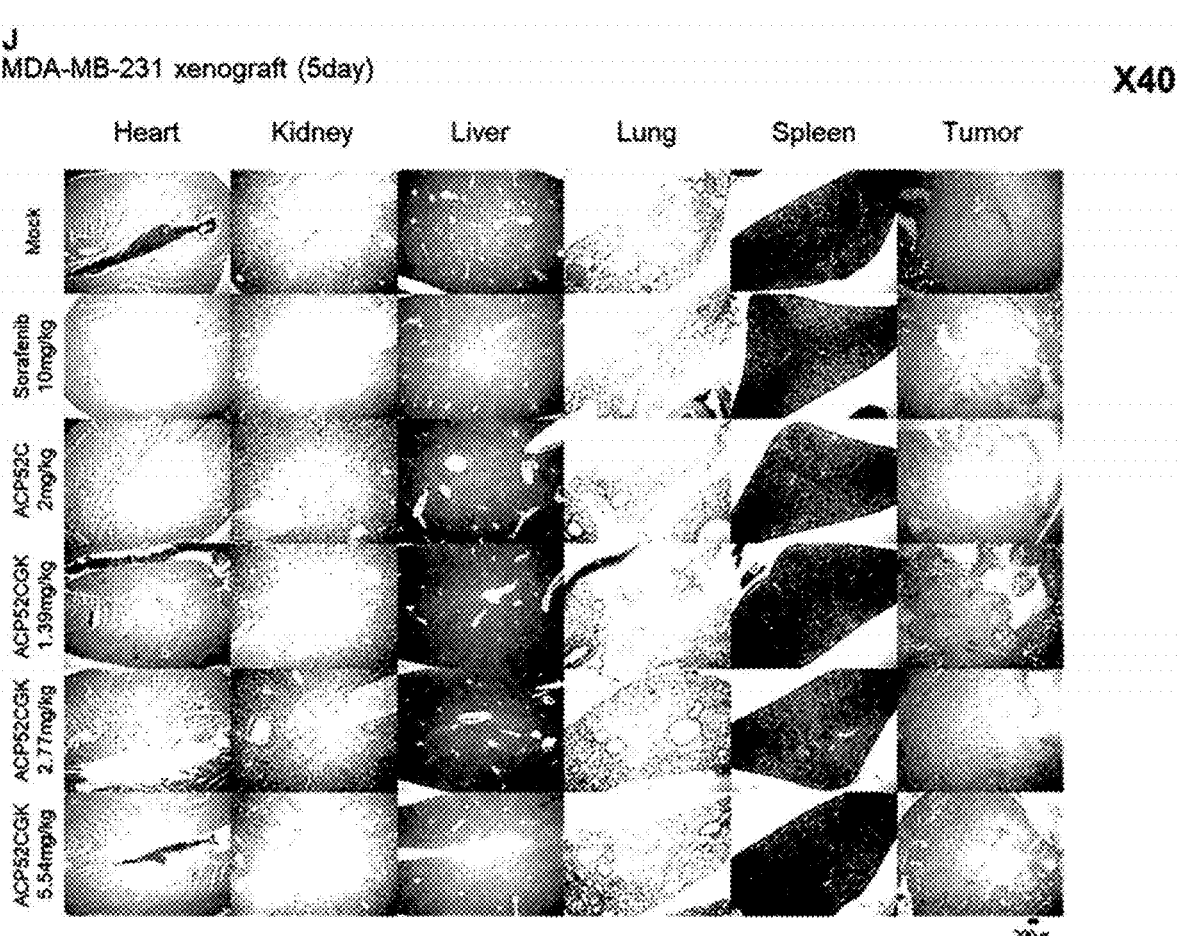
J
MDA-MB-231 xenograft (5day)

【FIG 18k】
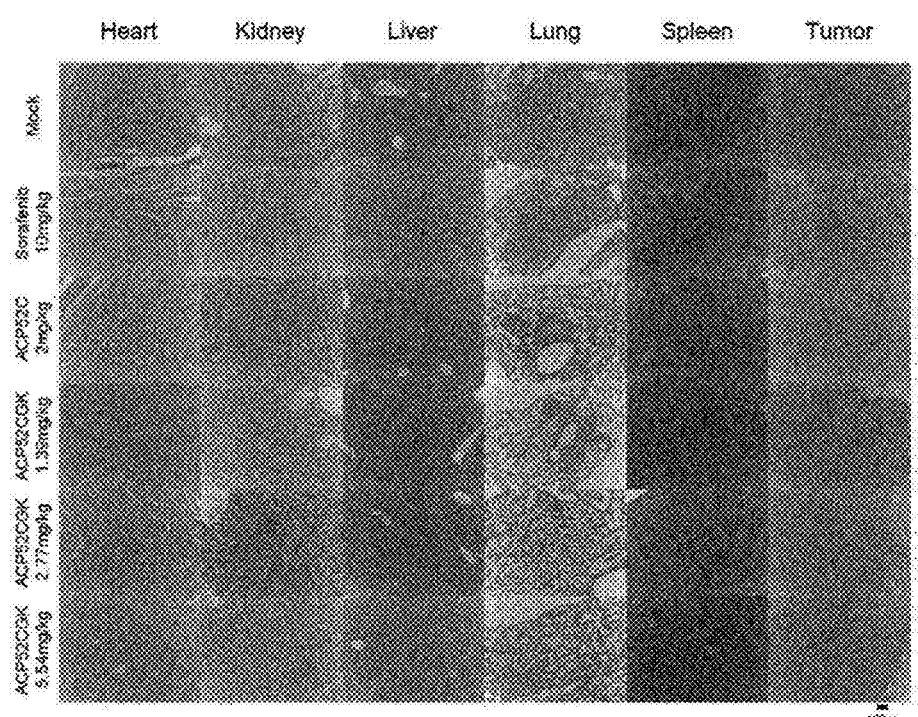
MDA-MB-231 xenograft (5day)     X100

[FIG 19a]
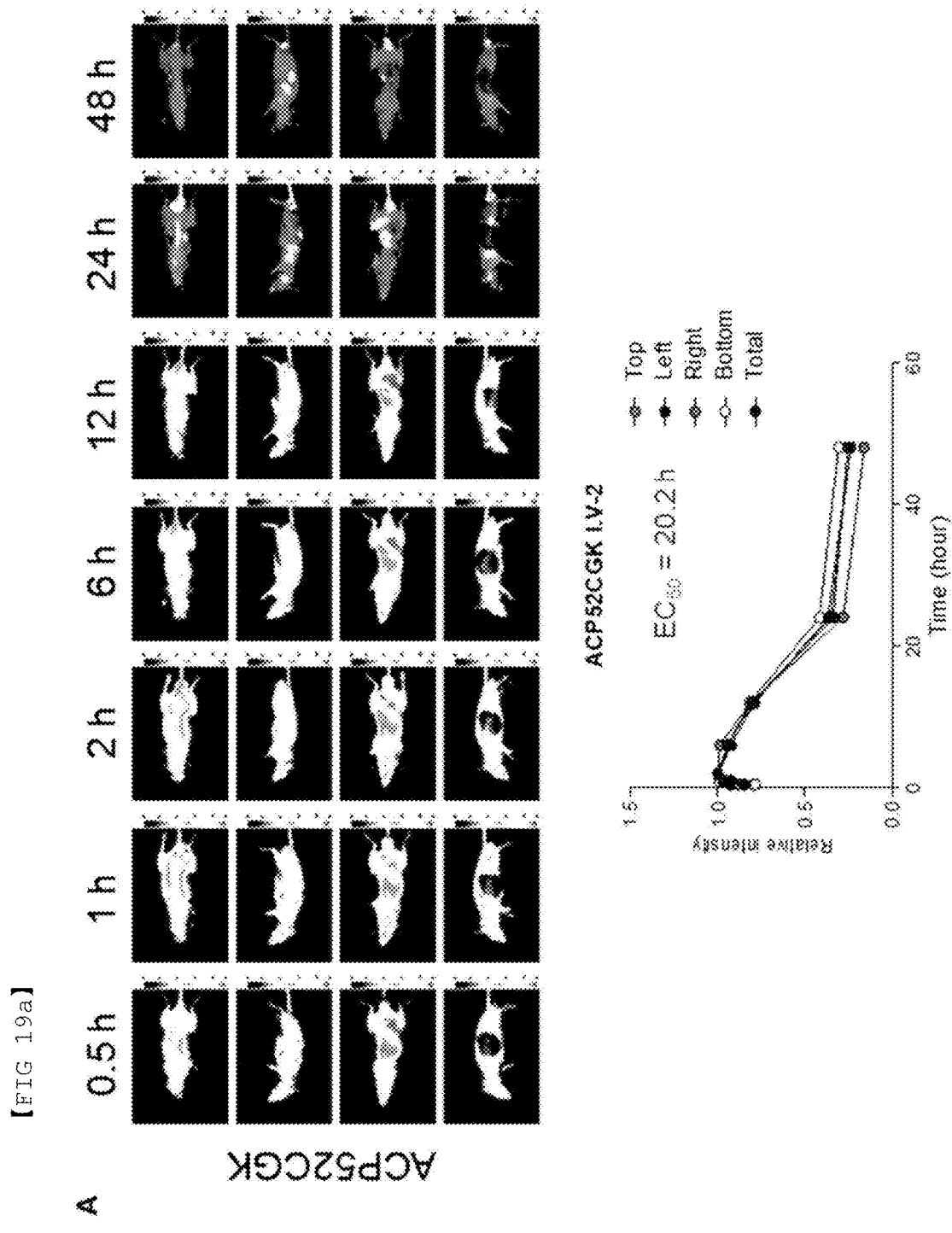

[FIG 19b]
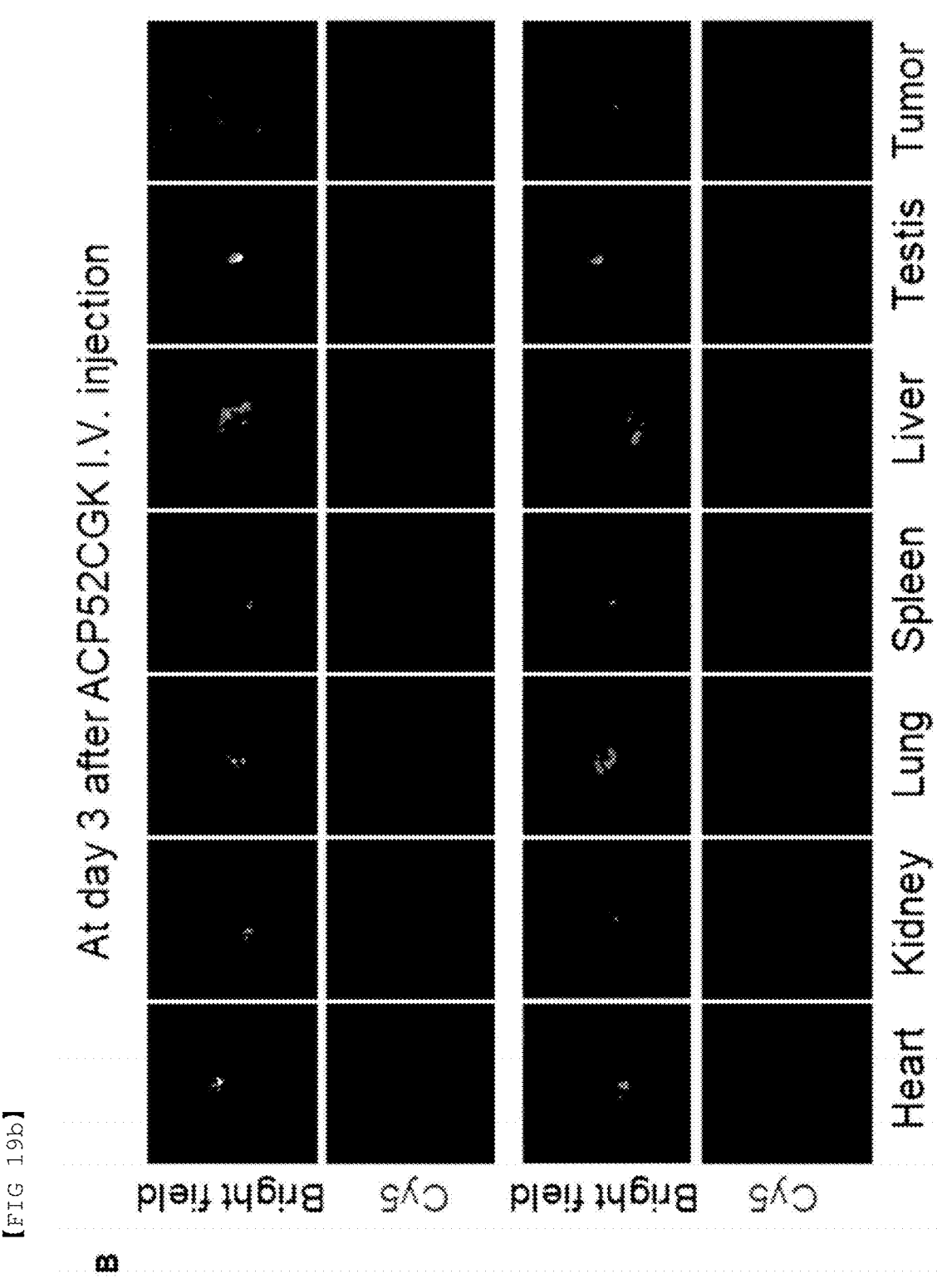
B

[FIG 20a]

ACP52CGK: Cellular efficacy (EC$_{50}$ = ~ 8 h)

・ Cytosol → nucleus → cytosol → mitochondria/lysosome → degradation

【FIG 20b】
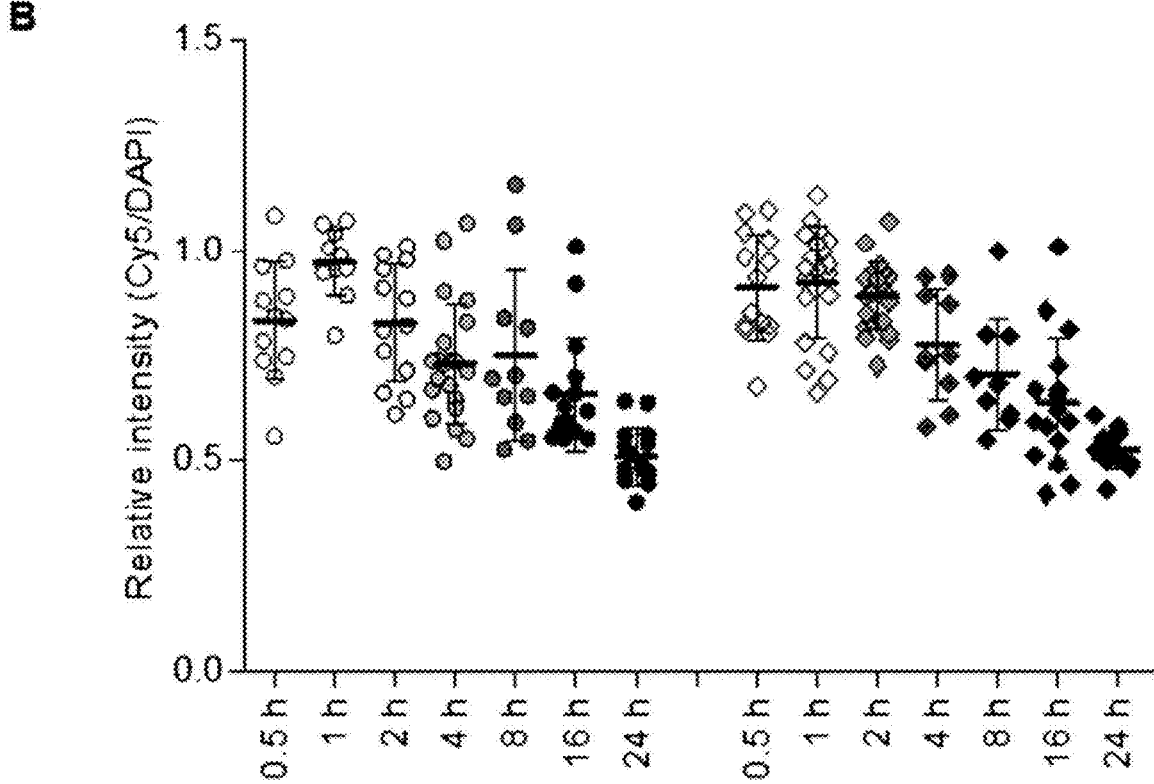

[FIG 21]
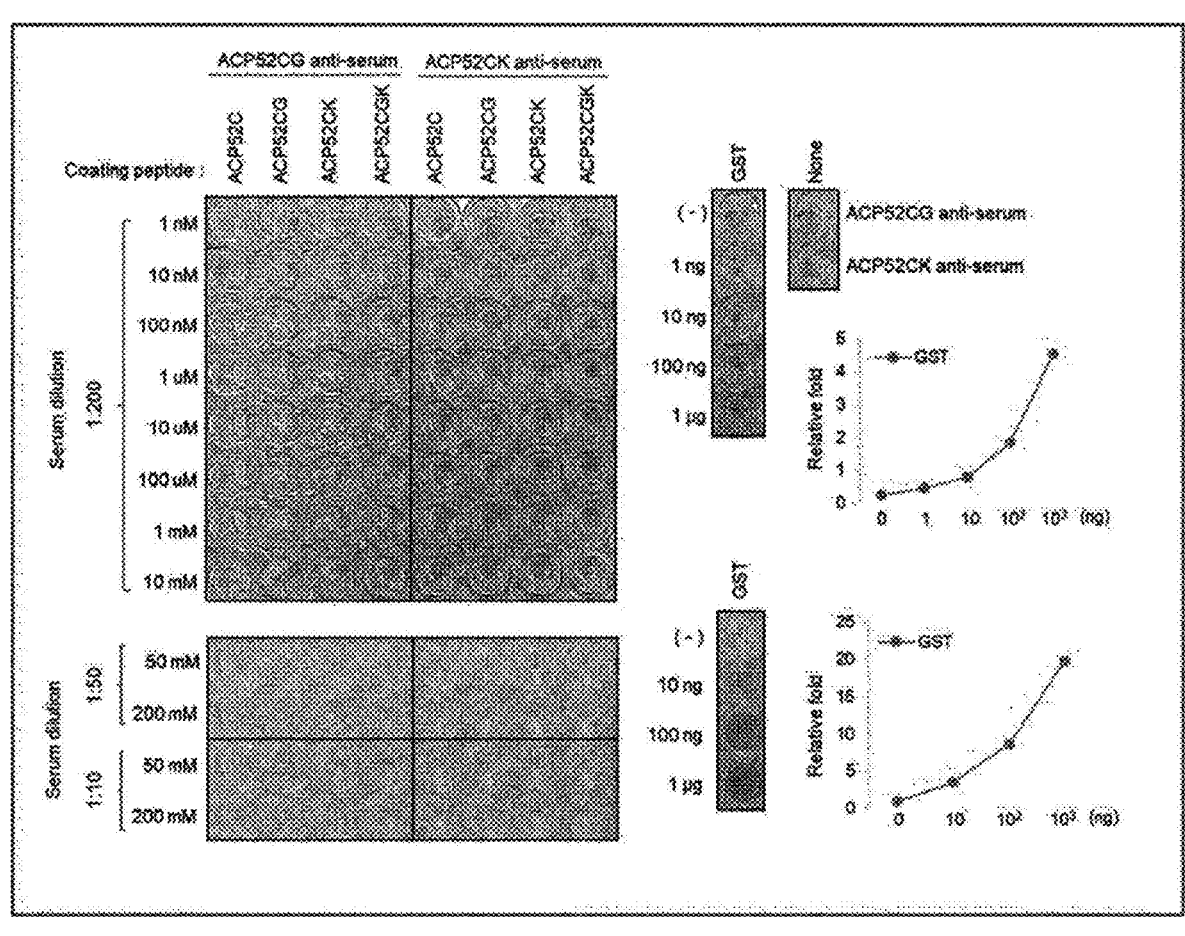

[FIG 22a]
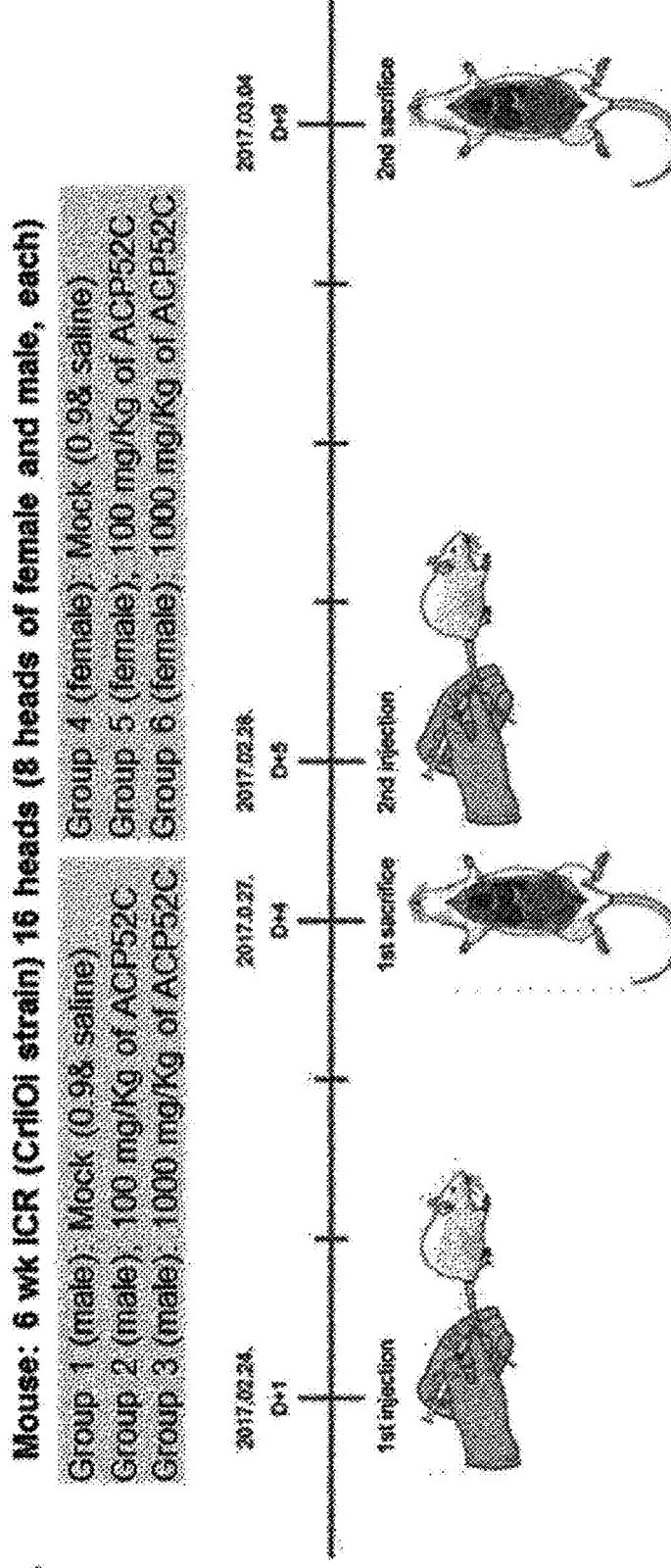

[FIG 22b]
B
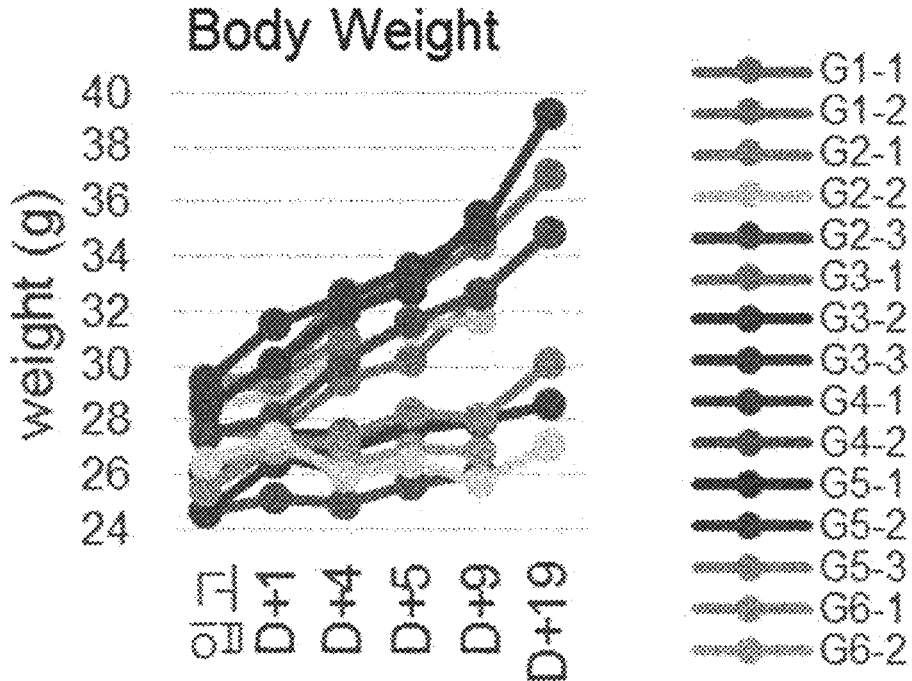

【FIG 22c】
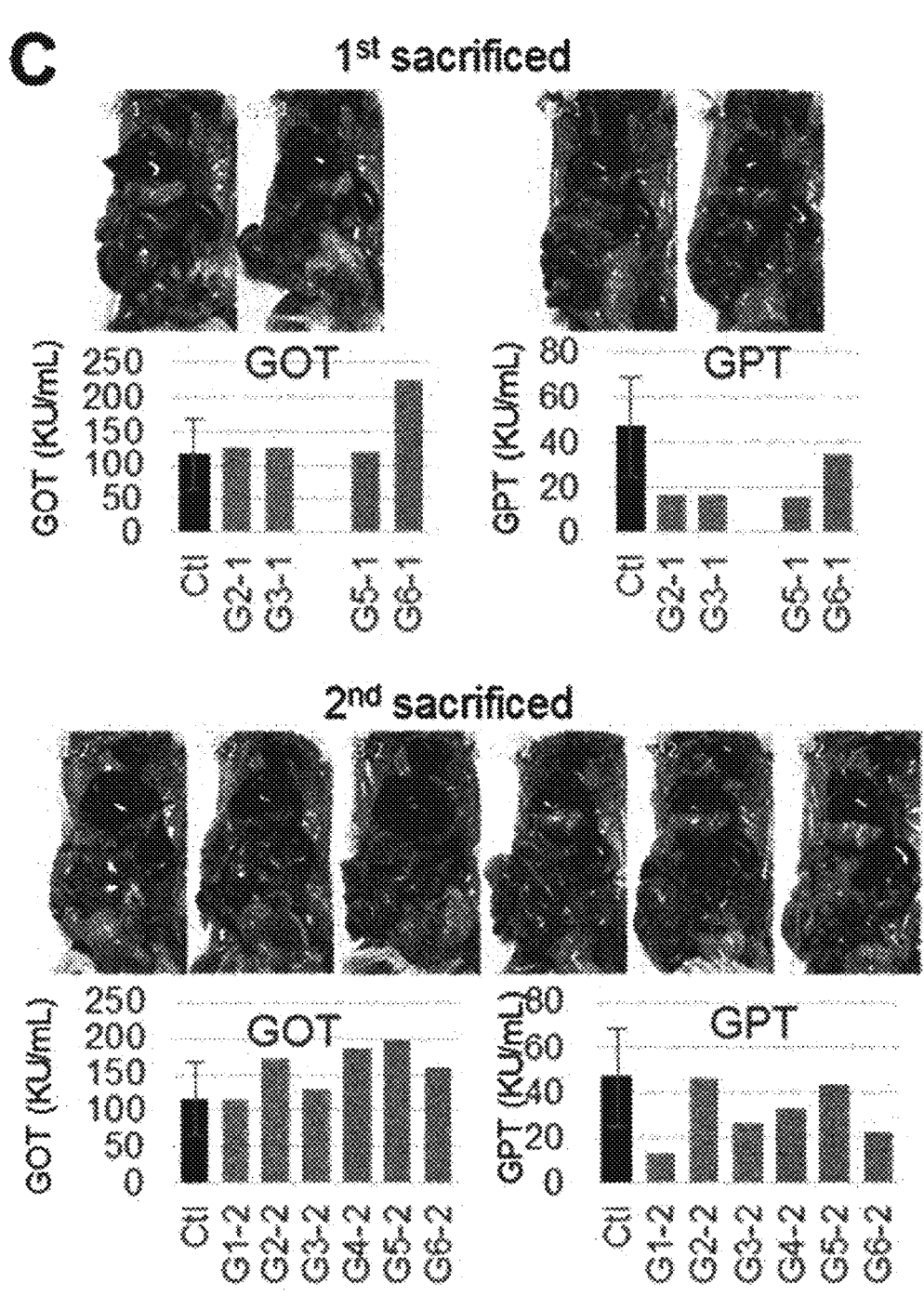

[FIG 22d]
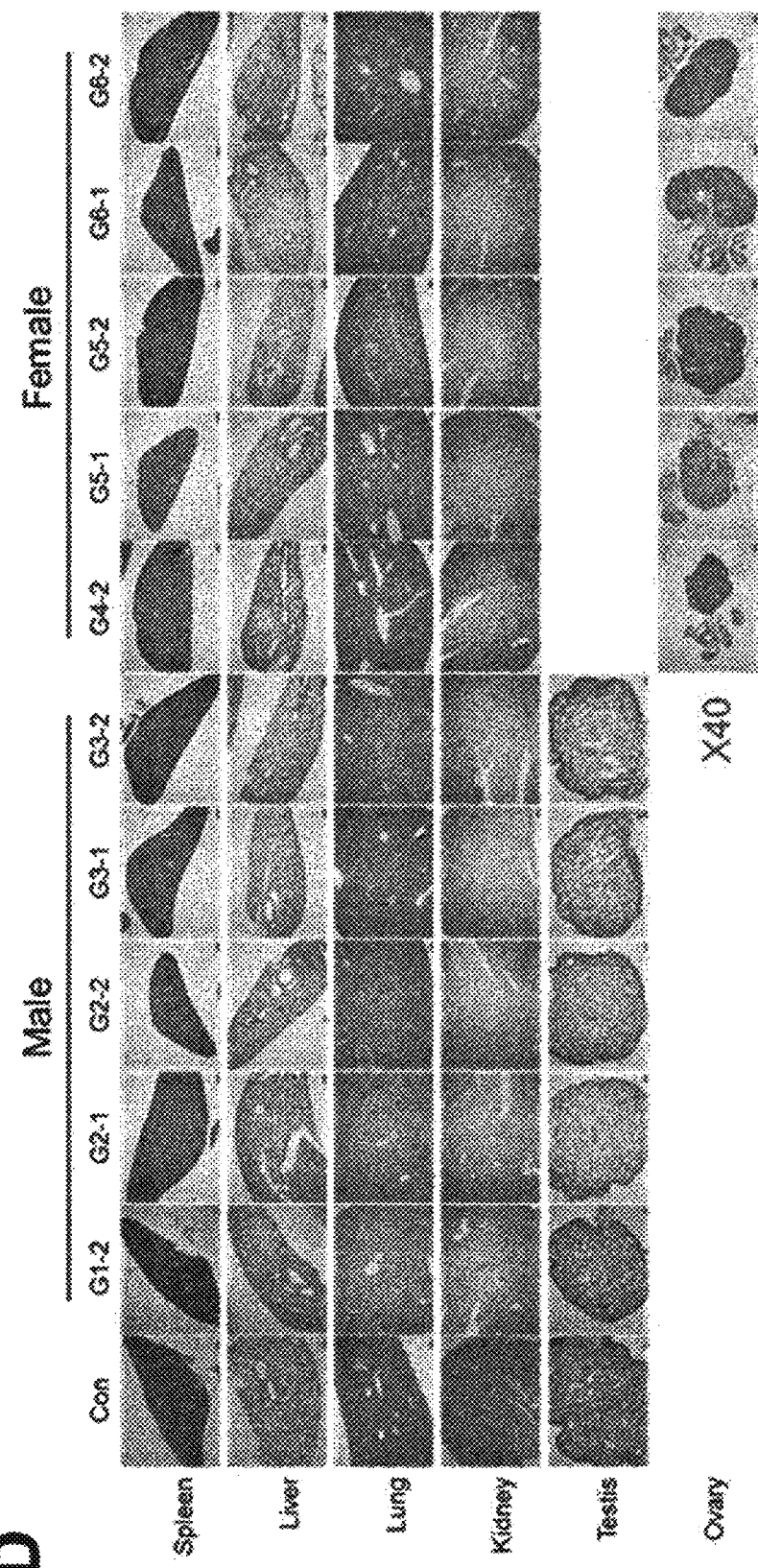

[FIG 22e]

[FIG 23]
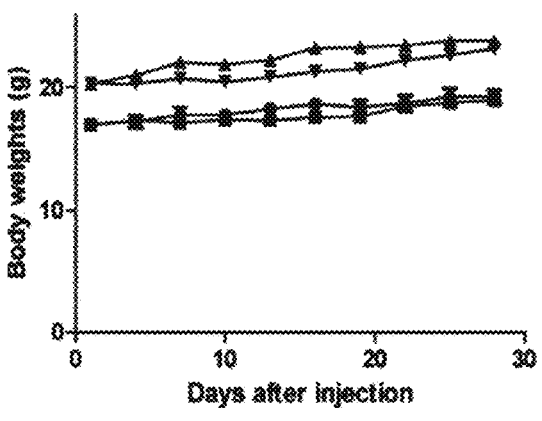
Legend:
- Female, vehicle
- Female, ACP52Cm (100 mg/kg)
- Male, vehicle
- Male, ACP52Cm (100 mg/kg)
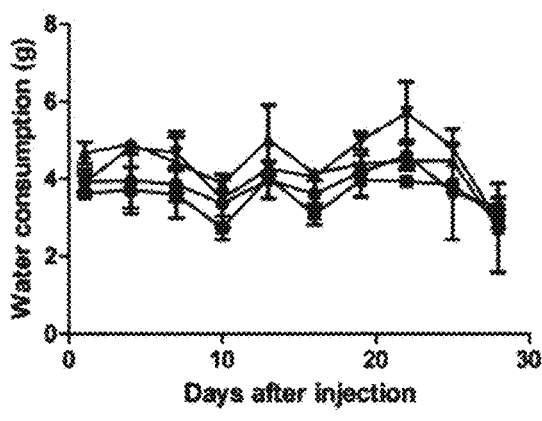
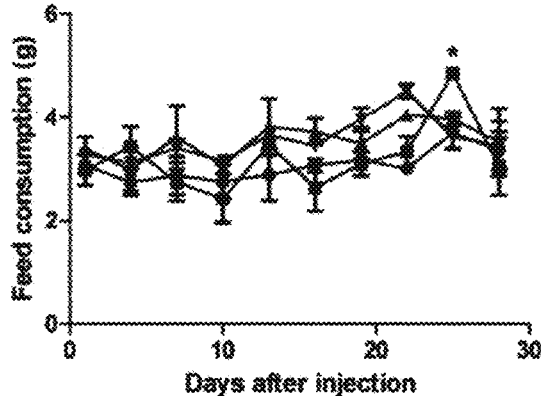

[FIG 24]
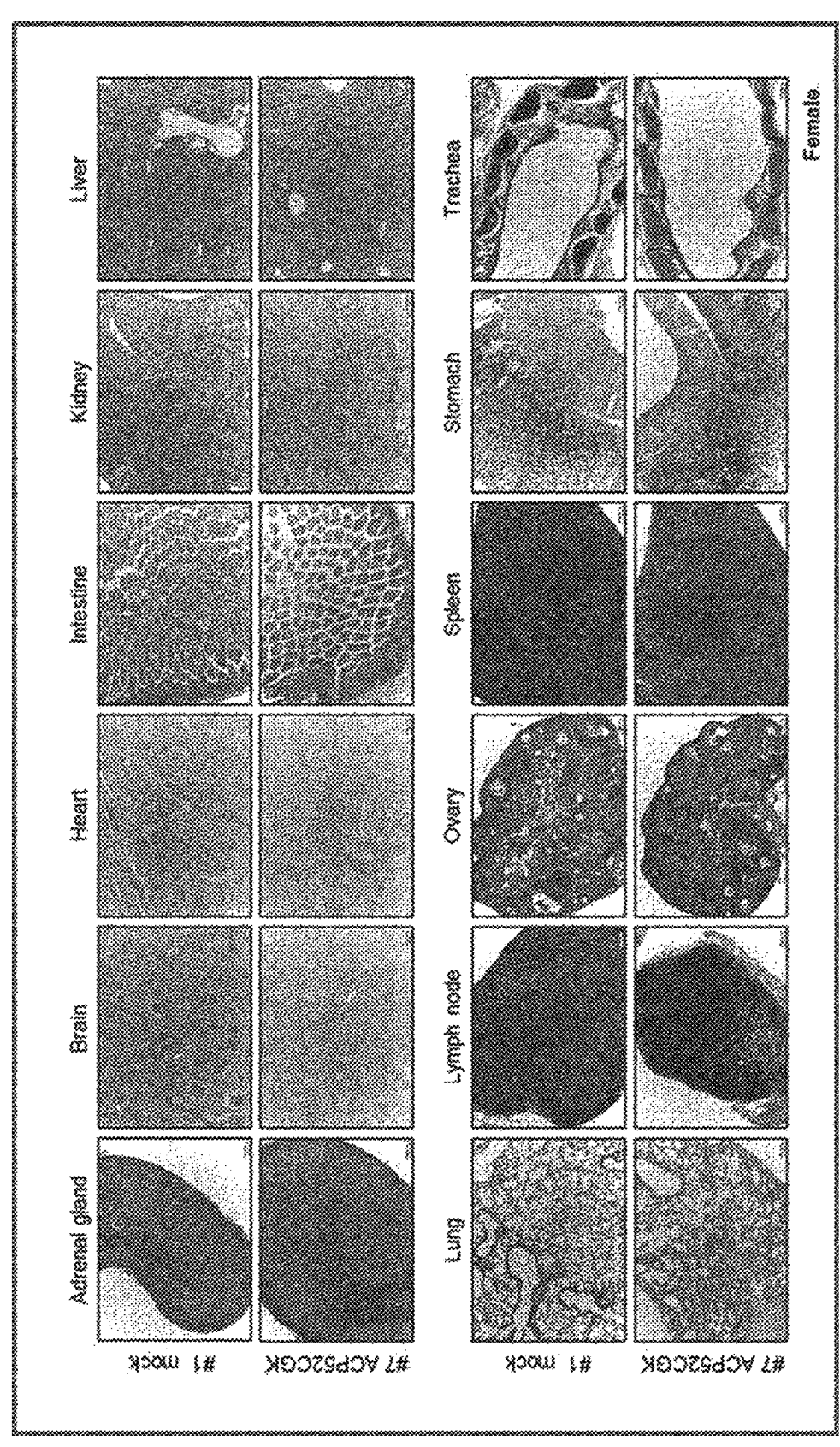

【FIG 25a】
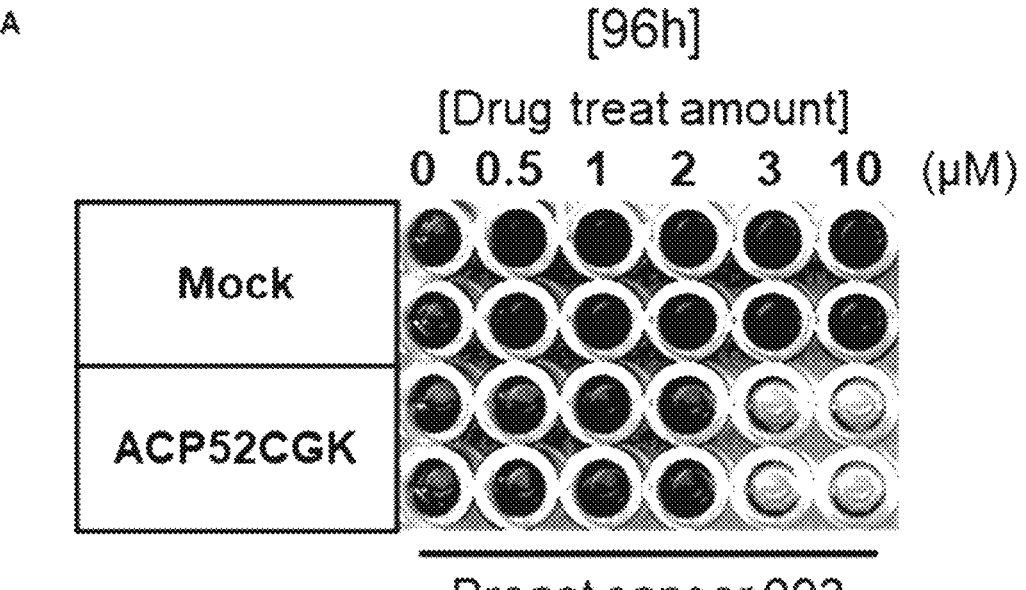
【FIG 25b】
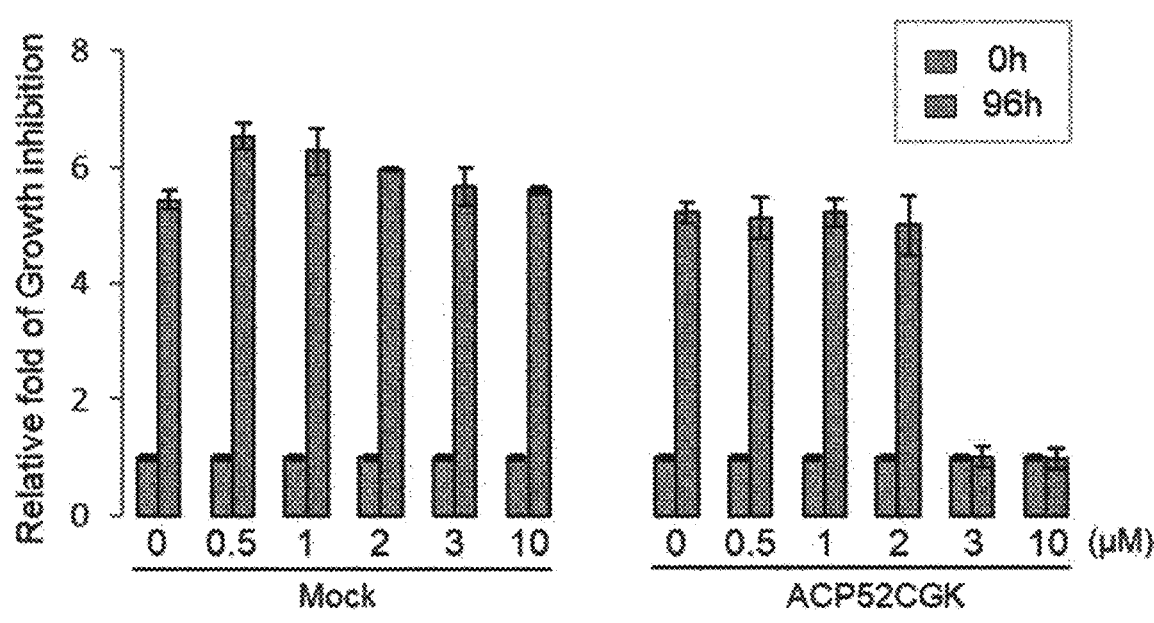

[FIG 25c]
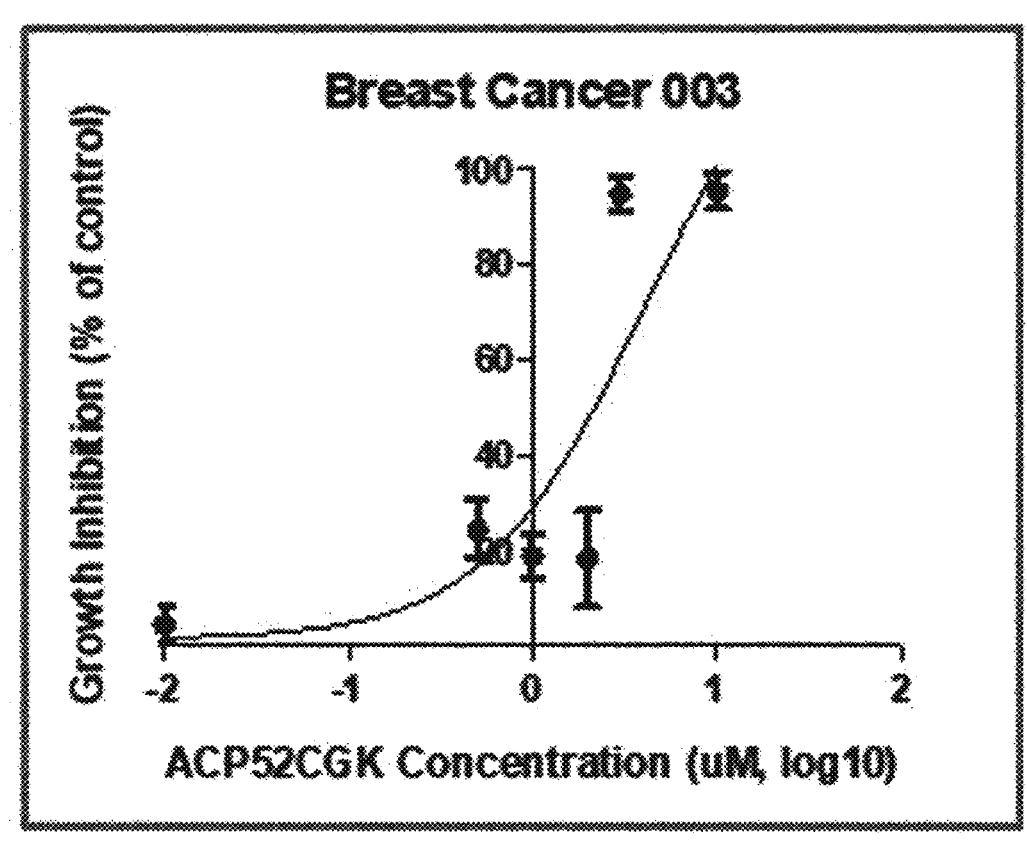
Breast Cancer 003
$GI_{50} = 2.13 \mu M$

[FIG 25d]
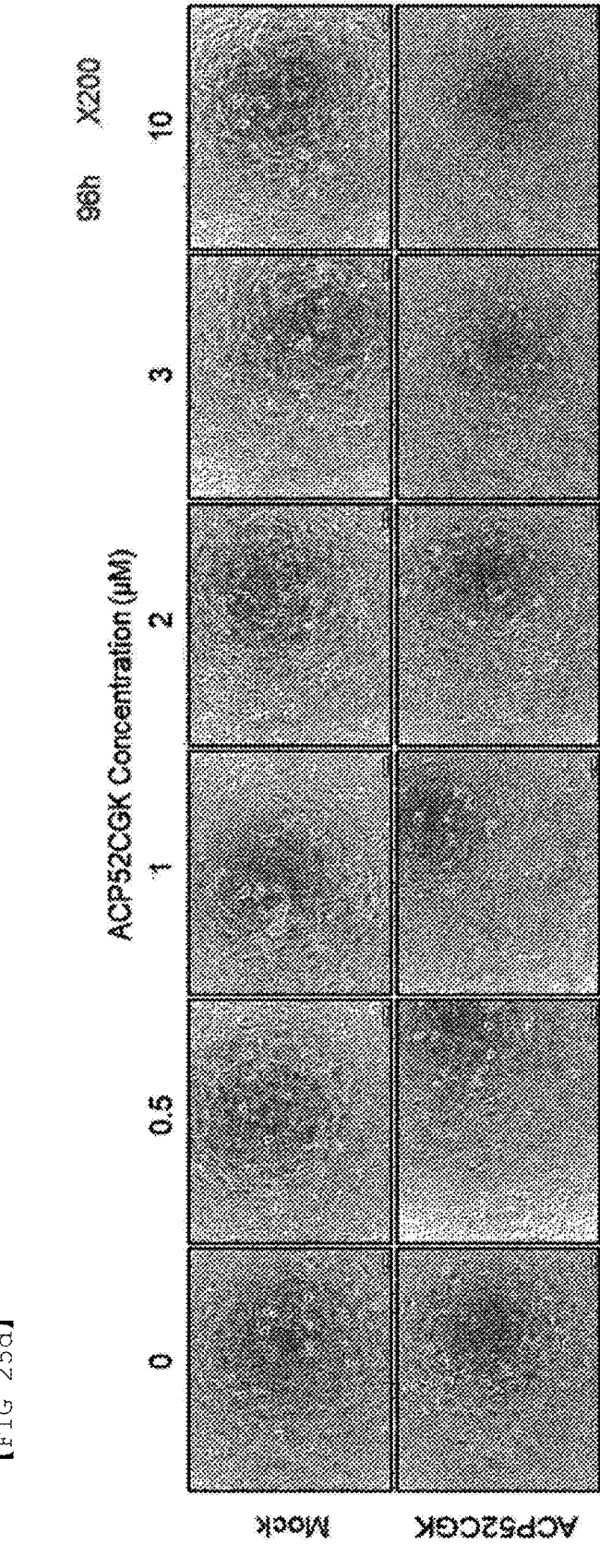

【FIG 26a】
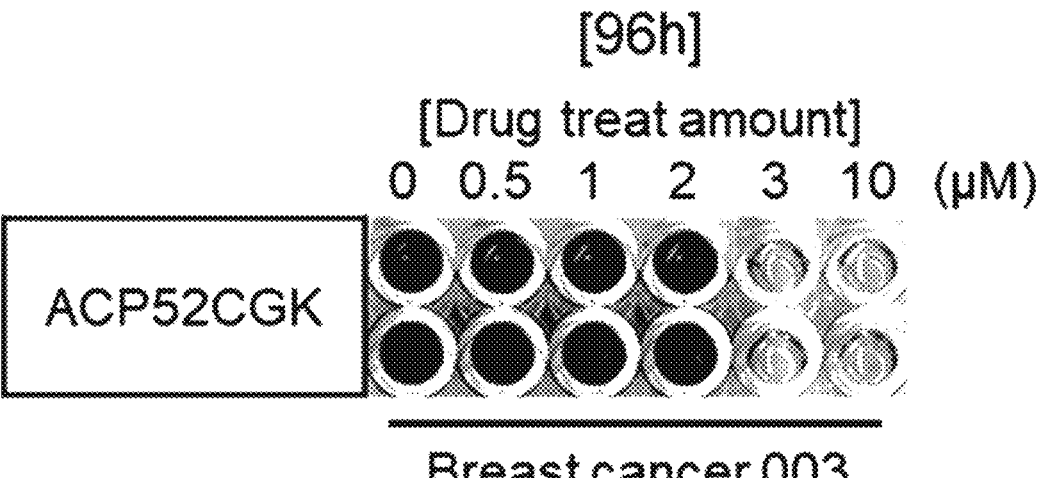
【FIG 26b】
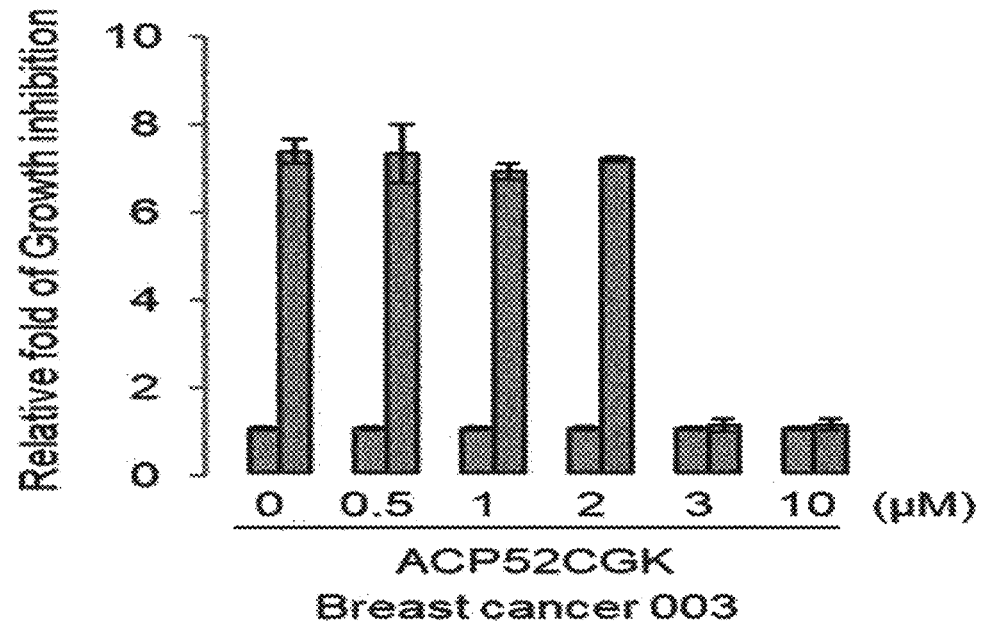

[FIG 26c]
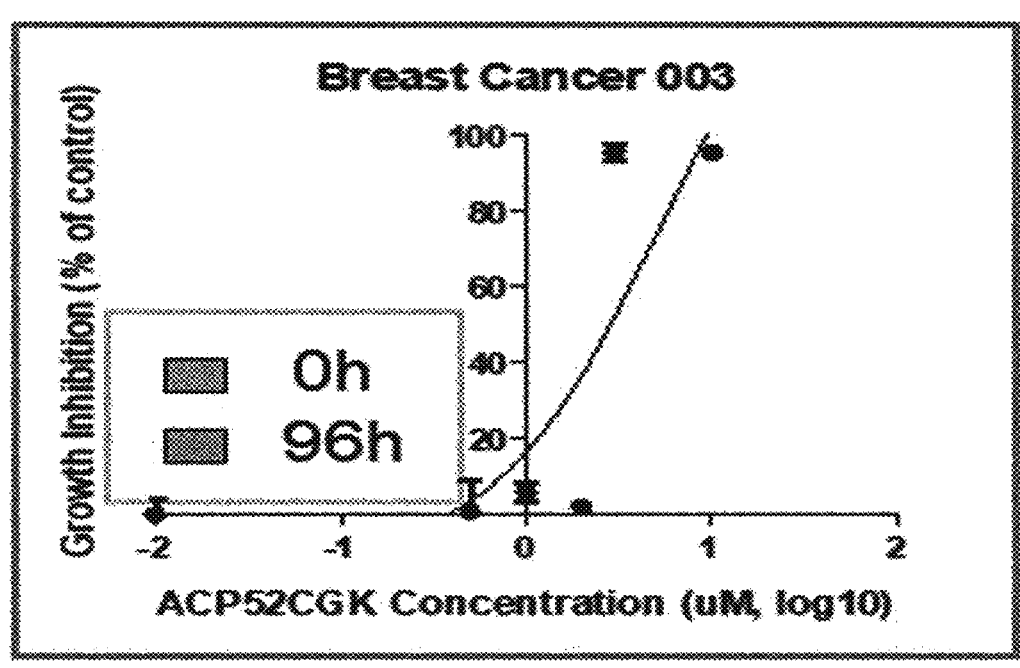
$GI_{50} = 2.89 \mu M$

[FIG 26d]
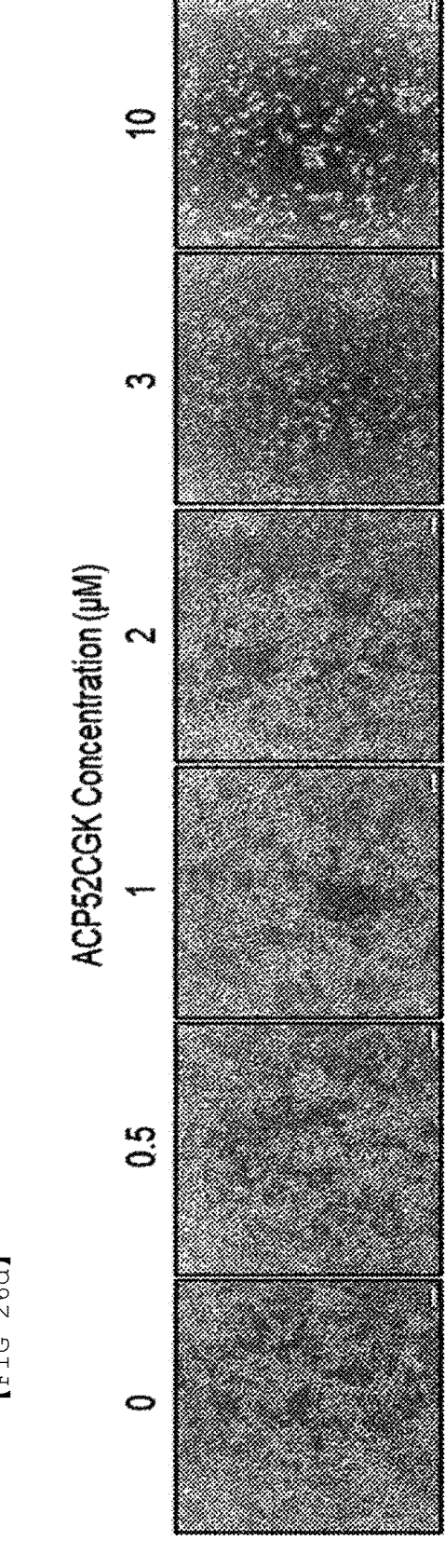

[FIG 27a]
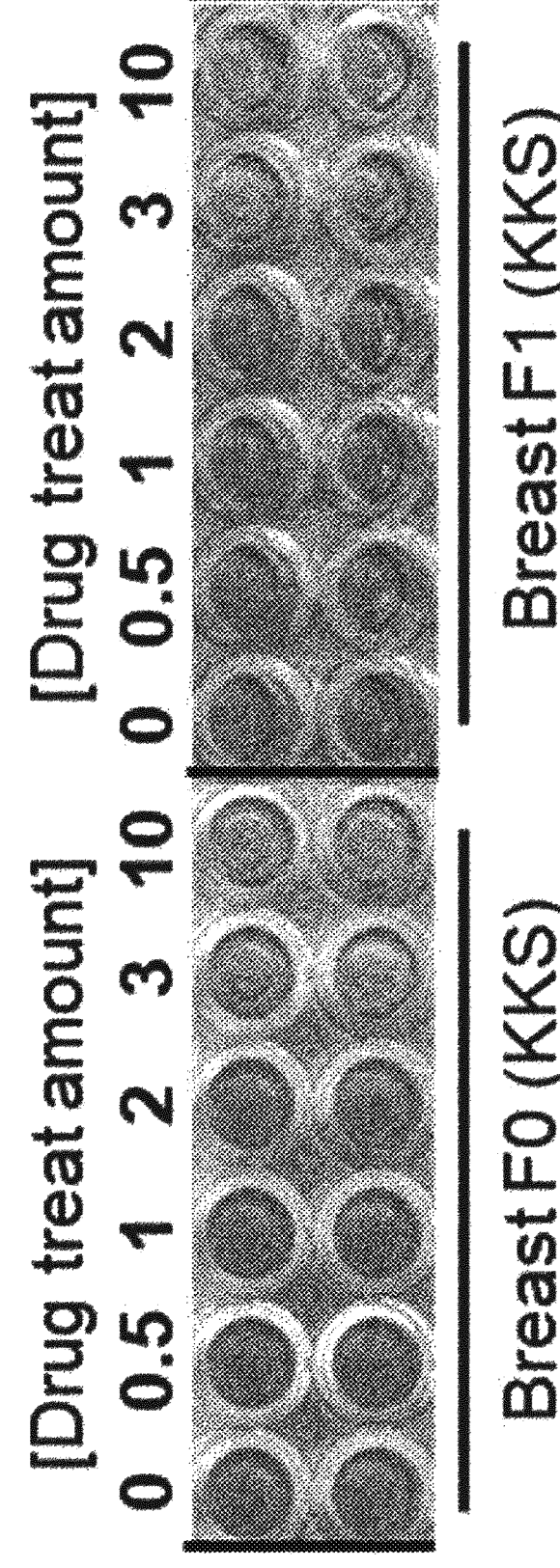

【FIG 27b】
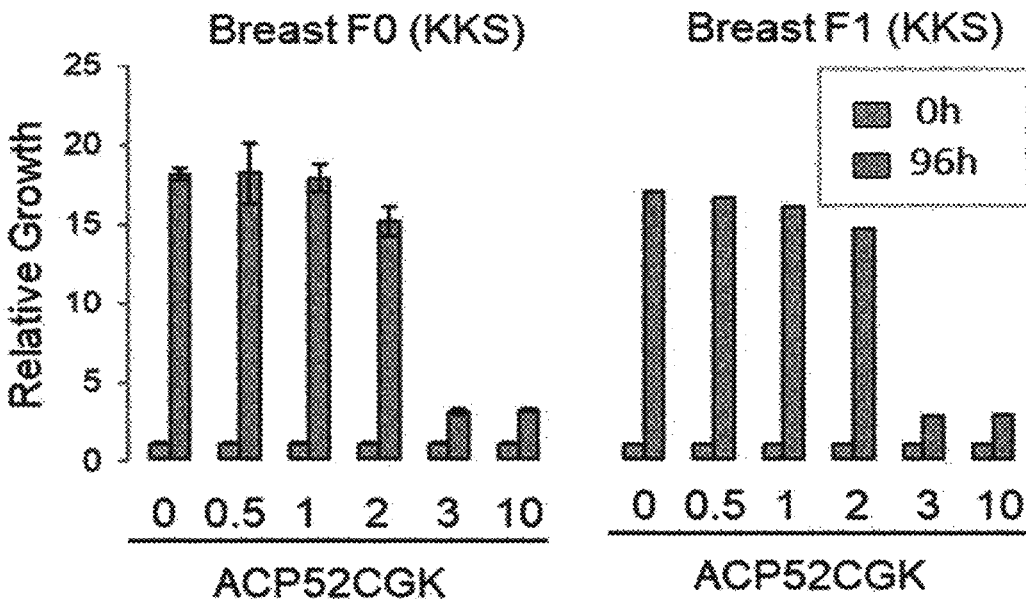
【FIG 27c】
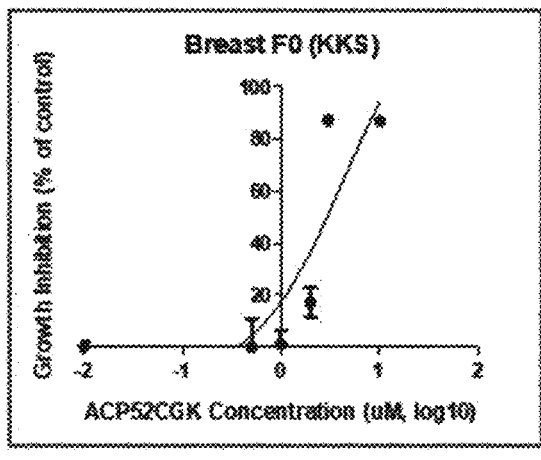
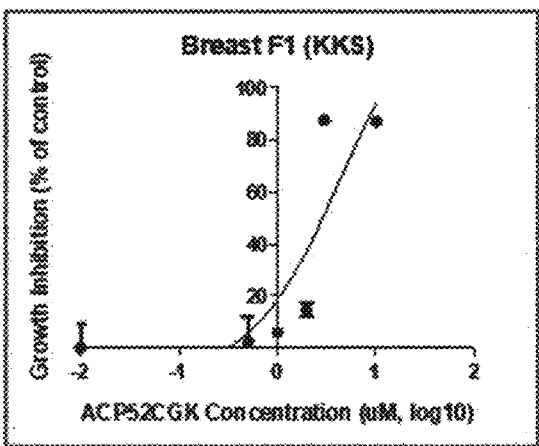

[FIG 27d]
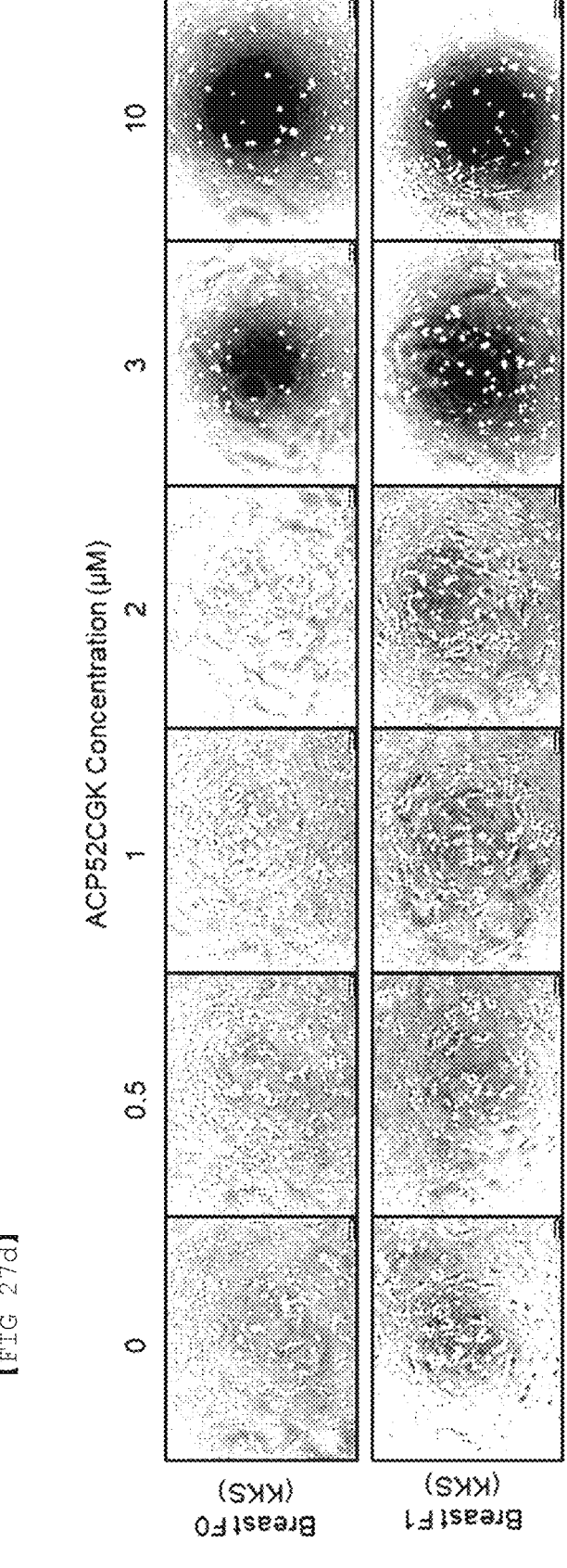

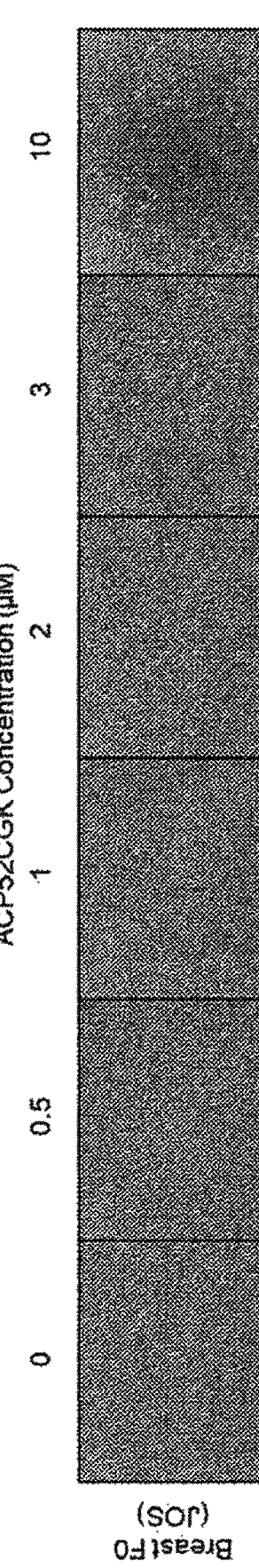
[FIG 28a]

[FIG 28b]
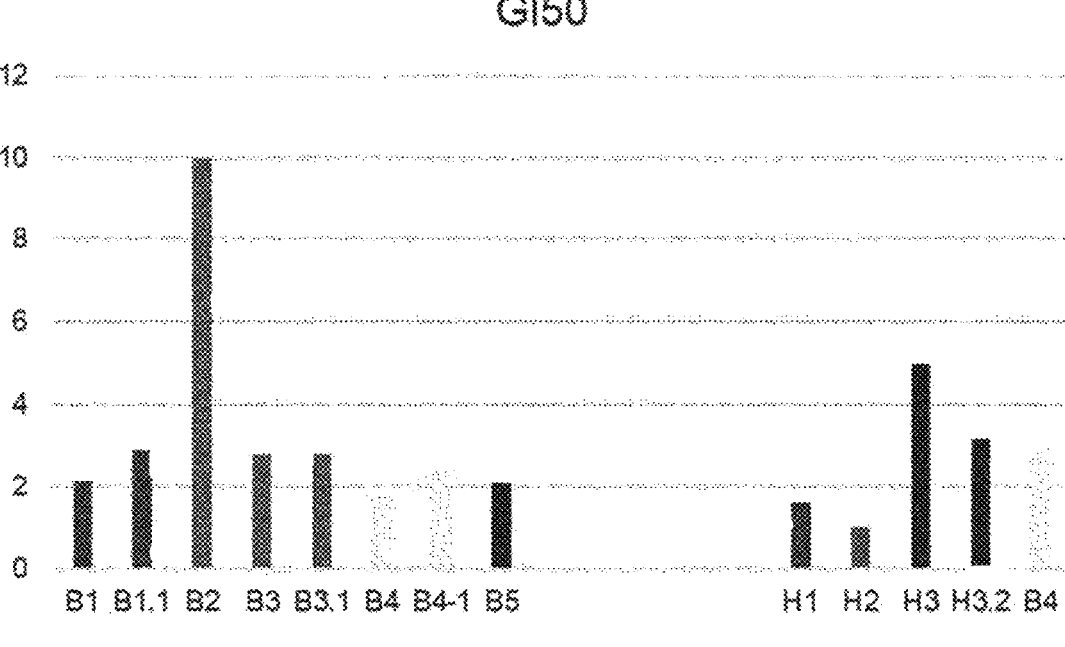

【FIG 29】
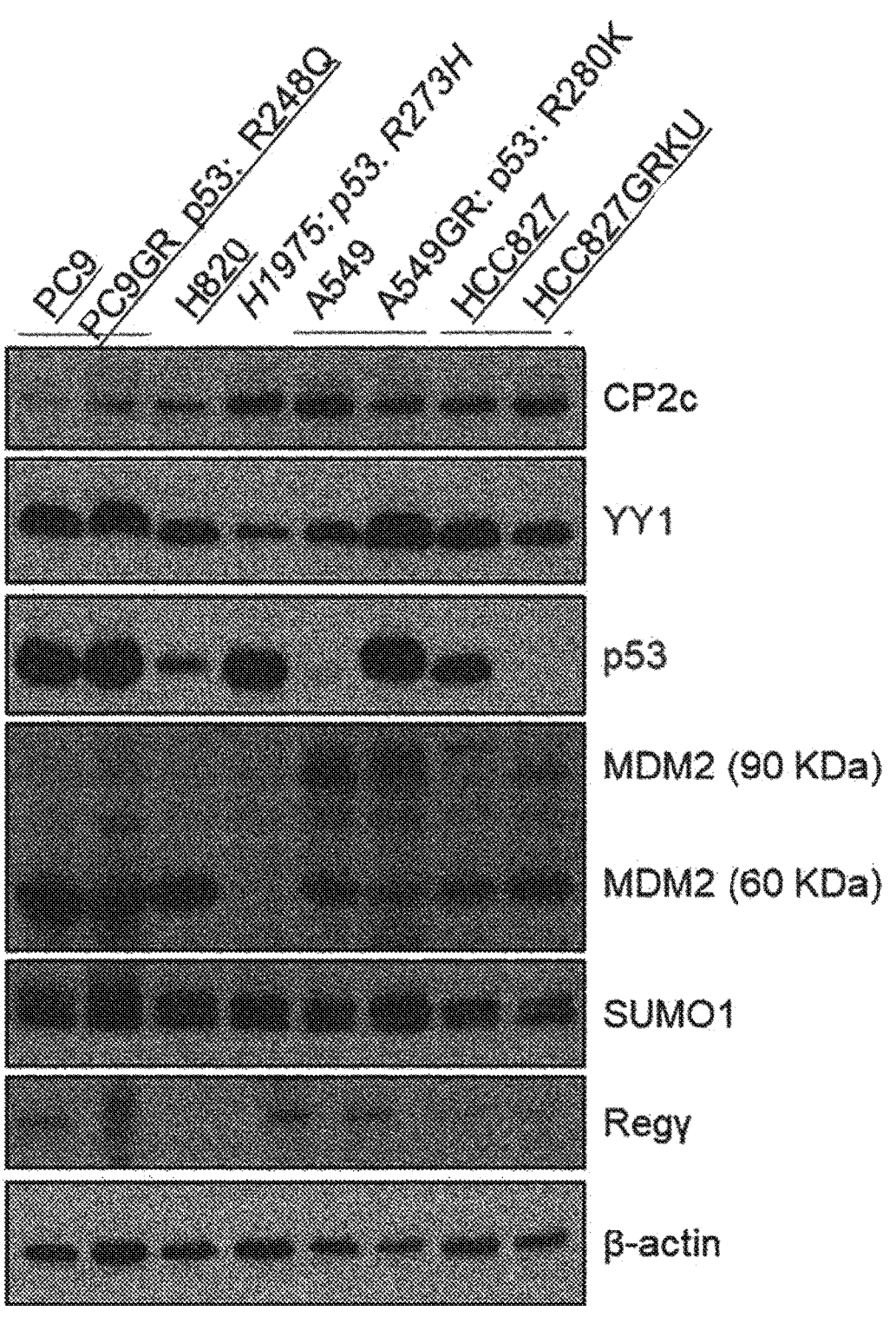

[FIG 30a]
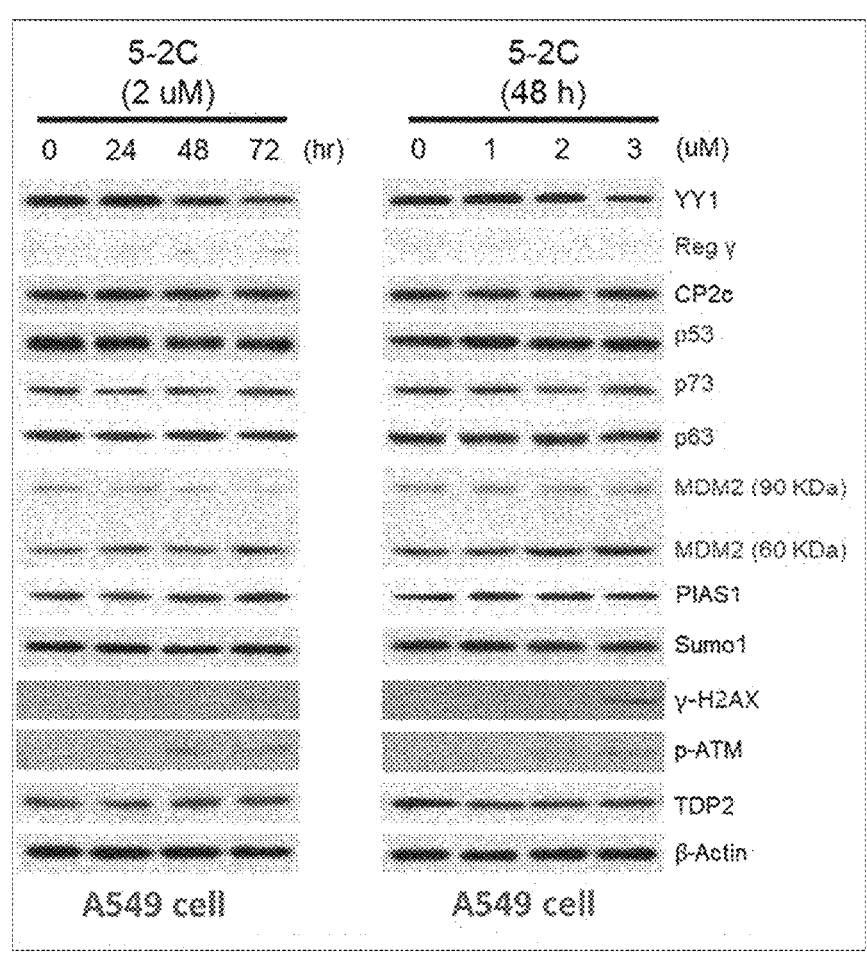

【FIG 30b】
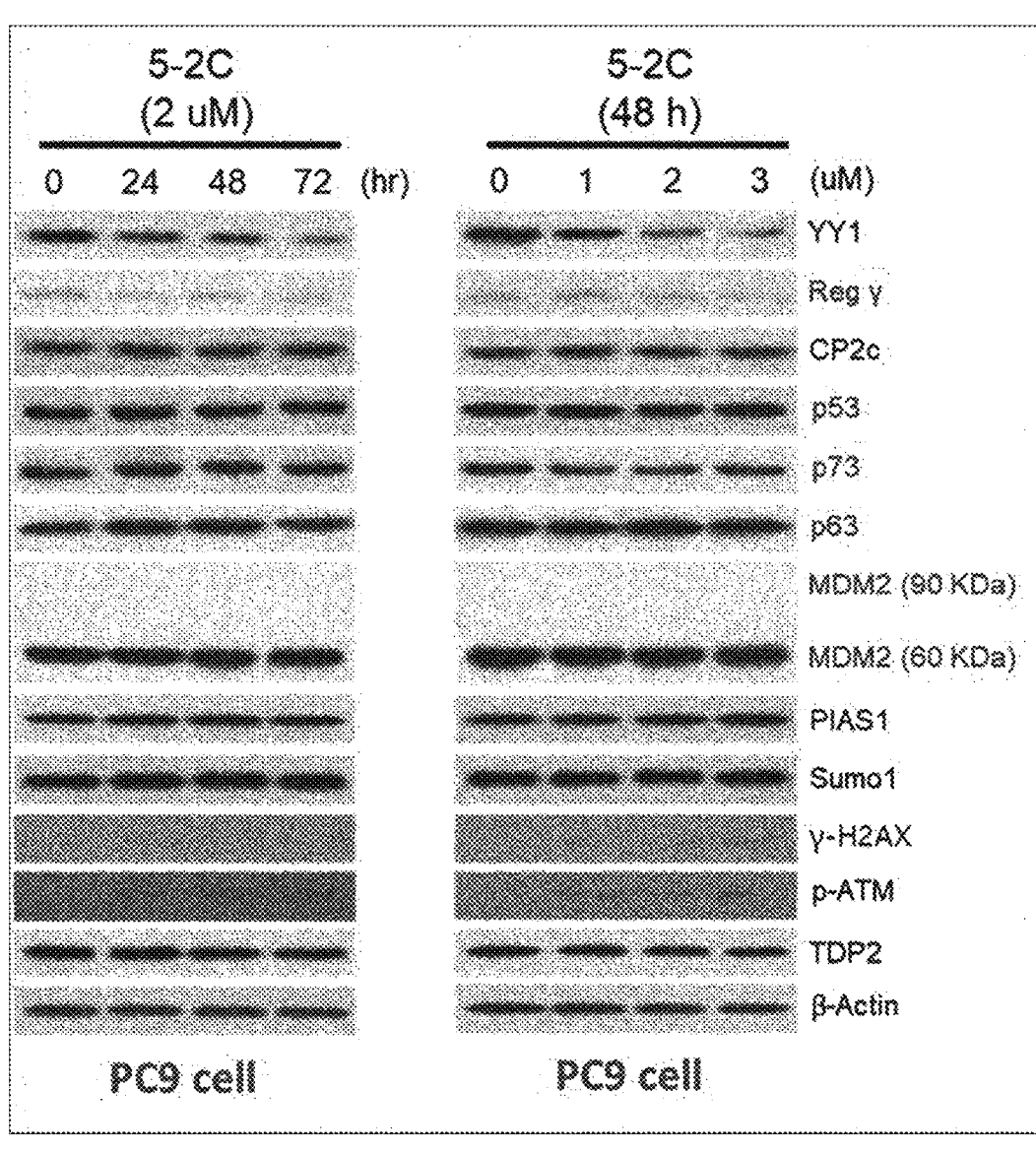

[FIG 30c]
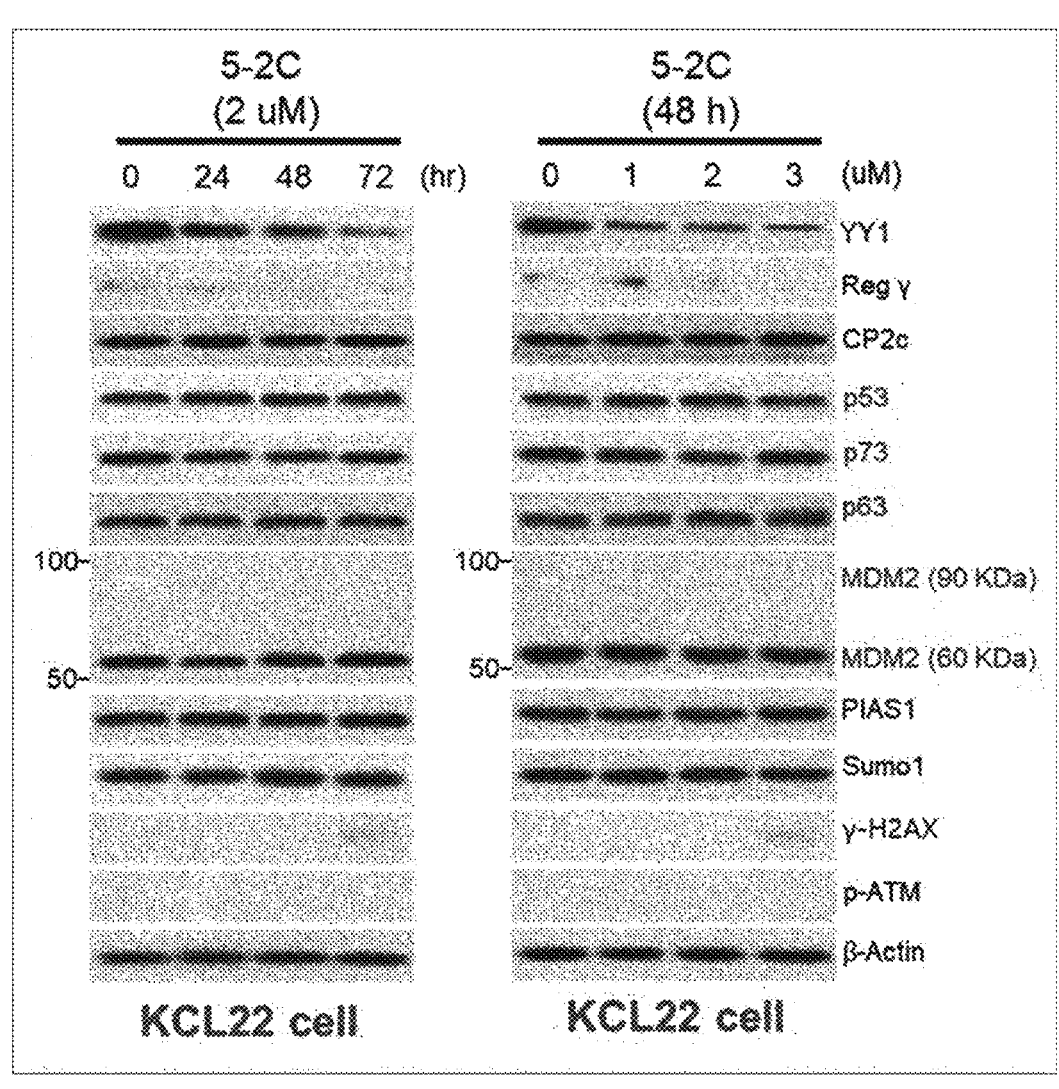

【FIG 31a】
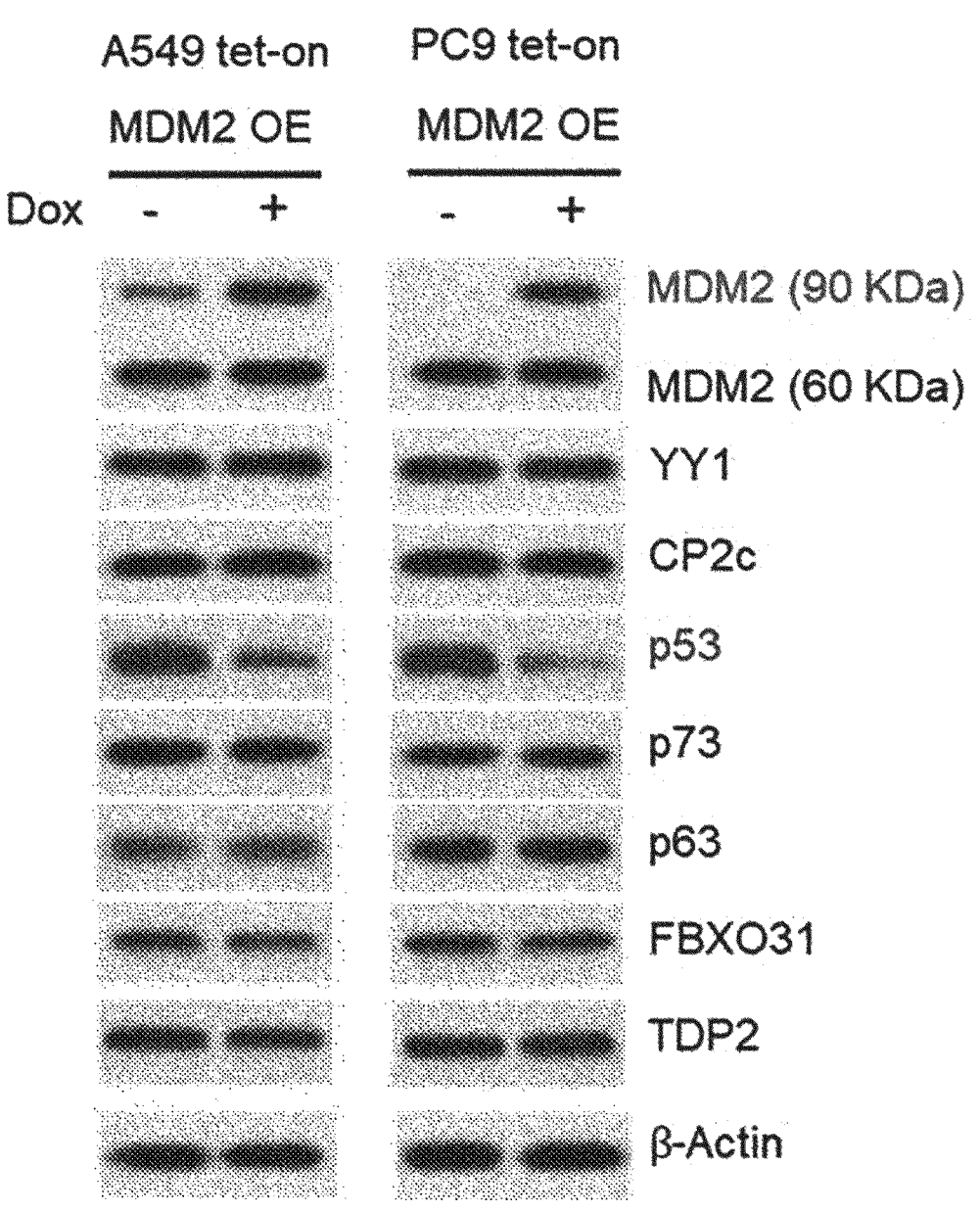

【FIG 31b】
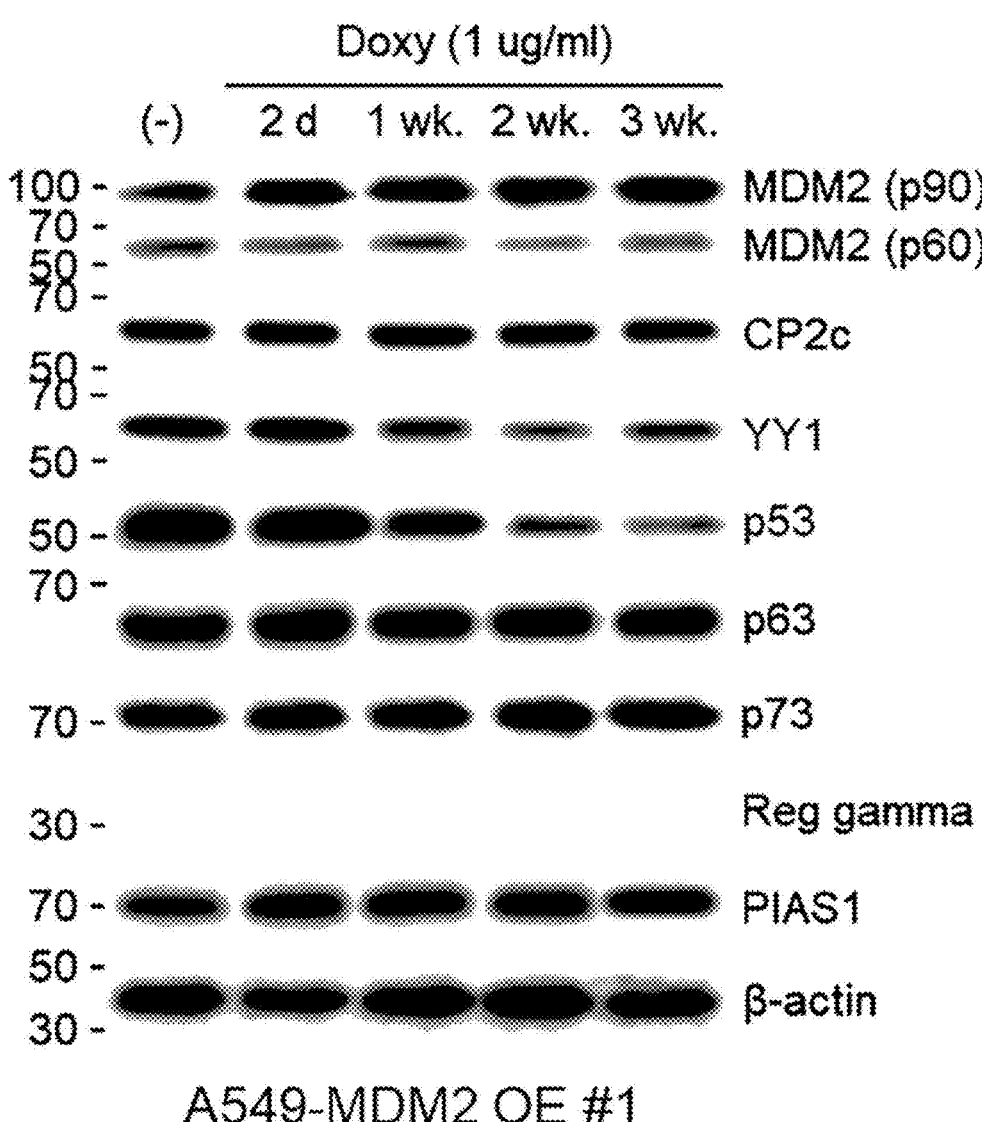

【FIG 32a】
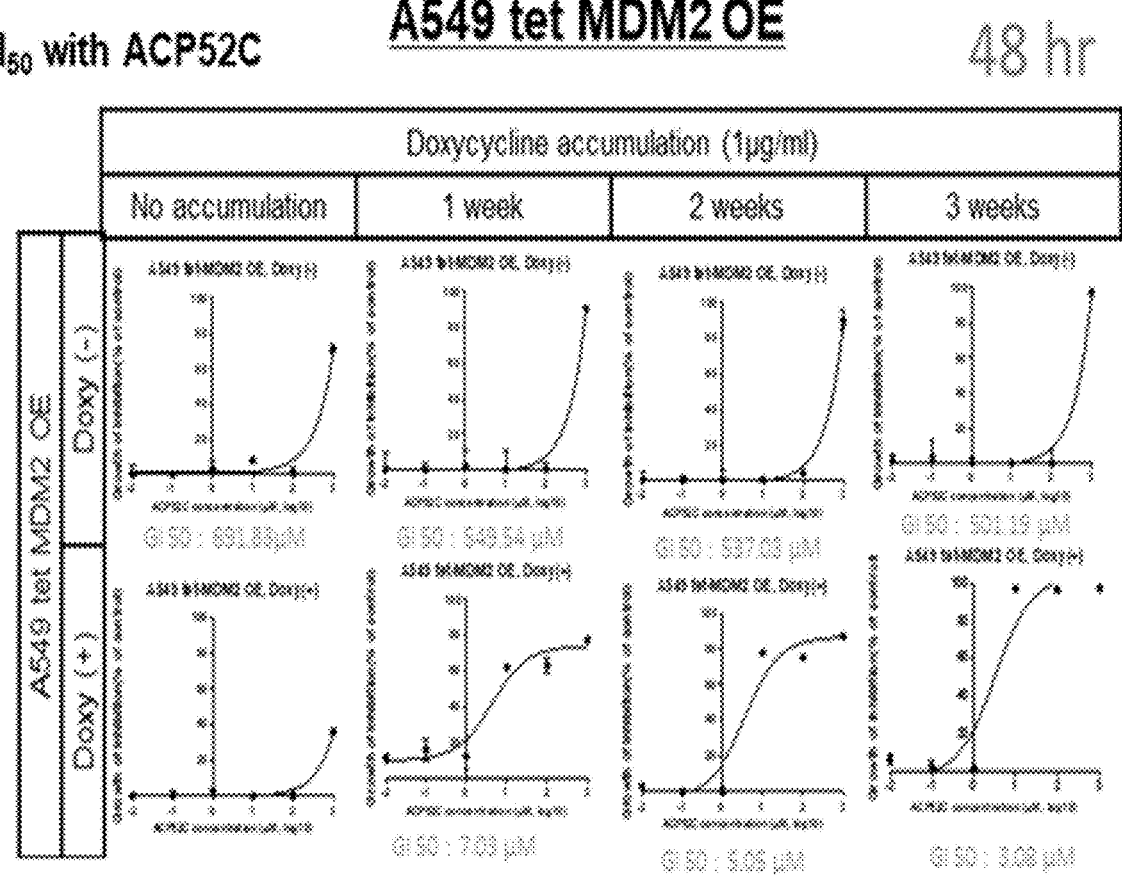

plate picture with ACP52c

【FIG 32c】
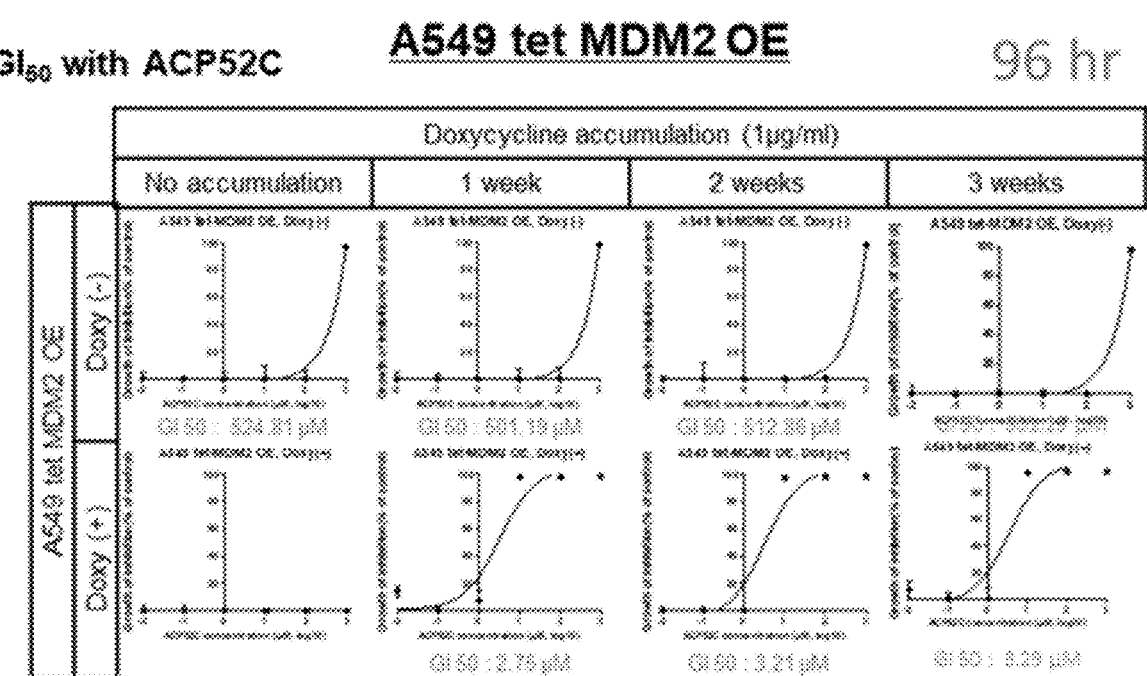

[FIG 32d]
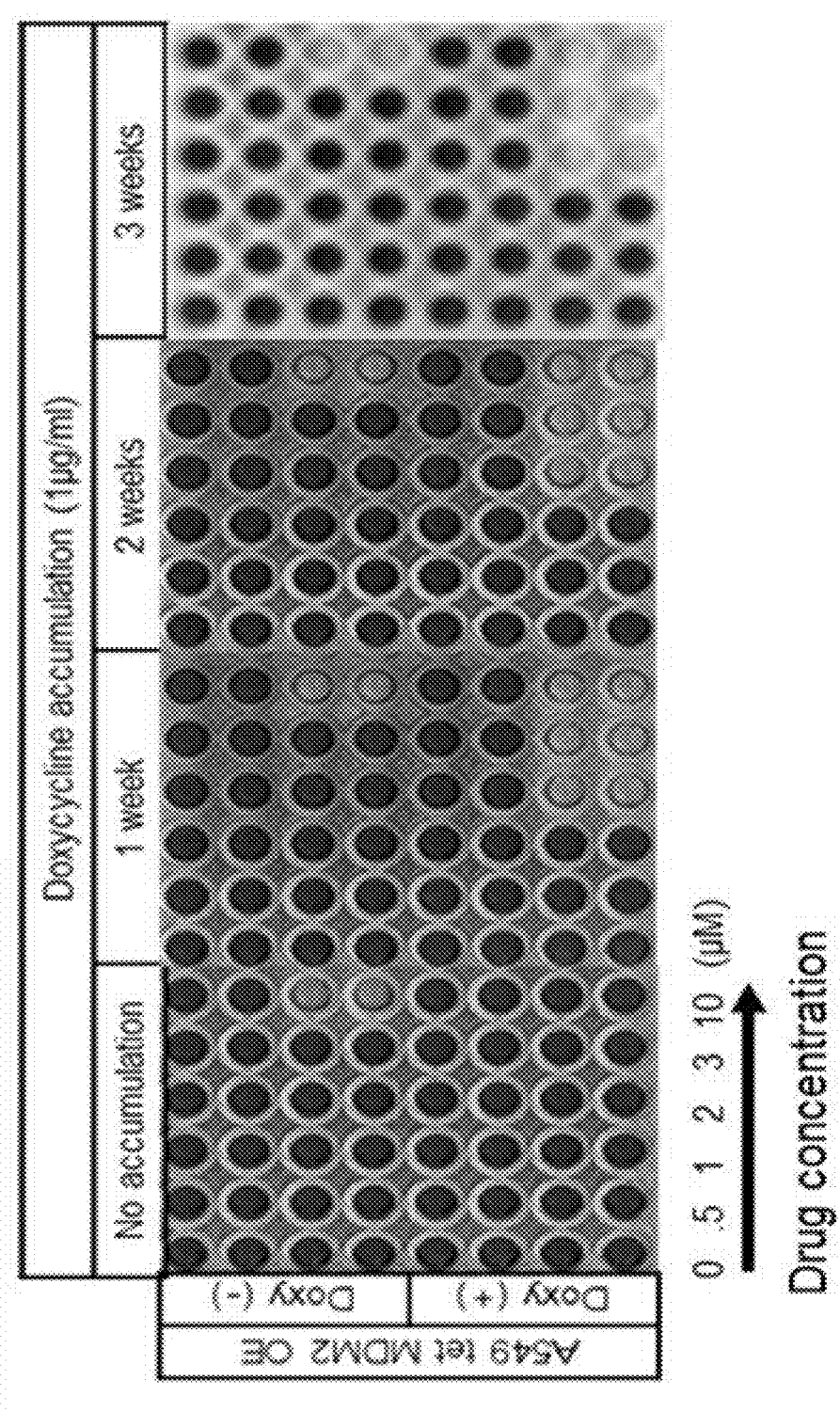
Plate picture with ACP52C

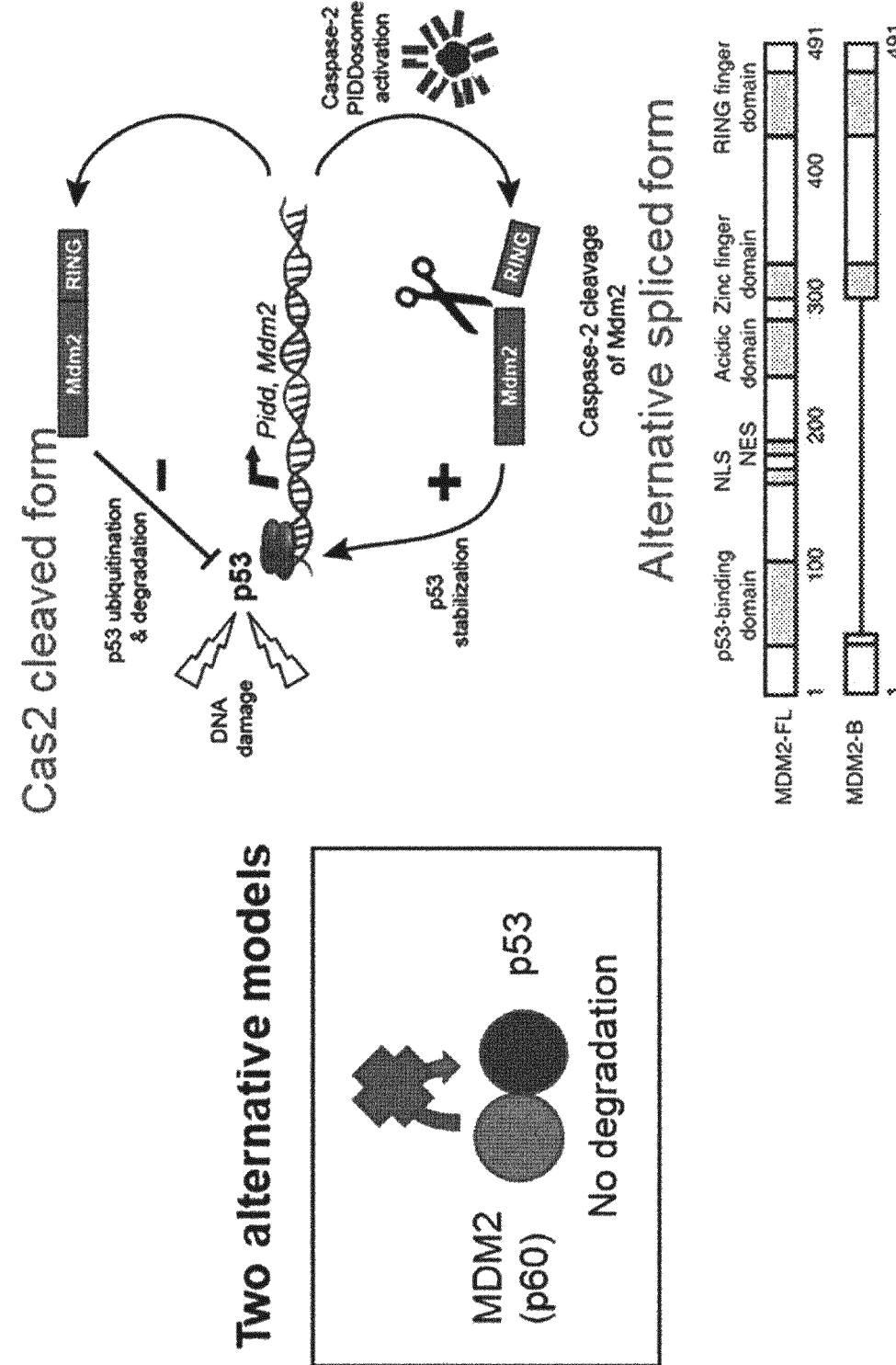
[FIG. 33a]

【FIG 33b】
B
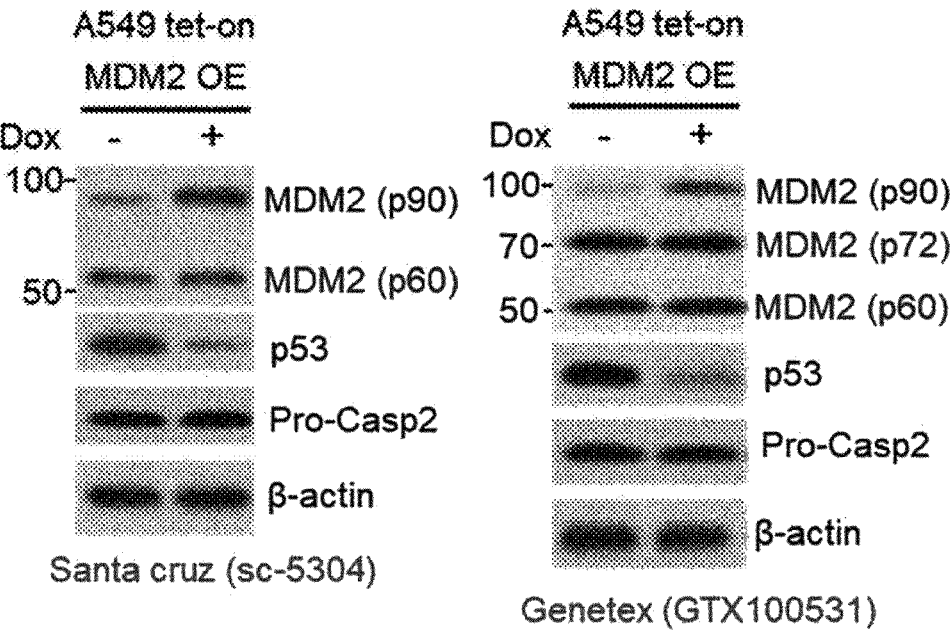

【FIG 33c】
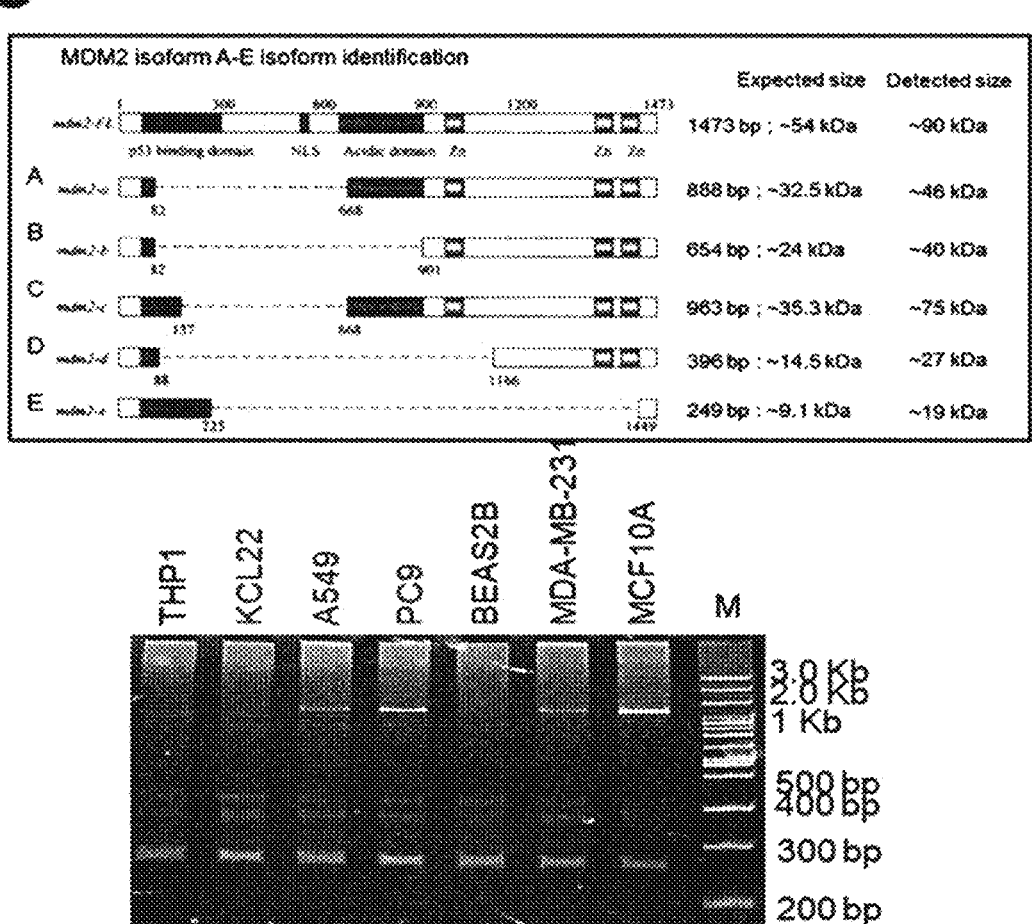

FIG. 33D

[FIG. 34a]
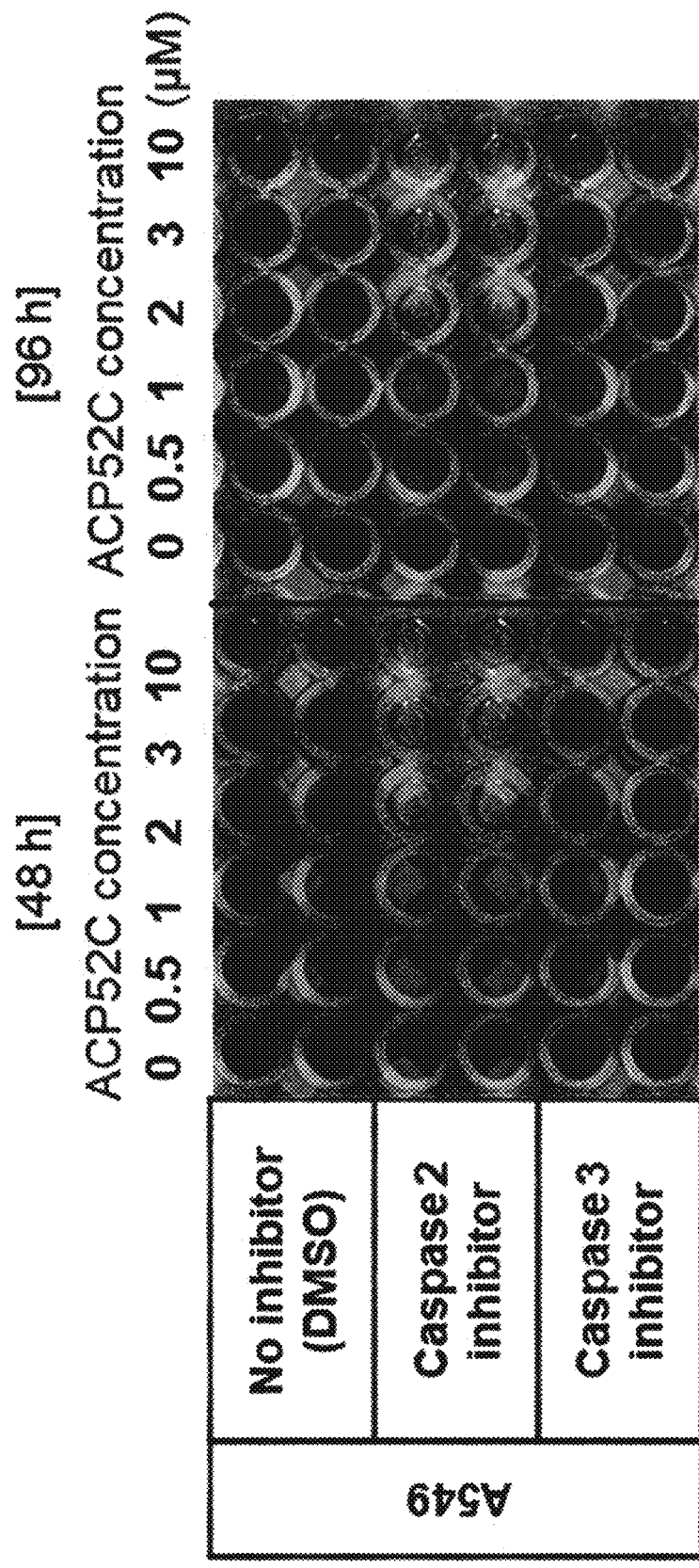

[FIG 34b]
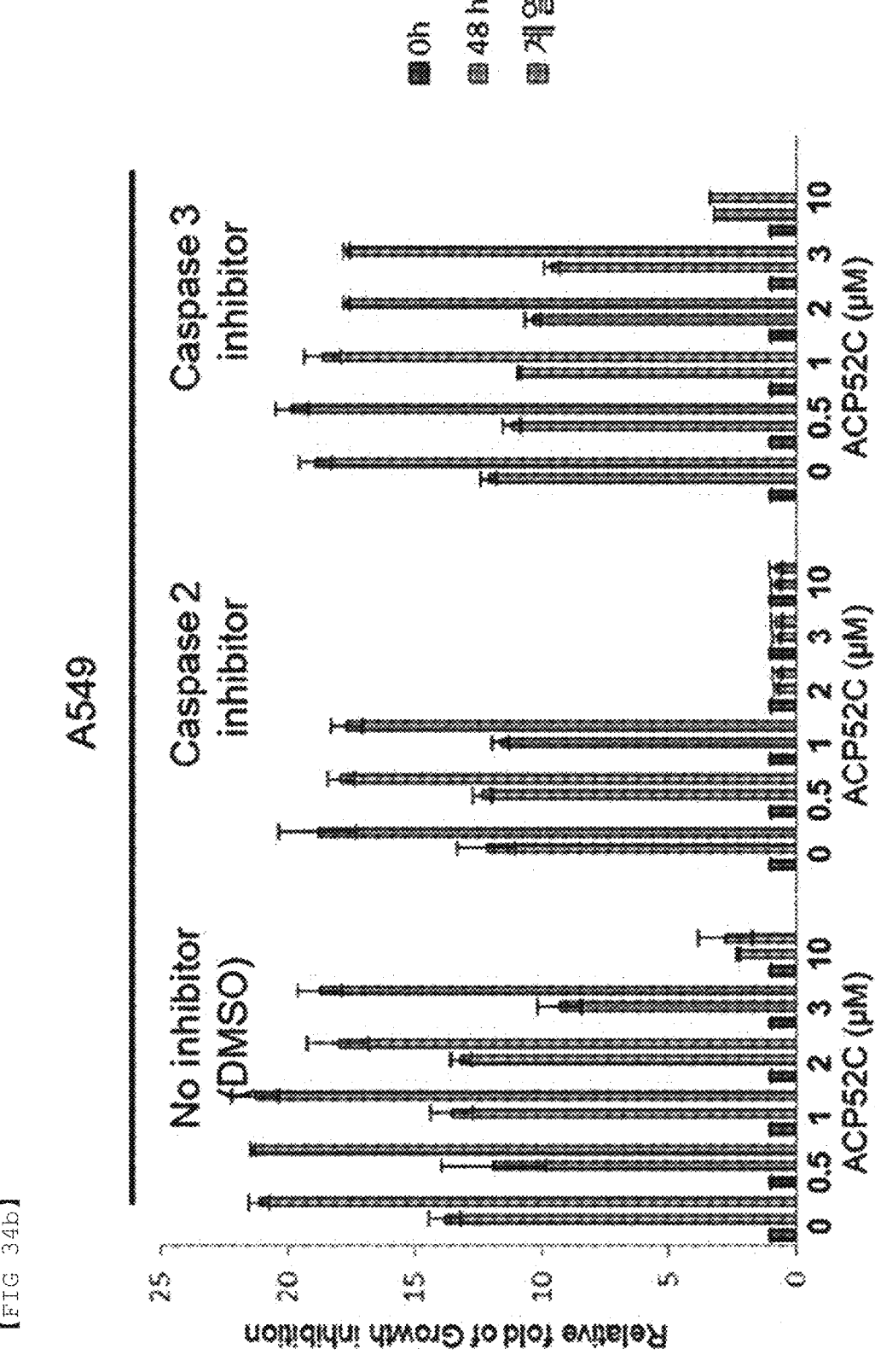

[FIG 34c]
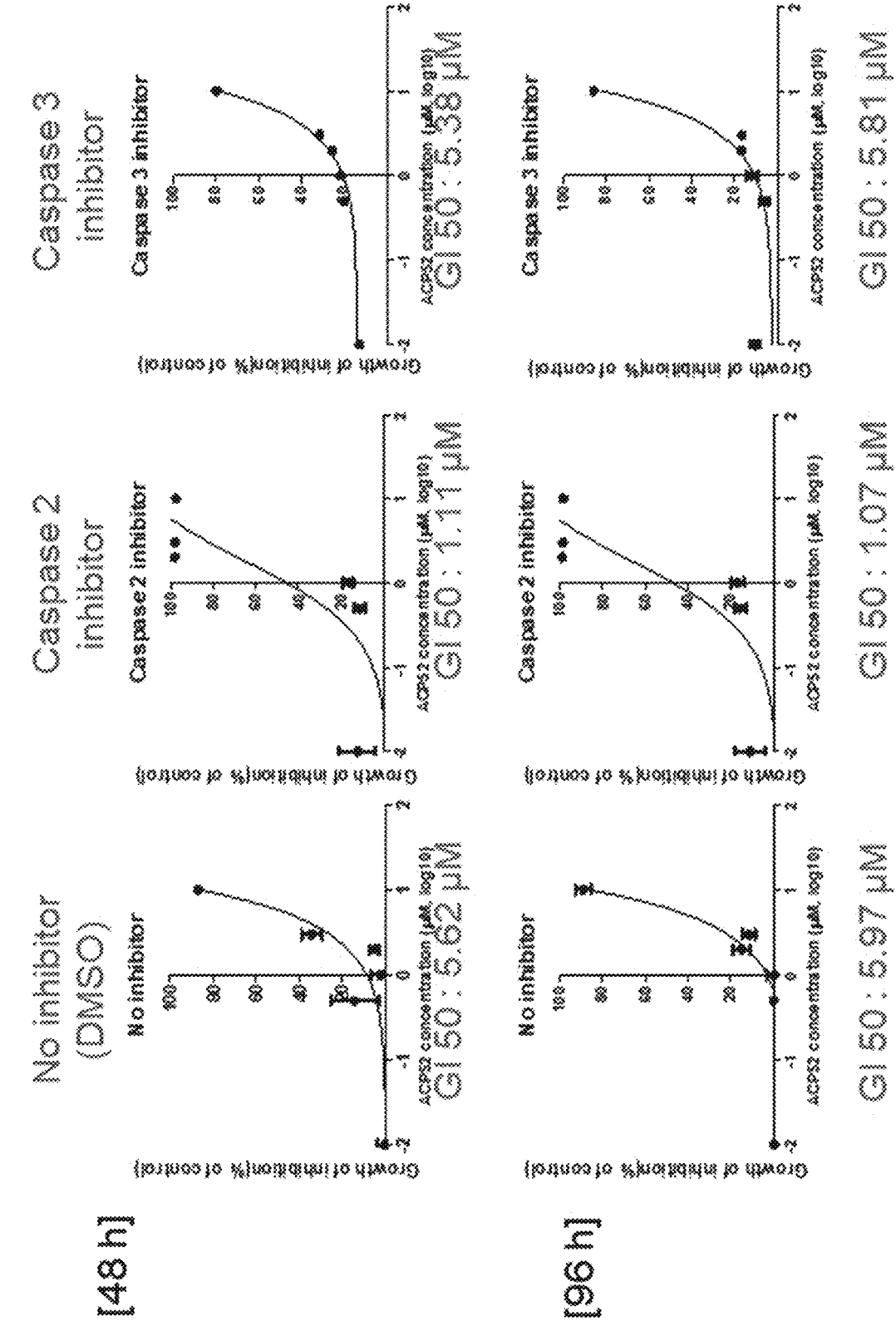

[FIG 34d]
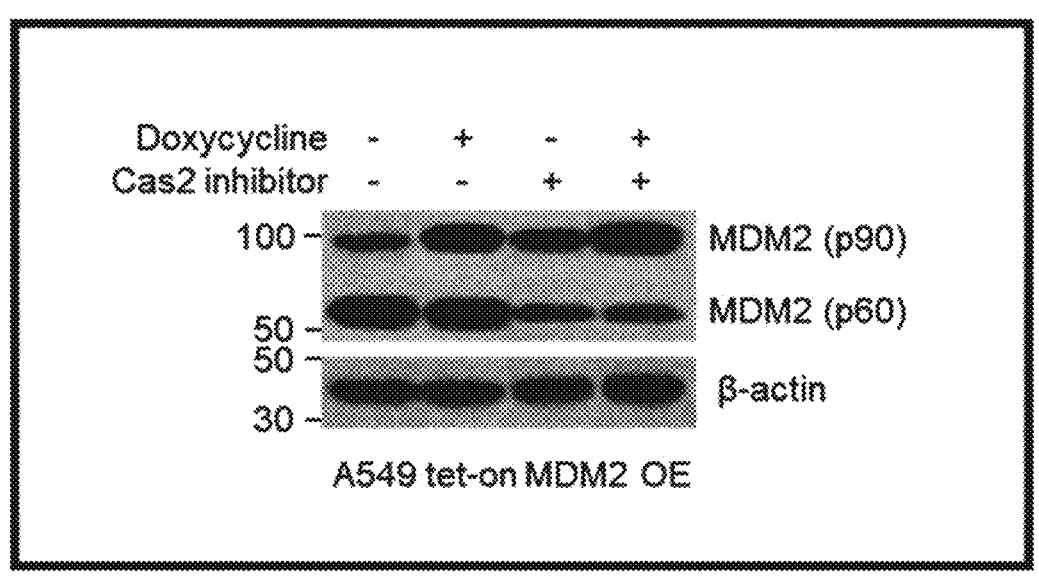
A549 tet-on MDM2 OE

[FIG 35]
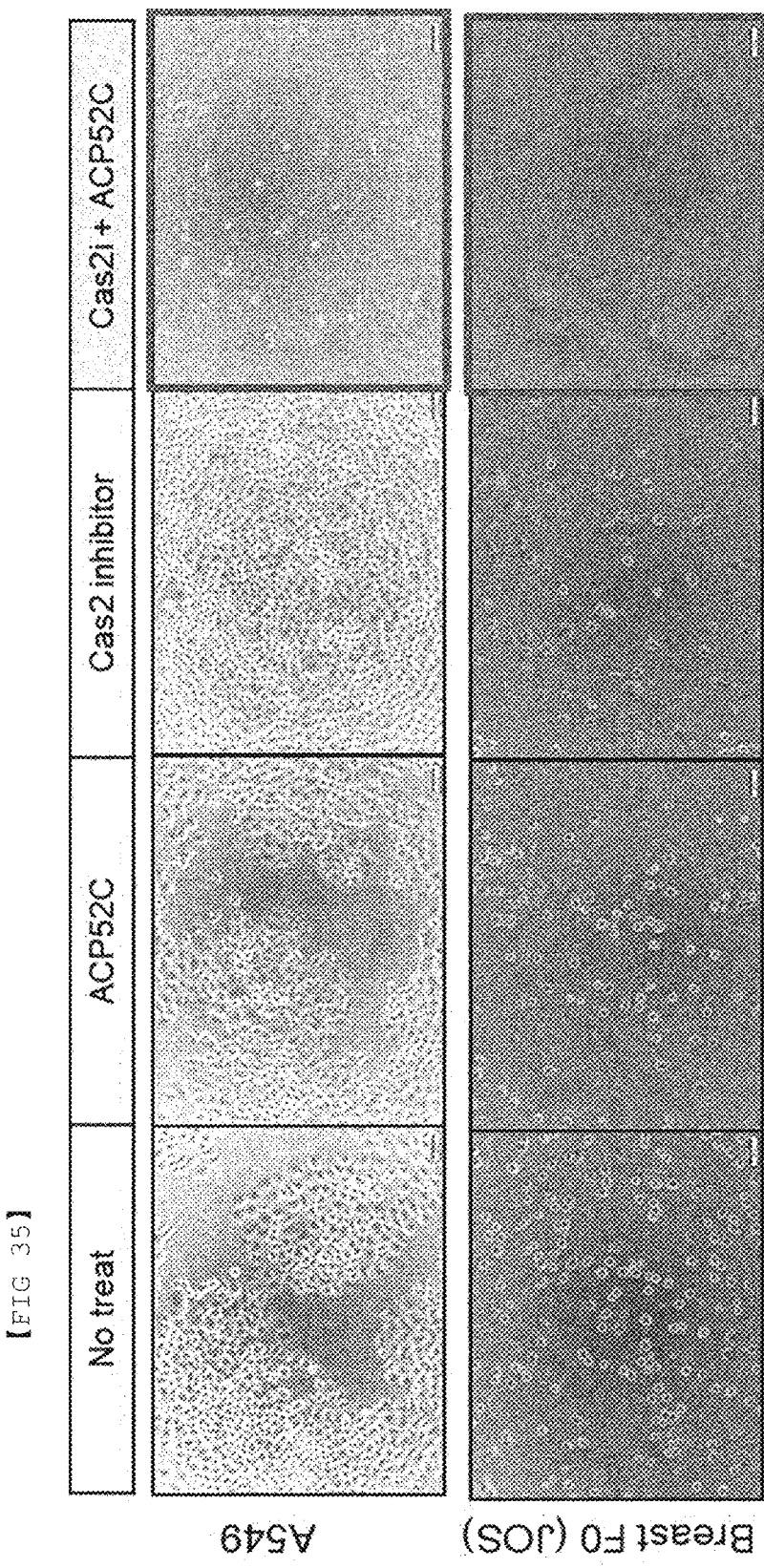

CP2C-TARGETING PEPTIDE-BASED ANTICANCER AGENT

CROSS REFERENCE TO RELATED APPLICATIONS

This application is a National Stage of International Application No. PCT/KR2020/004467 filed on Apr. 1, 2020, claiming priority based on Korean Patent Application No. 10-2019-0038023 filed on Apr. 1, 2019 and Korean Patent Application No. 10-2019-0085790 filed on Jul. 16, 2019.

INCORPORATION BY REFERENCE OF SEQUENCE LISTING

The content of the electronically submitted sequence listing, file name: Q267770_ST25.txt; size: 6,268 bytes; and date of creation: Jul. 10, 2025, filed herewith, is incorporated herein by reference in its entirety.

FIELD OF INVENTION

The presented invention relates to a CP2c-targeting peptide-based anticancer agent.

BACKGROUND OF INVENTION

While many protein/peptidic anticancer agents and low-molecular compound-based anticancer agents have already been developed and used, they do not selectively act only on cancer cells in vivo but cause serious side effects in normal cells, and their effects are sometimes insignificant due to the emergence of drug-resistant cancer cells. In addition, many protein/peptidic anticancer agents under development have a short half-life in vivo, so there are various studies underway to overcome this. As such, although efforts are being competitively made to develop anticancer drugs worldwide, anticancer drugs that are free from problems with in vivo stability, safety, and drug resistance have not yet been developed. Therefore, discovering a drug that can secure long-term stability in vivo, selectively remove only various types of cancer cells, and act on drug-resistant cancer cells, would be highly beneficial on a worldwide scale.

SUMMARY OF INVENTION

Technical Problem to be Solved

The presented invention has been made in view of the above problems, with a focus of providing a CP2c-targeting peptide-based anticancer agent capable of securing long-term stability in vivo, selectively removing only various types of cancer cells, and also acting on drug-resistant cancer cells.

Technical Solution

A CP2c-targeting peptide, according to the presented invention, refers to a peptide that binds to transcription factor CP2c to inhibit the formation of transcription factor complexes (CP2c homotetramer and CP2c/CP2b/PIAS1 heterohexamer) comprising CP2c, thereby inducing cancer cell-specific cell death. The CP2c-targeting peptide corresponds to Tyr-Pro-Gln-Arg (SEQ ID NO: 1), a peptide of the smallest size consisting only of amino acids essential for anticancer effect. Accordingly, a peptide essentially comprising the four amino acids and exhibiting anticancer effect by interacting with the CP2c protein can be used as the CP2c-targeting peptide according to the presented invention.

The CP2c-targeting peptide according to the presented invention may be a peptide consisting of 4 to 20 amino acids comprising the amino acid sequence of SEQ ID NO: 1. Preferably, the CP2c-targeting peptide according to the presented invention may be a peptide (ACP52) consisting of 6 amino acids (6 aa) 'NYPQRP (Asn-Try-Pro-Gln-Arg-Pro, SEQ ID NO: 2)'.

The CP2c-targeting peptide according to the presented invention may be bound to a cell-penetrating peptide (CPP: cell-penetrating peptide) so as to enhance cell-penetrating activity.

For example, the CP2c-targeting peptide according to the presented invention may be a peptide that comprises a peptide (ACP52) consisting of SEQ ID NO: 2; and an internalizing RGD (iRGD) peptide, consisting of 9 amino acids (9aa) 'CRGDKGPDC (Cys-Arg-Gly-Asp-Lys-Gly-Pro-Asp-Cys, SEQ ID NO: 3),' as a cell-penetrating peptide (CPP). 'ACP52C', as an example of the CP2c-targeting peptide according to the presented invention, is a peptide wherein an acetyl group (Ac) is bound to an N-terminal of ACP52, iRGD is bound to a C-terminal Pro, and an amide group ($NH_2$) is bound to a C-terminal of iRGD (see FIG. 7).

In addition, the presented invention has prepared a CP2c-targeting peptide-fatty acid conjugate, which is bound to a fatty acid, for the purpose of securing in vivo stability of the previously developed CP2c-targeting peptide. When a fatty acid is bound to the CP2c-targeting peptide, the resultant conjugate binds to albumin in the blood, thus increasing in vivo stability, and providing a high therapeutic effect.

The fatty acid may be (but not necessarily limited to) a $C_{12}$ to $C_{20}$ fatty acid. In an embodiment of the presented invention, the fatty acid may be a $C_{16}$ fatty acid, for example, palmitoyl acid (also expressed as 'pal'). In addition, in an embodiment of the presented invention, the fatty acid may be a modified fatty acid bound to glutamic acid (Glu, E), or an amino acid sequence represented by EGLFG (SEQ ID NO: 4) as a target sequence of the proteolytic enzyme Cathepsin B. In particular, the modified fatty acid may be formed through a peptide bond between a carboxyl group of a fatty acid and an amino group of glutamic acid or an amino group of glycine in an amino acid sequence represented by EGLFG (SEQ ID NO: 4). In the present specification, palmitoyl acid coupled with glutamic acid may be referred to as "E-pal", and palmitoyl acid coupled with an amino acid sequence represented by EGLFG (SEQ ID NO: 4) may be referred to as "EGLFG-pal. (SEQ ID NO: 12)"

In addition, the CP2c-targeting peptide-fatty acid conjugate, according to the presented invention, may comprise a CP2c-targeting peptide (e.g., ACP52) for CP2c targeting and a linker peptide for connecting CPP (e.g., iRGD) and/or a fatty acid to each other. The linker peptide may be an amino acid known in the art or a peptide consisting of a combination thereof, without specific limitation. In particular, the linker peptide may comprise glycine (Gly, G), e.g., Gn (where n is an integer of 1 to 6). In another embodiment of the presented invention, the linker peptide may consist of an amino acid sequence represented by $G_nKG_m$ (SEQ ID NO: 21) (where n and m are each independently an integer of 0 to 6). For example, lysine (Lys, K) may be located at an N-terminal or C-terminal of the linker peptide when n or m is 0, and lysine (Lys, K) may be located between glycine when n and m are not 0. For conjugation between the fatty acid and the peptide, lysine (Lys, K) is included in the linker peptide. A terminal functional group ($—NH_2$) of lysine may enable binding of additional amino acids.

In the CP2c-targeting peptide-fatty acid conjugate according to the presented invention, conjugation of the CP2c-targeting peptide and the fatty acid may be achieved through the linker peptide. In particular, the conjugation may be achieved through binding between glutamic acid, as a peptide bonded to the modified fatty acid, and lysine of the linker peptide. More specifically, the binding between the glutamic acid of the modified fatty acid and the lysine of the linker peptide may be formed through a peptide bond between the functional group ($NH_2$) of the lysine and the carboxyl group of the glutamic acid.

Meanwhile, N- and/or C-terminals of the peptides of the CP2c-targeting peptide-fatty acid conjugates used in the presented invention may be modified so as to obtain improved stability of the used peptide, enhanced pharmacological properties (half-life, absorption, potency, efficacy, etc.), altered specificity (for example, a broad spectrum of biological activity), and reduced antigenicity. Preferably, the modification may be a form wherein an acetyl group, a fluorenyl methoxy carbonyl group, an amide group, a formyl group, a myristyl group, a stearyl group, or polyethylene glycol (PEG) is bonded to the N- and/or C-terminal of the peptide, but a component capable of improving the modification of the peptide, particularly the stability of the peptide, may be included without limitation. As used in the presented invention, the term "stability" means not only in vivo stability that protects the peptide of the presented invention from attack by proteolytic enzymes in vivo, but also storage stability (e.g., room-temperature storage stability). In the CP2c-targeting peptide-fatty acid conjugate according to the presented invention, the N- and C-terminals of the peptide may be respectively modified with an acetyl group and an amide group.

CP2c-targeting peptide-fatty acid conjugates according to embodiments of the presented invention are as follows:

1) Ac-K (E-pal)-GG (SEQ ID NO: 13)—is bonded to an N-terminal, where Ac is absent, of ACP52C (C16-ACP52Cn, ACP52CG), 2) Ac-K (EGLFG-pal)-GG (SEQ ID NO: 14)—is bonded to an N-terminal, where Ac is absent, of ACP52C (C16-GFLG (SEQ ID NO: 15)-ACP52Cn, ACP52CK), 3) A functional group of K in a GG-K-GG (SEQ ID NO: 5) linker peptide located between ACP52 and iRGD is bonded to a glutamic acid alpha carbon carboxyl group of E-Pal (C16-ACP52Cm, ACP52GK)

4) A functional group of K in a GG-K-GG (SEQ ID NO: 5) linker peptide located between ACP52 and iRGD is bonded to a glutamic acid gamma carbon carboxyl group of E-Pal (γC16-ACP52Cm, ACP52CGK).

For example, the structures of ACP52GK and ACP52CGK in the CP2c-targeting peptide-fatty acid conjugate according to the presented invention are as presented in FIG. 36.

In an example of the presented invention, in vivo stability, anticancer effect, tumor metastasis inhibition effect, and physiological toxicity in mouse models xenografted with liver cancer cells (Hep3B) or breast cancer cells (MDA-MB-231) were analyzed using the four kinds of synthesized CP2c-targeting peptide-fatty acid conjugates. As a result, it was confirmed that in vivo stability, tumor inhibition effect, and tumor metastasis inhibition effect are excellent, and the conjugates are safe substances without toxicity to the body.

In addition, it was confirmed that, in a process of treating with the 4 kinds of synthesized CP2c-targeting peptide-fatty acid conjugates to investigate anticancer effect in an example of the presented invention, cells with resistance to the CP2c-targeting peptide-fatty acid conjugates were generated. Accordingly, it was confirmed that the generation mechanism and the cause of resistance were due to a decrease in the cellular MDM2p90 level in the cells treated with the CP2c-targeting peptide-fatty acid conjugates. Furthermore, it was confirmed that the resistant cancer cells to the CP2c-targeting peptide-fatty acid conjugates could be killed by the co-treatment of the CP2c-targeting peptide-fatty acid conjugates with the caspase2 inhibitor, which was capable of inhibiting the degradation of MDM2p90.

The presented invention provides a pharmaceutical composition and health functional food composition for preventing, improving, and treating cancer comprising the CP2c-targeting peptide-fatty acid conjugate as an active ingredient.

As another aspect of the presented invention, the presented invention also provides a method of treating an individual, the method comprising a step of administering the CP2c-targeting peptide-fatty acid conjugate, or a pharmaceutical composition comprising the same in a pharmaceutically effective amount to an individual in need of treatment.

In the presented invention, the cancer may also comprise a resistant cancer showing resistance to an anticancer agent, particularly, an anticancer agent based on the CP2c-targeting peptide-fatty acid conjugate according to the presented invention.

In the presented invention, the term "treatment" refers to any action in which the symptoms of cancer are improved or beneficially changed by the administration of the peptide according to the presented invention or a pharmaceutical composition containing the peptide.

In the presented invention, the term "administration" refers to introducing a predetermined substance, i.e. a peptide derivative according to the presented invention or a pharmaceutical composition comprising the same, to a subject by any suitable method. The route of the administration route may be any general route as long as a drug can reach the target tissue. For example, the route of administration may comprise, without being limited to, intraperitoneal administration, intravenous administration, intramuscular administration, subcutaneous administration, intradermal administration, oral administration, topical administration, intranasal administration, intrapulmonary administration, or rectal administration. However, since a peptide is digested upon oral administration, it is preferred to formulate an oral composition to be coated with an active agent or to be protected from degradation in the stomach. Preferably, the peptide would be administered in the form of an injection. In addition, a pharmaceutical composition according to the presented invention may be administered by any device capable of transporting an active substance to a target cell.

In the presented invention, the term "contained as an active ingredient" means an amount sufficient to treat a disease with a reasonable risk-benefit ratio applicable to medical treatment. The effective dose level may be determined depending upon the patient's disease type, severity, drug activity, drug sensitivity, administration time, administration route, excretion rate, treatment duration, factors comprising concomitant drugs, and other factors well-known in the field of medical. The peptide according to the presented invention or a pharmaceutical composition containing the same may be administered as an individual therapeutic agent or may be administered in combination with other therapeutic agents, may be administered sequentially or simultaneously with conventional therapeutic agents, and may be administered once or multiple times. It is important to administer a minimum amount that can obtain the maximum effect without side effects in consideration of all the aforementioned factors, which can be easily determined by those with medical expertise. The dosage and frequency of the pharmaceutical composition of the presented invention are determined based on the type of drug as an active ingredient, together with several related factors such as the type of disease, the route of administration, the age, sex, and weight of a patient, and the severity of the disease.

As used herein, the term "pharmaceutically effective amount" means an amount sufficient to treat a disease with a reasonable risk-benefit ratio applicable to medical treatment. A suitable dosage of the pharmaceutical composition of the presented invention varies depending on factors such as the formulation method, the administration method, the age, weight, and sex of a patient, disease severity, food, the time and route of administration, the administration route, the excretion rate, and response sensitivity, and an ordinary skilled physician can easily determine and prescribe an effective dosage for the desired treatment.

As used herein, the term "individual" of the presented invention comprises animals, such as horses, sheep, pigs, goats, camels, antelopes, dogs, or humans whose symptoms can be improved by administration of the therapeutic composition according to the presented invention. Disease can be effectively prevented and treated by administering the pharmaceutical composition according to the presented invention to an individual. The treatment method according to the presented invention may be a method of treating animals other than humans, but is not limited to them. That is, considering that humans can have a disease whose symptoms can be improved by administration of the composition according to the presented invention, it can be sufficiently used for human treatment.

Accordingly, the pharmaceutical composition according to the presented invention may comprise various pharmaceutically acceptable carriers as long as the peptide according to the presented invention is contained as an active ingredient. Pharmaceutically acceptable carriers may comprise binders, lubricants, disintegrants, excipients, solubilizers, dispersants, stabilizers, suspending agents, coloring agents, and flavoring agents for oral administration. An injection may be used by mixing a buffer, a preservative, an analgesic agent, a solubilizer, an isotonic agent, or a stabilizer. For topical administration, bases, excipients, lubricants, or preservatives may be used. The formulation of the pharmaceutical composition of the presented invention may be prepared in various ways by mixing with a pharmaceutically acceptable carrier as described above. For example, it may be prepared in the form of tablets, troches, capsules, elixirs, suspensions, syrups, or wafers for oral administration, and it may be prepared in the form of unit dose ampoules or multiple doses for injection. It may also be formulated in the form of other solutions, suspensions, tablets, pills, capsules, or sustained-release preparations.

Meanwhile, examples of carriers, excipients, and diluents suitable for formulation comprise lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, or mineral oil. In addition, a filler, an anti-agglomeration agent, a lubricant, a wetting agent, a flavoring agent, or a preservative may also be used.

The peptide according to the presented invention may also be contained as an active ingredient in a health functional food composition. A food composition according to the presented invention may be prepared in the form of a composition by mixing with a known active ingredient known to have anticancer function, and a scientifically acceptable food supplement additive may be further comprised. The health functional food composition of the presented invention comprises a composition for all types of food, such as functional food, nutritional supplements, health food, and food additives.

The above kinds of food compositions may be prepared in various forms according to conventional methods. For example, health food may be prepared in various forms such as tablets, pills, powders, capsules, gums, vitamin complexes, juices and drinks, and a food composition containing the peptide according to the presented invention as an active ingredient may be granulated, encapsulated, or powdered for ingestion. The food composition of the presented invention may comprise ingredients, such as proteins, carbohydrates, fats, nutrients and seasonings, which are commonly added during food production. For example, when prepared as a drink, citric acid, high fructose corn syrup, sugar, glucose, acetic acid, malic acid, fruit juice, jujube extract, or licorice extract can be added to the peptide of the presented invention. In addition, food additives, e.g., flavoring agents, coloring agents, fillers, or stabilizers, conventionally used in cooking, may be utilized as a food supplement additive. In addition, as in conventional beverages, various flavoring agents or natural carbohydrates may be included as additional ingredients. Specific examples of natural carbohydrates comprise, for example, monosaccharides such as glucose and fructose, disaccharides such as maltose and sucrose, polysaccharides such as dextrin and cyclodextrin, and sugar alcohols such as xylitol, sorbitol, and erythritol. As flavoring agents other than those described above, natural flavoring agents (thaumatin, *stevia* extract (e.g., rebaudioside A, glycyrrhizin, etc.)) and synthetic flavoring agents (saccharin, aspartame, etc.) may also be used.

Furthermore, the food composition of the presented invention may contain various nutrients, vitamins, minerals (electrolytes), flavoring agents such as synthetic and natural flavoring agents, coloring agents, thickening agents (cheese, chocolate, etc.), pectic acid and salts thereof, alginic acid and salts thereof, organic acids, protective colloidal thickeners, pH adjusters, stabilizers, preservatives, glycerin, alcohols, or carbonation agents used in carbonated beverages. These components may be used independently or in combination.

Hereinafter, the presented invention will be described in more detail with reference to the following examples. It should be understood that the examples are included merely to concretely explain the spirit of the invention, and do not serve as any sort of limits of the presented invention.

Effect of Invention

To identify a final candidate, which has improved in vivo stability, of transcription factor CP2c-targeting peptides ACP52C, which showed an effect as a general-purpose anticancer agent, a $C_{16}$ fatty acid was connected to the CP2c-targeting peptide lead material, ACP52C, and it was confirmed that the conjugate showed in vivo stability and anticancer effect in cancer cell-xenografted mouse models. In addition, the cancer cell-specific anticancer effect of the final anticancer candidate was confirmed in various cancer cells and normal cells. The anticancer effect of the final candidate was shown to be caspase2-dependent, and the therapeutic effect on cancer cells with anticancer drug resistance was confirmed by treatment with a combination of the caspase2 inhibitor and the final candidate.

BRIEF DESCRIPTION OF DRAWINGS

FIG. 1 illustrates $GI_{50}$ values dependent upon ACP52C treatment in various cancer cell lines.

FIGS. 2a to 2d illustrate that ACP52C treatment induces G2/M cell cycle arrest and cell death (subG1 cells) as revealed by FACS.

FIGS. 3a to 3c illustrate that ACP52C treatment causes an increase in the expression of p53 that regulates cell cycles and apoptosis.

FIGS. 4a to 4c illustrate that apoptosis is induced by ACP52C treatment.

FIG. 5 illustrates the time-dependent subcellular movement, localization, and amounts of ACP52C in the MDA-MB-231 cell line.

FIGS. 6a to 6h illustrate in vivo half-life analysis results of the ACP52C peptide.

FIG. 7 (SEQ ID Nos. 15 and 17-20) illustrates the construction of a $C_{16}$ fatty acid-binding peptide for improving in vivo stability.

FIGS. 9a to 9c illustrate cell growth analysis results dependent upon treatment with a $C_{16}$ fatty acid-binding peptides {ACP52C; ACP52CG (=ACP52CG-E); ACP52CK (=ACP52CG-GFLGE (SEQ ID NO: 16))} in various p53 mutant or null cancer cell lines.

FIGS. 10a to 10g illustrate cell growth analysis results dependent upon treatment with ACP52CGK (=γC16-ACP52 cm) in normal cell lines (BEAS2B and hMSC) and cancer cell lines (Hep3B, Hs746T, Caov-3, MDA-MB-231, U343, HCT116, PANC1, PC3, A549, and THP-1).

FIGS. 11a to 11e illustrate anticancer effect analysis results of ACP52CG (=ACP52CG-E) and ACP52CK (=ACP52CG-GFLGE (SEQ ID NO: 16)) in Hep3B cell line-xenograft mouse models.

FIGS. 12a to 12d illustrate anticancer effect analysis results of ACP52CK (=ACP52CG-GFLGE (SEQ ID NO: 16)) in liver cancer mouse models induced by DEN treatment.

FIGS. 13a to 13d illustrate anticancer effect analysis results of ACP52CG (=ACP52CG-E) and ACP52CK (=ACP52CG-GFLGE (SEQ ID NO: 16)) in liver cancer mouse models induced by DEN treatment.

FIGS. 14a to 14d illustrate anticancer effect analysis results of ACP52CG (=ACP52CG-E) and ACP52CK (=ACP52CG-GFLGE (SEQ ID NO: 16)) in MDA-MB-231 (LM1) cell line-xenograft mouse models.

FIGS. 15a to 15j illustrate analysis results of anticancer effects (tumor size and weight, body weight, and hematological analysis) and metastasis inhibition effects in Hep3B cell line-xenografted mouse models when treated with ACP52CGK in three different doses at 3-day intervals.

FIGS. 16a to 16k illustrate analysis results of anticancer effects (tumor size and weight, body weight, and hematological analysis) and metastasis inhibition effects in Hep3B cell line-xenografted mouse models when treated with ACP52CGK with three different doses at 5-day intervals.

FIGS. 17a to 17j illustrate analysis results of anticancer effects (tumor size and weight, body weight, and hematological analysis) and metastasis inhibition effects in MDA- MB-231 (LM1) cell line-xenografted mouse models when treated in ACP52CGK with three different doses at 3-day intervals.

FIGS. 18a to 18k illustrate analysis results of anticancer effects (tumor size and weight, body weight, and hematological analysis) and metastasis inhibition effects in MDA-MB-231 (LM1) cell line-xenografted mouse models when treated with ACP52CGK in three different doses at 5-day intervals.

FIGS. 19a to 19b illustrate in vivo half-life analysis results using fluorescently labeled ACP52CGK.

FIGS. 20a to 20b illustrate analysis results of the migration pathway, intracellular location, and intracellular residence time of ACP52CGK over time in the MDA-MB-231 cell line.

FIG. 21 illustrates analysis results through ELISA to investigate whether antibodies against ACP52C, ACP52CG, ACP52CK, and ACP52CGK are formed.

Figure 22E:
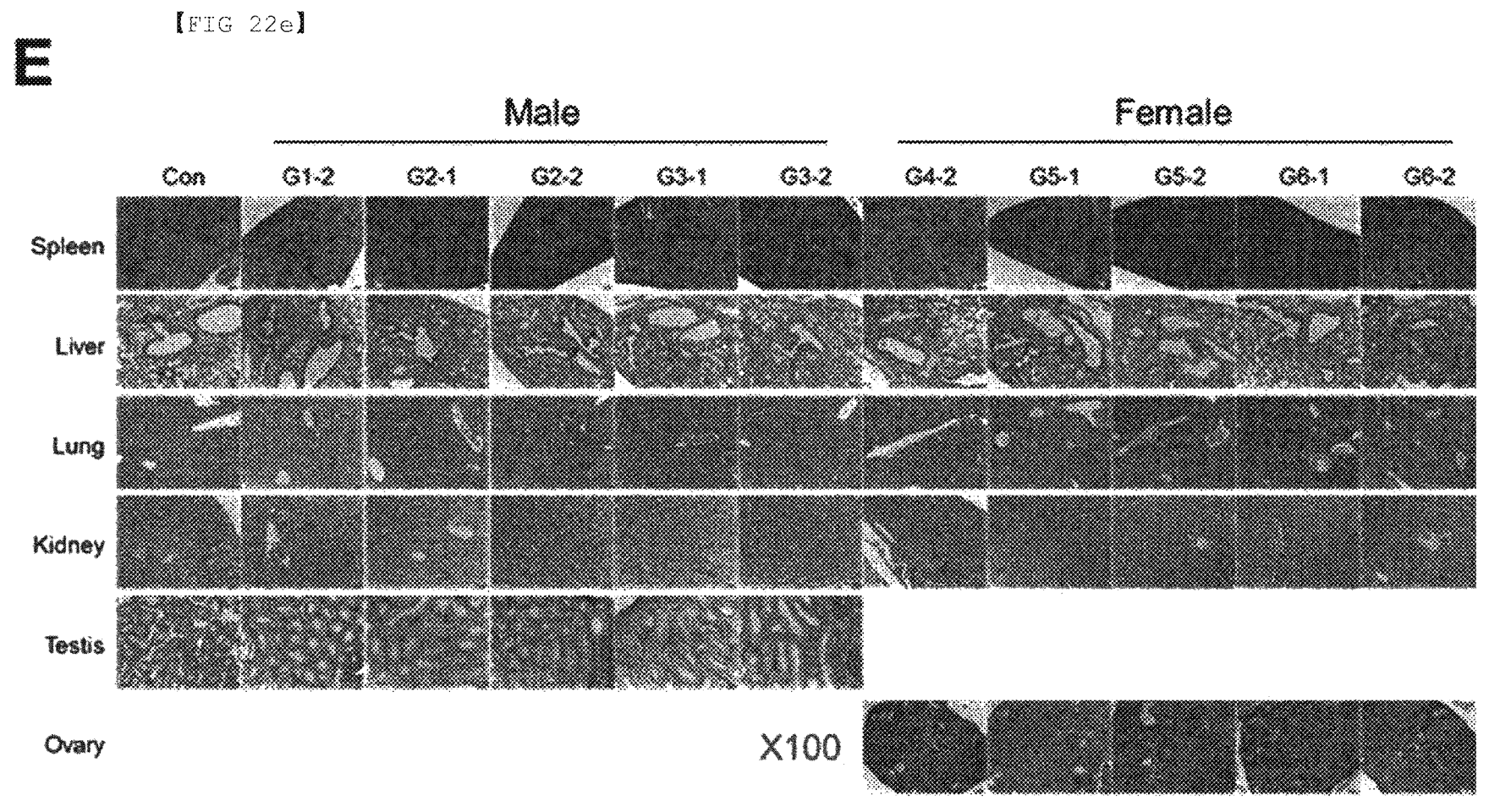

FIGS. 22a to 22e illustrate emergent and repeated in vivo toxicity test results of ACP52C.

FIG. 23 illustrates repeated toxicity test results of ACP52CGK (=γC16-ACP52 cm).

FIG. 24 illustrates histological analysis results of major organs whose toxicity test was repeated with ACP52CGK.

FIGS. 25a to 25d illustrate efficacy analysis results of ACP52CGK in cultures of cells derived from tumor tissues of breast cancer patients.

FIGS. 26a to 26d illustrate efficacy analysis results of ACP52CGK in cultures of cells derived from cryopreserved breast cancer patient cancer tissues.

FIGS. 27a to 27d illustrate efficacy comparison analysis results of ACP52CGK in cells cultured from PDX tumor tissues at specific generation.

FIGS. 28a to 28b illustrate efficacy and resistance analysis results of ACP52CGK in patient tumor tissue-derived cells.

FIG. 29 illustrates expression analysis results of CP2c transcription-activity-independent pathway proteins in lung cancer cell lines showing resistance to ACP52C.

FIGS. 30a to 30c illustrate ACP52C(=5-2C) treatment-dependent expression analysis results of CP2c transcription-activity-independent pathway proteins in lung cancer cell lines (A549, PC9, and KCL22).

FIGS. 31a to 31b illustrate MDM2 overexpression-dependent expression analysis results of CP2c transcription-activity-independent pathway proteins in lung cancer cell lines (A549 and PC9).

FIGS. 32a to 32d illustrate ACP52C treatment-dependent cell growth analysis results of the A549 cell line in which MDM2 overexpression is chronically induced.

Figure 33D:
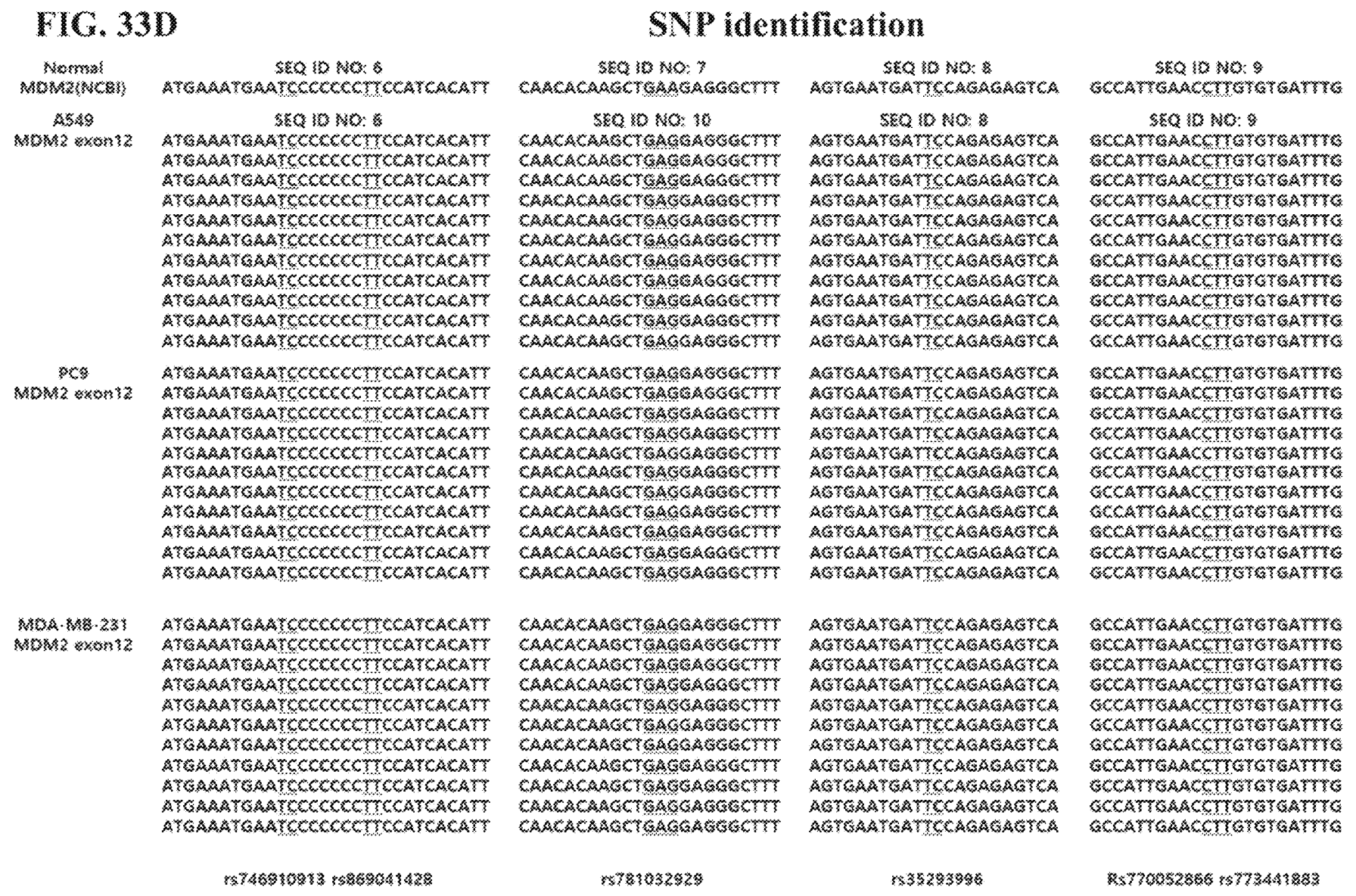

FIGS. 33a to 33d (SEQ ID nos. 6-10) illustrate MDM2p60 expression model and lung cancer cell line-specific alternative splicing and SNP analysis results.

FIGS. 34a to 34d illustrate efficacy analysis results, dependent upon the combined treatment of the Caspase2 inhibitor and ACP52C, in ACP52C resistant cells.

FIG. 35 illustrates cellular morphological changes, dependent upon the combined treatment of the Caspase2 inhibitor and ACP52C, in ACP52C resistant cells.

BEST MODE

Figure 8A:
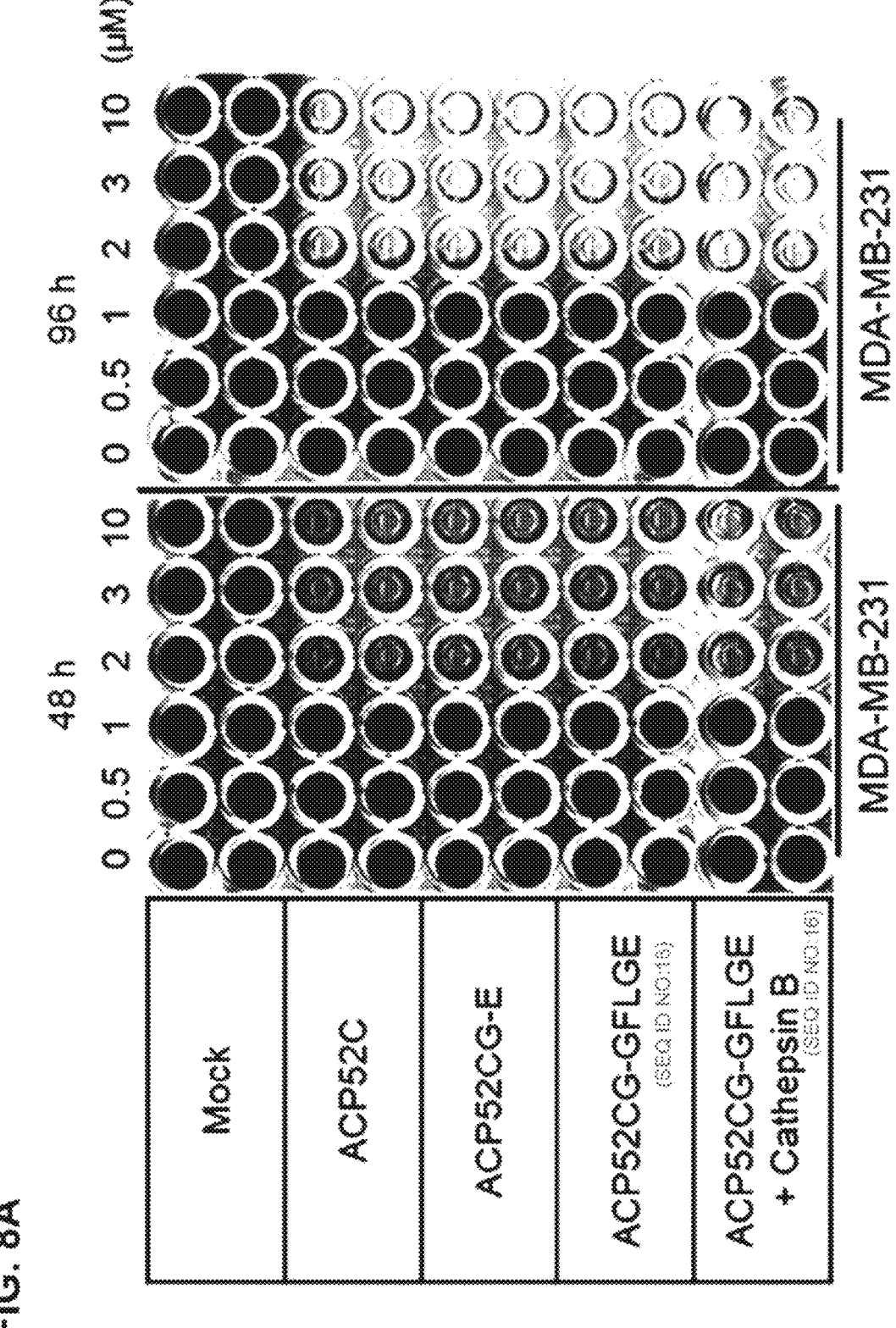
FIGS. 8a to 8d illustrate cell growth analysis results dependent upon treatment with $C_{16}$ fatty acid-binding peptides {ACP52C; ACP52CG (=ACP52CG-E); ACP52CK (=ACP52CG-GFLGE (SEQ ID NO: 16))} in various cancer cell lines.
Figure 8B:
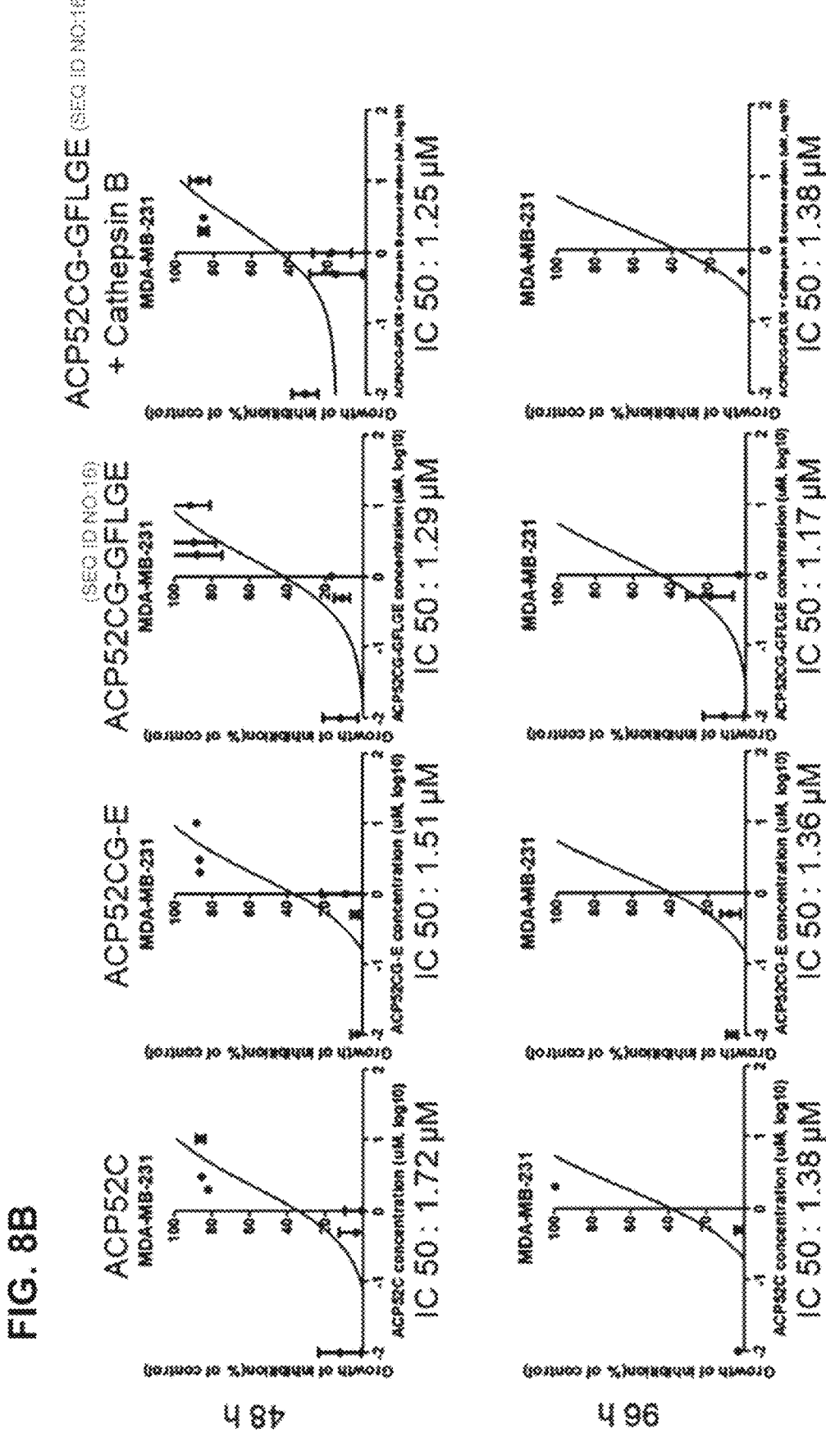
Figure 8C:
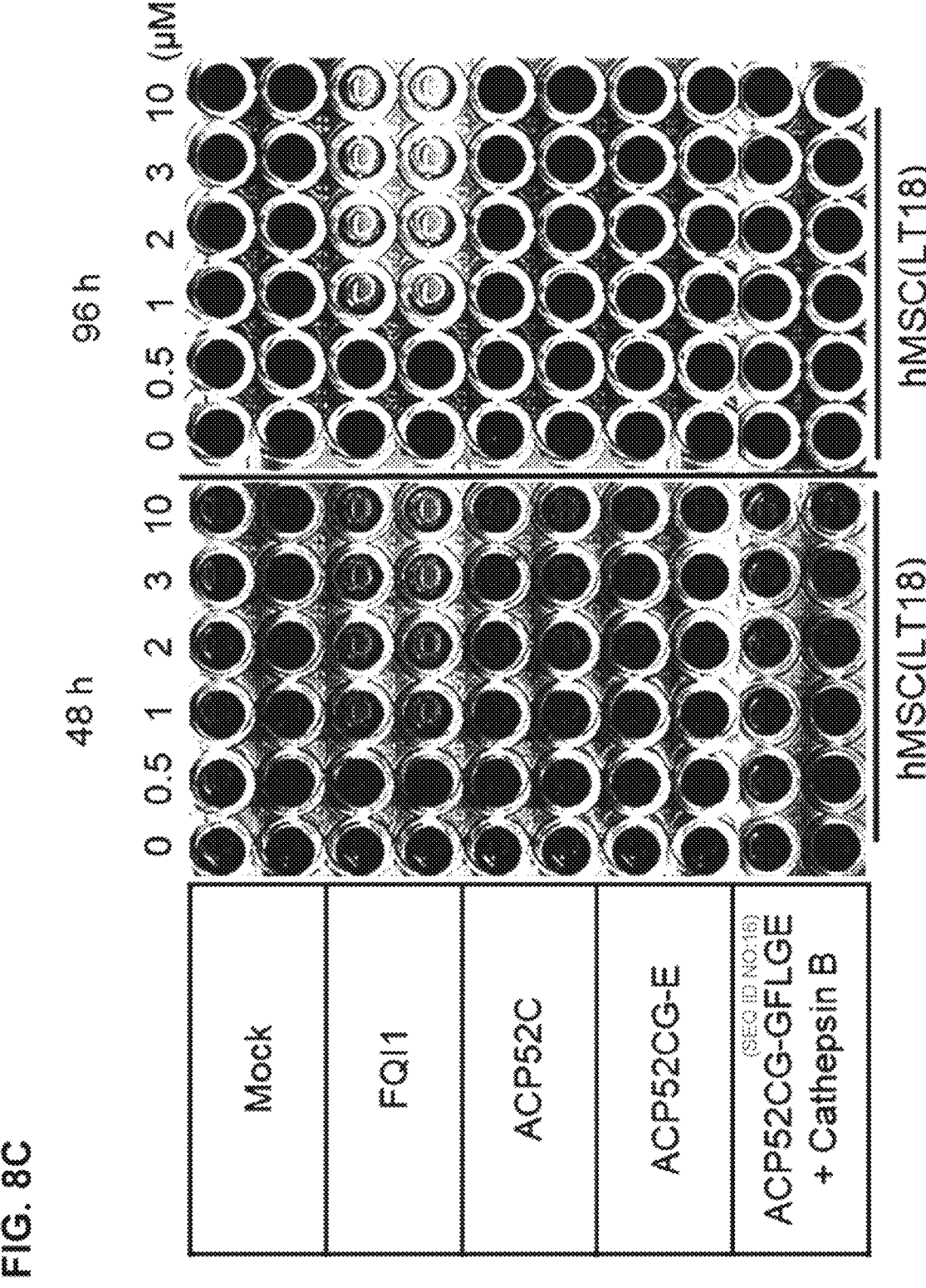
Figure 8D:
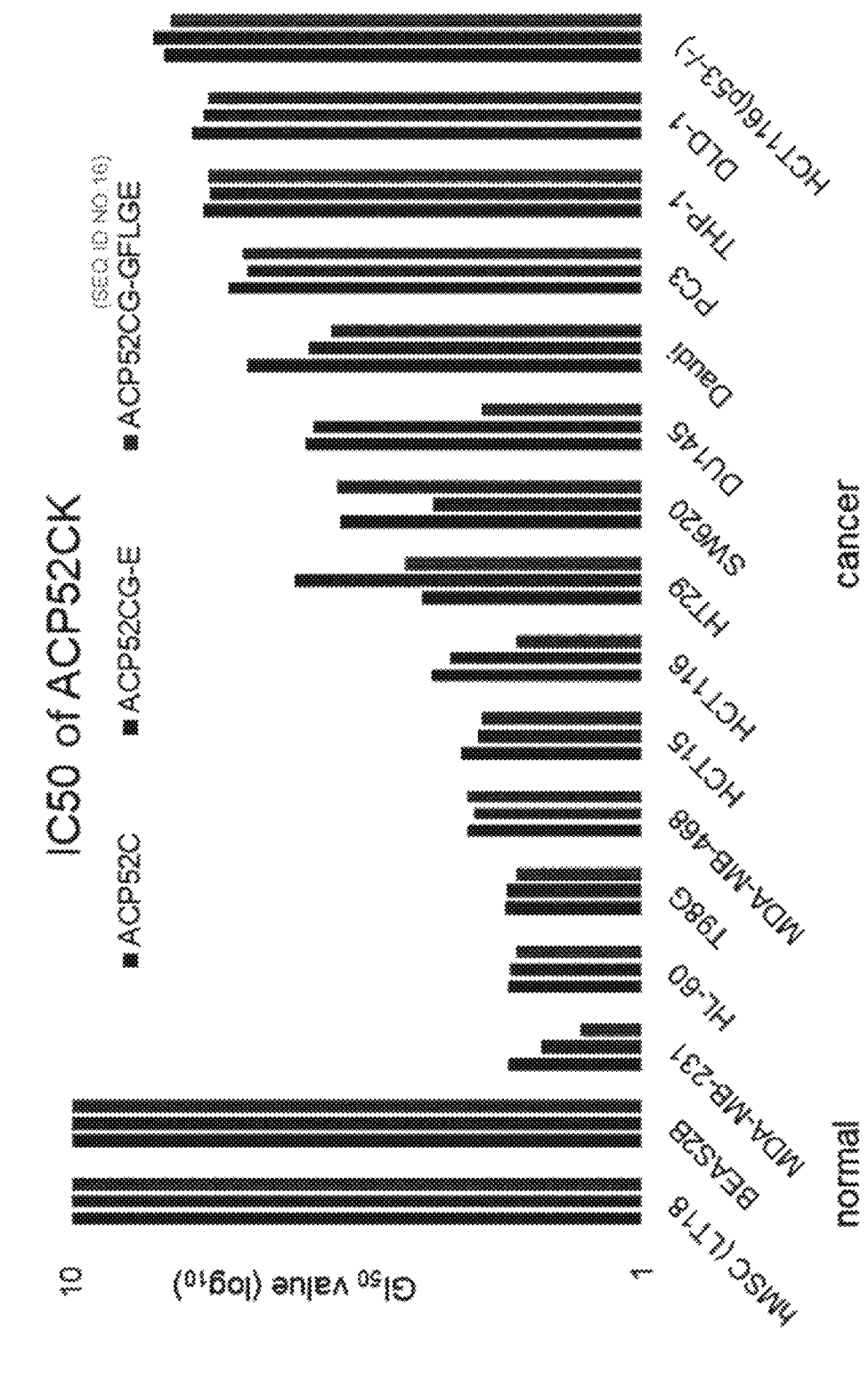

Hereinafter, the presented invention will be described in more detail with reference to the following examples. It should be understood that the examples are included merely to concretely explain the spirit of the invention, and do not serve as any sort of limits of the presented invention.

[Preparation Example 1] Preparation of CP2c-Targeting Peptide Conjugated with Cell-Penetrating Peptide The transcription factor CP2c is known to be overexpressed in various cancers. According to a study by a US research team, it was reported that inhibition of CP2c expression in liver cancer cell lines inhibited cell growth, whereas overexpression of CP2c caused cancer malignancy and metastasis [Grant et al., Antiproliferative small-molecule inhibitors of transcription factor LSF reveal oncogene addiction to LSF in hepatocellular carcinoma, *Proc. Natl. Acad. Sci.* 2012; 109 (12): 4503-4508].

The present inventors identified peptides binding to transcription factor CP2c (also known as Tfcp2, LSF, LBP1, UBP1, etc.) by a phage display method [Kang et al., Identification and characterization of four novel peptide motifs that recognize distinct regions of the transcription factor CP2, *FEBS Journal* 2005; 272:1265-1277], selected one type of peptide (CP2c-targeting peptide, SEQ ID NO: 2) that was derived from one peptide interfering with DNA binding of CP2c among the identified peptides, and synthesized an ACP52C lead material by binding the internalizing RGD (iRGD) peptide consisting of 9 amino acids (9 aa) 'CRGDKGPDC' (Cys-Arg-Gly-Asp-Lys-Gly-Pro-Asp-Cys, SEQ ID NO: 3) as a cell-penetrating peptide (CPP) to the CP2c-targeting peptide so as to improve cell permeability (FIG. 7).

[Example 1] Confirmation of Anti-Cancer Effect of ACP52C

The selected peptide binds to CP2c and inhibits the formation of a transcription factor complex including CP2c (CP2c homotetramer and CP2c/CP2b/PIAS1 heterohexamer), thereby indirectly interfering with DNA binding of CP2c. As a result of analyzing the anticancer effect in various carcinomas targeting the synthesized ACP52C, it was confirmed that it exhibits cancer cell-specific growth inhibition and cell death efficacy (FIG. 1).

The growth inhibitory and cell death-inducing efficacy of ACP52C was confirmed by FACS analysis by treating cells with ACPS2C after synchronizing the cell cycle to the G1/S phase through a double thymidine block method. As a result, it was confirmed that a polyploid was formed while with cell cycle arrest at the G2/M phase. On the other hand, it was confirmed that, when ACP52C was applied to the cell line synchronized to the G2/M phase with thymidine/nocodazole treatment, the cell cycle was arrested at the subG1 phase and cell death was induced (FIGS. 2a to 2d).

It was confirmed that the ACP52C-induced G2/M phase arrest was caused by the increased expression of CHK1/2 protein and the decreased expression of CDC25c, CDK1, and cyclin B proteins, whereas the cell death induction was caused by the increased expression of pro-apoptotic proteins along with the decreased expression of anti-apoptotic marker proteins, and the apoptosis via activation of caspases (FIGS. 3a to 3c, FIGS. 4a to 4c).

The subcellular movement, localization, and stability of ACP52C in the cells treated with the Cy5-labeled peptide (Cy5-ACP52C) for 30 minutes were analyzed by confocal microscopy over time. The most peptide passed through the cytoplasm, located in the nucleus from 4 hours, moved back to the cytoplasm at 8 hours, and degraded in the cytoplasm at 16 hours. It was confirmed that the Cy5-ACP52C peptide was co-located with CP2c in the nucleus from 1 hour after treatment, and CP2c also tends to be distributed in the cytoplasm at 8 hours after treatment along with Cy5-ACP52C (FIG. 5).

The ACP52C half-life in the solution containing serum was analyzed by HPLC (model: UHPLC DIONEX Ultimate 3000; Flow=1.000 ml/min) after incubation of ACP52C in the solution containing 10% serum for various times and then removing serum proteins with Centricon (Mw10,000) before HPLC analysis. As a result of the experiment, ACP52C was not degraded at all until 24 hours. Meanwhile, after injecting ACP52C into the mouse via tail vein, blood samples were extracted over time and the degree of ACP52C degradation in the blood samples was analyzed by HPLC. As a result, EC50 (time retaining 50% of the intact ACP52C) was about 2 hours. Additionally, when the remained intensity of fluorescence in the mouse body was measured by live imaging process over time in the Cy5-labeled peptide (Cy5-ACP52C)—injected mouse via tail vein, ACP52C was observed in cancer tissues even 5 days after injection although the total fluorescence intensity in the mouse body was halved at 7.95 hours after treatment (FIGS. 6a to 6h).

[Preparation Example 2] Synthesis of CP2c-Targeting Peptide-Fatty Acid Conjugates Our data suggest that ACP52C might be unstable in vivo although ACP52C showed a good anticancer activity. As an effort to improve in vivo stability of ACP52C, 4 types of albumin-affinity $C_{16}$ fatty acid (palmitoyl acid)-conjugated peptides were synthesized (FIG. 7). Each peptide whose N-terminus and C-terminus were modified was synthesized, and then a $C_{16}$ fatty acid was conjugated to each of them.

Figure 9B:
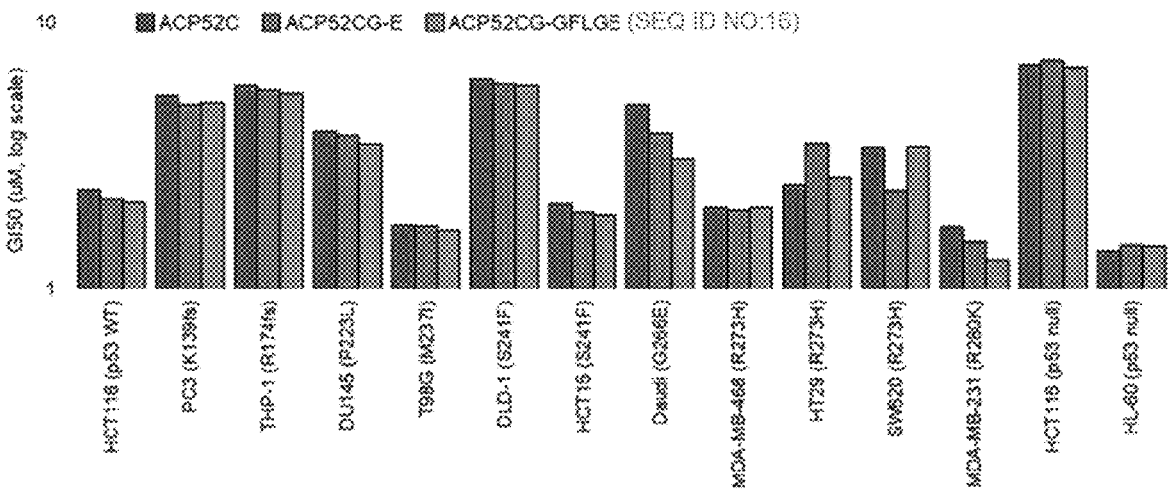
Figure 9C:
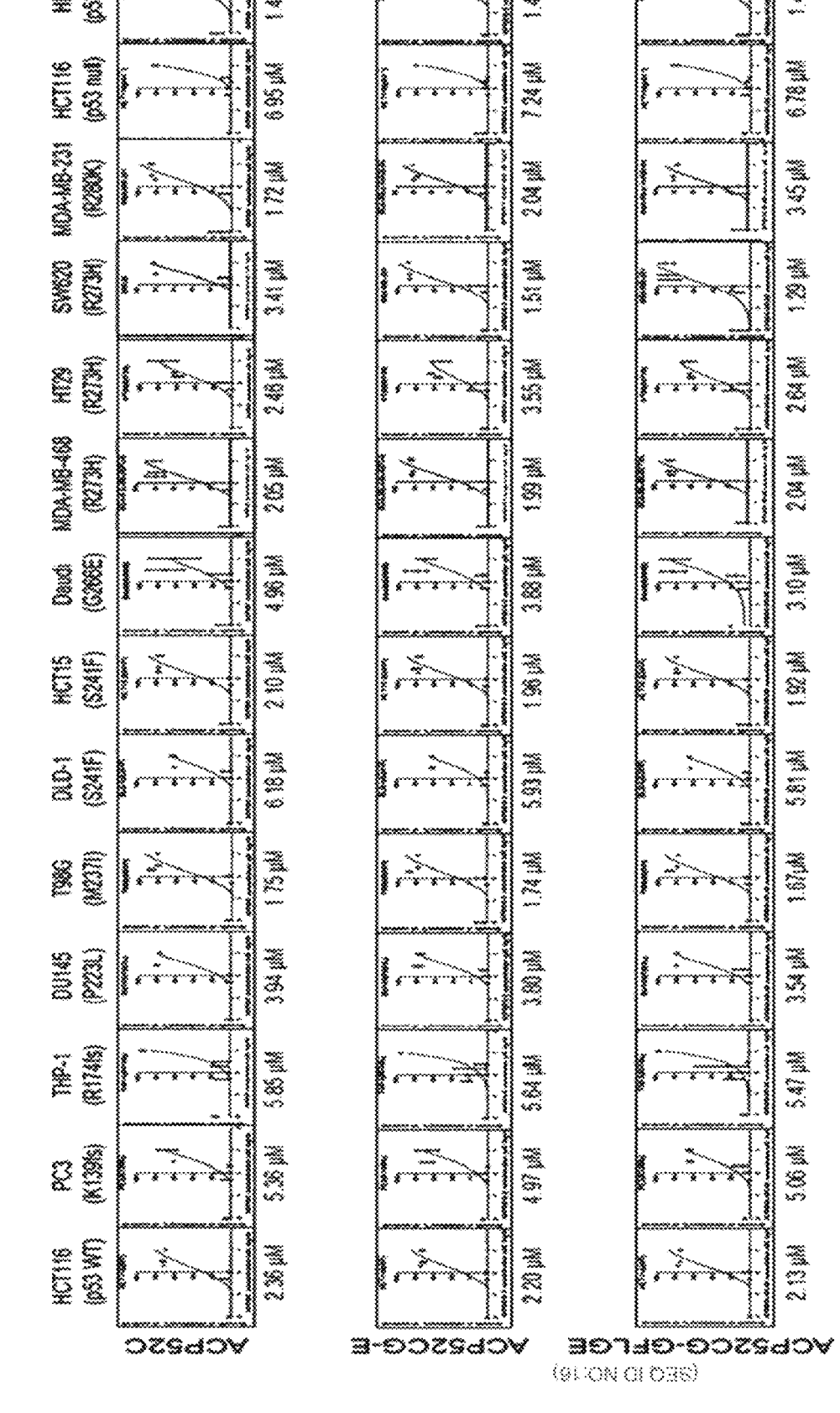
Figure 10C:
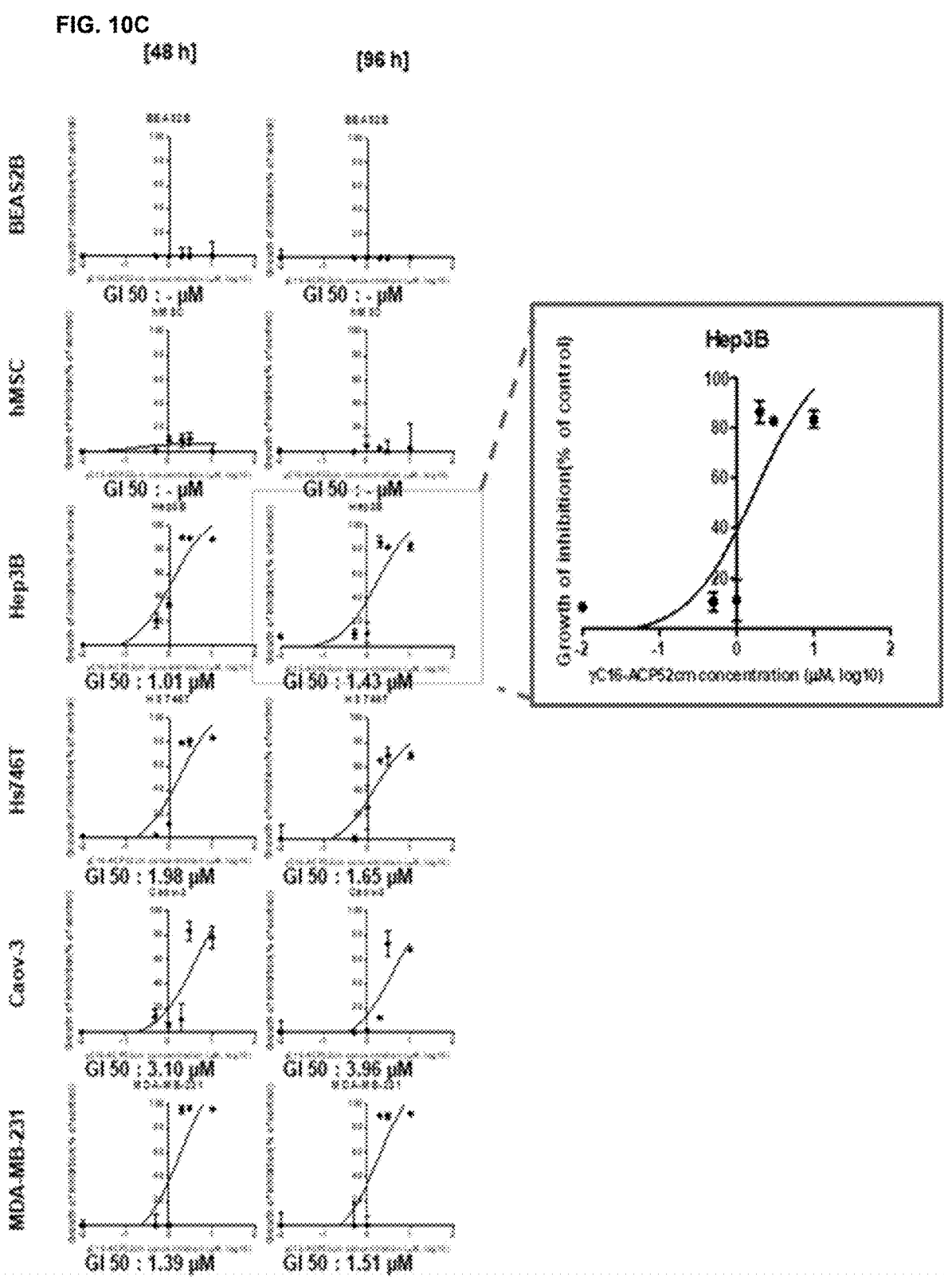
Figure 10F:
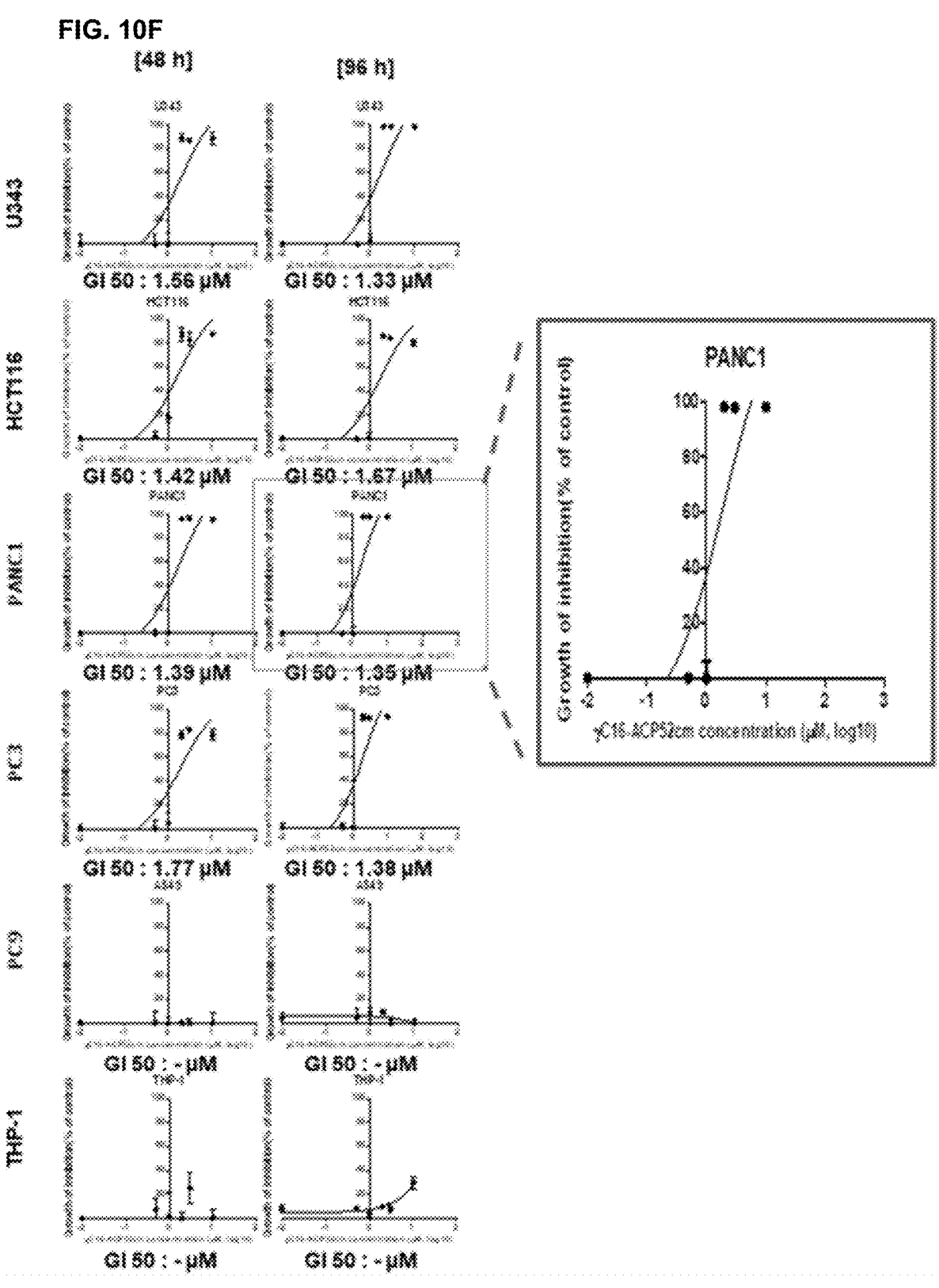
Figure 12B:
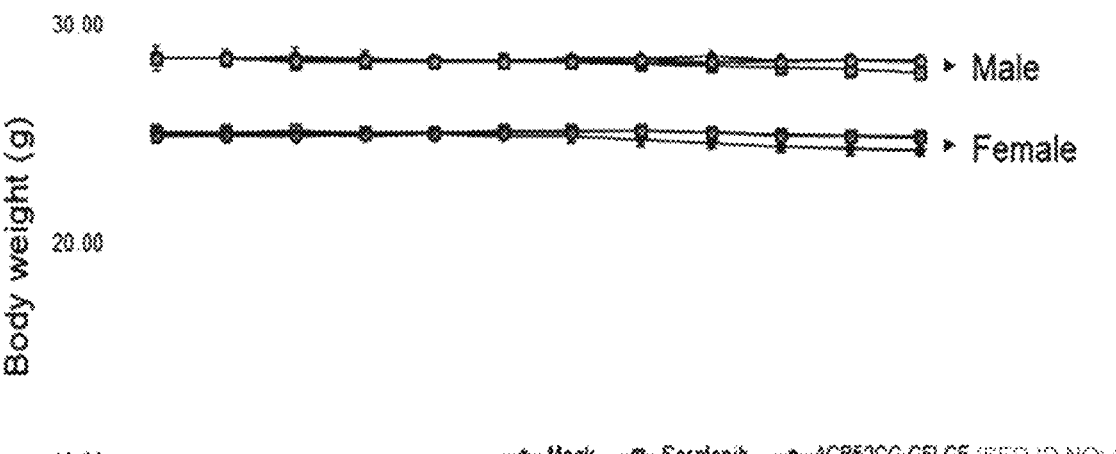
Figure 12C:
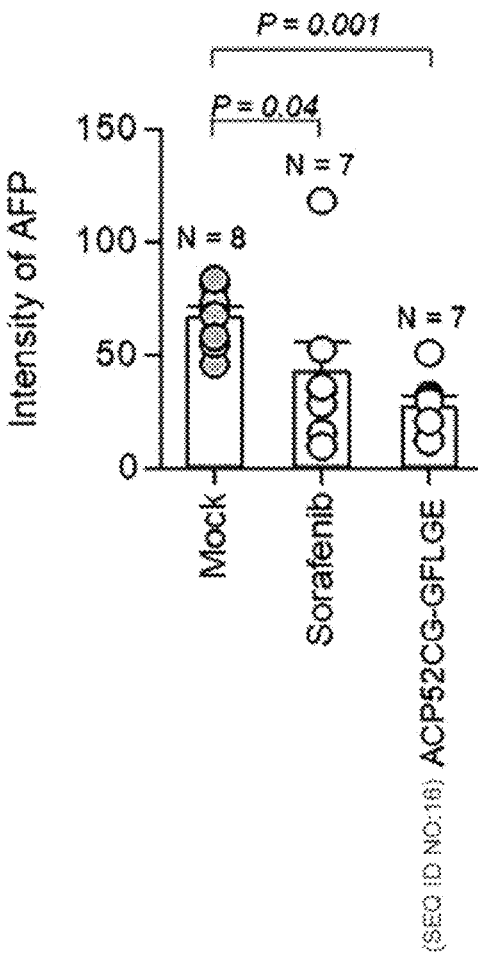
Figure 12D:
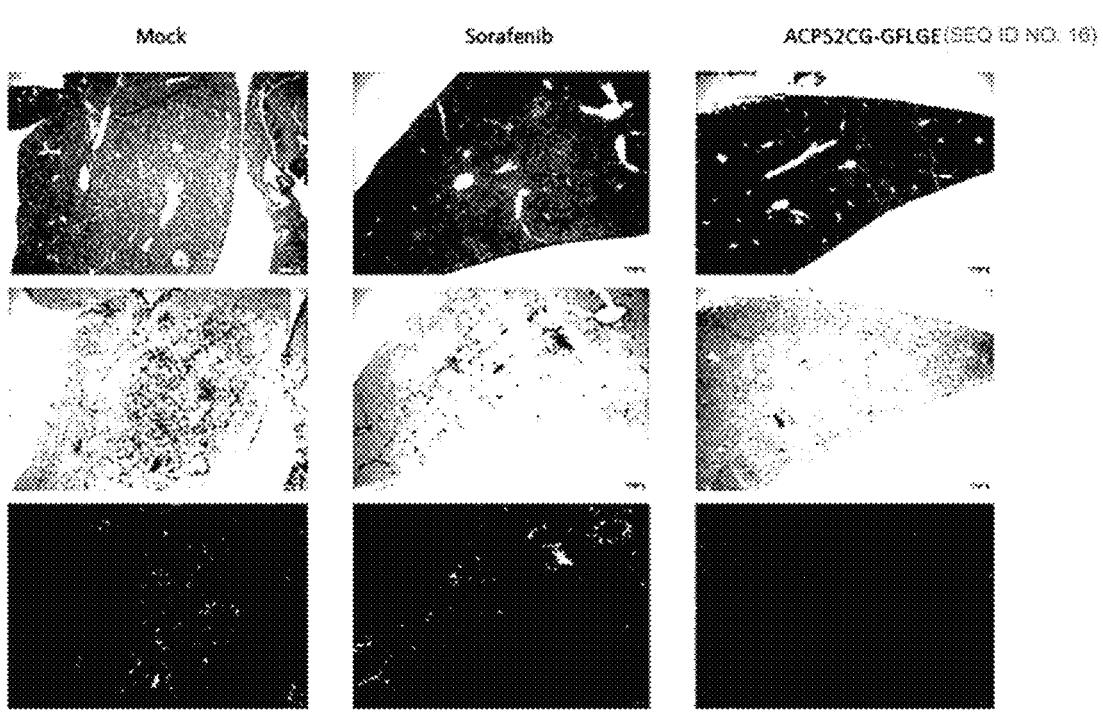
Figure 13C:
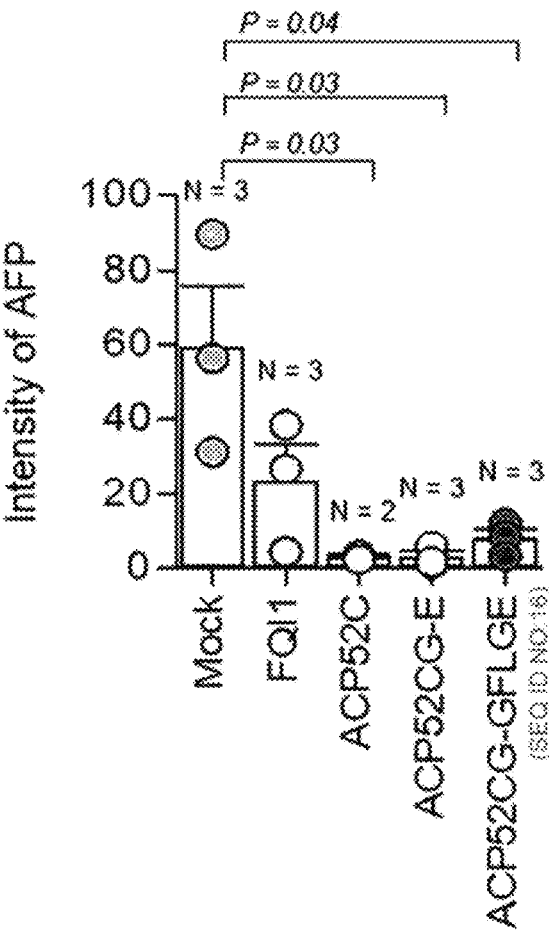
Figure 13D:
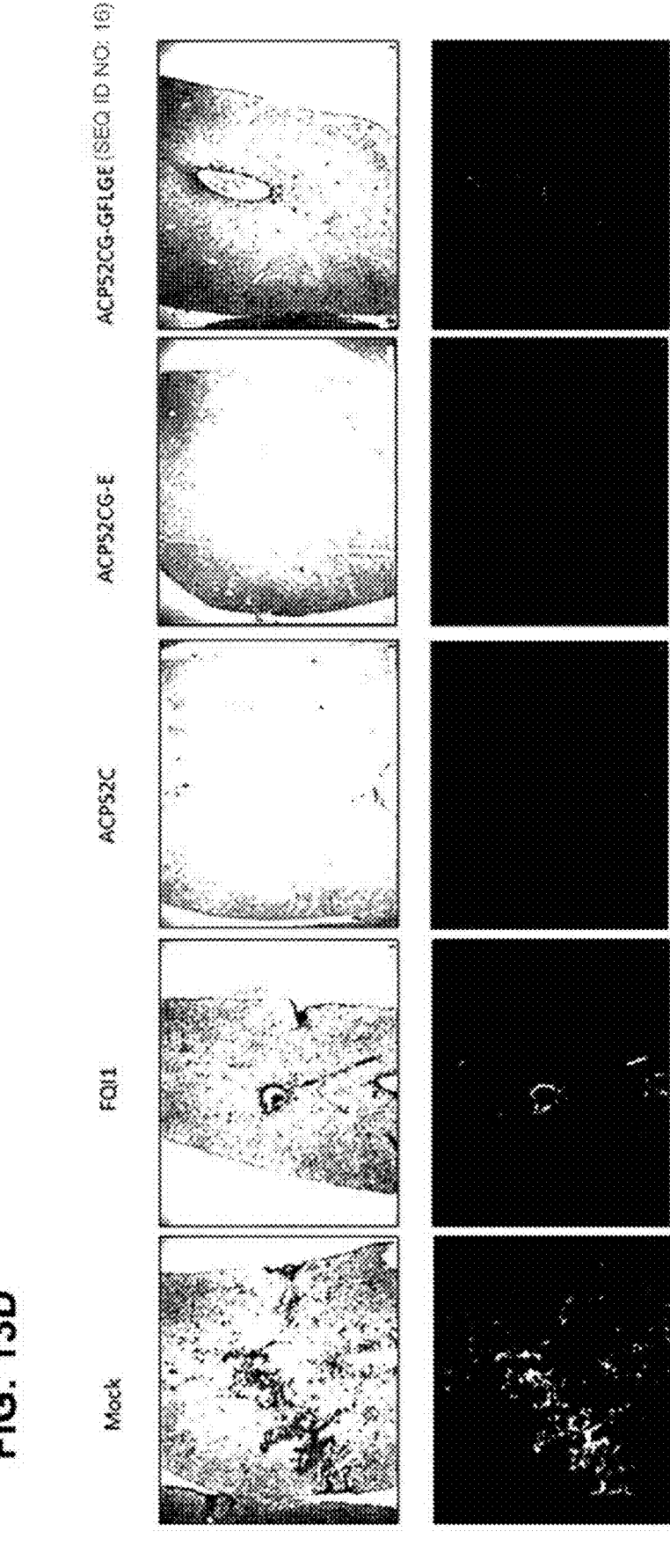
Figure 16J:
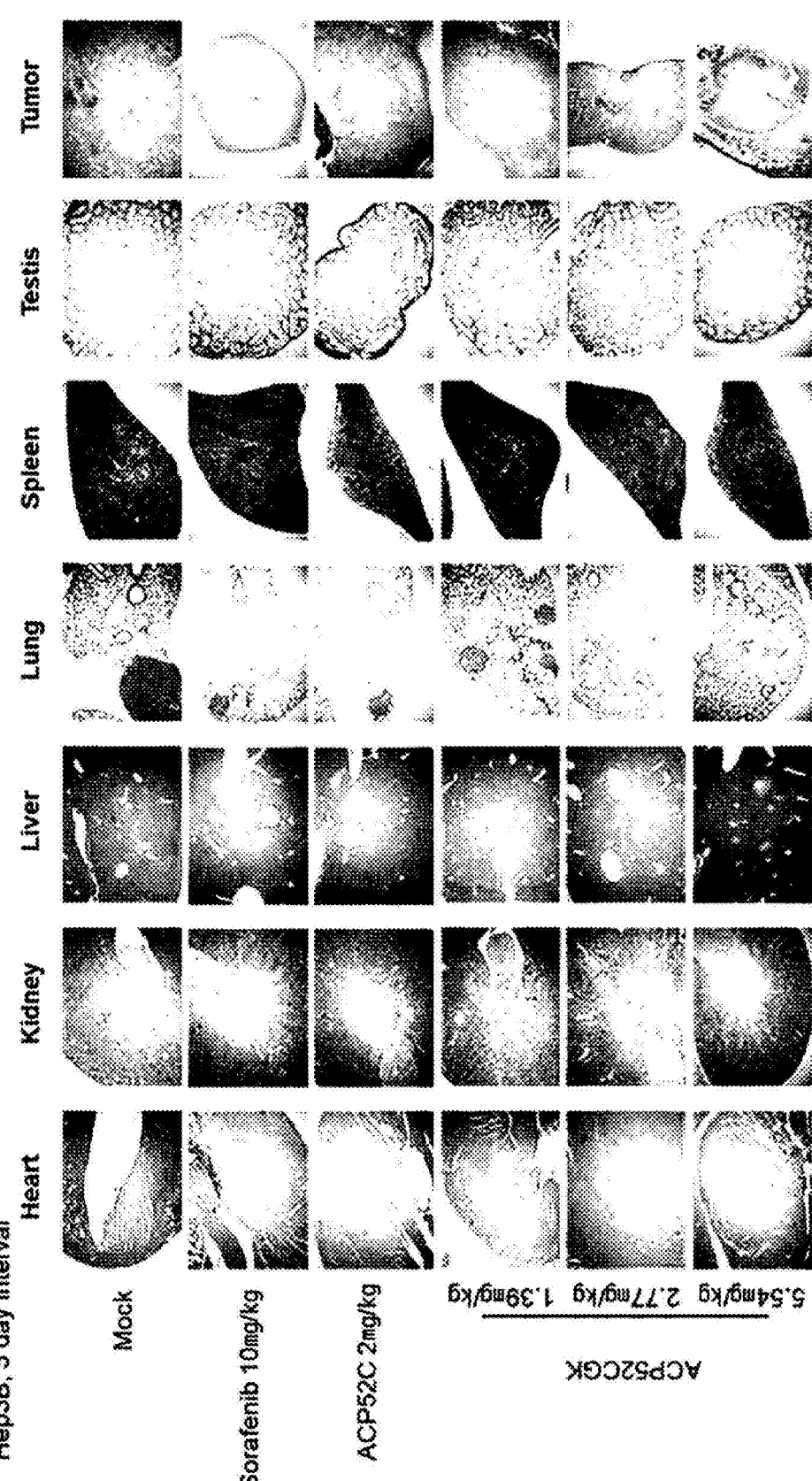
Figure 32B:
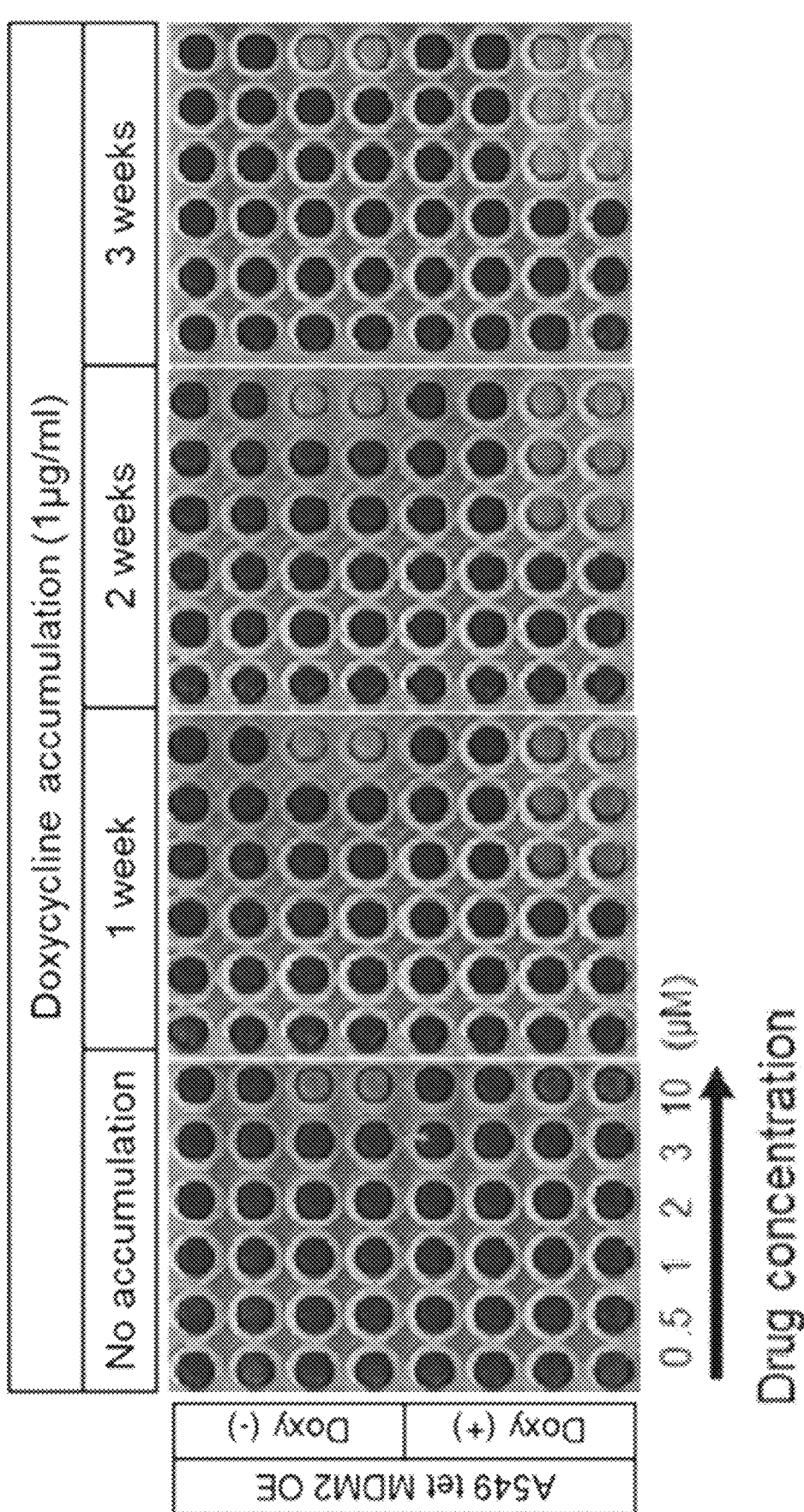
Figure 36:
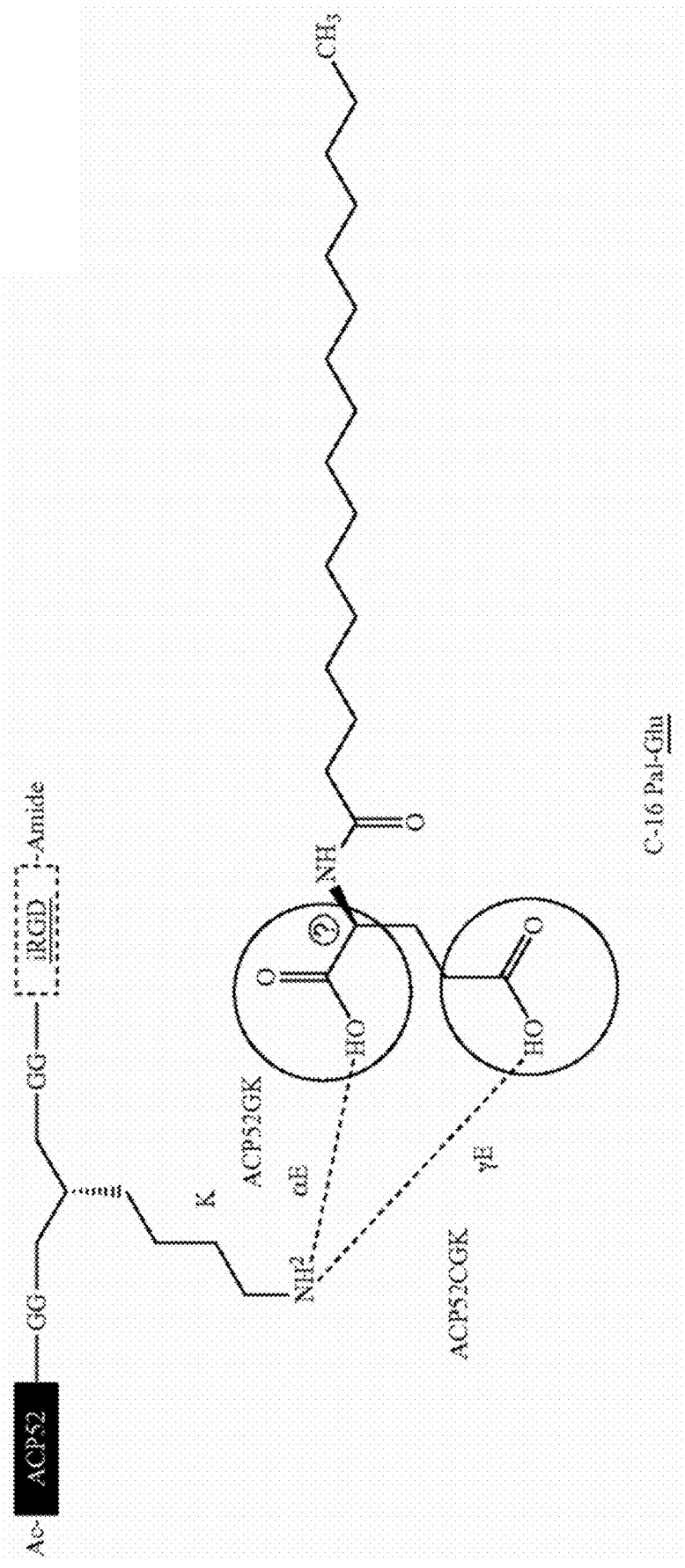

[Example 2] Confirmation of In Vitro Anticancer Effect of CP2c-Targeting Peptide-Fatty Acid Conjugate The anticancer effect of the CP2c-targeting peptide-fatty acid conjugate synthesized in Preparation Example 2 was analyzed in various cancer cells. As a result, all three types of $C_{16}$ fatty acid-binding peptides {ACP52CG (=ACP52CG-E), ACP52CK (=ACP52CG-GFLGE (SEQ ID NO: 16)), and ACP52CGK} induced cancer cell-specific cell death similarly to the control group (ACP52C), and the $GI_{50}$ values calculated at 48 hours after treatment were like or more efficient than that of the control (FIGS. 8a to 8d, FIGS. 10a to 10g). In addition, after treatment with ACP52CG and ACP52CK for various cancer cell lines with different p53 mutations, cell survival curves and $GI_{50}$ values were calculated through MTT assay. As a result, although the $GI_{50}$ value for each cell line showed a deviation, it was 10 mM or less, which was clearly distinguished from the result of the normal cell line (about 1,000 mM) (FIGS. 9a to 9c). In conclusion, the anticancer effects of ACP52CG, ACP52CK and ACP52CGK were similar to those of ACP52C, and the fatty acids bound to the complexes did not show any negative effects on cancer cells and normal cells.

[Example 3] Confirmation of Tumor Growth Inhibitory Effect and General Physiological Toxicity Dependent Upon Treatment with CP2c-Targeting Peptide-Fatty Acid Conjugates in Mouse Models Transplanted with Various Cancer Cell Lines

[3-1] Confirmation of Tumor Growth Inhibitory Effect and General Physiological Toxicity of ACP52CG (=ACP52CG- E), ACP52CK (=ACP52CG-GFLGE (SEQ ID NO: 16)), and ACP52GK (=C16-ACP52cm) in Mouse Models Transplanted with Liver and Breast Cancer Cell Lines To analyze the anticancer efficacy of the CP2c target peptide-fatty acid conjugates synthesized in Preparation Example 2 in animal models, ACP52CG and ACP52CK were injected into the Hep3B xenograft mice via tail vein 5 times at 3-day intervals. As a result, both ACP52CG and ACP52CK showed similar efficacy to sorafenib, but their efficacy was inferior to that of ACP52C. However, no specific abnormalities were found in normal tissues and blood levels, and no toxicity was observed (FIGS. 11a to 11e).

In addition, the mice that passed 22 weeks after DEN treatment were classified into 3 groups (7 to 8 mice/group), such as a control group (mock) treated with only a vehicle, a sorafenib group (an approved drug for liver cancer treatment), and an ACP52CG-GFLGE (SEQ ID NO: 16) (ACP52CK) group. The drug was injected through the tail vein a total of 12 times at a concentration of 5 mg/kg at 3-day intervals. As a result of the analysis, the sorafenib treatment group showed a significant anticancer effect (p=0.04) compared to the control group, and the ACP52CG-GFLGE (SEQ ID NO: 16) (ACP52CK) treatment group showed a similar anticancer effect (p=0.001) to the sorafenib treatment group (FIGS. 12a to 12d). Furthermore, efficacy analysis results of ACP52CG and ACP52CK in mice 15 weeks after DEN treatment were also superior to another control, FQI1, but did not show any superior efficacy compared to ACP52C (FIGS. 13a to 13d).

When ACP52CG and ACP52CK were injected into MDA-MB-231 (LM1) xenograft mice via tail vein 5 times at 3-day intervals, both ACP52CG and ACP52CK showed tumor regression efficacy, but the anticancer effect was not significant. No specific abnormalities were found in blood levels, so toxicity was not observed (FIGS. 14a to 14d).

When ACP52GK (=C16-ACP52 cm) was injected into Hep3B xenograft mice via tail vein 5 times at 3-day intervals, and then the efficacy was analyzed, it was confirmed that the ACP52GK efficacy was lower than that of ACP52C, but the effect was superior to that of the control FQI1 group.
[3-2] Confirmation of Tumor Growth Inhibitory Effect, Metastasis Inhibition Effect, and General Physiological Toxicity of ACP52CGK in Mouse Models Transplanted with Liver and Breast Cancer Cell Lines ACP52CGK was injected into the Hep3B xenograft mice via tail vein at 3 different concentrations (1.39, 2.77, or 5.54 mg/kg) 5 times at 3-day intervals. The tumor volume was measured at every three days after drug injection. The tumor and major tissues were excised from the mice sacrificed on the 24th day after the tumor cell injection. The tumor was weighed and fixed with 4% formaldehyde together with major organs. After making tissue slides through paraffin sections, hematoxylin/eosin staining was performed. The collected blood samples were subjected to basic CBC analysis using a Coulter LH 750 hematology analyzer. The acquired data were statistically processed using an Excel program.

As a result, ACP52CGK exhibited a tumor suppressive effect similar to that of ACP52C, and no abnormalities were found in normal tissues and blood levels (FIGS. 15a to 15d and 15g to 15j). In addition, according to FIGS. 15e to 15f showing the average and standard deviation of the tumor area metastasized to the lung, it was confirmed that ACP52CGK had a superior to ACP52C in the tumor metastasis inhibition effect.

ACP52CGK was injected into Hep3B xenograft mice via tail vein 5 times at intervals of 5 days at 3 different concentrations (1.39, 2.77, 5.54 mg/kg), and the anticancer effect was evaluated in the same manner as described above. As a result, all three concentrations of ACP52CGK showed tumor inhibition and metastasis inhibition effects superior to the sorafenib and ACP52C treatment groups, and the inhibition effects were concentration-dependent (FIGS. 16a to g). In addition, ACP52CGK injected by 5-day intervals showed more effective tumor inhibition and metastasis inhibition effects to those injected by 3-day intervals (compare FIGS. 15a to 15j with FIGS. 16a to k). As a result of a comprehensive analysis of all the results, 2.77 mg/kg was the optimal concentration. In addition, no particular abnormality was found in blood levels, so toxicity was not observed (FIGS. 16h to 16k).

The anticancer effect of ACP52CGK was analyzed in MDA-MB-231 (LM1) xenograft mice in the same manner as in the Hep3B xenograft mouse model experiments. Similarly, tumor suppression and metastasis inhibition effects were superior to those of the sorafenib and ACP52C-treated groups at all three concentrations (1.39, 2.77, or 5.54 mg/kg) of ACP52CGK (FIGS. 17a to 17f and 18a to 18g). A superior anticancer effect was observed when injected at intervals of 5 days rather than at intervals of 3 days, and 2.77 mg/kg was the optimal concentration. In addition, no particular abnormality was found in blood levels, so toxicity was not observed (FIGS. 17g-j and 18h-k).

[Example 4] Stability and Safety Evaluation of CP2c-Targeting Peptide-Fatty Acid Conjugates To analyze the in vivo half-life of ACP52CGK, Cy5-labeled ACP52CGK was injected into the tail vein of the mouse, and then the fluorescence intensity remaining in the mouse body was measured over time by live imaging process. As a result, the half-life was about 20.2 hours (FIGS. 19a to 19b). These results indicate that the conjugation with the fatty acids caused significantly improved in vivo stability, compared to the lead material ACP52C showing a half-life of 7.95 hours.

Figure 20A:
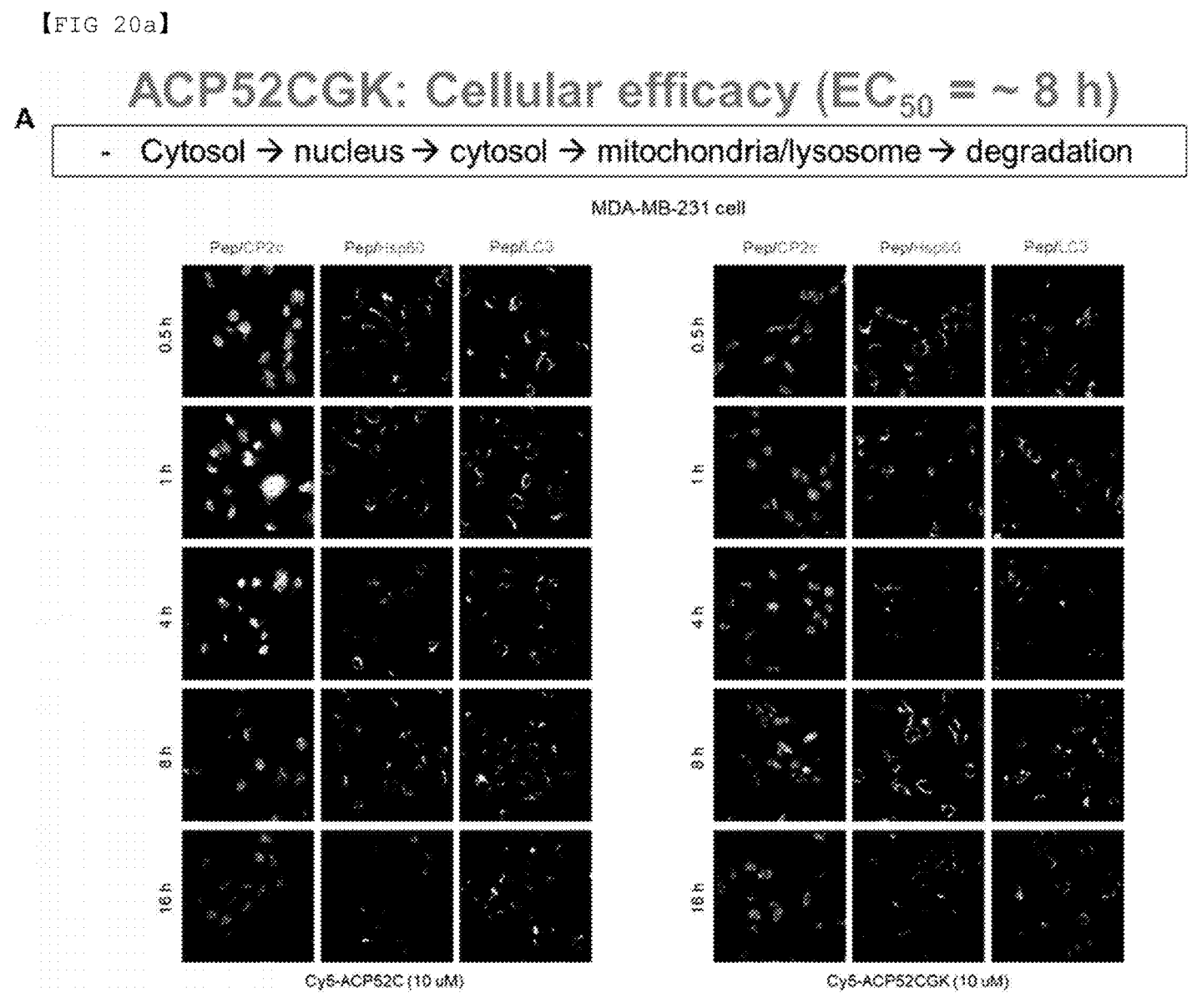

To analyze the subcellular movement, localization, and stability of ACP52CGK in cultured cells, Cy5-labeled ACP52CGK was treated in cell culture media for 30 minutes, and then the subcellular movement of the peptide was traced over time. In addition, subcellular movement was analyzed by confocal microscope whether Cy5-labeled ACP52CGK also migrated into mitochondria (Hsp60) and lysosomes (LC3). As a result, ACP52CGK passed through the cytoplasm and was located mostly in the nucleus from 4 hours, and came out of the cytoplasm after 8 hours; some thereof was in the mitochondria, but eventually migrated to the lysosome and degraded at 16 hours. These subcellular movement, localization, and stability phenomena of ACP52CGK were not different from those in ACP52C (FIGS. 20a to 20b).

Meanwhile, it was speculated that the ACP52C would not exhibit immunogenicity since it is consisting of 15 amino acids. To verify this, immunogenicity of ACP52CG and ACP52CK was directly tested in the process of deriving the final new drug candidate. Since the final candidate material might be a C-16 palmitoyl acid-conjugated ACP52C peptide, which is not different with ACP52CG and ACP52CK in terms of chemical composition, it was decided to analyze whether antibodies were formed on ACP52CG and ACP52CK. As a result of performing ELISA analysis on sera isolated from rabbits injected with ACP52CG and ACP52CK three times, both rabbit sera did not induce immune responses in ACP52CG, ACP52CK, and ACP52CGK, including ACP52C. Therefore, it was concluded that the final candidate material (ACP52CGK) would also not show immunogenicity in the human body (FIG. 21).

A repeated toxicity test for the in vivo administration of ACP52CGK was conducted using female and male mice. As a preliminary experiment, when 100 mg/kg and 1000 mg/kg of ACP52C were repeatedly administered twice, all the mice survived, and any liver toxicity or adverse effect on major organs was not observed. As a full-scale experiment, after intravenous infusion of ACP52CGK for 28 days at 3-day intervals into the solvent group and high-dose group (100 mg/Kg) of 6 males and females each, the weight change, drinking water intake, and main histological analysis of organs, organ weight, hematological tests and blood biochemical tests were analyzed. Overall, no abnormal findings were detected (FIGS. 22a to 22e, 23, and 24, and Tables 1, 2, 3 and 4).

TABLE 1

Absolute organ weights (g) of mice treated or non-treated with ACP52CGK

|  | Female (vehicle) | Female (ACP52Cm, 100 mg/kg) | Male (vehicle) | Male (ACP52Cm, 100 mg/kg) |
|---|---|---|---|---|
| Liver | 0.8000 ± 0.0353 | 0.8049 ± 0.0350 | 0.9050 ± 0.0732 | 0.9011 ± 0.0916 |
| Kidney | 0.2305 ± 0.0124 | 0.2417 ± 0.0184 | 0.3188 ± 0.0174 | 0.3055 ± 0.0220 |
| Adrenal Gland | 0.0045 ± 0.0014 | 0.0059 ± 0.0009 | 0.0046 ± 0.0014 | 0.0040 ± 0.0013 |
| Spleen | 0.0625 ± 0.0070 | 0.0620 ± 0.0051 | 0.0604 ± 0.0076 | 0.0573 ± 0.0084 |
| Ovary (Testis) | 0.0046 ± 0.0016 | 0.0059 ± 0.0012 | 0.1863 ± 0.0083 | 0.1693 ± 0.0169 |
| Uterus (Epididymis) | 0.0503 ± 0.0188 | 0.0638 ± 0.0227 | 0.0518 ± 0.0052 | 0.0482 ± 0.0127 |
| Lung | 0.1423 ± 0.0182 | 0.1432 ± 0.0075 | 0.1411 ± 0.0186 | 0.1476 ± 0.0105 |
| Thymus | 0.0394 ± 0.0055 | 0.0338 ± 0.0022 | 0.0402 ± 0.0127 | 0.0408 ± 0.0144 |
| Heart | 0.0919 ± 0.0097 | 0.0950 ± 0.0072 | 0.1072 ± 0.0066 | 0.1078 ± 0.0087 |
| Brain | 0.4077 ± 0 0196 | 0.4034 ± 0.0291 | 0.4013 ± 0.0157 | 0.3943 ± 0.0168 |

TABLE 2

Relative organ weights (%) of mice treated or non-treated with ACP52CGK

|  | Female (vehicle) | Female (ACP52Cm, 100 mg/kg) | Male (vehicle) | Male (ACP52Cm, 100 mg/kg) |
|---|---|---|---|---|
| Liver | 4.45 ± 0.17 | 4.47 ± 0.14 | 4.17 ± 0.25 | 4.41 ± 0.41 |
| Kidney | 1.28 ± 0.06 | 1.34 ± 0.06 | 1.47 ± 0.09 | 1.50 ± 0.08 |
| Adrenal Gland | 0.0250 ± 0.0076 | 0.0324 ± 0.0047 | 0.02 ± 0.01 | 0.02 ± 0.01 |
| Spleen | 0.35 ± 0.04 | 0.35 ± 0.03 | 0.28 ± 0.03 | 0.28 ± 0.04 |
| Ovary (Testis) | 0.0255 ± 0.0087 | 0.0326 ± 0.0054 | 0.86 ± 0.05 | 0.83 ± 0.08 |
| Uterus (Epididymis) | 0.28 ± 0.10 | 0.35 ± 0.12 | 0.24 ± 0.02 | 0.24 ± 0.07 |
| Lung | 0.79 ± 0.10 | 0.79 ± 0.03 | 0.65 ± 0.07 | 0.72* ± 0.05 |
| Thymus | 0.22 ± 0.03 | 0.19 ± 0.02 | 0.19 ± 0.06 | 0.20 ± 0.06 |
| Heart | 0.51 ± 0.04 | 0.53 ± 0.03 | 0.49 ± 0.03 | 0.53 ± 0.04 |
| Brain | 2.27 ± 0.12 | 2.24 ± 0.18 | 1.85 ± 0.05 | 1.93 ± 0.12 |

TABLE 3

Hematology of mice treated or non-treated with ACP52CGK

|  | Female (vehicle) | Female (ACP52Cm, 100 mg/kg) | Male (vehicle) | Male (ACP52Cm, 100 mg/kg) |
|---|---|---|---|---|
| WBC ($10^3$/ul) | 2.26 ± 0.15 | 2.34 ± 0.62 | 2.42 ± 0.98 | 2.83 ± 1.04 |
| Neutrophils (%) | 16.33 ± 5.14 | 17.77 ± 0.91 | 18.17 ± 2.59 | 25.83 ± 12.58 |
| Eosinophils (%) | 14.47 ± 5.42 | 14.83 ± 1.7 | 3.83 ± 1.76 | 6.70 ± 2.17 |
| Basophils (%) | 0.97 ± 0.31 | 1.20 ± 0.66 | 1.30 ± 0.90 | 0.73 ± 0.38 |
| Lymphocytes (%) | 66.57 ± 1.92 | 65.23 ± 0.91 | 75.10 ± 5.12 | 65.53 ± 13.98 |
| Monocytes (%) | 1.27 ± 0.32 | 1.07 ± 0.06 | 0.93 ± 0.71 | 0.77 ± 0.67 |
| RBC ($10^6$/ul) | 9.66 ± 0.45 | 9.91 ± 0.08 | 10.59 ± 0.29 | 10.39 ± 1.39 |
| Hematocrit (%) | 54.80 ± 4.30 | 54.50 ± 1.47 | 57.50 ± 1.71 | 58.30 ± 9.33 |
| Hemoglobin (g/dl) | 14.67 ± 0.32 | 14.93 ± 0.50 | 16.07 ± 0.45 | 15.53 ± 2.18 |
| MCV (fl) | 56.53 ± 0.32 | 55.00 ± 1.64 | 54.33 ± 1.47 | 56.00 ± 2.30 |
| MCH (pg) | 17.03 ± 1.70 | 15.07 ± 0.49 | 15.17 ± 0.12 | 14.97 ± 0.15 |
| MCHC (g/dl) | 28.60 ± 2.12 | 27.43 ± 0.32 | 27.97 ± 0.61 | 26.70 ± 0.80 |
| Platelets ($10^3$/ul) | 892.67 ± 111.54 | 906.33 ± 145.82 | 964.33 ± 125.51 | 1038 ± 30.51 |

TABLE 4

Serum biochemistry of mice treated or non-treated with ACP52CGK

| | Female (vehicle) | Female (ACP52Cm, 100 mg/kg) | Male (vehicle) | Male (ACP52Cm, 100 mg/kg) |
|---|---|---|---|---|
| ALT (U/l) | 11.53 ± 1.68 | 13.93 ± 3.23 | 45.40 ± 10.18 | 23.20 ± 5.94 |
| AST (U/l) | 66.67 ± 9.28 | 68.37 ± 5.46 | 96.00 ± 7.06 | 93.30 ± 19.39 |
| T-proteins (g/dl) | 4.50 ± 0.10 | 4.63 ± 0.55 | 4.77 ± 0.32 | 4.43 ± 0.35 |
| Albumin (g/dl) | 3.33 ± 0.06 | 3.20 ± 0.17 | 2.93 ± 0.12 | 2.73 ± 0.25 |
| Cholesterol (mg/dl) | 82.73 ± 4.53 | 79.60 ± 8.56 | 99.13 ± 11.12 | 90.63 ± 2.97 |
| Triglycerides (mg/dl) | 23.43 ± 6.55 | 18.90 ± 12.34 | 22.25 ± 25.39 | 23.67 ± 6.43 |
| HDL (mg/dl) | 40.03 ± 2.30 | 39.47 ± 4.97 | 77.50 ± 23.19 | 72.85 ± 7.42 |
| LDL (mg/dl) | 4.77 ± 0.90 | 4.43 ± 0.91 | 4.10 ± 0.35 | 3.57 ± 0.23 |
| BUN (mg/dl) | 27.70 ± 4.19 | 26.50 ± 3.32 | 31.83 ± 17.33 | 23.53 ± 4.76 |
| Creatinine (mg/dl) | 0.35 ± 0.01 | 0.36 ± 0.02 | 0.37 ± 0.03 | 0.37 ± 0.03 |
| LDH (U/l) | 147.70 ± 17.08 | 141.10 ± 44.08 | 308.33 ± 73.74 | 357.73 ± 91.87 |

To investigate whether the efficacy of ACP52CGK tested on cancer cell lines and xenograft mouse models can be equally applied in actual clinical practice, the efficacy of ACP52CGK was evaluated in cells cultured from the tumor tissue of breast cancer patients in a fresh state. As a preliminary result, it was confirmed that ACP52CGK induces cell death at $GI_{50}$: ~2 µM, similar to those in the cancer cell line experiments (FIGS. 25a to 25d). Accordingly, the cancer tissues of breast cancer patients in cryo-preservation were thawed and the primary culture was performed. When effect of ACP52CGK was analyzed on the cells obtained therefrom, it was also confirmed that cell death is induced at $GI_{50}$: ~2 µM. (FIGS. 26a to 26d).

[Example 5] Analysis of Resistance Causation of Cells Exhibiting Resistance to CP2c-Target Peptide-Fatty Acid Conjugate As a result of analyzing the efficacy of ACP52CGK in cells primary cultured from PDX (patient derived xenograft) tumor tissue for each generation, it was confirmed that the sensitivity to ACP52CGK was not significantly different in cells derived from the same origin (FIGS. 27a to 27d). However, primarily cultured cells from some PDX tumor tissues showed resistance to ACP52CGK (FIGS. 28a to 28b).

The cells exhibiting resistance to ACP52CGK (mainly lung cancer cell lines) tended to show a low expression level of MDM2p90 and a relatively high expression of MDM2p60. In fact, it was confirmed by immunoblot that the expression of YY1 was decreased in the three lung cancer cell lines (A549, PC9, KCL22) treated with ACP52C, but the expression of p53, p63 and p73 did not show any change. There was no decrease in the expression of MDM2 (p90 and p60) in these cell lines. Since MDM2p60 is known to be a protein in which the C-terminal region of MDM2p90 comprising sites (S386, S395, and S407) phosphorylated by ATM is deleted, it was speculated that the MDM2 degradation would not be properly regulated by ACP52C treatment (FIG. 29, FIGS. 30a to 30c). In accordance with this, by treatment with doxycycline for 3 weeks, MDM2p90 was continuously overexpressed and, interestingly, the expression of p53 protein and YY1 among the CP2c transcriptional activity-dependent and independent marker proteins were decreased by week by immunoblot. Meanwhile, because of analyzing the induction of cell death according to ACP52C treatment by MTT assay, it was confirmed that cell death was induced from the second week. Therefore, it was demonstrated that the low expression of MDM2p90 in lung cancer cell lines is the cause of ACP52C resistance (FIGS. 31a to 31b, FIGS. 32a to 32d).

Two models have been proposed that the generation of MDM2p60 is due to caspase2 cleavage of MDM2p90 or alternative splicing. When we performed RT-PCR using a primer set capable of detecting an alternative splicing form of MDM2 in various cancer cell lines, a lung cancer cell-specific splice form was not found. In addition, when we tested the nucleotide sequence analysis of genomic DNA after PCR cloning to determine whether MDM2p60 is generated from the truncated mRNA due to the presence of SNPs in the MDM2 gene specifically for lung cancer cell lines, lung cancer cell-specific SNPs were not observed (FIGS. 33a to 33d).

Meanwhile, when a caspase2 inhibitor (AC-VDVAD (SEQ ID NO: 11)-CHO) was treated to identify a phenomenon that occurs due to the high activity of caspase2 specifically in lung cancer cells, it was found by immunoblot that the protein amount of MDM2p90 increased, while the protein amount of MDM2p60 decreased according to the treatment with the Caspase2 inhibitor. Therefore, we concluded that the MDM2p60 form, which is overexpressed in lung cancer cells, is the result of cleavage of MDM2p90 by caspase2. Based on these results, the cell death-inducing effect was analyzed by treating cells (A549 and PDX cells; Breast F0-JOS), which showed resistance to ACP52C, with a combination of caspase 2 inhibitor and ACP52C. As a result, efficacy was observed around $GI_{50}$~1 µM in the group treated with the combination of the caspase 2 inhibitor and ACP52C (FIGS. 34a to 34d, FIG. 35).

Therefore, the ACP52CGK peptide improved in vivo stability compared to the existing ACP52C peptide and showed growth inhibition/cell death in all carcinoma cells as in ACP52C, but had no significant effect on normal cells. In addition, it was confirmed that cancer cells exhibiting resistance to ACP52C could be killed by the combined treatment of ACP52C with a caspase 2 inhibitor.

The invention claimed is:

1. A CP2c-targeting peptide-fatty acid conjugate, comprising:
   a transcription factor CP2c-targeting peptide comprising the amino acid sequence of SEQ ID NO: 2, wherein the N-terminus of the transcription factor CP2c-targeting peptide is modified with an acetyl group;
   a linker peptide at the C-terminus of the transcription factor CP2c-targeting peptide, wherein the linker peptide consists of the amino acid sequence of $G_nKG_m$ (SEQ ID NO: 21), wherein n and m are each independently an integer of 1 to 6;
   a cell-penetrating peptide (CPP) consisting of the amino acid sequence of SEQ ID NO: 3 at the C-terminus of the linker peptide, wherein the C-terminus of the cell-penetrating peptide (CPP) is modified with an amide group; and
   a fatty acid conjugated with lysine (Lys, K) of the linker peptide, wherein the fatty acid is $C_{16}$ palmitoyl acid bonded to glutamic acid (Glu, E).

2. The CP2c-targeting peptide-fatty acid conjugate according to claim 1, a functional group of lysine (Lys, K) of the amino acid sequence of $G_nKG_m$ (SEQ ID NO: 21) is bonded to a gamma carbon carboxyl group of the glutamic acid, wherein n and m are each independently an integer of 0 to 6.

3. A pharmaceutical composition for treating cancer, comprising the CP2c-targeting peptide-fatty acid conjugate according to claim 1 as an active ingredient.

4. A health functional food composition for alleviating cancer, comprising the CP2c-targeting peptide-fatty acid conjugate according to claim 1 as an active ingredient.

5. A pharmaceutical composition for treating cancer comprising the CP2c-targeting peptide-fatty acid conjugate according to claim 1 and Caspase2 inhibitor as an active ingredient.

* * * * *

SEQUENCE LISTING

<160> NUMBER OF SEQ ID NOS: 21

<210> SEQ ID NO 1
<211> LENGTH: 4
<212> TYPE: PRT
<213> ORGANISM: Artificial Sequence
<220> FEATURE:
<223> OTHER INFORMATION: Synthetic construct of peptide for targeting
      CP2c

<400> SEQUENCE: 1

Tyr Pro Gln Arg
1

<210> SEQ ID NO 2
<211> LENGTH: 6
<212> TYPE: PRT
<213> ORGANISM: Artificial Sequence
<220> FEATURE:
<223> OTHER INFORMATION: Synthetic construct of peptide for targeting
      CP2c

<400> SEQUENCE: 2

Asn Tyr Pro Gln Arg Pro
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct of cell-penetrating peptide

<400> SEQUENCE: 3

Cys Arg Gly Asp Lys Gly Pro Asp Cys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic construct of amino acid sequence

<400> SEQUENCE: 4

Glu Gly Leu Phe Gly
1               5

<210> SEQ ID NO 5
<211> LENGTH: 5
<212> TYPE: PRT
<213> ORGANISM: Artificial Sequence
<220> FEATURE:
<223> OTHER INFORMATION: linker peptide

<400> SEQUENCE: 5

Gly Gly Lys Gly Gly
1               5

<210> SEQ ID NO 6
<211> LENGTH: 30
<212> TYPE: DNA
<213> ORGANISM: Homo sapiens

<400> SEQUENCE: 6
atgaaatgaa tccccccctt ccatcacatt                                   30

-continued

```
<210> SEQ ID NO 7
<211> LENGTH: 23
<212> TYPE: DNA
<213> ORGANISM: Homo sapiens

<400> SEQUENCE: 7
caacacaagc tgaagagggc ttt                                           23

<210> SEQ ID NO 8
<211> LENGTH: 22
<212> TYPE: DNA
<213> ORGANISM: Homo sapiens

<400> SEQUENCE: 8
agtgaatgat tccagagagt ca                                            22

<210> SEQ ID NO 9
<211> LENGTH: 23
<212> TYPE: DNA
<213> ORGANISM: Homo sapiens

<400> SEQUENCE: 9
gccattgaac cttgtgtgat ttg                                           23

<210> SEQ ID NO 10
<211> LENGTH: 23
<212> TYPE: DNA
<213> ORGANISM: Homo sapiens

<400> SEQUENCE: 10
caacacaagc tgaggagggc ttt                                           23

<210> SEQ ID NO 11
<211> LENGTH: 5
<212> TYPE: PRT
<213> ORGANISM: artificial sequence
<220> FEATURE:
<223> OTHER INFORMATION: synthetic construct, caspase2 inhibitor

<400> SEQUENCE: 11

Val Asp Val Ala Asp
1               5

<210> SEQ ID NO 12
<211> LENGTH: 5
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (5)..(5)
<223> OTHER INFORMATION: Palmitoyl acid bound to glycine

<400> SEQUENCE: 12

Glu Gly Leu Phe Gly
1               5

<210> SEQ ID NO 13
<211> LENGTH: 4
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
```

```
<222> LOCATION: (2)..(2)
<223> OTHER INFORMATION: Palmitoyl acid bound to glutamic acid

<400> SEQUENCE: 13

Lys Glu Gly Gly
1

<210> SEQ ID NO 14
<211> LENGTH: 8
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (6)..(6)
<223> OTHER INFORMATION: Palmitoyl acid bound to glycine

<400> SEQUENCE: 14

Lys Glu Gly Leu Phe Gly Gly Gly
1               5

<210> SEQ ID NO 15
<211> LENGTH: 4
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MOD_RES
<222> LOCATION: (1)..(1)
<223> OTHER INFORMATION: Palmitoyl acid bound to glycine

<400> SEQUENCE: 15

Gly Phe Leu Gly
1

<210> SEQ ID NO 16
<211> LENGTH: 5
<212> TYPE: PRT
<213> ORGANISM: Artificial Sequence
<220> FEATURE:
<223> OTHER INFORMATION: The sequence is artificially synthesized

<400> SEQUENCE: 16

Gly Phe Leu Gly Glu
1               5

<210> SEQ ID NO 17
<211> LENGTH: 19
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: SITE
<222> LOCATION: (1)..(1)
<223> OTHER INFORMATION: N-term Ac
<220> FEATURE:
<221> NAME/KEY: MOD_RES
<222> LOCATION: (2)..(2)
<223> OTHER INFORMATION: Palmitoyl acid bound to glutamic acid
<220> FEATURE:
<221> NAME/KEY: SITE
<222> LOCATION: (19)..(19)
<223> OTHER INFORMATION: C-term NH2

<400> SEQUENCE: 17

Lys Glu Gly Gly Asn Tyr Pro Gln Arg Pro Cys Arg Gly Asp Lys Gly
1               5                   10                  15
```

Pro Asp Cys

<210> SEQ ID NO 18
<211> LENGTH: 23
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: SITE
<222> LOCATION: (1)..(1)
<223> OTHER INFORMATION: N-term Ac
<220> FEATURE:
<221> NAME/KEY: MOD_RES
<222> LOCATION: (6)..(6)
<223> OTHER INFORMATION: Palmitoyl acid bound to glycine
<220> FEATURE:
<221> NAME/KEY: SITE
<222> LOCATION: (23)..(23)
<223> OTHER INFORMATION: C-term NH2

<400> SEQUENCE: 18

Lys Glu Gly Leu Phe Gly Gly Gly Asn Tyr Pro Gln Arg Pro Cys Arg
1               5                   10                  15

Gly Asp Lys Gly Pro Asp Cys
            20

<210> SEQ ID NO 19
<211> LENGTH: 21
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: SITE
<222> LOCATION: (1)..(1)
<223> OTHER INFORMATION: N-term Ac
<220> FEATURE:
<221> NAME/KEY: MOD_RES
<222> LOCATION: (10)..(10)
<223> OTHER INFORMATION: Palmitoyl acid bound to glutamic acid
<220> FEATURE:
<221> NAME/KEY: SITE
<222> LOCATION: (21)..(21)
<223> OTHER INFORMATION: C-term NH2

<400> SEQUENCE: 19

Asn Tyr Pro Gln Arg Pro Gly Gly Lys Glu Gly Gly Cys Arg Gly Asp
1               5                   10                  15

Lys Gly Pro Asp Cys
            20

<210> SEQ ID NO 20
<211> LENGTH: 21
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: SITE
<222> LOCATION: (1)..(1)
<223> OTHER INFORMATION: N-term Ac
<220> FEATURE:
<221> NAME/KEY: MOD_RES
<222> LOCATION: (10)..(10)
<223> OTHER INFORMATION: Palmitoyl acid bound to gamma glutamic acid
<220> FEATURE:
<221> NAME/KEY: SITE
<222> LOCATION: (21)..(21)
<223> OTHER INFORMATION: C-term NH2

-continued

```
<400> SEQUENCE: 20

Asn Tyr Pro Gln Arg Pro Gly Gly Lys Glu Gly Gly Cys Arg Gly Asp
1               5                   10                  15

Lys Gly Pro Asp Cys
            20

<210> SEQ ID NO 21
<211> LENGTH: 5
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: VARIANT
<222> LOCATION: (1)..(1)
<223> OTHER INFORMATION: Gly residue can be repeated up to four times or
      absent
<220> FEATURE:
<221> NAME/KEY: VARIANT
<222> LOCATION: (4)..(4)
<223> OTHER INFORMATION: Gly residue can be repeated up to four times or
      absent

<400> SEQUENCE: 21

Gly Gly Lys Gly Gly
1               5
```